(12) United States Patent
Hadad et al.

(10) Patent No.: US 11,672,446 B2
(45) Date of Patent: Jun. 13, 2023

(54) INSULIN DELIVERY RECOMMENDATIONS BASED ON NUTRITIONAL INFORMATION

(71) Applicant: MEDTRONIC MINIMED, INC., Northridge, CA (US)

(72) Inventors: Yaron Hadad, San Francisco, CA (US); Jonathan Lipnik, Ramat Gan (IL)

(73) Assignee: MEDTRONIC MINIMED, INC., Northridge, CA (US)

( * ) Notice: Subject to any disclaimer, the term of this patent is extended or adjusted under 35 U.S.C. 154(b) by 1083 days.

(21) Appl. No.: 16/359,611

(22) Filed: Mar. 20, 2019

(65) Prior Publication Data
US 2019/0290172 A1 Sep. 26, 2019

Related U.S. Application Data

(60) Provisional application No. 62/783,100, filed on Dec. 20, 2018, provisional application No. 62/647,552, filed on Mar. 23, 2018.

(51) Int. Cl.
| | |
|---|---|
| A61B 5/145 | (2006.01) |
| A61B 5/00 | (2006.01) |
| G06N 20/00 | (2019.01) |
| G06F 16/9032 | (2019.01) |
| G16H 20/60 | (2018.01) |

(52) U.S. Cl.
CPC ........ *A61B 5/14532* (2013.01); *A61B 5/0022* (2013.01); *G06F 16/90324* (2019.01); *G06N 20/00* (2019.01); *G16H 20/60* (2018.01)

(58) Field of Classification Search
None
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,640 A | 9/1999 | Szabo |
| 5,954,643 A | 9/1999 | Van Antwerp et al. |
| 6,017,328 A | 1/2000 | Fischell et al. |

(Continued)

OTHER PUBLICATIONS

Stephen Webb, Quantify Life-Feed Yourself/QuaLiFY, Grant Agreement No. 613783, Collaborative Project, RTD Services, Vienna, Austria, Feb. 8, 2016, URL: http://www.qualify-fp7.eu/uploads/2018/06/D2-4-QuaLiFY_Final-implementation-of-QSP.pdf.

*Primary Examiner* — Kristy A Haupt
(74) *Attorney, Agent, or Firm* — Weaver Austin Villeneuve & Sampson LLP

(57) ABSTRACT

Disclosed herein are techniques related to insulin delivery recommendations based on nutritional information. In some embodiments, the techniques may involve obtaining user input indicative of quantitative information for a food item. The techniques may further involve determining, based on the user input, nutritional information for the food item. Additionally, the techniques may involve generating, based on the nutritional information, an insulin delivery recommendation.

20 Claims, 71 Drawing Sheets

(56) References Cited

U.S. PATENT DOCUMENTS

| | | |
|---|---|---|
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,837,111 B2 | 11/2010 | Yang et al. |
| 7,879,010 B2 | 2/2011 | Hunn et al. |
| 7,882,150 B2 | 2/2011 | Badyal |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,974,881 B2 | 7/2011 | Culver et al. |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,376,750 B1 | 2/2013 | Murphy-Aniceto et al. |
| 8,647,121 B1 | 2/2014 | Witlin et al. |
| 9,011,153 B2 | 4/2015 | Bennett et al. |
| 9,721,008 B1 | 8/2017 | Byron et al. |
| 9,734,426 B2 | 8/2017 | Divakaran et al. |
| 2005/0192494 A1* | 9/2005 | Ginsberg ............... G16H 20/17 600/365 |
| 2007/0123819 A1 | 5/2007 | Mernoe et al. |
| 2007/0141540 A1 | 6/2007 | Borg |
| 2009/0275002 A1 | 11/2009 | Hoggle |
| 2010/0136508 A1 | 6/2010 | Zekhtser |
| 2010/0160861 A1 | 6/2010 | Causey, III et al. |
| 2011/0009708 A1 | 1/2011 | Boyes |
| 2011/0053122 A1 | 3/2011 | Hill et al. |
| 2011/0125783 A1 | 5/2011 | Whale et al. |
| 2011/0166881 A1 | 7/2011 | Brazzo et al. |
| 2012/0041978 A1 | 2/2012 | Tischer |
| 2012/0083669 A1 | 4/2012 | Abujbara |
| 2012/0179665 A1 | 7/2012 | Baarman et al. |
| 2013/0108993 A1 | 5/2013 | Katz |
| 2014/0099614 A1 | 4/2014 | Hu et al. |
| 2014/0255882 A1 | 9/2014 | Hadad et al. |
| 2015/0370766 A1 | 12/2015 | Kossmann et al. |
| 2017/0220558 A1 | 8/2017 | Pinel et al. |
| 2018/0211139 A1 | 7/2018 | Bui Tran et al. |
| 2018/0240359 A1 | 8/2018 | Hujsak |
| 2019/0006040 A1 | 1/2019 | Fleming et al. |
| 2019/0102523 A1* | 4/2019 | Buckley ............... G06T 19/006 |
| 2019/0252079 A1 | 8/2019 | Constantin et al. |
| 2020/0350052 A1* | 11/2020 | Saint ..................... G16H 20/30 |

\* cited by examiner

| Name | Edit params | Edit pipeline | Precision | Recall | F1 | Utilization | Delete? |
|---|---|---|---|---|---|---|---|
| glutenfree | Edit | Edit | 0.9911764705888 | 0.6087313432284 | 0.7684063582884 | 1.0 | ☐ |
| dairyfree | Edit | Edit | 0.9889281024575 | 0.7677286101866 | 0.8636784946948 | 1.0 | ☐ |
| noeggs | Edit | Edit | 0.9925057853398 | 0.7397880299979 | 0.8471454886309 | 1.0 | ☐ |
| nofish | Edit | Edit | 0.8962204933508 | 0.8853238365425 | 0.8875 | 1.0 | ☐ |
| nosoy | Edit | Edit | 0.8513181818188 | 0.3483448069 | 0.5373978141 | 1.0 | ☐ |
| nopeanuts | Edit | Edit | 0.9929888807595 | 0.9773967725422 | 0.9846876638 | 1.0 | ☐ |
| notreenuts | Edit | Edit | 0.9916434454039 | 0.8639803861643 | 0.9216886752091 | 1.0 | ☐ |
| noshellfish | Edit | Edit | 0.9877425644484 | 0.967 | 0.9772612439362 | 1.0 | ☐ |
| vegetarian | Edit | Edit | 1.0 | 0.9128640303601 | 0.9544419134 | 1.0 | ☐ |

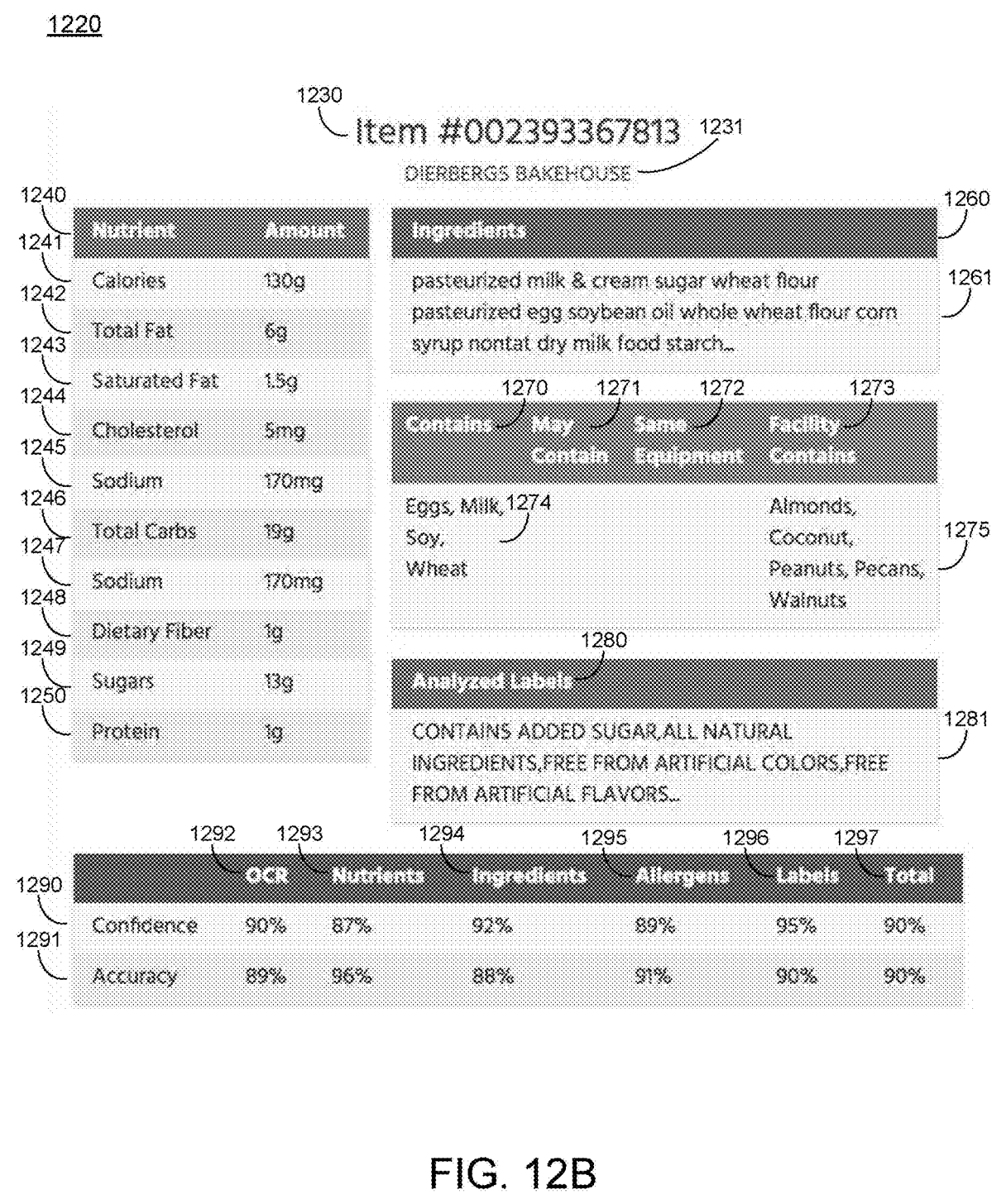

1230 — Item #002393367813 — 1231
DIERBERGS BAKEHOUSE

| Nutrient | Amount |
|---|---|
| Calories | 130g |
| Total Fat | 6g |
| Saturated Fat | 1.5g |
| Cholesterol | 5mg |
| Sodium | 170mg |
| Total Carbs | 19g |
| Sodium | 170mg |
| Dietary Fiber | 1g |
| Sugars | 13g |
| Protein | 1g |

1240 – 1250 label nutrient rows (1241–1250)

Ingredients (1260)

pasteurized milk & cream sugar wheat flour pasteurized egg soybean oil whole wheat flour corn syrup nonfat dry milk food starch... (1261)

| Contains (1270) | May Contain (1271) | Same Equipment (1272) | Facility Contains (1273) |
|---|---|---|---|
| Eggs, Milk, Soy, Wheat (1274) | | | Almonds, Coconut, Peanuts, Pecans, Walnuts (1275) |

Analyzed Labels (1280)

CONTAINS ADDED SUGAR, ALL NATURAL INGREDIENTS, FREE FROM ARTIFICIAL COLORS, FREE FROM ARTIFICIAL FLAVORS... (1281)

| | OCR (1292) | Nutrients (1293) | Ingredients (1294) | Allergens (1295) | Labels (1296) | Total (1297) |
|---|---|---|---|---|---|---|
| Confidence (1290) | 90% | 87% | 92% | 89% | 95% | 90% |
| Accuracy (1291) | 89% | 96% | 88% | 91% | 90% | 90% |

FIG. 12B

General Product Information

| | |
|---|---|
| EAN / UPC | 5000108469013 |
| Manufacturer | Dierbergs Bakehouse |
| Brand | Dierbergs Bakehouse |
| Sub Brand | |
| Variant | |
| Product Title | Lemon Cheesecake |
| Size 1 | 550 |
| Size 1 UOM | Grams |
| Super Group | |
| Product Group | |
| Category | Cake |
| Country of Origin | |
| Storage | Ambient |
| Packaging | Box |

PRODUCT DATA

Ingredients

Ingredient List: Rolled Oats (54%), Sugar, Glucose Syrup, Raisins (10%), Sunflower Oil, Cereal Crisps (Rice Flour, Wheat Flour), Humectant: Glycerol, Oat Bran, Honey, Colour (Plain Caramel), Natural Raisin Flavouring, Antioxidant (Tocopheral)

Allergy Text: For allergens, see ingredients in bold
Also, may contain Nuts and Barley Allergy Advice:
Barley - May Contain
Oats - Contains
Wheat - Contains
Nuts - May Contain Nutrition

FIG. 12C

| | Product Id | Images | Ingredients | Nutrients | Allergens | Labels | Confidence |
|---|---|---|---|---|---|---|---|
| ☐ | 00239336781 | +9 more | 24 Detected | 21 Detected | 9 Detected | 45 positive 95 negative | 90% |
| ☐ | 08800645765 | +7 more | 19 Detected | 23 Detected | 4 Detected | 62 positive 56 negative | 93% |
| ☐ | 08163720200 | +6 more | 15 Detected | 14 Detected | 6 Detected | 37 positive 88 negative | 89% |
| ☐ | 06466489356 | +4 more | | | | | |
| ☐ | 06161360017 | +7 more | | | | | |
| ☐ | 00778650801 | +8 more | | | | | |
| ☐ | 00415730176 | +9 more | | | | | |
| ☐ | 00414200214 | +5 more | | | | | |

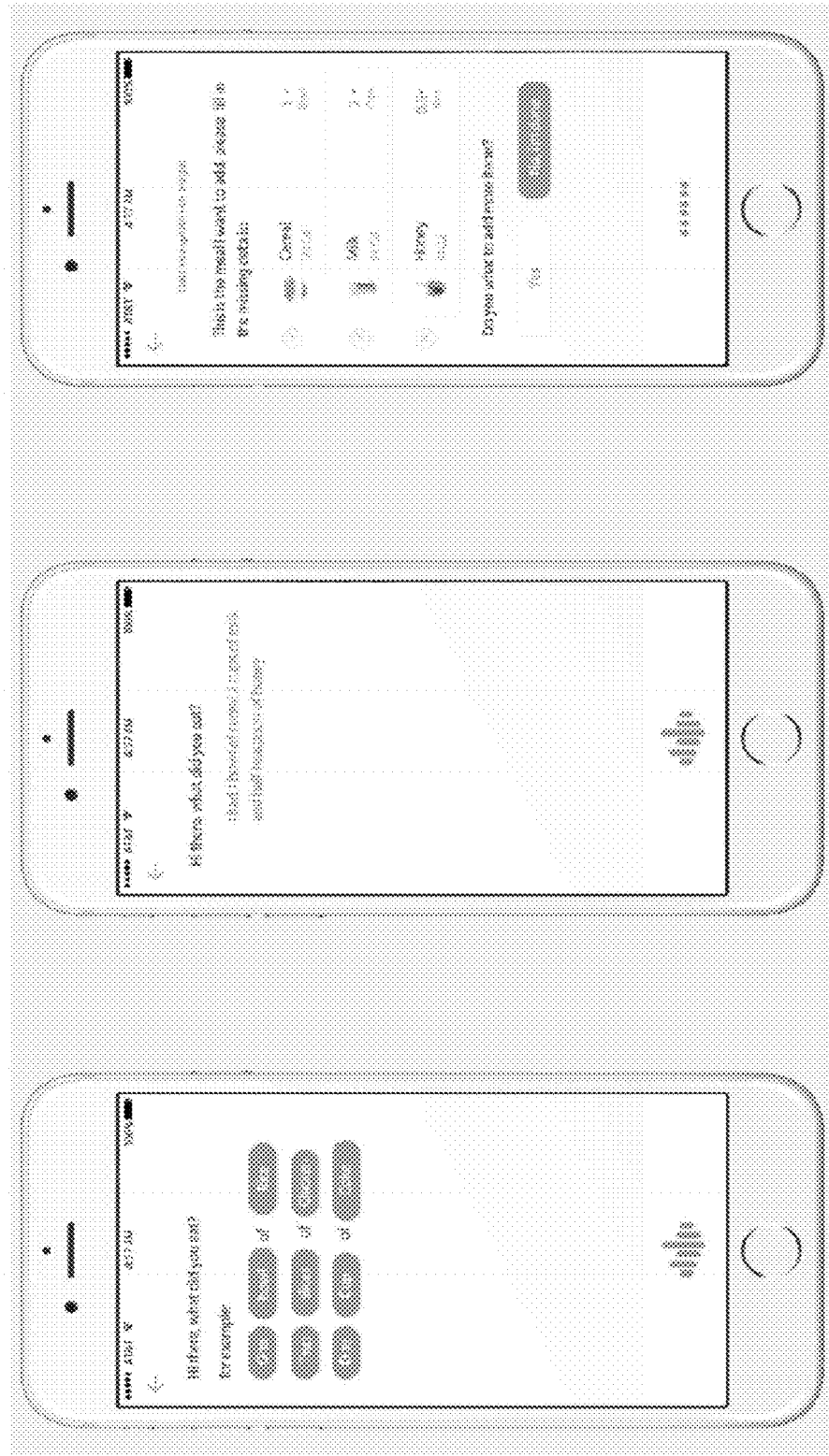

Spot The Difference
 
770cals      405cals
FIG. 19A
Spot the Difference
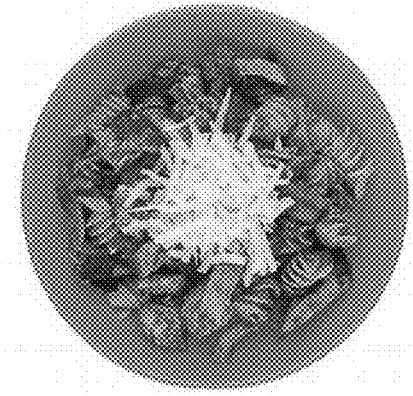 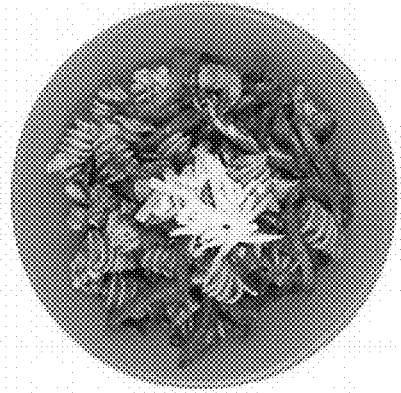
800cals      380cals
FIG. 19B

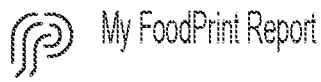 My FoodPrint Report
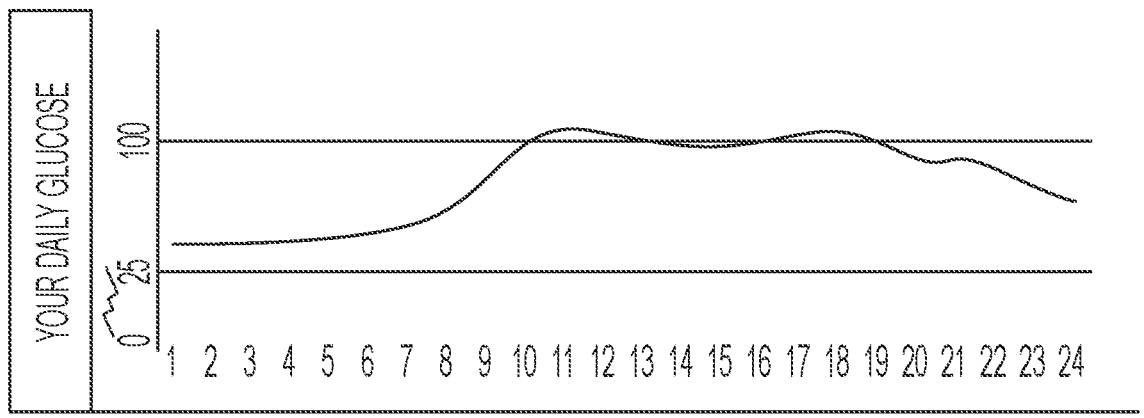
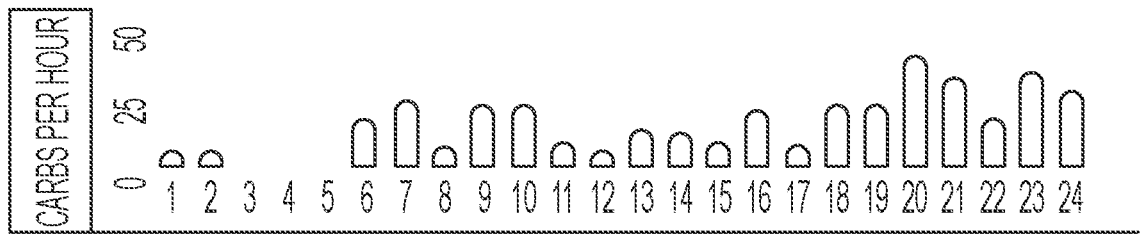
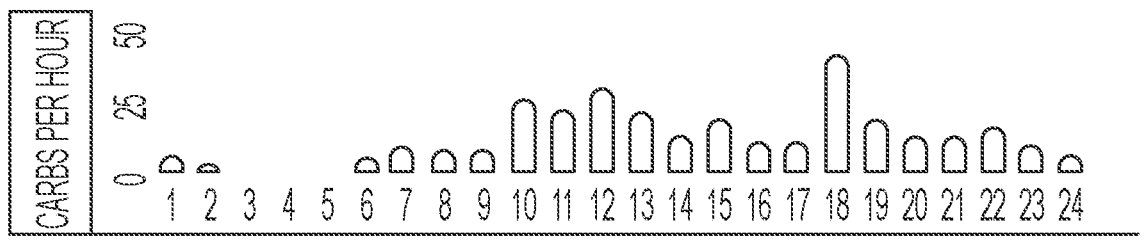
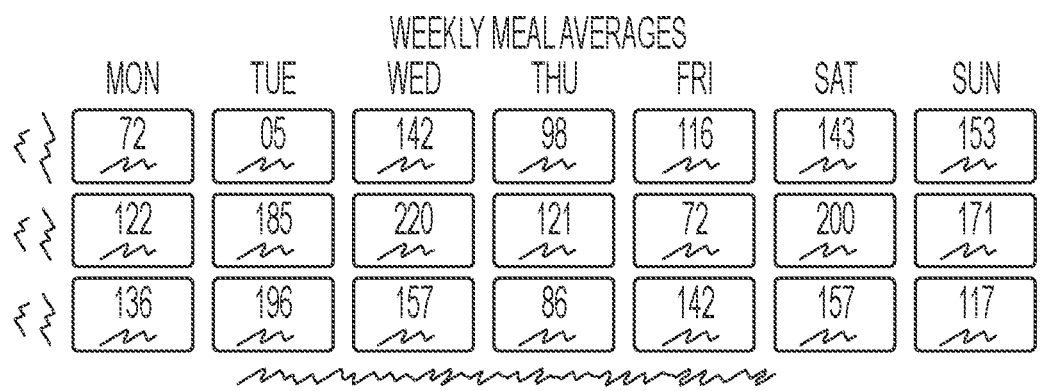
FIG. 34A

FIG. 54

```
Enter search term ('q' to quit): blt
12 samples found
Associations:

bacon (0.917)
tomato (0.750)
sandwich (0.667)
lettuce (0.500)
basil (0.333)
```

*FIG. 57A*

```
Enter name of selected nodes: egg
3307 samples

External associations:

cheese (0.240)
bread (0.160)
bacon (0.158)
coffee (0.153)
butter (0.103)
sausage (0.083)
turkey (0.078)
cheddar cheese (0.074)
creamer (0.063)
whole wheat (0.061)
spinach (0.059)
pepper (0.053)
smoked (0.048)
onion (0.047)
muffin (0.047)
pork (0.042)
ham (0.042)
cheddar (0.032)
mushroom (0.032)
coconut oil (0.023)
salsa (0.022)
ketchup (0.019)
pan fried (0.018)
hash brown (0.012)
cured (0.012)
hickory (0.011)
orange juice (0.009)
grit (0.006)

Internal associations:

egg (1.000)
boiled (0.148)
fried (0.081)
poached (0.032)
omelette (0.013)
```

*FIG. 57B*

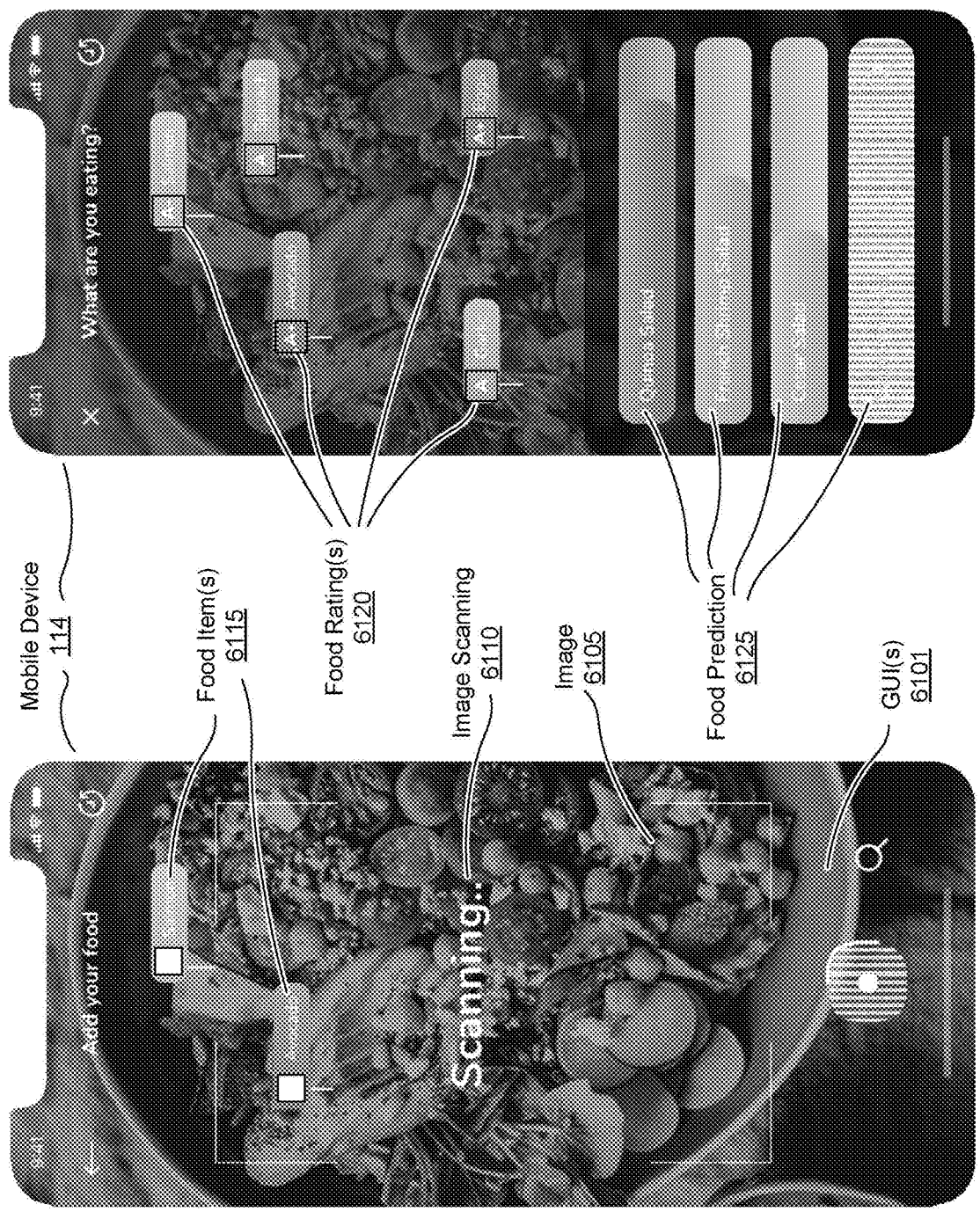

INSULIN DELIVERY RECOMMENDATIONS BASED ON NUTRITIONAL INFORMATION

CROSS-REFERENCE TO RELATED APPLICATIONS

This application claims priority to U.S. Provisional Patent Application No. 62/647,552 filed Mar. 23, 2018, and U.S. Provisional Patent Application No. 62/783,100 filed Dec. 20, 2018, which applications are incorporated herein by reference in their entirety for all purposes.

BACKGROUND

A plethora of databases and services are available to offer food and nutrition advices. Examples of such databases and services include healthcare providers, food or nutrition manufacturers, restaurants, online and offline food recipes, and scientific articles. Whether it be for recreational, cosmetic, medical, or other purposes, individuals inevitably have to rely on multiple sources of information to make food and nutrition-related decisions every day.

Numerous attempts have been made to generate a collection of data on nutrition information of commonly consumed foods, as well as their effects on human health. However, these databases usually struggle with inconsistences, unreliability, and generally low quality as data are often collected or crowd-sourced from user inputs. In addition, because many of the attempts have targeted specific populations, geographies, or food categories within a defined period of time, the resulting databases are often fragmented in scope and time. Such fragmentation limits their applicability. Furthermore, these databases depend on different sources of data (e.g., mobile devices, glucose monitors, social media, etc.) that are often incompatible with each other. Without an alternative, individuals continue to be dependent on limited and incomplete databases and/or services to piece together decisions for food and nutrition.

Thus, there is a need for systems and methods that can continuously collect a vast amount of data (e.g., ingredients in a dish, nutrition information, glucose levels, blood pressures, temperature, etc.) from discrete sources, analyze and restructure the data into a common format, assess and predict correlations between an individual's consumed foods and biomarkers, and provide personalized nutrition recommendations based on the individual's health and metabolic state at any given time.

BRIEF SUMMARY

Disclosed herein are techniques related to insulin delivery recommendations based on nutritional information. The techniques may be practiced using a processor-implemented method; a system comprising one or more processors and one or more processor-readable storage media; and/or one or more non-transitory processor-readable storage media.

In some embodiments, the techniques may involve obtaining user input indicative of quantitative information for a food item. The techniques may further involve determining, based on the user input, nutritional information for the food item. Additionally, the techniques may involve generating, based on the nutritional information, an insulin delivery recommendation.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 11 illustrates an exemplary table of problem solvers and their statistical analyses, in accordance with some embodiments;

FIGS. 12A-12C illustrate abstracting and classifying information from a consumer food package, in accordance with some embodiments;

FIG. 13 illustrates an exemplary table of abstracted and classified consumer food packages, in accordance with some embodiments;

FIG. 15 illustrates an exemplary table of information abstracted from restaurants menus in accordance with some embodiments;

FIGS. 18A-18C illustrate exemplary windows of a GUI-based software interface for voice recognition analysis, in accordance with some embodiments;

FIGS. 19A and 19B illustrate side-by-side comparisons of similar looking foods that have substantially different caloric content, in accordance with some embodiments;

FIGS. 34A-34C illustrate exemplary windows of a GUI-based software interface showing a compressive report by insights and recommendation engine, in accordance with some embodiments;

FIG. 54 shows a graphical user interface (GUI) for managing a training set for food classification in accordance with some embodiments;

FIGS. 57A and 57B illustrate an exemplary process of using one or more computer algorithms to generate statistical associations among foods;

FIGS. 61A and 61B illustrate exemplary windows of a GUI-based software interface for food image rating, in accordance with some embodiments;

DETAILED DESCRIPTION

Reference will now be made in detail to some exemplary embodiments of the disclosure, examples of which are illustrated in the accompanying drawings. Wherever possible, the same reference numbers will be used throughout the drawings and disclosure to refer to the same or like parts.

Introduction

Not only can two people respond differently to an identical food, but a single individual can respond differently to the identical food at different times. However, the current state of food and nutrition services continues to rely on previously generated, static databases to provide generic, non-customized suggestions on food and health management.

Currently available databases for food and nutrition are inconsistent due to user input dependency, limited in their scope and time scale, and often incompatible with each other. Thus, there is presently a lack of systems and methods that can curate the fragmented food-related information into a single format, assess relationship between foods and biomarkers for each individual, and provide personalized nutrition recommendations that continuously evolve with the individual's lifestyle.

The disclosure herein can provide the solutions to the above by (1) creating and/or using a food ontology that is continuously being updated from various sources (e.g., from the internet, pre-existing databases, user input, etc.) to organize and analyze any obtainable information of all food types (e.g., elementary foods, packaged foods, recipes, restaurant dishes, etc.), (2) generating a personalized data network among a multitude of data collection devices and services (e.g., mobile devices, glucose sensors, healthcare provider databases, etc.) to integrate any obtainable information of biomarkers that can be affected by or can affect metabolism (e.g., sleep, exercise, blood tests, etc.), and (3) connecting the food ontology and the personalized data network to draw insights on how foods can affect each individual, and generate personalized food, health, and wellness recommendations for each individual.

Examples of foods include elementary foods (e.g., fruits, vegetables, meat, salt, sugar, etc.), packaged foods, and restaurant dishes. The foods can also include beverages (e.g. liquids, water, coffee, tea, alcohol, juices, shakes, powdered drinks, etc.).

Next, various embodiments of the disclosure will be described with reference to the drawings.

Platform

Embodiments of the present disclosure can be implemented as an ecosystem of devices, database(s), and a platform to provide users with personalized nutrition insights.

Figure 1:
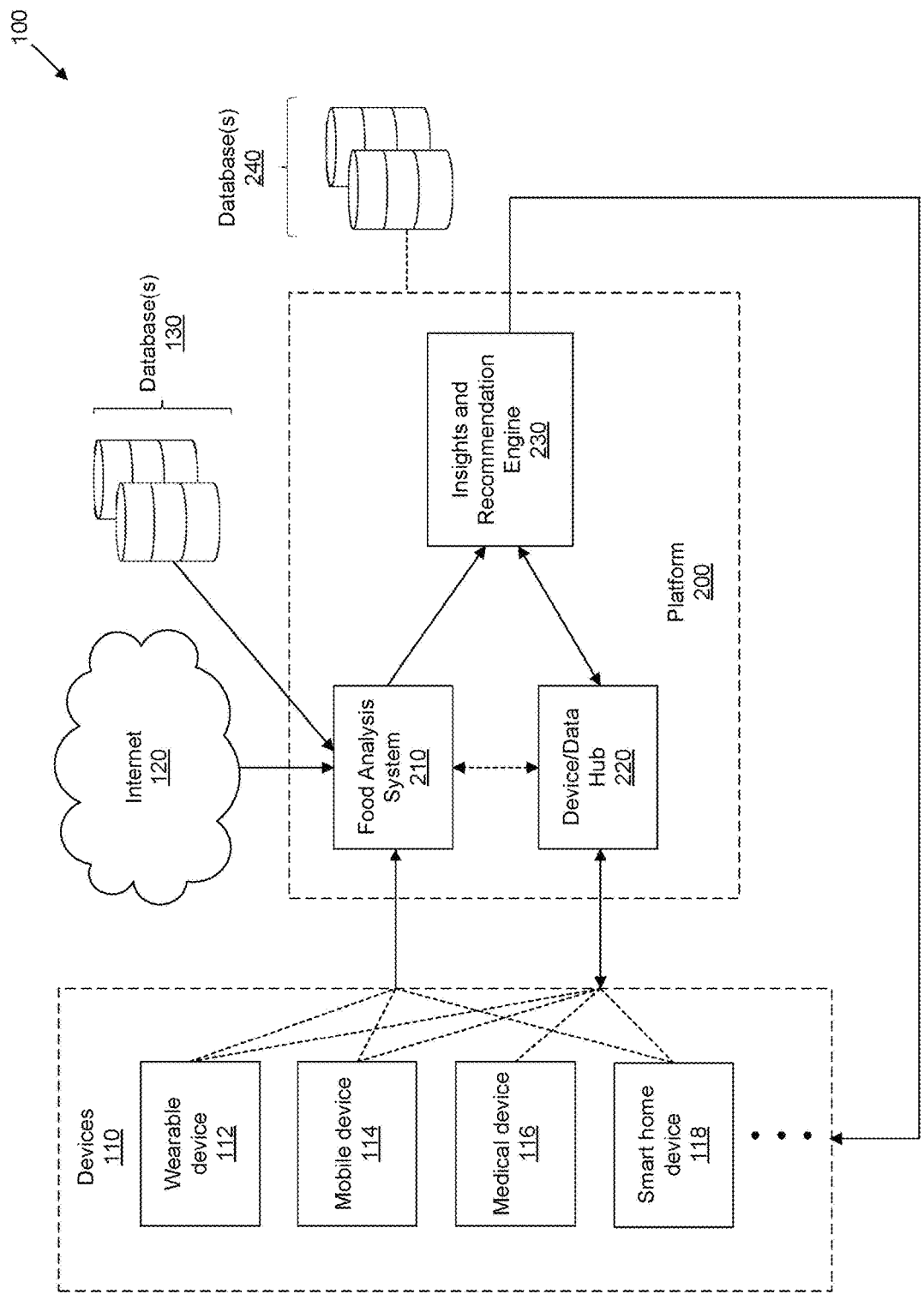
FIG. 1 illustrates an ecosystem for food analysis and personalized health management, in accordance with some embodiments.

FIG. 1 illustrates an ecosystem 100 in accordance with some embodiments. In one aspect, the ecosystem 100 can include a platform 200. The platform 200 can include three components: a food analysis system 210, a device/data hub 220, and an insights and recommendation engine 230. The three components in the platform 200 can be standalone or interconnected to one another. The ecosystem 100 can also include devices 110. The devices 110 can include a wearable device 112 (e.g., a smart watch, fitness tracker, etc.), a mobile device 114 (e.g., a cell phone, a smart phone, a voice recorder, etc.), a medical device 116 (e.g. a glucose monitor, insulin pump, heart rate monitor (HRV), skin temperature sensor, etc.), or more. One or more of the devices 110 (e.g., the mobile device 114) can have access to one or more social network service (SNS) accounts (e.g., Facebook, Instagram, Twitter, Snapchat, Reddit, Yelp, Google+, Tumblr, etc.), thereby to allow any information or data (e.g., images, videos, texts, audio records, etc.) of the user accessible to the platform 200. The devices 110 can be in communication with each other. The platform 200 can be in communication with the devices 110. The platform 200 can be in communication with the Internet 120 and database(s) 130 (e.g., other food, nutrition, or healthcare providers). In some cases, the database(s) 130 can include genome databases to retrieve genomic information of the user. Examples of the genome databases can include, but are not limited to, 23andMe, deCODE Genetics, Gene by Gene, Gene Planet, DNA Ancestry, uBiome, and healthcare providers. The platform 200 can also be in communication with an additional database(s) 240 to store any data or information that is collected and generated by the platform 200. The additional database(s) 240 may be a collection of secure cloud databases.

The food analysis system 210 can create, update, and/or utilize the food ontology. The food analysis system 210 can be connected to various sources of data including the devices 110 (e.g., the wearable device 112, the mobile device 114, etc.), the Internet 120, and the existing databases 130. The food analysis system 210 can serve as a content management system to continuously receive, analyze, and organize nutrition information of all food types (e.g., elementary foods, packaged foods, recipes, restaurant dishes, etc.) into the food ontology.

The device/data hub 220 can generate a user's personalized data network between the devices 110. The device/data hub 220 can automatically aggregate biomarker and health data of the user (e.g., sleep, exercise, blood tests, genetic tests, etc.) from multiple application programming interfaces (APIs) and healthcare provider databases.

The insights and recommendation engine 230 can be in communication with the food analysis system 210 and the device/data hub 220. As such, the engine 230 can create and analyze any correlation between information from the food ontology and information from the personalized data network. The engine 230 constitutes the "brains" of the platform 200, and functions as a food global positioning system (food GPS) for the user. The engine 230 can account for the user's own day-to-day nutritional needs based on how the user's biomarkers react to different foods at different times. Thus, the engine 230 can generate personalized food, health, and wellness recommendations for the user. The engine 230 can be in communication with the devices 110 directly or through communication with the device/data hub 220. In an example, the engine 230 may use the devices 110 to relay the recommendations to the user in a visible format.

The platform 200 can be implemented using one or more graphical user interfaces (GUIs; not shown in FIG. 1) to enable a user to select and employ features of the three components: the food analysis system 210, the device/data hub 220, and the insights and recommendation engine 230. Generally, GUIs can be a type of interface that allows users to interact with electronic devices through graphical icons and visual indicators such as secondary notation, as opposed to text-based interfaces, typed command labels or text navigation. The GUIs can be rendered on a display screen on a user device. Actions in the GUIs can be performed through direct manipulation of the graphical elements. In addition to computers, the GUIs can be rendered on hand-held devices, such as a smartphones, portable media players, gaming devices, and office and industry equipment. The GUIs of the platform 200 can be provided in a software, software application, web browser, etc. The GUIs may be displayed on a user device. The GUIs can be provided through a mobile application. One or more GUIs of the present disclosure can be referred to as the platform GUIs. The platform GUIs can be in communication with other GUIs, such as the wearable device 112, mobile device 114, the medical device 116, the smart home device 118 (e.g., a smart refrigerator), etc. End users of the platform can include a baby, a teenager, a college student, adults, healthy individuals, patients, participants of wellness programs, insurees of various providers, etc.

Food Analysis System

Figure 2:
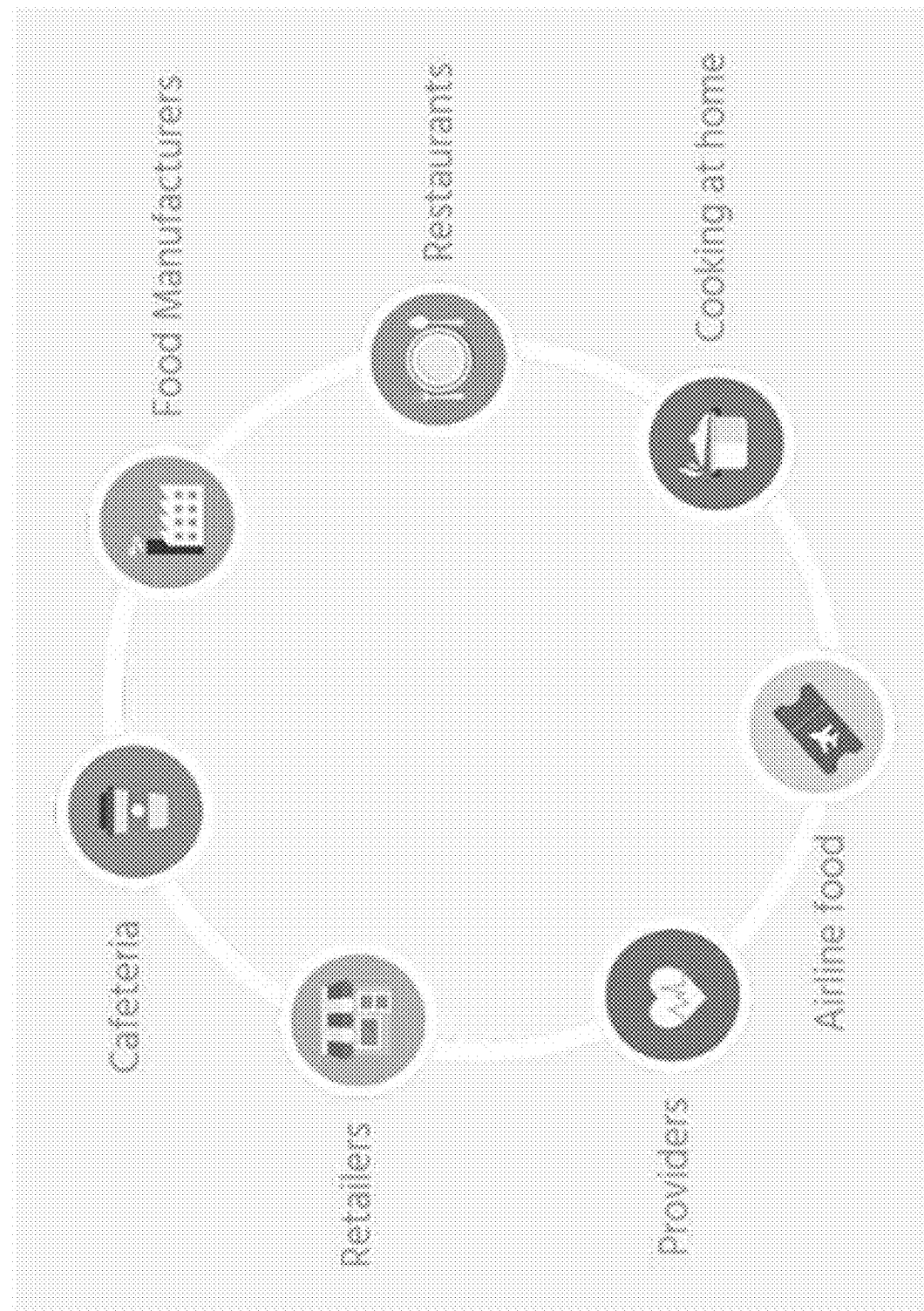
FIG. 2 illustrates examples of sources for food-related data in accordance with some embodiments.

The food analysis system 210 can map foods by abstracting information from data relating to the foods to develop the food ontology. The food analysis system 210 can continuously receive, analyze, and organize nutrition information from data relating to all food types into the food ontology. The food ontology can otherwise be referred to as a web of foods. The food-related data can be obtained from a plurality of sources. The plurality of sources can include the devices 110 (e.g., the wearable device 112, the mobile device 114, etc.), the Internet 120, and the existing database(s) 130. Examples of sources for the food-related data are illustrated in FIG. 2. Examples of sources for the food-related data can include food manufacturers, restaurants, grocery stores, cafeteria, airline foods, healthcare providers, etc. The existing database(s) 130 can be the food databases of competitors.

The food-related data can be classified into a plurality of different categories, for example 2, 3, 4, 5 or more categories. In some cases, a category may include one or more subcategories.

In some embodiments, the food-related data that is analyzed by the food analysis system 210 may be separated into four different categories, for example (1) elementary foods, (2) recipes, (3) packaged foods, and (4) restaurant dishes. The foods can include beverages (e.g. water, coffee, tea, alcohol, etc.).

Elementary foods in category (1) may include commonly eaten foods and ingredients. Elementary foods may be further separated into two or more constituents, for example (a) elementary ingredient and (b) elementary recipe. An elementary ingredient is a food item that contains a single ingredient other than water. Examples of elementary ingredients may include banana, almond, frozen blueberries, raw blueberries, and so forth. An elementary recipe is an abstraction of commonly eaten foods that contain more than a single ingredient. Examples of elementary recipes may include Pad Thai, chicken lo mein, french fries, and so forth.

Recipes in category (2) may include foods comprising of multiple ingredients together with preparation instructions. Recipes in category (2) may only include specific recipes, and may be fundamentally different than the elementary recipes in category (1). For example, a generic "Pad Thai" in category (1) is an abstraction of the notion of a dish known as Pad Thai (which generally includes noodles, oil, peanuts, etc.), and is therefore an elementary recipe. In contrast, different Pad Thai recipes (e.g. those found on various Internet sources) are specific recipes, and are realizations of the elementary recipe "Pad Thai" and are therefore (non-elementary) recipes. Other examples of recipes in category (2) may include, e.g. multiple recipes for fettuccine alfredo from different sources.

Packaged foods in category (3) may include foods that have a barcode and are sold as a package, e.g. a Chocolate Clif bar with a specific universal product code (UPC). Most packaged foods may be considered to include a recipe by the food manufacturer, since a recipe is needed to prepare the packaged foods. However, since the amounts of each ingredient and the exact preparation instructions are not usually provided or listed on packaged foods, the category of packaged foods can therefore be separate from recipes. The separate categories may be needed because packaged foods and recipes often need to be analyzed differently by the machine learning models disclosed elsewhere herein.

Restaurant dishes in category (4) may include menu items from restaurants, for example McDonald's Big Mac. In practice, these restaurant dishes are created from recipes internal to the restaurant themselves. However, in most restaurants, the exact ingredients list and the preparation instructions are not provided or known to the customers. Accordingly, restaurant dishes are distinguished from recipes since they need to be addressed (analyzed) differently from recipes.

In general, nutrition-related data on food is often partial (incomplete) as some of the information is typically missing or difficult to obtain. For example, elementary foods in category (1) may lack labels, and adding new food items and new nutrients can be challenging. Packaged foods in category (2) usually do not show the amounts of different ingredients. Also, most food labels on packaged foods may only include a limited number of nutrients (e.g. 10-14) when there could be more nutrients. Furthermore, data for the food label may be captured in an image form, and there could be discrepancies between the actual contents of the packaged food and the information on the food label. As for the recipes in category (3), there are usually no labels on recipes, and thus the nutritional information may be inaccurate. Likewise, for the restaurant dishes in category (4), restaurant menus typically do not have labels and may not include nutritional information. The ingredients in a restaurant dish are often part of the free text in the description for the restaurant dish. Furthermore, data for restaurant dishes is typically captured in an image form (e.g. of a menu), and there is a wide variation in the way dishes are being described or depicted on restaurant menus.

In view of the above, each of the above food categories (1)-(4) individually may possess certain gaps or limitations. However, those gaps or limitations can be addressed by the algorithms described herein, such that the food analysis system can generate a complete understanding of each food object by leveraging data within and between different categories. In most cases, knowledge about the ingredients and amounts of each food can allow additional data about each food to be determined.

The food analysis system 210 can leverage one or more algorithms comprising at least one machine learning algorithm to abstract information from the data relating to foods. The food analysis system can classify the abstracted data into one or more categories of the food ontology. The categories can be abstraction layers. One or more algorithms can include a natural language processing (NLP), a computer vision system, or a statistical model. The computer vision system can include artificial intelligence (AI), deep learning, or optical character recognition (OCR) capabilities. The computer vision system, in combination with NLP, can convert images of consumer packaged foods or images of restaurant menu into structured data that can be analyzed and classified into the food ontology.

The categories, or abstraction layers, of foods in the food ontology can include name, description, user ratings, images, characteristics (e.g. dietary needs, allergies, cuisine, flavors, textures, etc.), ingredients breakdown (types and amounts), nutrients break down (types and amounts), processing information, and food geolocation and/or availability information. The food analysis system may use at least one machine learning algorithm to generate additional abstraction layers or metadata of foods. The additional abstraction layers or metadata of foods may be incorporated into the food ontology. A food item can have one or more abstraction layers. An abstraction layer can be used to describe one or more food items.

Dietary needs can be an abstraction layer of the food ontology. The dietary needs can include a vegetarian, lacto-ovo-vegetarian, pescatarian, lacto-vegetarian, ovo-vegetarian, vegan diet, or any other diet depending or based on popularity in a specific region. A vegetarian generally may not eat meat or fish. A lacto-ovo-vegetarian may avoid flesh of all animals, both meat and fish. A pescatarian may eat fish but not meat. A lacto-vegetarian may consume dairy products but no eggs. An ovo-vegetarian may consume eggs but no dairy. A vegan may avoid all animal-based foods, including honey.

The dietary needs can include a gluten free diet. The gluten free diet can be important for individuals with celiac disease (celiacs), a serious autoimmune disorder of gluten indigestion that can damage the small intestine. The celiac disease can affect 1 in 100 people worldwide. Examples that cannot be used for the gluten free diet include wheat, barley, rye, and oats. Examples of common processed foods containing the wheat, barley, rye, or oats can include malted products, cereals, cold cuts, gravies, seasoned rice mixes, trail mixes, and imitation fish or bacon.

The dietary needs can include a diabetic diet for individuals with type 1 or type 2 diabetes. The diabetes can be diseases that result in too much sugar (e.g. glucose) in the blood. The diabetic diet can include fiber-rich foods, including fruits, vegetables, whole grains, legumes (beans, lentils, and lentils) and low-fat dairy products. The diabetic diet can include fish that are rich in omega-3 fatty acids, including salmon and mackerel. The diabetic diet may not include foods that are high in sugar (carbohydrates). For example, an individual with diabetes on a 1,600 calorie diet may consume no more than about 50% of these calories from carbohydrates.

The dietary needs can include various religious diets, including Halal and Kosher diets. The Halal diet can be according to what is permissible or lawful in traditional Islamic dietary laws. In an example, the Halal diet may not include pork or pig meat products. The Kosher diet can be according to what is permissible or lawful to a set of Jewish religious dietary laws called kashrut. In an example, the Kosher diet may not include a hare, hyrax, camel, and pig. The food analysis system 210 can be in communication with several food certification programs, including the Islamic Food and Nutrition Council of America (IFANCA), the Kosher Supervision of America (KSA), etc. to continuously monitor and update its algorithms for the religious diets.

The dietary needs can include a lactose free diet for individuals with lactose intolerance. The lactose intolerance can be a condition related a decreased ability to digest lactose, a sugar found in milk products. The individuals with lactose intolerance can show symptoms including abdominal pain, bloating, diarrhea, gas, and nausea after consuming milk-containing or milk-based products without any medication (e.g. lactase). Thus, the food analysis system 210 can analyze and report whether a food item can contain milk or milk-based ingredients.

The dietary needs can include an organic foods diet. The organic foods can include products that come from animals that are not given any antibiotics or growth hormones. The organic foods can include plants that do not use conventional pesticides or fertilizers that are made with synthetic ingredients. Examples of terms used in labels of commercially available organic products can include "100% Organic," "Organic," and "Made with Organic Ingredients."

The dietary needs can include a non-genetically modified organisms (non-GMO) diet. A GMO ingredient can be a plant or animal that is created by means of genetic engineering in a lab environment that goes beyond traditional crossbreeding. The genetic engineering can be combining genes from different species to create a new one. Because organic foods can be prohibited from using one or more GMO ingredients, an organic food can be, generally, a non-GMO food. Examples of terms used in labels of commercially available non-GMO products can include "Non-GMO Project Verified." The "Non-GMO Project Verified" label can be certified by the Non-GMO Project.

The dietary needs can include other diets preferred by a user, such as Atkins diet, Zone diet, Ketogenic diet, and raw food diet. The Atkins diet may be a weight-loss program devised by Robert Atkins. The Atkins diet can be a first variation of a low-carbohydrate diet. The Zone diet can be a second variation of the low-carbohydrate diet. The Zone diet can require a specific food ratio of 40% carbohydrates, 30% fats, and 30% protein in each meal. The Zone diet can recommend eating five times a day to help prevent overeating. The Ketogenic diet can be used for children with epilepsy. The Ketogenic diet can be a third variation of the low-carbohydrate diet. The Ketogenic diet can encourage a high-fat diet. The Ketogenic may cause a breakdown of fat deposits in the body for fuel and create substances called ketones through a process called ketosis. The Ketogenic diet can encourage consumption of oils from avocados, coconuts, Brazil nuts, olives, and oily fish. The raw food diet can encourage consumption of foods and drinks that are not processed. The raw food diet may not include food products with artificial food preservatives, including calcium propionate, sodium nitrate, butylated hydroxyanisole (BHA), and butylated hydroxytoluene (BHT). The food analysis system 210 can leverage at least one machine learning algorithm to detect or estimate presence of one or more artificial food preservatives from consumer packages foods.

Allergies can be an abstraction layer of the food ontology. For information regarding food allergies, the food analysis system 210 can be in communication with existing databases such as the Food Allergy Research and Resource Program (FARRP) to continuously monitor and update its algorithms to abstract information from or classify allergenic foods. The allergenic foods can be broken down to one or more groups, including wheat or gluten (barley, corn, maize, oat, rice, rye, wheat, other gluten-containing grains, etc.), lactose or dairy products (cow, goat, sheep milk, etc.), eggs (hen, goose, duck), tree nuts (almond, brazil nut, cashew nut, chestnut, hazelnut, macadamia nut, pecan nut, pistachio, walnut, etc.), legumes (chickpea, lentil, lupin, peanut, pea, etc.), fish (Alaska pollock, carp, cod, dogfish, mackerel, salmon, sole, tuna, etc.), and crustacean shellfish (crab, lobster, shrimp, etc.). Additional allergenic foods can include fruits (acerola, apple, apricot, banana, cherry, coconut, date, fig, grape, mango, melon, orange, peach, pineapple, etc.) and vegetables (asparagus, avocado, carrot, celery, etc.).

Food flavors can be an abstraction layer of the food ontology. The food flavors can include sensory impression of foods. The food flavors can be determined by chemical senses of taste and smell. Some examples of tastes can include sweet, sour, bitter, salty, and savory (also known as umami). Some examples of smell, or odor that can be distinguished by human olfactory system, can include fragrant (e.g., florals and perfumes), fruity (all non-citrus fruits), citrus (e.g., lemon, lime, orange), woody or resinous (e.g., pine or fresh cut grass), chemical (e.g., ammonia, bleach), sweet (e.g. chocolate, vanilla, caramel), minty (e.g., eucalyptus and camphor), toasted or nutty (e.g., popcorn, peanut butter, almonds), pungent (e.g., blue cheese, cigar smoke), and decayed (e.g. rotting meat, sour milk). Alternatively or in addition to, the food flavors can be determined by a range of temperature (e.g., hot, room temperature, cold, frozen, etc.).

The food flavors can be flavorants, or flavorings, as a substance in a food. Some examples of natural or artificial flavorants for taste can include glutamic acid, glycine, guanylic acid, inosinic acid, disodium 5'-ribonucleotide, acetic acid, ascorbic acid, citric acid, fumaric acid, lactic acid, malic acid, phosphoric acid, and tartaric acid. Some examples of natural or artificial flavorants for odor can include diacetyl, acetylpropionyl, acetoin, isoamyl acetate, benzaldehyde cinnamaldehyde, ethyl propionate, methyl anthranilate, limonene, ethyl decadienoate, allyl hexanoate, ethyl maltol, ethylvanillin, methyl salicylate, and manzanate.

The food flavors can also include color. The color of a food can affect an individual's expectations of one or more flavors of the food. In an example, adding more red color to a drink can increase sweetness of the drink. The colors can be labelled by the food analysis system 210 in one or more ways. The colors can be labelled by a standard nomenclature, including red, orange, yellow, green, blue, navy, purple, black, etc. The colors can be labelled as a position in a predefined color palette, or a color wheel. Alternatively or in addition to, the colors can be labelled in terms of a food's characteristic absorption profile in at least a portion of the electromagnetic spectrum. The characteristic absorption profile can be defined by a position and intensity for at least a portion of the electromagnetic spectrum. At least a portion of the electromagnetic spectrum can be the visible spectrum. The visible spectrum can include electromagnetic radiation in a range from about 400 nanometers to about 750 nanometers. Labeling the colors as the position and intensity within the electromagnetic spectrum may avoid bias against users with or without color blindness.

Nutritional characteristics can be an abstraction layer of the food ontology. The nutritional characteristics can include one or more dietary goals or restrictions suggested to or defined by a user. The dietary goals can include low fat, high fat, and high calcium. The nutritional characteristics can include nutritional recommendations for pregnancy. The nutritional recommendations for pregnancy can include: pasteurized foods to prevent Listeria infection; foods with high folic acid, calcium, or iron; foods or drinks with low caffeine; and avoiding or consuming no more than 6 ounces per week fish with a high level of mercury. The fish with the high level of mercury can include king mackerel, marlin, swordfish, tilefish, and tuna.

Textures can be an abstraction layer of the food ontology. The textures can include: soft, firm, creamy, crumbly, crunchy, crisp, brittle, tender, chewy, tough, thick, thin, sticky, airy, fluffy, greasy, gooey, moist, mushy, lumpy, pulpy, grainy, etc.

The food ontology generated by the food analysis system 210 can be compatible with any suitable food database including existing food databases. General databases of foods include U.S. Department of Agriculture (USDA) database, Open Food Facts, and ItemMaster. Databases on packaged foods include Nutritionix, Fatsecret, and Myfitnesspal. Databases on recipes include Yummly, BBC Good Food, Allrecipes, The Kitchn, EatingWell, and MyRecipes. Databases on restaurant dishes include HealthyDiningFinder, Nutritionix, MyNetDiary, FatSecret, HealthyOut, and OpenMenu. Alternatively or in addition to, the food ontology generated by the food analysis system 210 can complement limitations of the existing food databases. The existing food databases can have low quality of data due to complete or partial dependency on user generated and reported content. The existing food databases can have a limited scope as they may not cover all food categories and/or have targeted specific populations and/or geographies during data collection. Also, the existing food databases can be static or outdated due to dependency on data that has been collected in the past. Additionally, the existing food databases may not maintain a robust ontology of foods with detailed abstracting layers (e.g. characteristics, ingredients breakdown, etc.).

Figure 3:
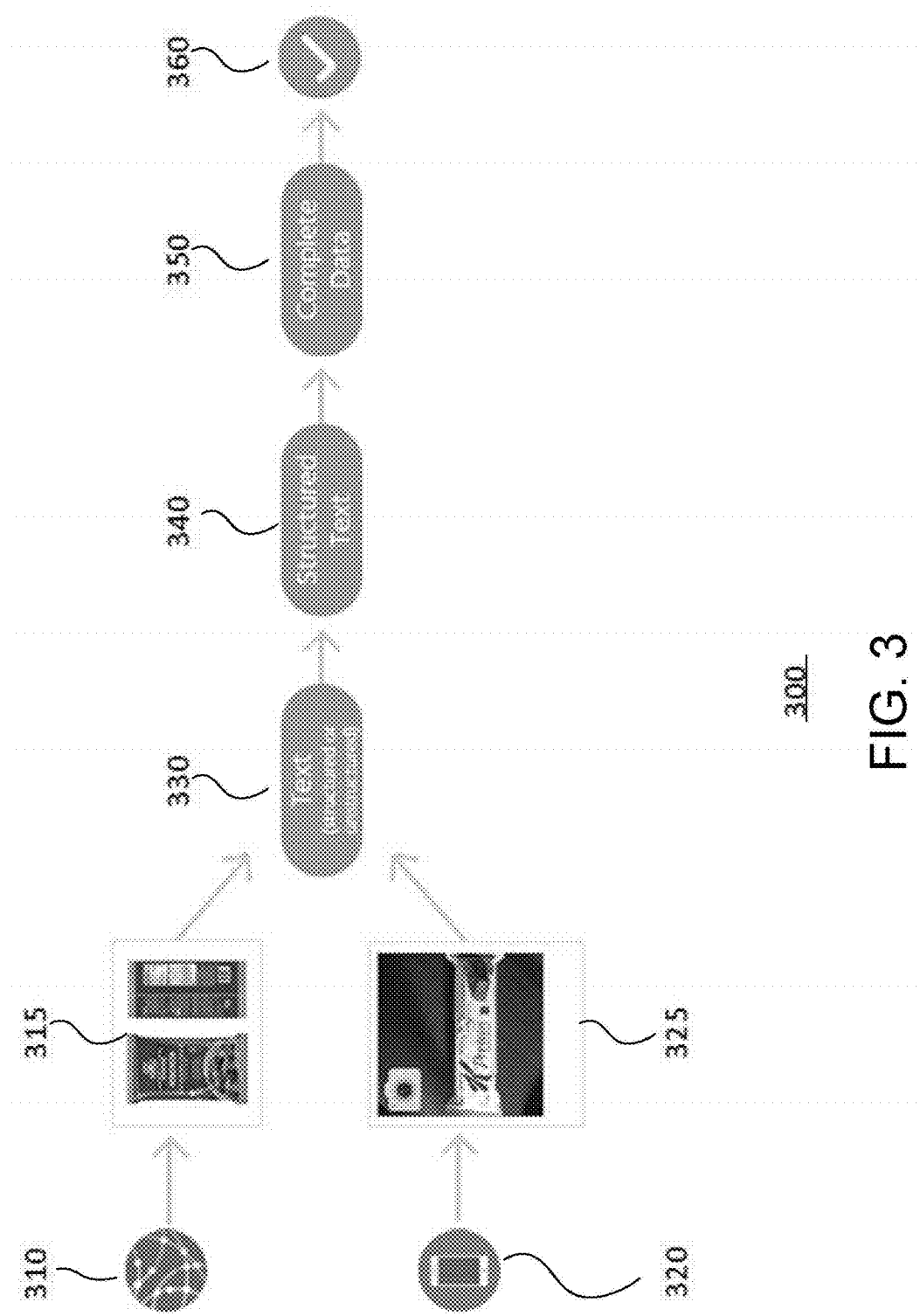
FIG. 3 is a flow chart of a method of food analysis, in accordance with some embodiments.

FIG. 3 is a flow chart of a method 300 of the food analysis system 210. The food analysis system 210 can connect to the Internet 310 and collect images related to foods. The foods can include consumer packaged foods. The images can include front and back pictures of Immaculate Bakery Gluten Free Chocolate Chunk Cookies 315. The images can include a nutrition facts label. The food analysis system 210 can also be configured to connect to a user's mobile device 320 and collect food-related images 325 taken or saved by the user. The food analysis system 210 can also collect food-related texts (e.g. publications, text messages, etc.) from the Internet 310, the mobile device 320, or other sources. The food analysis system 210 can use various algorithms including OCR to automatically isolate food-related textual information 330 from the images 315, 325. The food analysis system 210 can use NLP and other machine learning algorithms to parse the collected food-related texts into a structured format 340, analyze their characteristics 350, and validate that a resulting analysis is correct 360. The food analysis system 210 can use the validated characteristics to map the foods in the food ontology.

In some embodiments, the food analysis system can perform optical character recognition (OCR) to extract textual information from the images. The food analysis system can also implement a convolutional neural network to extract information from various icons that often appear on packaged foods. Examples of OCR techniques that are used in embodiments of the present disclosure are next described.

Figure 42:
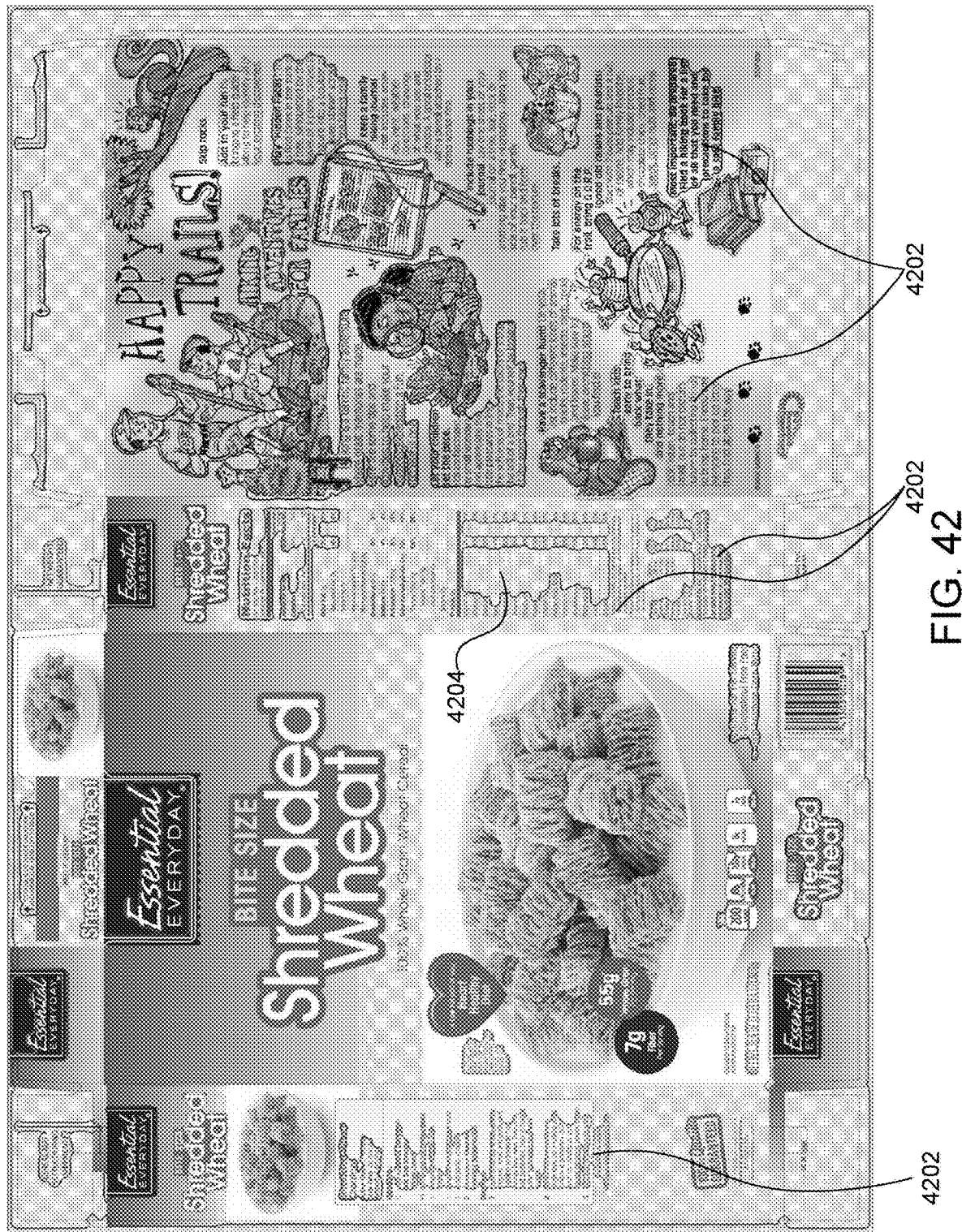
FIG. 42 shows an example of standard deviation image areas in accordance with some embodiments.
Figure 43:
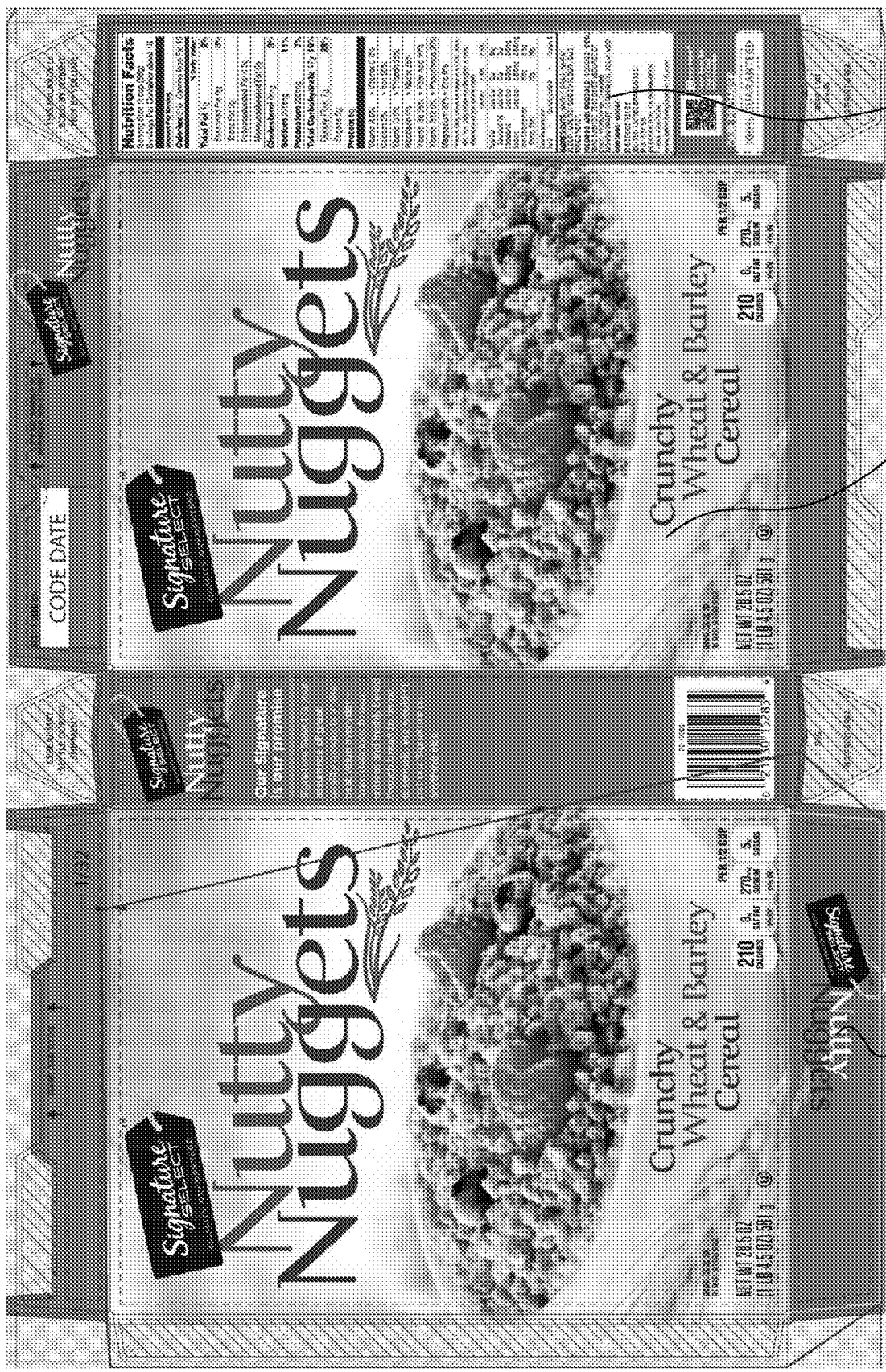
FIG. 43 shows an example of rectangle detection image areas in accordance with some embodiments.

Nutritional information extraction as described herein may comprise extracting the nutritional facts, ingredients or allergens of a consumer product using an image of the product. This can be implemented by first dividing the image into multiple sub-images containing areas with text, using for example an image crop algorithm. The image crop algorithm may comprise a method for extracting parts of an image containing text. The method implemented by the image crop algorithm may comprise the following steps: (1) search and extract rectangles in the image; (2) calculate the standard deviation image and pull areas with large standard deviation; (3) remove overlapping areas and calculate the difference between standard deviation areas overlapping with rectangle areas; and (4) return a list of the areas pulled from the images. FIG. 42 shows an example of standard deviation image areas, and FIG. 43 shows an example of rectangle detection image areas. Referring to FIG. 42, the standard deviation image areas may include a plurality of free-form contours 4202 around the text and empty spaces 4204 therebetween. Referring to FIG. 43, the rectangle detection image areas include a plurality of rectangle boxes 4302 surrounding the text. Accordingly, areas (sub-images) of various shapes and sizes can be cropped from the original image.

Next, an OCR algorithm can be implemented on each of the cropped sub-images. Words pertaining to allergens, ingredients or nutritional facts can be searched in the paragraph of the extracted text.

Figure 44:
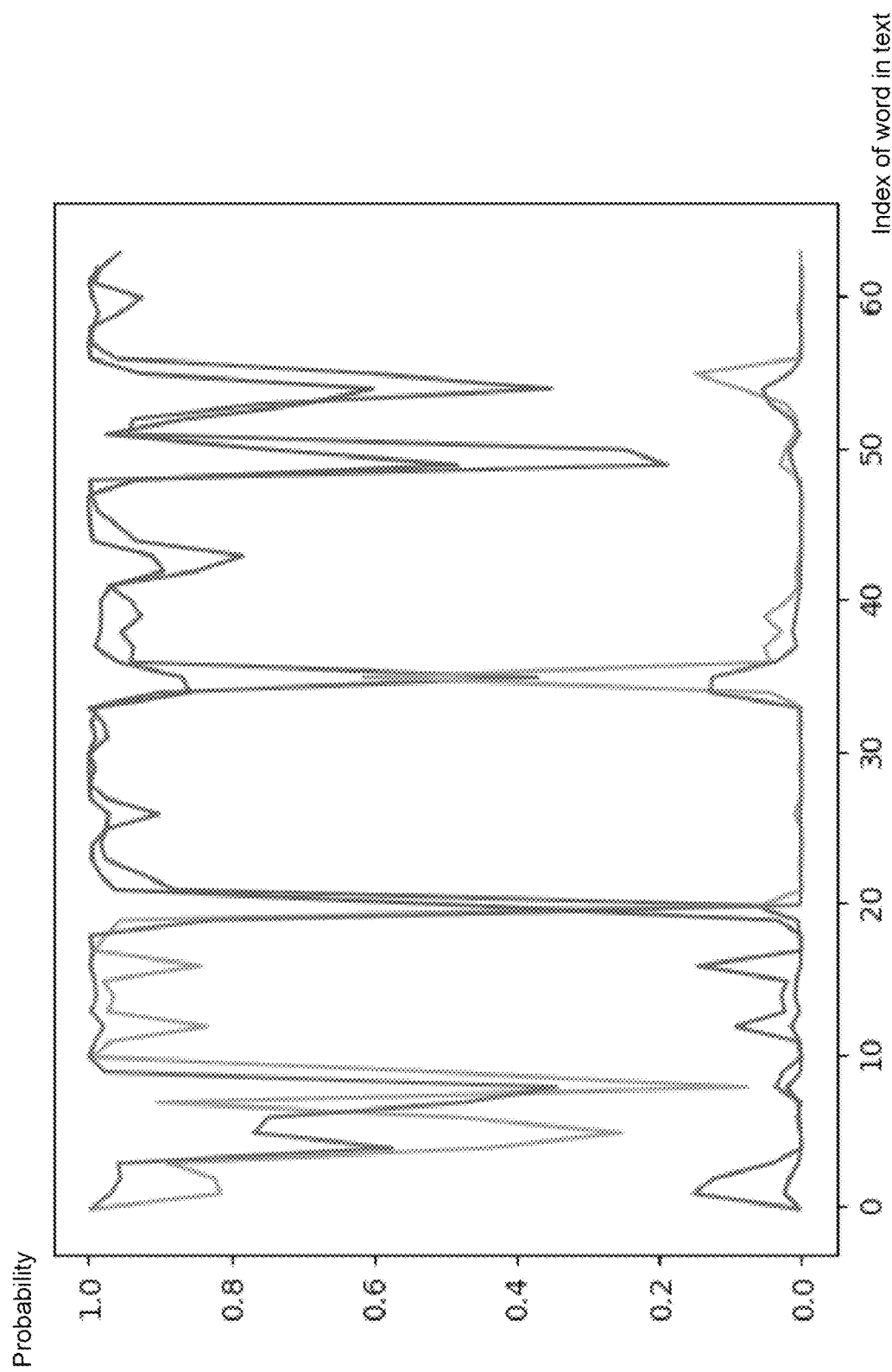
FIG. 44 shows an example of a stalactite cave OCR text type separation in accordance with some embodiments.

For allergens and ingredients, their spelling may be first corrected using a specialized spell checker. The spell checker can be used to correct words that were misspelled by the OCR. The frequency of each word in a training set is used to determine their probability, for example as set by Zipf's law which states that given some corpus of natural language utterances, the frequency of any word is inversely proportional to its rank in the frequency table. For each word detected by the OCR, the food analysis system can check if the word is in the stored vocabulary. If the word is not in the stored vocabulary, the following options may be available: (1) Assume there is a spelling mistake, look for a predetermined number of top matches (e.g. top eight matches) in the vocabulary, and choose the one with the highest probability, or (2) Assume that the detected word is a result of two different words concatenated by the OCR, and then choose the split that offers the highest probability. After the spelling has been corrected, each extracted text can be divided into sections of ingredients and allergens by maximizing their confidence, using for example a stalactite cave algorithm. The stalactite cave algorithm can be used to detect parts of text containing an ingredients paragraph and an allergens paragraph. The stalactite cave algorithm can be implemented by a training a model to classify an expression to three classes, for example: (i) ingredients, (ii) allergens and (iii) others. The model can include tfidf transformation and a logistic regression classifier. The confidence on every three words can be checked using the model. Dynamic programming can be used to assert the parts containing each group (ingredients and allergens), such that the area under the confidence graph is maximized. FIG. 44 shows an example of a stalactite cave OCR text type separation. The x-axis of the graph of FIG. 44 shows the index of the word in the text (e.g. for a food dish). The y-axis of the graph of FIG. 44 shows the probability that a pair of words starting on the index belongs to the various classes (e.g., ingredients, allergens, etc.). After each extracted text has been divided into sections of ingredients and allergens, the paragraph with the highest confidence is selected as being most relevant for allergens and ingredients.

For nutritional facts, the food analysis system described herein can assert for each line whether the line contains a nutritional fact. Next, the line is divided into name (by fitting to a word bank), amount, and measurement. The paragraph with the highest confidence is then selected as being most relevant for nutritional facts.

Figure 45:
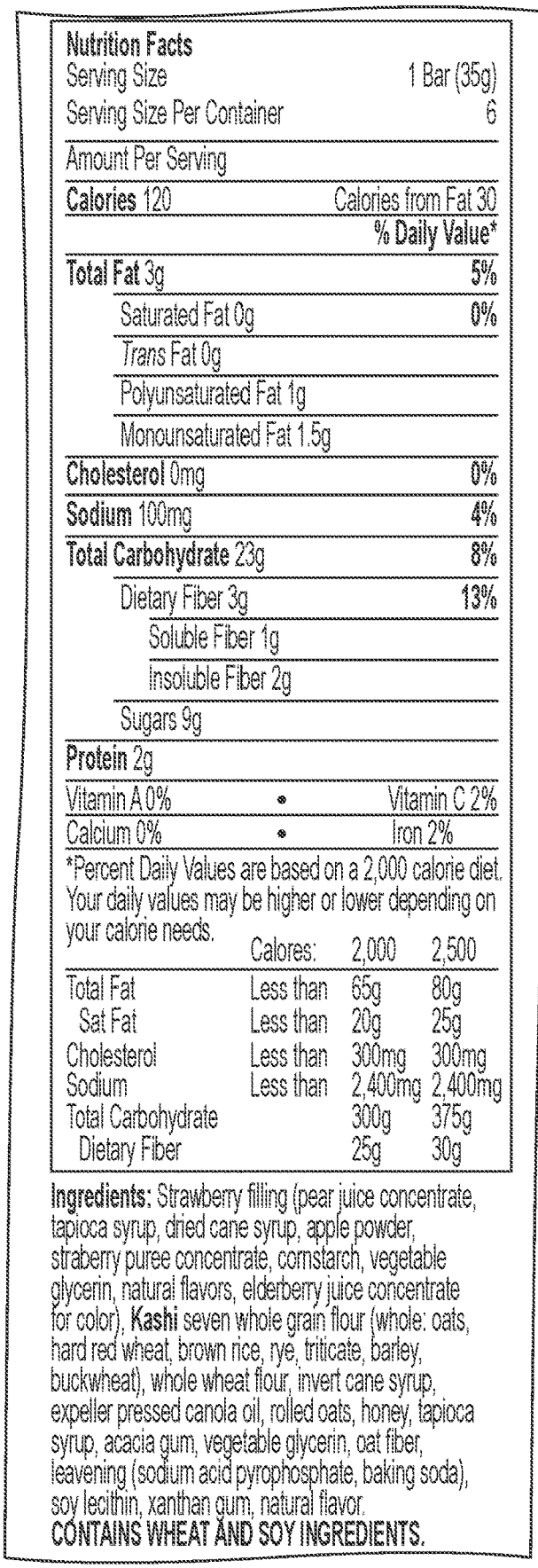
FIG. 45 shows an exemplary image of a packaged food label from which nutritional information is to be extracted.

An example of nutritional information extraction is next described with reference to FIG. 45 which shows an image of a packaged food label. The OCR output is provided as follows:

Allergens: Contains Wheat and Soy Ingredients.

Ingredients: Strawberry filling pear juice concentrate, tapioca syrup, dried cane syrup, apple powder, strawberry puree concentrate, constarch, vegetable glycerin, natural flavors, elderberry juice concentrate for color Kashi seven whole grain flour whole: cats, hard red wheat, brown rice, rye, triticale, barley, buckwheat whole wheat flour, invert cane syrup, expeller pressed canola oil, rolled cats, honey, tapioca syrup, acacia gum, vegetable glycerin, coat fiber, leavening sodium acid pyrophosphate, baking soda soy lecithin, xanthan gum, natural flavor.

Nutritional facts:

| Name | Amount | Percentage | Unit |
| --- | --- | --- | --- |
| Dietary Fiber | 3 | 12 | g |
| Sugars | 9 | — | g |
| Iron | 2 | 2 | |
| Polyunsaturated Fat | 1 | — | g |

-continued

| Name | Amount | Percentage | Unit |
| --- | --- | --- | --- |
| Saturated Fat | 0 | 0 | g |
| Insoluble Fiber | 2 | — | g |
| Sodium | 100 | 4 | mg |
| Calories | 120 | | |
| Monounsaturated Fat | 1.5 | — | g |
| Calcium | 0 | 0 | |
| Vitamin A | 0 | 0 | |
| Soluble Fiber | 1 | — | g |
| Total Fat | 3 | 5 | g |
| Cholesterol | 0 | 0 | mg |
| Total Carbohydrate | 23 | 8 | g |
| Protein | 2 | 4 | g |
| Trans Fat | 0 | — | g |

Figure 46:
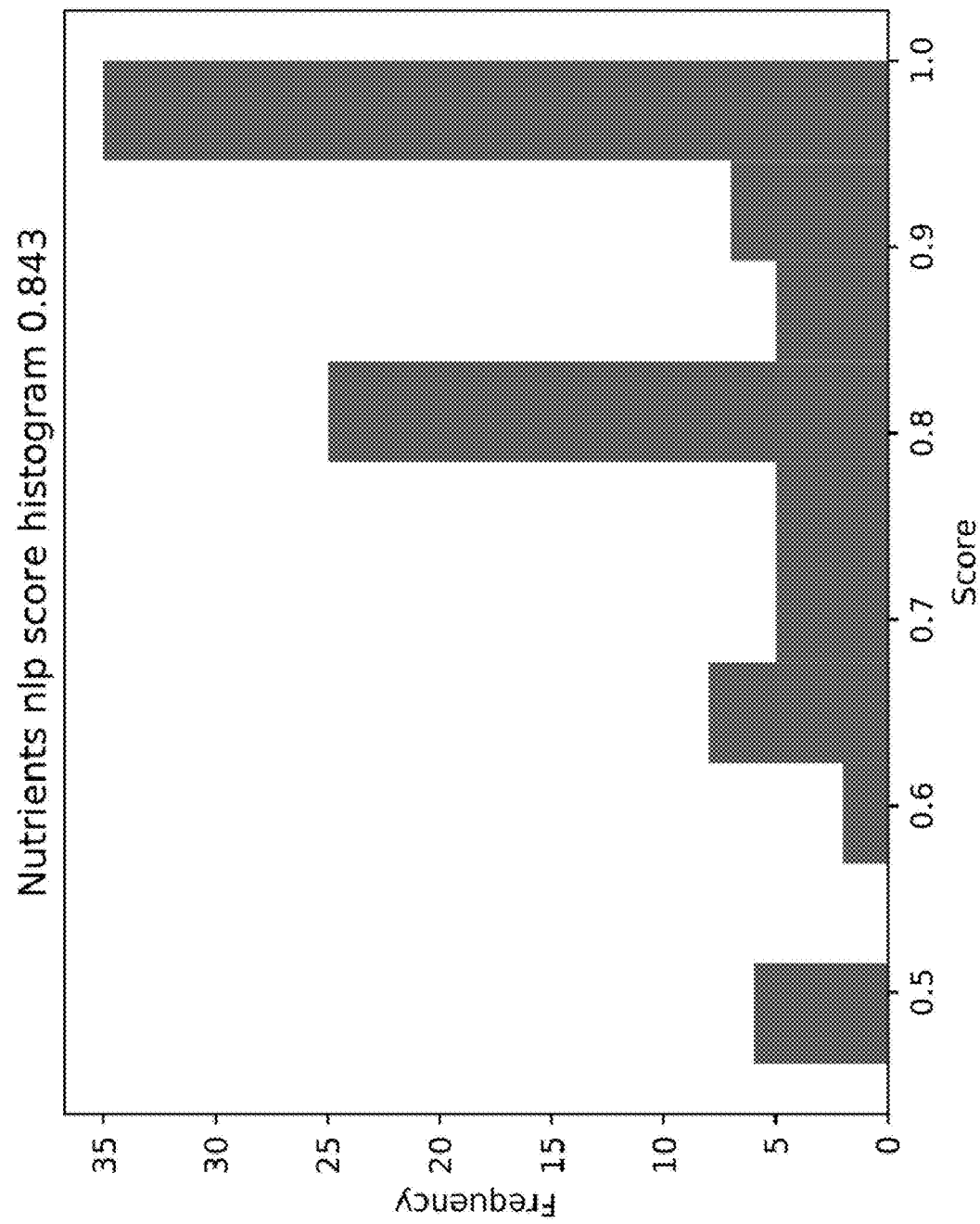
FIG. 46 illustrates a nutrients NLP score histogram based on nutritional information extraction on over 40000 food products, in accordance with some embodiments.
Figure 47:
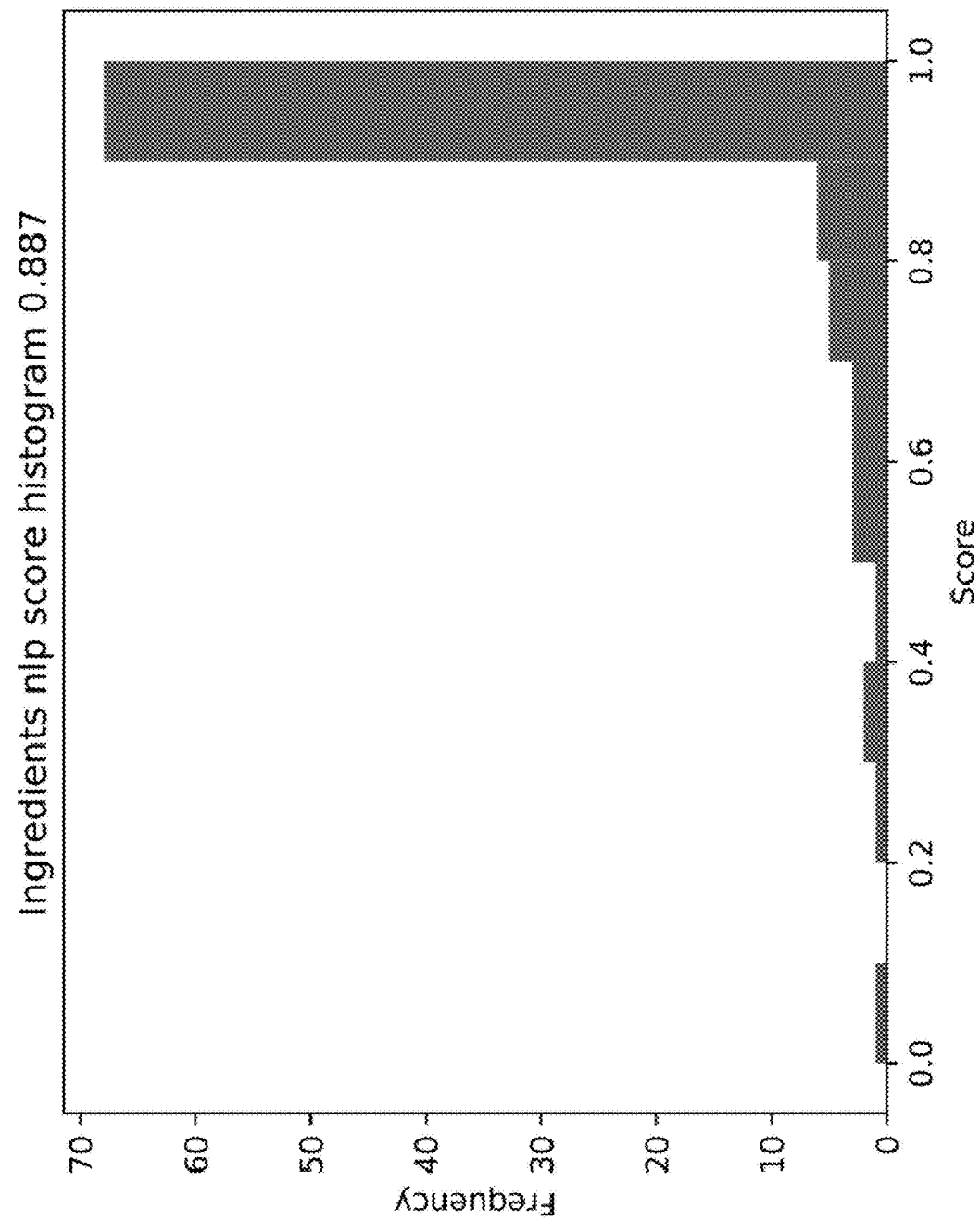
FIG. 47 illustrates an ingredients NLP score histogram based on nutritional information extraction on over 40000 food products, in accordance with some embodiments.
Figure 48:
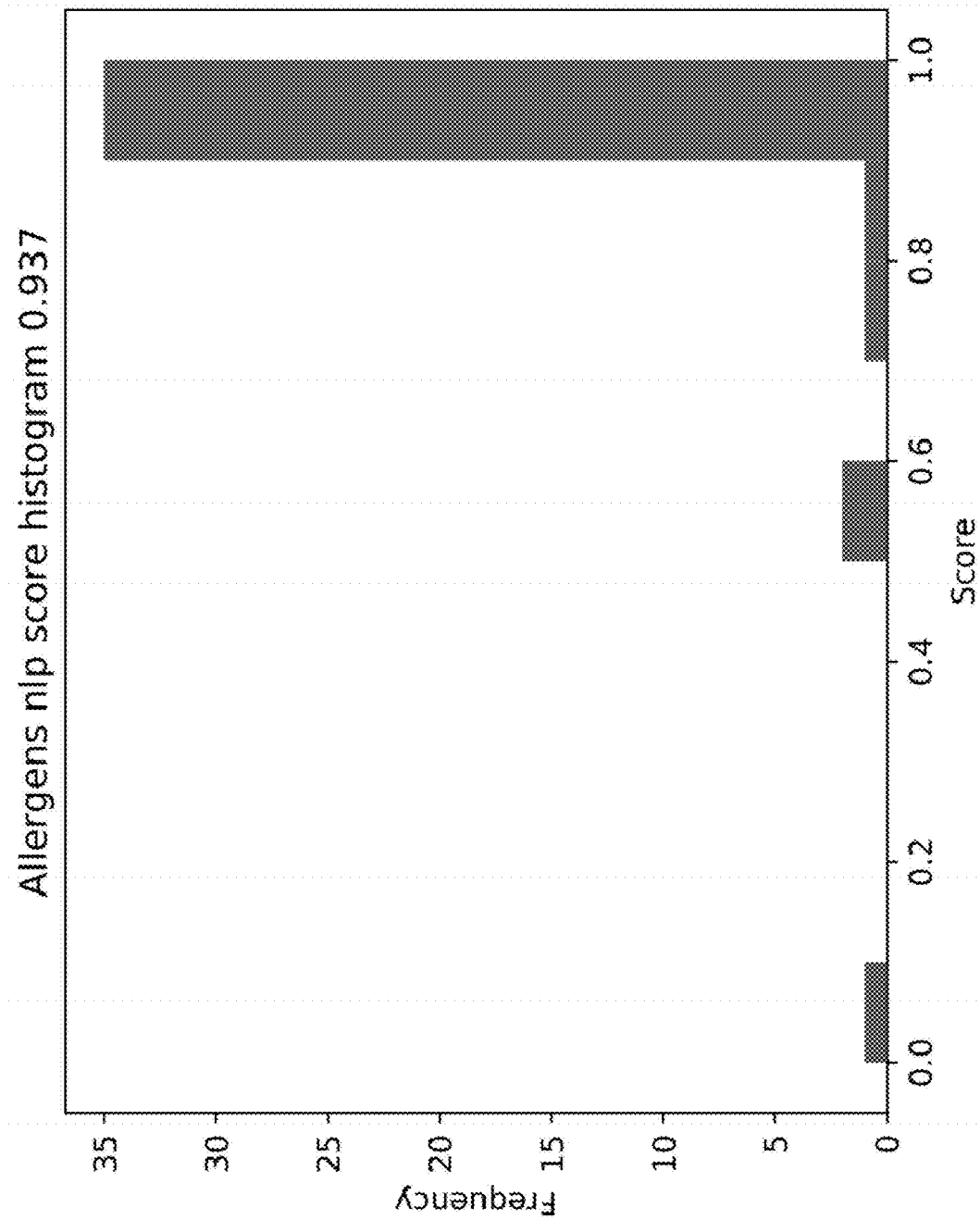
FIG. 48 illustrates an allergens NLP score histogram based on nutritional information extraction on over 40000 food products, in accordance with some embodiments.

FIGS. 46-48 illustrate the results of nutritional information extraction on more than 40000 food products. Specifically, FIG. 46 is illustrative of the nutritional facts accuracy showing a nutrients NLP score histogram of 0.843. FIG. 47 is illustrative of the ingredients accuracy showing an ingredients NLP score histogram of 0.887. FIG. 48 is illustrative of the allergens accuracy showing an allergens NLP score histogram of 0.937. Based on the above results, it can be observed that the various algorithms utilized in the nutritional information extraction process described herein are capable of extracting highly accurate information on nutritional facts, ingredients, and allergens.

In some embodiments, the packaged foods OCR described herein may further include a logo recognition technique. The logo recognition technique may be applied alone, or in conjunction with the nutritional information extraction technique described above. Two main classifiers may be provided for logo recognition: (1) a text based classifier, and (2) an image classifier.

The text classifier can utilize OCR to extract text from an image. A tfidf vectorizer can be used to transform the text to numeric vectors. Classification of the text vectors can be performed using one or more of the following: Logistic Regression, Decision Tree, or Random Forest.

Figure 49:
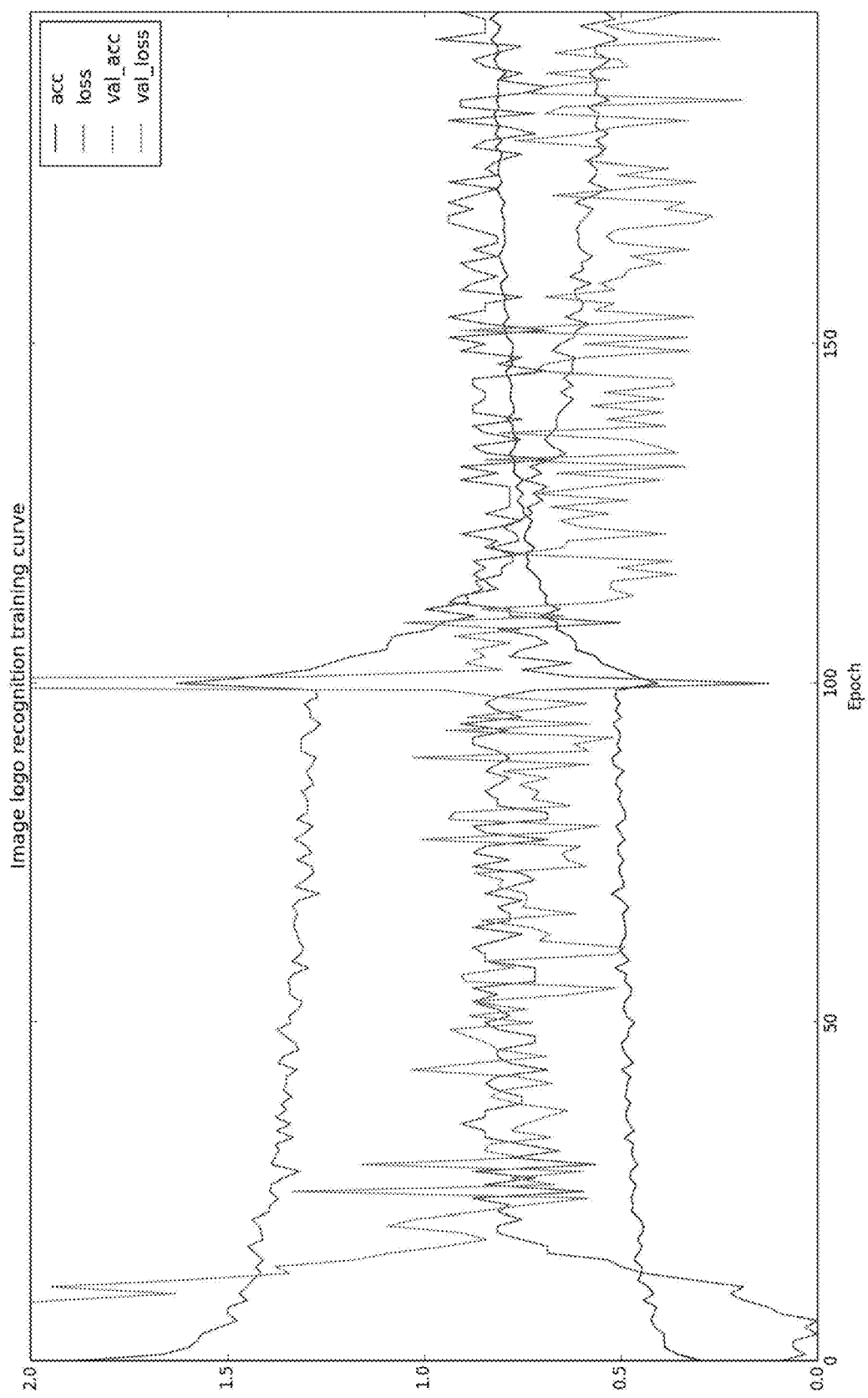
FIG. 49 shows a graph of image logo training results in accordance with some embodiments.
Figure 50:
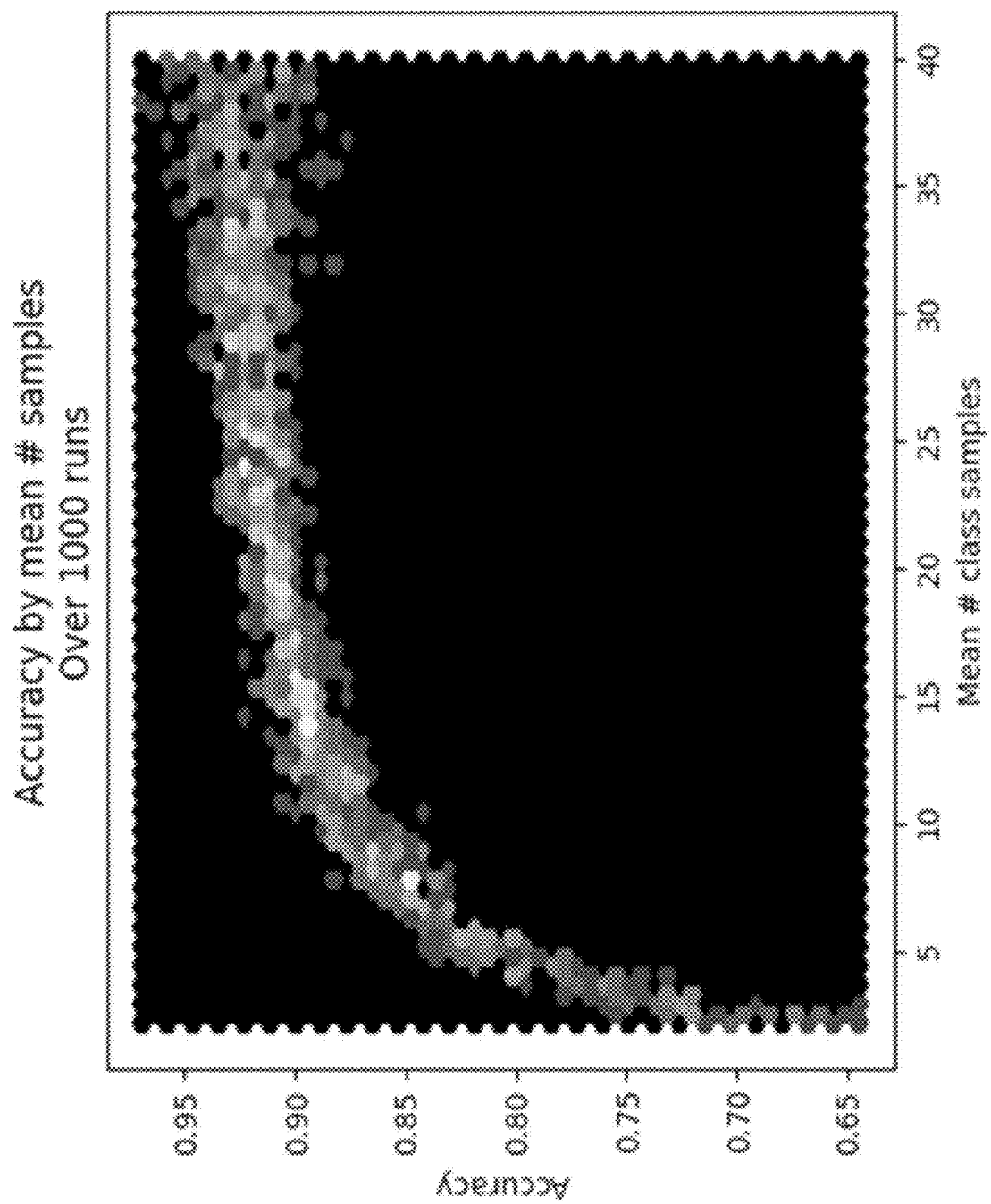
FIG. 50 shows a graph of text logo recognition results in accordance with some embodiments.
Figure 51A:
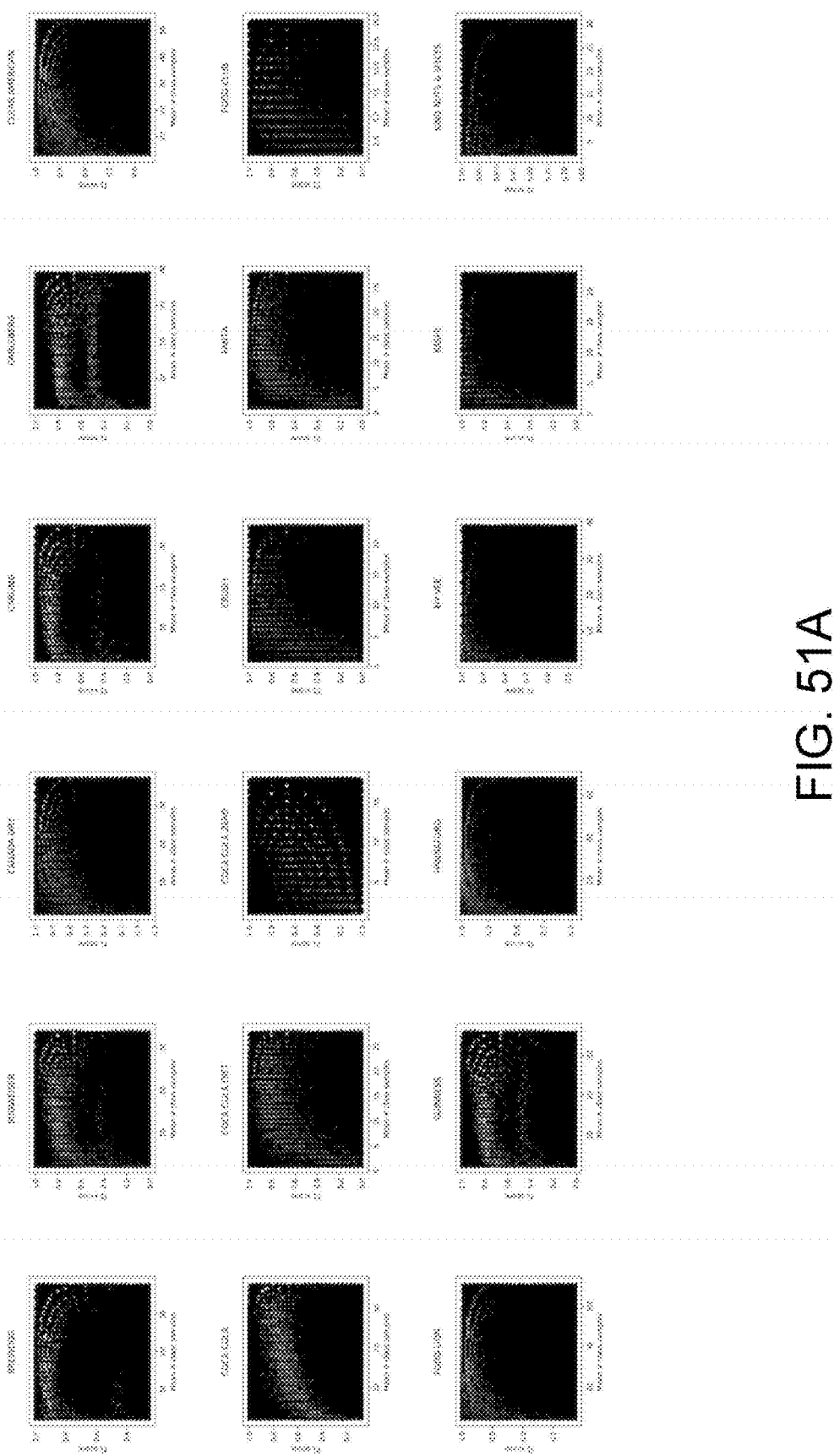
FIGS. 51A and 51B illustrate the results per logo for a plurality of different logos in accordance with some embodiments.
Figure 51B:
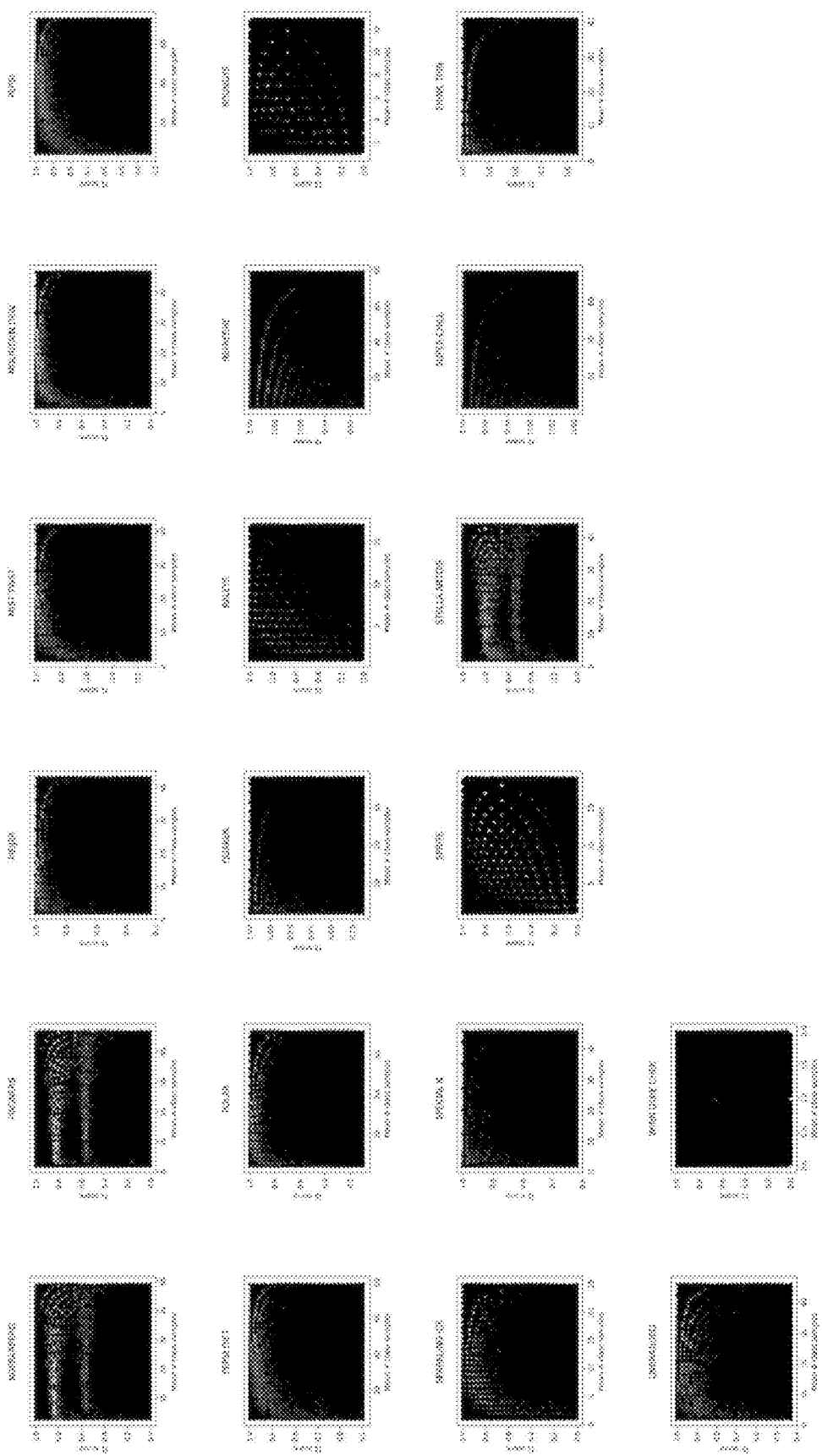

The image classifier can be based on Deep Residual Learning for Image Recognition (ResNet50) pre-trained on imagenet data. Multiple layers (e.g. 3 layers) of multilayer perceptron (MLP) can be attached to the output of ResNet50 and trained. The neural network can be fine-tuned by training all but the first n layers (e.g. first 50 layers). The training can be performed on a small set of images by including a specialized image augmentation. The image augmentation can include making the following random changes to images with logos: (a) image rotation, (b) gamma correction, (c) brightness change, and (d) averting to gray scale image. Conversely, images without logos can be used to enlarge the logo image trainset by inserting logos into those images that do not have logos. The following steps can be performed to ensure a large variety in logo insertion: (i) warping logo image with homography transformation, and (ii) adding logo to a random location in the image. FIG. 49 shows an example of image logo training results. Fine-tuning was performed after 100 epochs. FIG. 50 shows an example of text logo recognition results, specifically accuracy per mean number of samples over 1000 runs for a plurality of different logos. FIGS. 51A and 51B further illustrates the results per logo, for the plurality of different logos.

In some embodiments, the food analysis system disclosed herein may include a food image recognition engine. The food image recognition engine may be a computer vision system that is configured to classify foods from images, and analyze the content, volume and nutritional values of the foods.

Conventional commercially available food image analysis systems are typically limited to food classification alone, and lack the ability to estimate volumes of individual contents within the foods. Existing food image analysis systems may have other deficiencies as well. For example, existing food image analysis systems analyze foods based on food contents that are shown on the images, and are unable to account for ingredients that are not visually apparent from the images. Some of those ingredients (that are not visible from the images) can significantly disrupt and alter the nutritional estimation of a given food. An example of such ingredients is the oil family, where 1 tbsp of oil can contribute over 100 calories. FIGS. 19A and 19B each illustrates side-by-side comparisons of similar looking foods, but that have substantially different caloric content due to differences in individual food content amounts and other ingredients (such as oil) that are not visually apparent. For example, in FIG. 19A, the two bowls contain the same ingredients but in different amounts. The bowl on the left of FIG. 19A contains: 180 g untrimmed steak cooked in 1 tsp oil. 2 cups Lettuce, 4 rings red onion, 50 g avocado, 1 cup cooked rice noodles, 30 g cucumber, 2 cherry tomatoes, 2 tsp sesame oil, 2 tsp lime juice, 1 tsp soy sauce. The bowl on the right of FIG. 19A contains: 100 g trimmed steak (grilled), and has the same amount of lettuce, red onion and lime juice as the bowl on the left. However, the bowl on the right has half the avocado and rice noodles, 50 g Cucumber, double the cherry Tomatoes, ½ a medium carrot and half the sesame oil compared to the bowl on the left. As such, the left bowl contains 770 calories whereas the right bowl contains only 405 calories. Referring to FIG. 19B, the bowl on the left contains: 200 g chicken cooked in 2 tsp extra virgin olive oil, 30 g semi-trimmed bacon, 2 cups cooked pasta, 30 g full fat cheddar, 2 large Florets Broccoli, 1 medium mushroom. The bowl on the right of FIG. 19B contains: 100 g poached chicken, 1 cup cooked pasta, 1 tsp capers, 10 g low fat cheddar, ¼ large capsicum, 4 large florets broccoli, 2 medium mushrooms. As a result of the extra pasta, the left bowl contains 800 calories whereas the right bowl contains only 380 calories.

Convention/existing food image analysis systems may be limited for the following reasons.

First, studies have shown that 50% of the meals in the U.S are eaten out. This means that for a model to produce good real world results, it must be capable to handle restaurant dishes with high accuracy. The majority of the leading academic papers on the topic, as well as the commercial food image analysis solutions available, expect to have sufficient number of images for each dish of every restaurant. In the U.S. alone, there are over 700,000 restaurants, with an average of 61 dishes in each restaurant, which yields an enormous lower bound of over 42 million dishes. Unfortunately, the majority of the restaurants do not provide enough images of their dishes (even chain restaurants usually have only a few images of each dish). Furthermore, online sources of dishes images (such as those found on Yelp™) do not solve the problem. This means that in order for a solution to provide very accurate results in real world data, it must overcome the "eat out data gap". Namely, the model has to be able to identify images of dishes even if it has never been exposed to images from a specific restaurant.

Second, as discussed with reference to FIGS. 19A and 19B, there are many foods that appear to be very similar, yet can be very different (e.g. noodle dishes such as pad thai, lo mein, and others). While deep neural networks may perform fairly well at distinguishing objects in many cases, this is not always possible. For this purpose, there is ample value in identifying both the dishes as well as their ingredients, and try to use the former to provide more information about the latter, and vice versa in a bidirectional or multidirectional manner. To achieve this, one will have to leverage the structure of dishes and their relationships to ingredients (namely a food ontology such the one described herein).

Third, in many cases, existing systems may provide several suggestions for a given image, many of which may be poorly classified. This is mainly due to the fact that many foods can be deceptive when analyzed from an image, and no computer vision system can perform perfectly. Specifically in the case of digital nutrition (and other digital healthcare solutions), receiving poor results can reduce a user's confidence in the computer vision system. Users may stop using such systems. This means that there is ample value in providing only correct or sufficiently accurate results. While it is generally impossible for a computer vision system to always be accurate, there is a delicate balance between specificity of a classification (e.g. Noodles dish→Pad Thai→Pad Thai with chicken) and the system's confidence level. Current existing systems tend not to generalize results that they are uncertain about. For example, current existing systems may not be capable of generating more accurate (but more generalized) results to the users.

Lastly, a problem exists in the non-uniqueness of mapping from a food image to nutritional values. Many existing systems attempt to map food images into nutritional values, but are not configured to know the features that are lacking in order to complete the mapping. Nor are the existing systems configured to assist the users in bridging the knowledge gap.

The food image recognition engine described herein can address the above shortcomings of existing systems. The food image recognition engine disclosed herein is capable of one or more of the following: (1) Identify which foods are definitely (i.e. 100% probability) in the image; (2) Identify foods which may be in the image (probabilities), either by studying the image, the context in which it was taken, the user's history, or the likelihoods of certain foods appearing together; (3) Distinguish between dishes (e.g. Pad Thai) and ingredients (e.g. peanuts) they may contain; and (4) Leverage historical eating patterns of a user, and the context in which the user is eating to estimate volume and thus nutritional values. In particular, this can include using known menus when the user is eating out.

To achieve the above goals, the food image recognition engine can include an algorithm comprising the following. First, a complete ontology of visual cues for foods (VICUF) is constructed. This is an ontology of any visual cue that human beings (or computers) may use to identify the food that is before them, and may include: (1) Combo food items (e.g. Greek salad, or a burrito); (2) Ingredients (e.g. banana, apple, shrimps); and (3) Other cues (e.g. cup, liquid, fried, etc.). Knowing the entire ontology of VICUF can be used in conjunction with other inputs to obtain a more accurate identification of restaurant dishes. Next, a robust corpus for each label in VICUF is created. Ideally each label in the training set is to be annotated. Next, a convolutional neural network (CNN) is trained on each label in the VICUF (binary classifier), or a CNN capable of multi-labeling is trained. The latter CNN may provide better results since certain foods often appear together, while other foods do not. Next, each time a new image is supplied, the CNN will map it to a probability vector, where each component represents the probability that a specific food-related visual cue is in the image. The above steps may be sufficient to create a food logging experience. Given an image, the food image recognition engine can sort items in the food logger depending on their probability value in the output vector. A threshold can be included such that items with low probability do not appear.

In some embodiments, additional sensors and inputs, for example based on spectroscopy and non-visible light (infrared), can be used to detect the subtleties between similar-looking foods and individual volumes/contents. In some embodiments, the volume/content can be estimated based on a sequence of images or video for 3D reconstruction of foods. In some embodiments, distance estimation can be performed using an infrared system that is configured to measure distances from various points on a plate of food.

The food analysis system 210 can include a labeling machine. The labeling machine can be a machine learning system to discover categories or abstraction layers (herein also referred to as labels) about foods. The labeling machine can be an automated system for textual analysis of food objects and labeling them. This allows adding another layer of metadata, which the system is using to understand various characteristics of every food. These characteristics (labels) can be used in different ways by the system, for example by a personalized recommendation engine.

Examples of labels can include at least one ingredient (e.g., beef, pork, acorn, celery, etc.), at least one nutrient (e.g., vitamin A, vitamin C, calcium, iron, etc.), at least one dietary need (e.g., vegetarian, vegan, gluten free, etc.), at least one allergy (e.g., peanut free, gluten free, etc.), at least one dish type (e.g., salad, sandwich, soup, etc.), at least one cuisine (e.g. ethnic and/or religious cuisines, etc.), at least one flavor (e.g., sweet, fruity, etc.), at least one nutritional characteristic (e.g., low fat, high protein, etc.), and at least one texture (e.g., soft, firm, etc.). The labels can be generally classified into one or more of the following categories, for example: dietary needs (including diets and allergens), processing method, taste, meal, and dish. Dietary needs are food labels that allow a personalized recommendation engine to filter foods that a certain individual will never eat due to certain dietary restrictions. The labels can be generated automatically by the labeling machine. Dietary needs can be generally classified into two kinds: (1) dietary needs that are due to food allergies and (2) dietary needs that are due to specific diets that users often follow for ethical, religious or environmental reasons. Examples of dietary needs relating to food allergies may include gluten-free, dairy-free, no shellfish, no fish, no soy, no eggs, no peanuts, etc. Other examples of dietary needs may include vegetarian, pescatarian, or vegan.

The labeling machine can use a machine learning approach or a non-machine learning heuristic approach to develop a food labeler that can discover characteristics about foods. The machine learning approach can be referred to as a "label classifier" approach. The non-machine learning heuristic approach can be referred to as a "heuristic labeler" approach. The label classifier approach or the heuristic labeler approach can generate at least one algorithm for at least one food labeler to identify and label at least one particular abstraction layer of at least one food. The identification and labeling of particular abstraction layer of food can be referred to as food labeling. The label classifier and the heuristic labeler can use one or more logical entities known as an analyzer and a problem solver for food labeling. Both the label classifier and the heuristics labeler can be evaluated using a corpus of pre-defined food data to assess how well each food labeler can perform. The labeling machine can use various statistical models (e.g. precision, recall, etc.) to evaluate performance of the food labeler.

As a logical entity of the labeling machine, an analyzer can be a single model with a specific logic. The analyzer can be used to determine a specific attribute of a food item (e.g., whether the item is vegan or not). Thus, multiple analyzers can be required to determine multiple attributes of the food item. The analyzer can include a training set. For each analyzer, one or more training sets can be created, and each training set can have a distinguishable name (e.g., "English" or "Spanish" for different languages, or "gluten free" or "vegan" for different dietary needs). A problem solver can be a combination of two or more analyzers to determine an attribute for the food item based on the combined logics of its encompassing analyzers. The problem solver can include at least one label classifier analyzer or one heuristic labeler analyzer. The problem solver can encompass at least one additional problem solver.

For both the label classifier and the heuristic labeler approaches, labeling and classifying a food data is a process with three main processes: (1) training various analyzers; (2) defining at least one combination of two or more analyzers to form a problem solver; and (3) running the problem solver to identify, label, and classify one or more features from the food data. Furthermore, the training the different analyzers process can include two sub-processes: (i) establishing at least one training set for each analyzer, and (ii) performing a training based on at least one training set.

The labeling machine can use the label classifier approach to develop an analyzer. In the label classifier approach, a training set for an analyzer can contain at least one pair of input data and its corresponding correct answer, also known as a target. The target can be a "gold standard" for the analyzer. The analyzer's learning algorithm can find one or more patterns in the training set between the input data and the target, and generate an improved machine learning algorithm that can capture one or more patterns. The analyzer can be trained with more than one training sets, respectively, to generate more than one improved machine learning algorithms for an identical characteristic. Successively, a test set can be used to test accuracies of the more than one improved machine learning algorithms of the analyzer, and the best performing algorithm can be selected for use. Selecting the best performing algorithm can involve comparing statistical analyses from each algorithm's accuracy test, including a recall value, a precision value, and an $F_1$ score. The recall value can indicate how many of items that should have been labelled are actually selected. The precision value can indicate how many of the items were correctly labeled. The $F_1$ score can be a harmonic mean of the recall and precision values as a measure of accuracy, according to the following equation:

$$F_1 = 2 \cdot \frac{\text{recall} \cdot \text{precision}}{\text{recall} + \text{precision}}$$

where the $F_1$ score can reach its best value at 1 and its worst value at 0. Thus, if multiple analyzer algorithms are trained to label a same food characteristic, an analyzer algorithm with the highest F1 score can be selected as a working analyzer.

Figure 4:
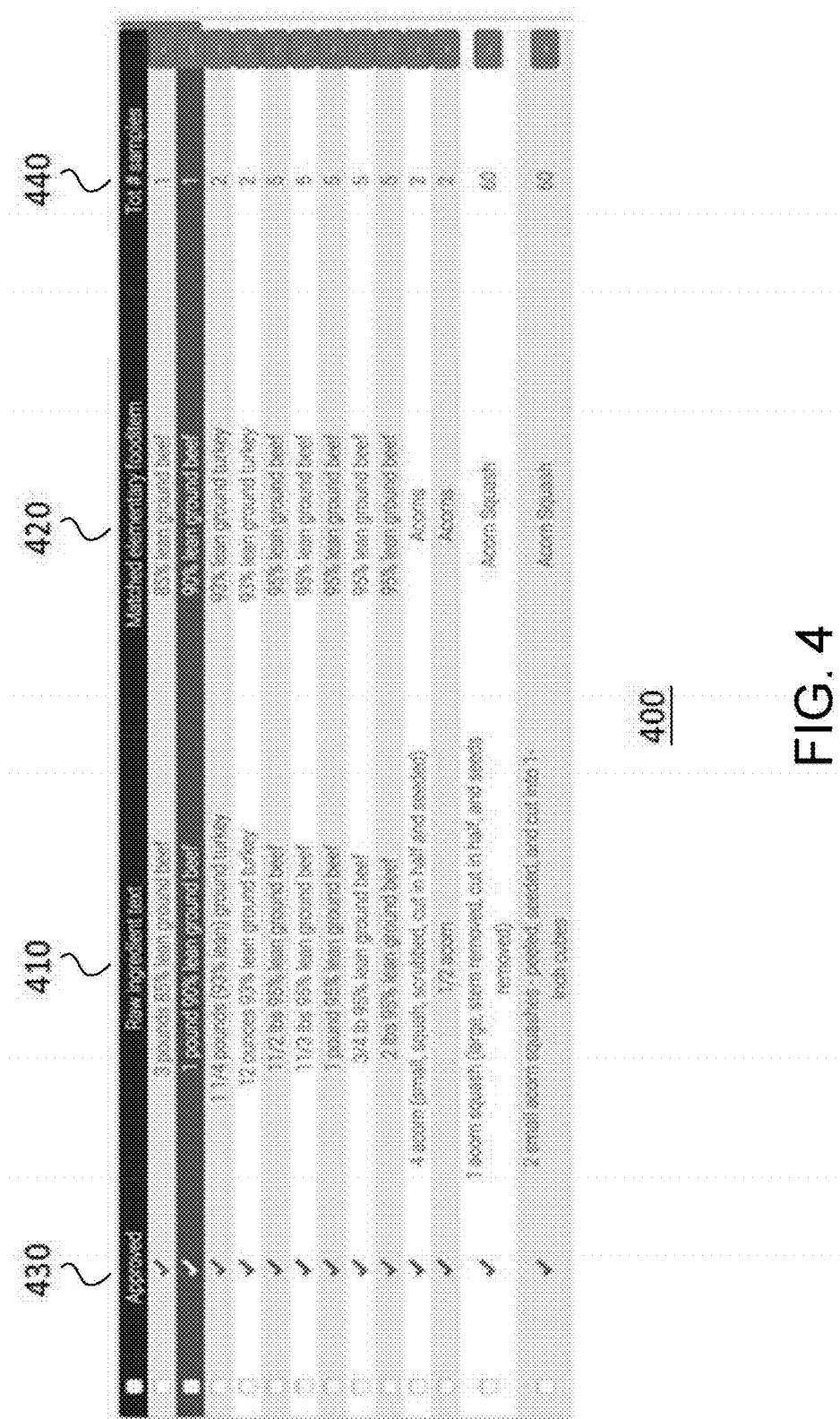
FIG. 4 illustrates an exemplary table of a training set for a food analysis algorithm, in accordance with some embodiments.

FIG. 4 illustrates a table of a training set 400 for an analyzer based on the label classifier approach. The analyzer can be tasked to classify ingredients from an input data 410

Figure 5:
FIG. 5 illustrates an exemplary table of results from testing a food analysis algorithm, in accordance with some embodiments.
Figure 52:
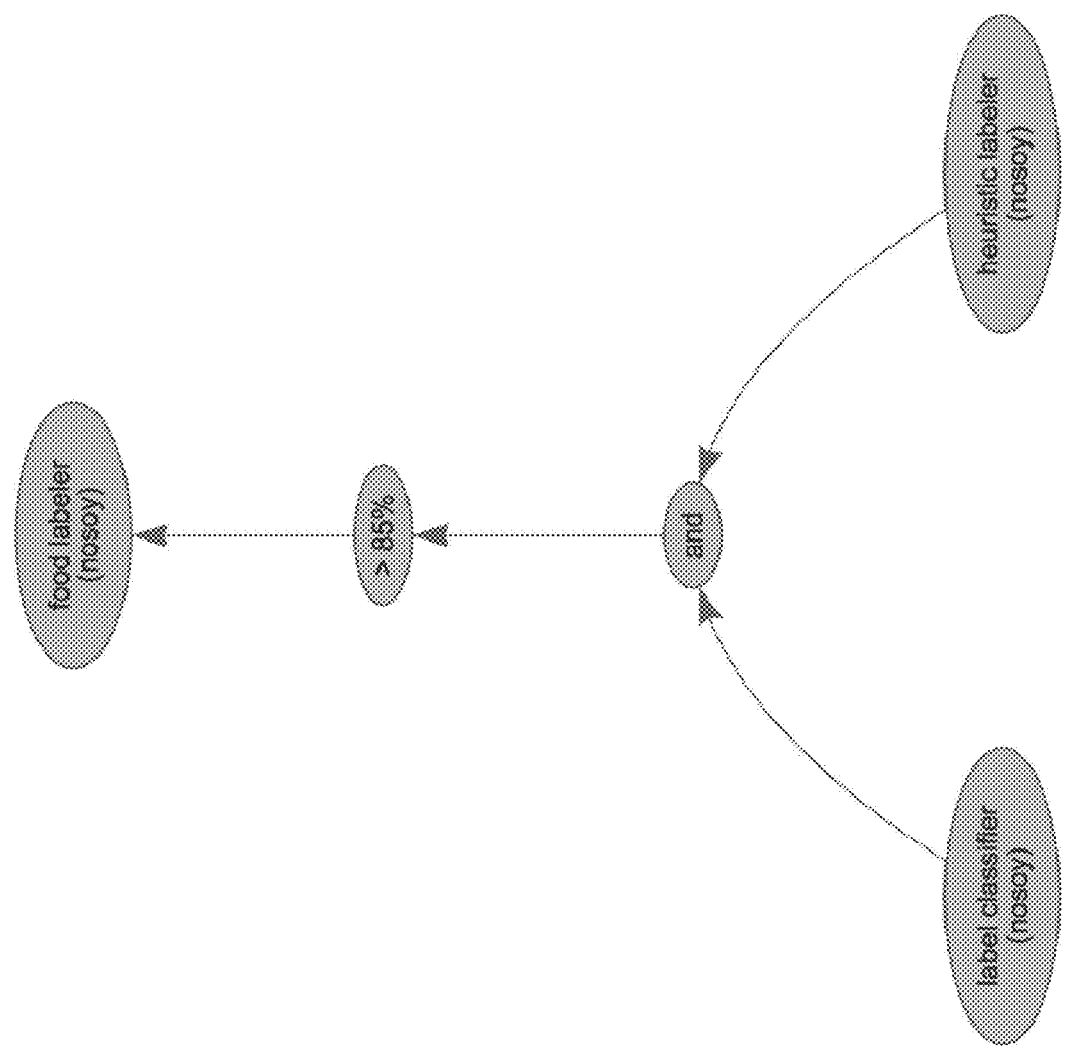
FIG. 52 illustrates a model for classifying whether a food-item is free from soy, in accordance with some embodiments.

(Raw ingredient text). The particular training set can be named "English" as the training set is designed to train the analyzer to classify ingredients written in English. Each input data is provided with a corresponding target 420 (Matched elementary food item). In this example, an input data of "1 pound 90% lean ground beef" can have a corresponding target of "90% lean ground beef." The table of the training set 400 can also indicate when an input data-corresponding target pair is selected for use 430 (Approved). A content developer may unselect an input data-corresponding target pair from the training set. The table of the training set 400 can also display a number of samples 440 (Tot # samples), in the database(s) of the platform 200, that contain a same corresponding target. FIG. 5 illustrates a table of results 500 from testing multiple trained analyzers. Each analyzer is trained to identify and label ingredients written in English. The table indicates the recall value 510, the precision value 520, and the F1 score 530 of each analyzer tested. In some embodiments, the label classifier can use a pipeline comprising of word singularization, For example, CountVectorizer and logistic regression can be used to determine whether a food item is to be tagged with a certain label. The label classifier can use as a training set, the same validation set used by the heuristic labeler described herein. As an example, a complete model for classifying whether a food-item is free from Soy or not can structured as shown in FIG. 52. Thus, only food-items which are classified as Soy-free by both classifiers, and for which the combined classification confidence is over 85%, can be considered to be Soy-free. To investigate the effect of the model composition, the precision and recall of the separate models can be examined, as well as the composed model (for the above example of the Soy-free labeler), and summarized in the table below. It can be observed that the model is greatly benefited from the composition, improving the precision (in this case) by around 20%:

| Model | Precision | Recall |
| --- | --- | --- |
| Heuristic | 71% | 96% |
| Classifier | 74% | 90% |
| Composed | 93% | 94% |

Figure 53:
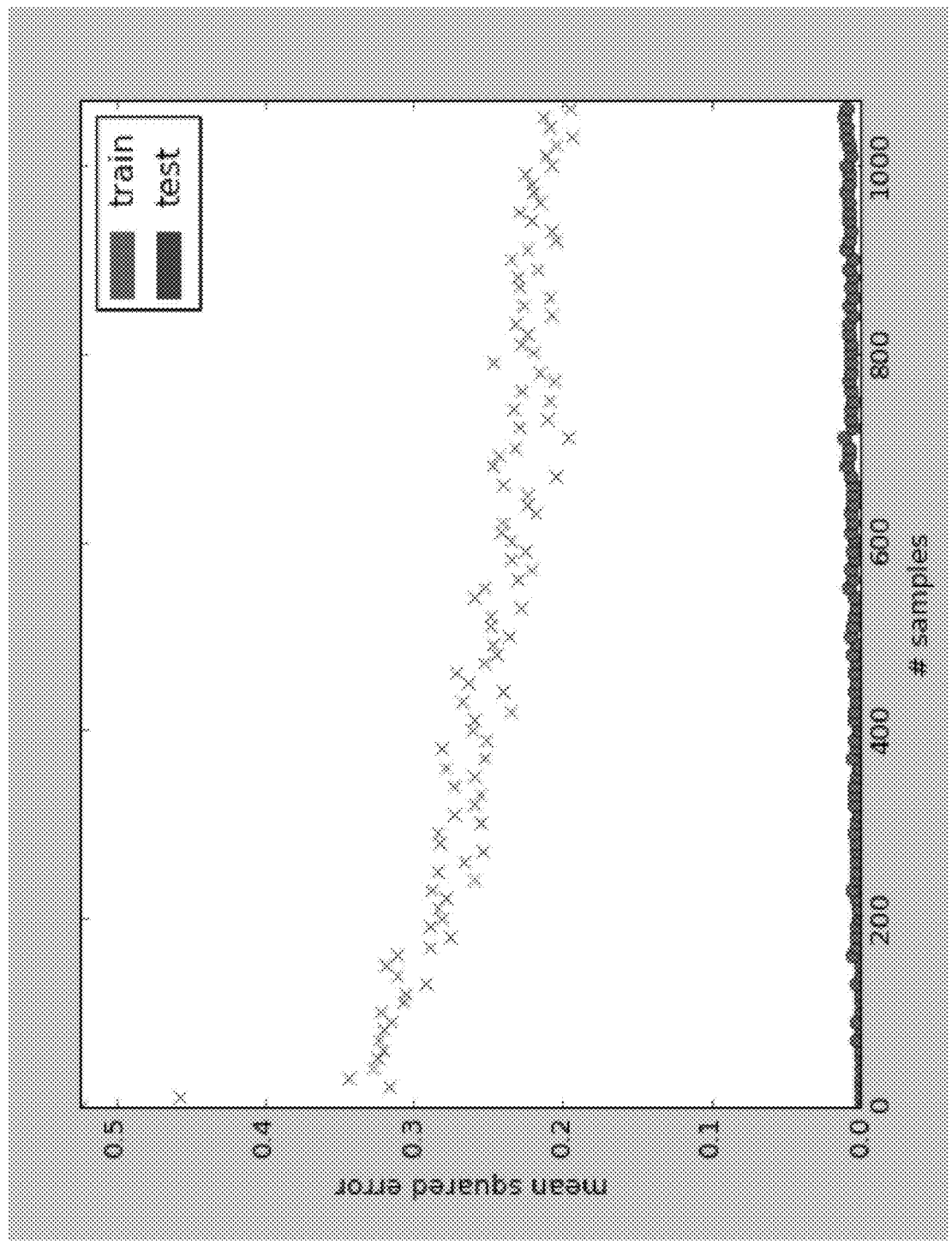
FIG. 53 illustrates an example of a learning curve in accordance with some embodiments.

FIG. 53 illustrates an example of a learning curve for most of the classifiers described herein. It can be observed that the model is capable of learning the training set almost entirely, and that the model is able to generalize. The learning curve also shows that obtaining more data can likely improve the generalization further.

Alternatively or in addition to, the labeling machine can use the heuristic labeler approach to develop an analyzer. The analyzer of the heuristic labeler approach can analyze food items for a specific characteristic of foods (e.g. dietary needs, such as vegetarian, vegan, gluten free, etc.). Such analyzer can use a special vocabulary list that is pre-defined for each specific characteristic to determine whether a new food item should be labeled with the characteristic or not. Each analyzer of the heuristic labeler approach can contain three components: a vocabulary list, a labeling logic, and a training set.

The analyzer of the heuristic labeler approach can include the vocabulary list. The vocabulary list can contain groups of words that are correlated to a food characteristic (e.g. gluten free), also referred to as a food label. When a textual data from a food item is provided as an input, the heuristic labeler approach compares words found in the textual data to the groups of words in the vocabulary list. The groups of words in the vocabulary list can include negative terms, positive terms, menu positive terms, and non-negative terms. Having at least one matching negative term can indicate that the food item may not belong to the food label. Having at least one matching positive term despite having at least one matching negative term can indicate that the food item may belong to the food label. Having at least one matching menu positive term can indicate that the food item may belong to the particular food label only when the word is from a menu category title. Lastly, the non-negative terms can be words that used to be negative terms but have been verified not to be so. The non-negative terms can be kept to ensure that such terms may not be added as a negative term again.

Figure 6:
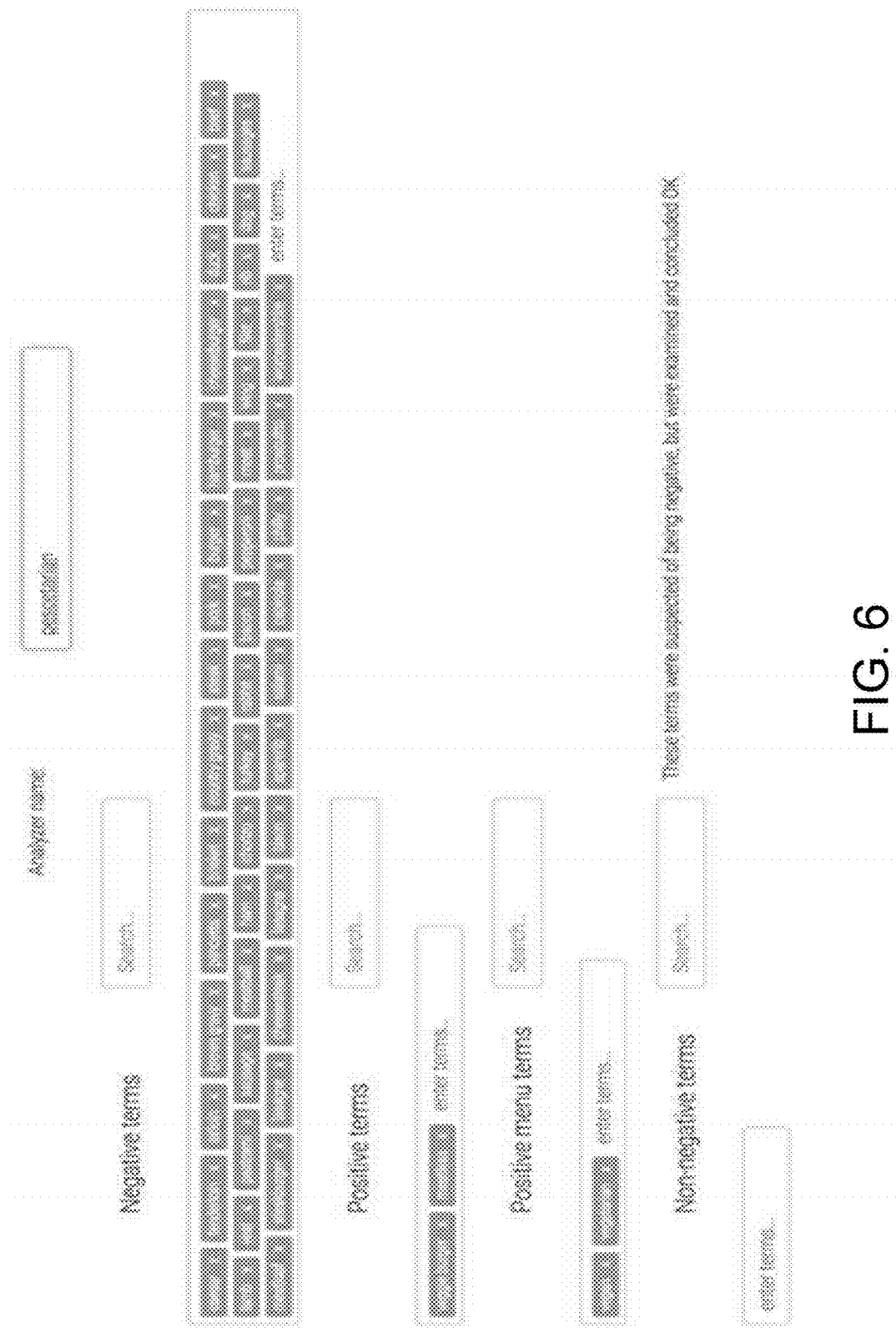
FIG. 6 illustrates an exemplary vocabulary list for a food analysis algorithm, in accordance with some embodiments.

FIG. 6 illustrates an exemplary vocabulary list for a food label "pescatarian." A pescatarian can be a person who does not eat meat, but eats fish. The vocabulary list for the food label "pescatarian" can have negative terms, positive terms, positive terms, and, optionally, non-negative terms. The negative terms can include caesar, tenderloin, sirloin, brown gravy, pancetta, brisket, country gravy, steak, pork, burger, hamburger, cheeseburger, duck, chicken, beef, lamb, veal, pastrami, sausage, meatball, ham, chorizo, turkey, rabbit, bacon, pepperoni, meat, wing, filet, rib, dog, sausages, meatloaf, steakburger, lasagna, cheesesteak, lasagna, bison, sparerib, salami, capocollo, philly, prosciutto, and Worcestershire. The positive terms can include veggie burger and meatless. The positive menu terms can include vegan and vegetarian. There may or may not be a non-negative term discovered.

The analyzer of the heuristic labeler approach can include the labeling logic. Based on the vocabulary list, the labeling logic can have three rules for labeling a food item. Firstly if there is not a matching negative term, positive term, or menu positive term in the food item's name, description, or menu category title, then the food item can be tagged with the label. Secondly if there is at least one matching negative term, in the absence of any other matching terms, then the food item cannot be tagged with the label. Thirdly if there is at least one matching positive term or at least one matching menu positive term in the food item's menu or sub-menu, then the food item can be tagged with the label. The third rule of the labeling logic can remain valid even if there is also at least one matching negative term.

In addition to the vocabulary list and the labeling logic, the analyzer of the heuristic labeler approach can include the training set. A purpose of the training set can be to verify that the vocabulary list generated for a certain food label is sufficient. The training set can include a list of food items with known characteristics. The corresponding vocabulary list can be applied to each food item in the training set to assess if the labeling should be applied or not. Afterwards, the training set can determine whether the labeling assessment was correct, and report a precision value (%) of the vocabulary list.

Figure 7:
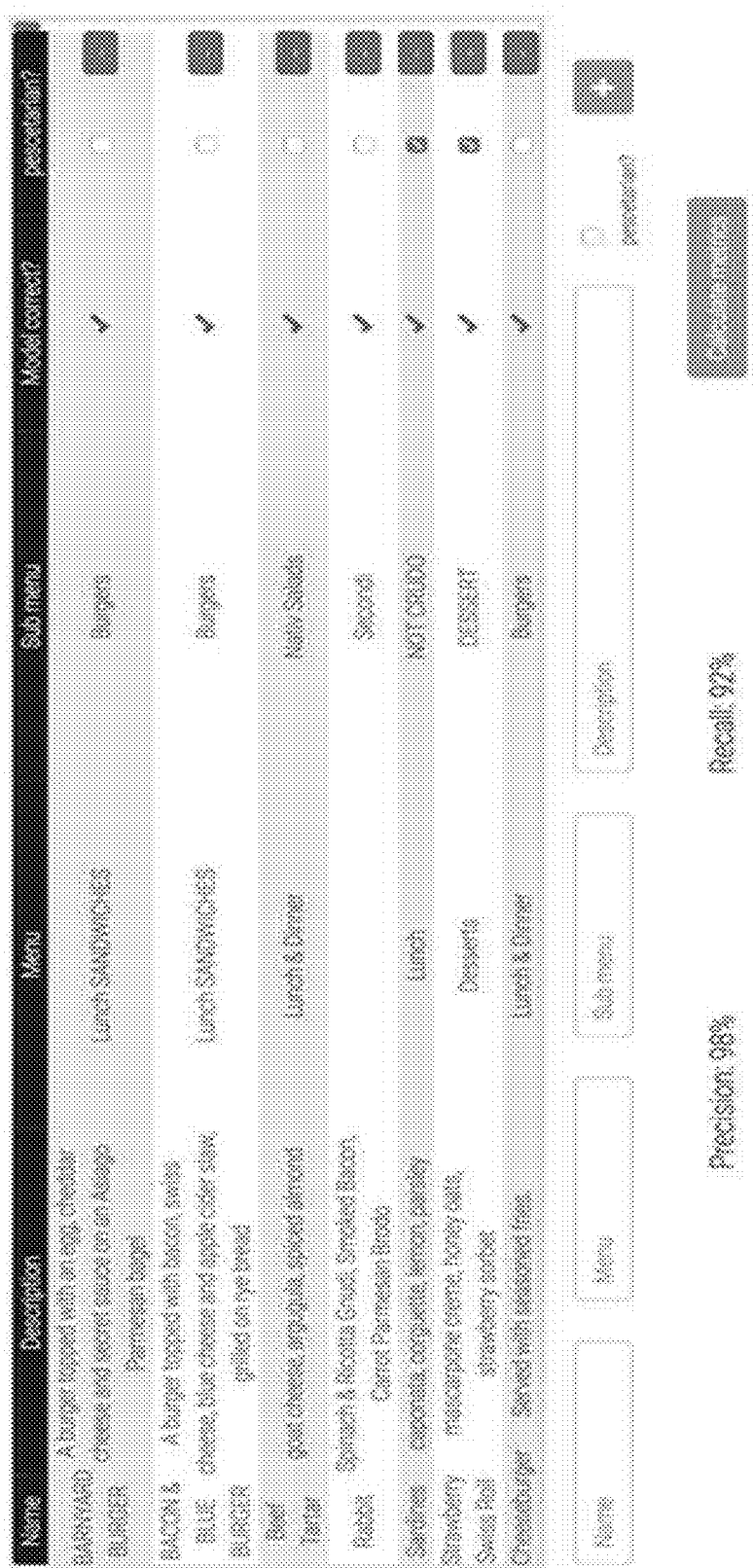
FIG. 7 illustrates an exemplary table of a training set for a different food analysis algorithm, in accordance with some embodiments.

FIG. 7 illustrates an exemplary table of a training set for the food label "pescatarian" based on the heuristic labeler approach. The training set can include various food items, including food items that a pescatarian can or cannot eat. Each of the various food items can be defined by a following list: name (e.g. Strawberry Swiss Roll), description (e.g. mascarpone crème, honey oats, and strawberry sorbet), menu (desserts), and sub-menu (desserts). If a food item is listed in a menu without a sub-menu, then the sub-menu can be listed as identical to the menu. Testing the vocabulary list can involve applying the vocabulary list to analyze the various food items in the training set, and recording whether or not the vocabulary list can correctly distinguish pescatarian-friendly food items. The training set can also report a precision value (e.g., 98%) and a recall value (e.g. 92%) to determine reliability and validity of the vocabulary list. In this example, the precision value can indicate how many of the items analyzed were correctly labeled "pescatarian." The recall value tells you how many of the items that should have been labelled "pescatarian" were actually selected.

During training or in use, an analyzer based on the heuristic labeler approach can detect one or more words, extracted from a food item, that are not found in an appropriate vocabulary list. If one or more unknown words is assessed (e.g. by machine learning) to be related to at least one negative term, the analyzer can store one or more words in the databases 240 along with at least one word found in the vocabulary list that may be related. One or more words can later be examined (e.g. by machine learning or a content developer) and added as a new term in the appropriate vocabulary list of the analyzer (e.g. as a new negative term). One or more words added can expand capacity and efficiency of the analyzer.

As a logical entity of the labeling machine, a problem solver can be a combination of at least two analyzers to integrate the logics of at least two analyzers. In some examples, an analyzer from the machine learning approach (label classifier) for a particular food attribute and an analyzer from the heuristic approach (heuristic labeler) for the particular food attribute can be combined as a problem solver to label foods that have the particular food attribute. The resulting problem solver can be denoted as an "attribute" food labeler. For example, a problem solver for identifying and labeling gluten free foods can be called a "gluten free" food labeler.

Figure 8:
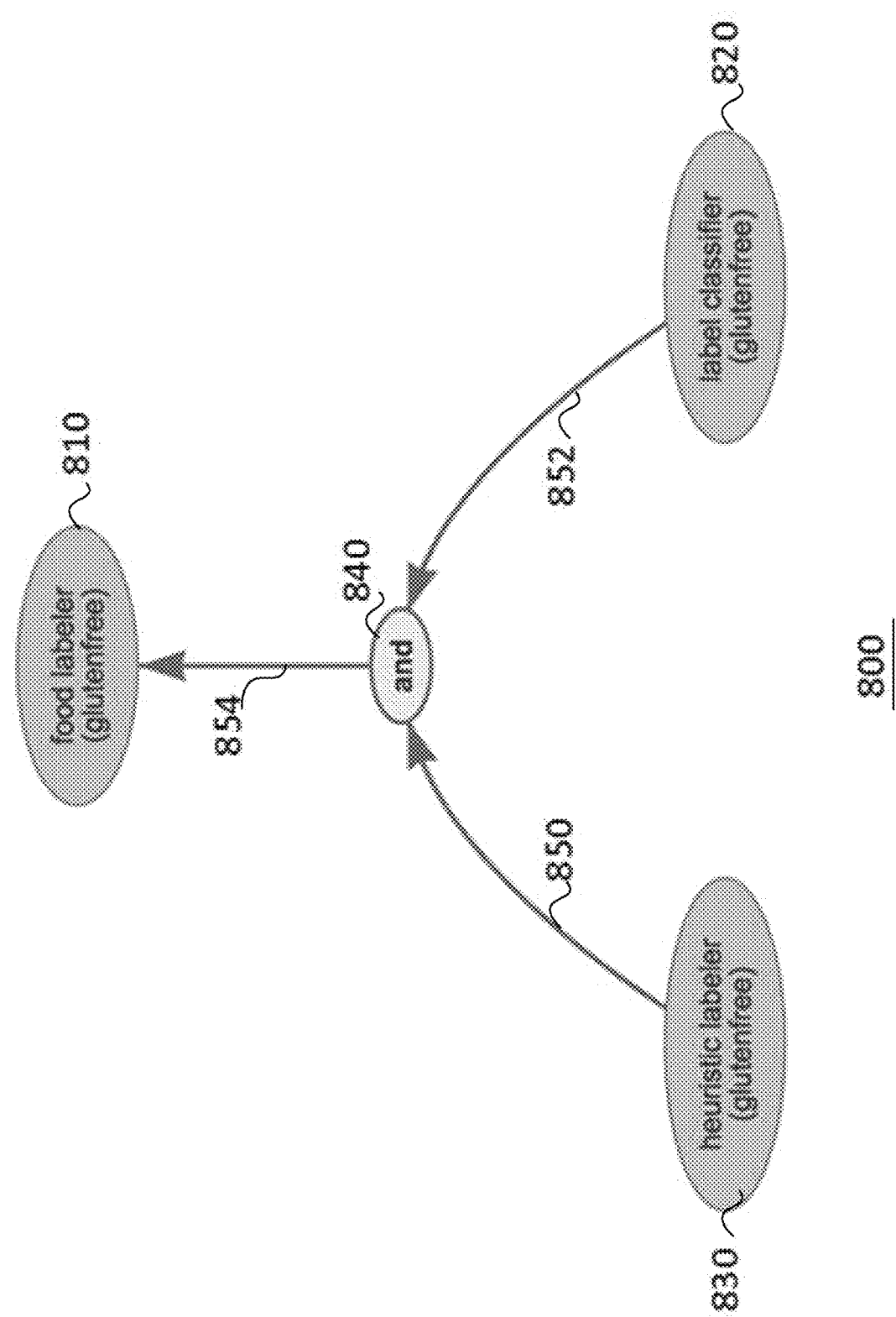
FIG. 8 illustrates an exemplary pipeline of a food labeler in accordance with some embodiments.

FIG. 8 illustrates an exemplary pipeline 800 of the "gluten free" food labeler. The pipeline can be a diagram representing a combination of different analyzers. The "gluten free" food labeler 810 can be designed by combining two analyzer nodes: a label classifier 820 and a heuristic labeler 830 that are both trained to identify the "gluten free" attribute. A relationship between the two analyzer nodes to define the food labeler 810 can be described by a logic node. The logic node can be an AND node or an OR node. The AND node can combine results of two analyzers in a strict approach. As illustrated in FIG. 8, if the "gluten free" food labeler is defined by the AND node 840, the food item may then be labeled as "gluten free" only when both analyzer nodes believe that the food item is "gluten free." On the other hand, the OR node, in use, can combine results of two analyzers in a less-strict approach. For example (not shown in FIG. 8), if a "gluten free" food labeler is defined by the OR node, the food item may then be labeled as "gluten free" when at least one of the two analyzers believes it is "gluten free." The pipeline also includes arrows 850, 852, 854 that connect the relationship among the nodes.

Figure 9:
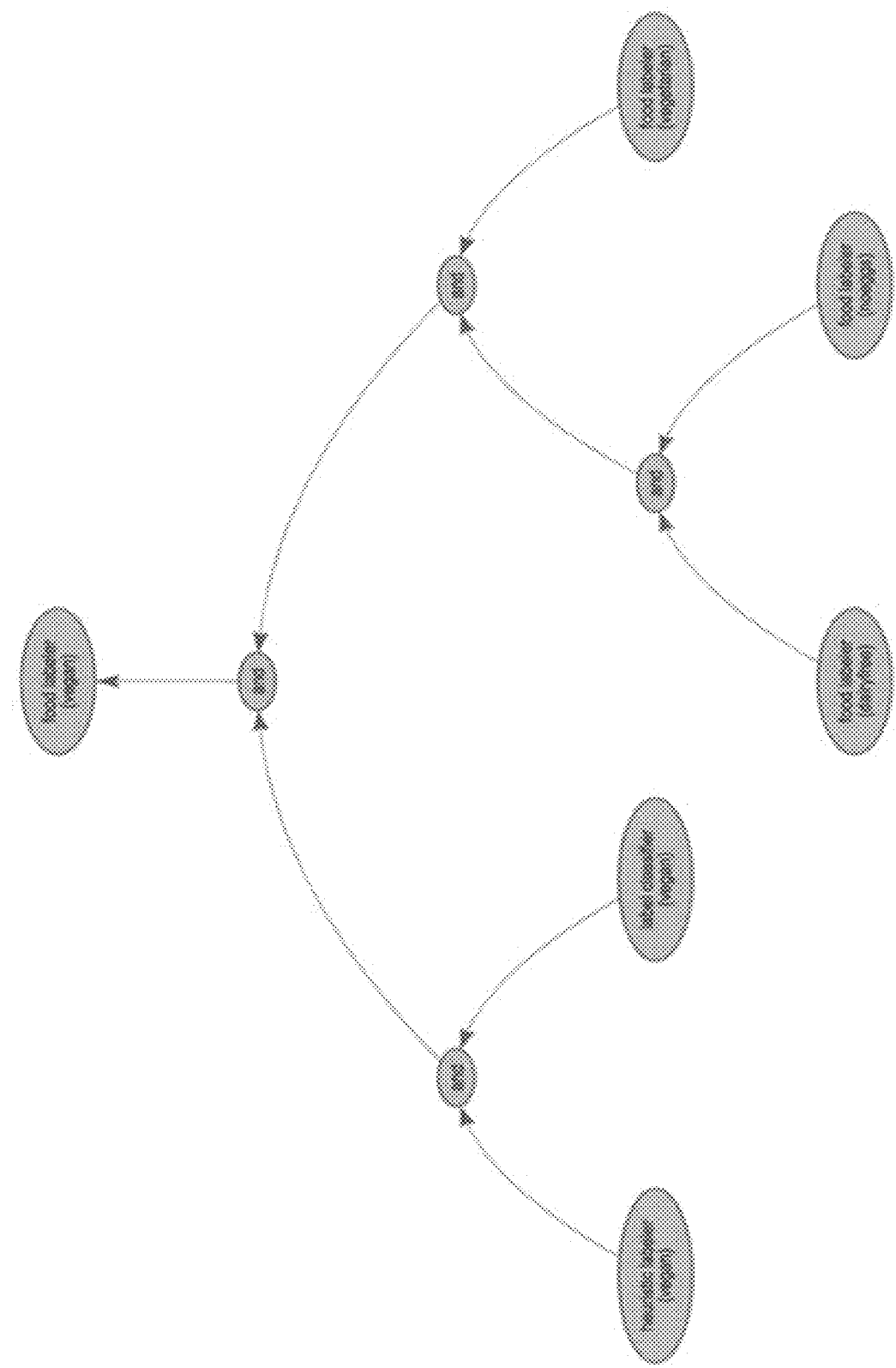
FIG. 9 illustrates a second exemplary pipeline of a food labeler in accordance with some embodiments.

A problem solver can be a combination of multiple problem solvers to integrate the logics of the multiple problem solvers to fine a food attribute. The resulting problem solver can also be denoted as an "attribute" food labeler. FIG. 9 illustrates an exemplary pipeline of a "vegan" food labeler. The "vegan" food labeler can be defined by a combination of multiple nodes, including a label classifier for the "vegan" attribute, a heuristic classifier for the "vegan" attribute, and additional pre-defined food labelers for additional food attributes. A relationship between the "vegan" label classifier and the "vegan" heuristic classifier is defined by an AND logic node. Each of the additional pre-defined food labelers can be a combination of a label classifier and a heuristic classifier for one of the additional food attributes. The additional food attributes can be "dairy free," "no eggs," and "vegetarian," and their relationships are defined by AND logic nodes. The resulting "vegan" food labeler can label a food item as "vegan" only when the following four requirements are true: (1) the "vegan" label classifier and the "vegan" heuristic classifier both believe that the food item is "vegan"; (2) the "dairy free" food labeler believes that the food item is "dairy free"; (3) the "no eggs" food labeler believes that the food item is "no eggs"; and (4) the "vegetarian" food labeler believes that the food item is "vegetarian." The "vegan" food labeler in FIG. 9 will not label the food "vegan" if any of the four requirements are not true.

Every version of a problem solver (or a food labeler) can be tested using a training set, and analyzed using statistics. Statistics from a problem solver can be different from the analyzers' statistics because a problem solver is a combination of the results of its encompassing analyzers. Along with the precision, recall, and F1 scores, a utilization value can also be reported. The utilization value can be a fraction of the training set items that can pass a confidence threshold defined in the problem solver's pipeline. A problem solver with a pre-defined confidence threshold can have high precision and recall values, but a low utilization value. The low utilization value can signify that a high portion of the problem solver's results are not accurate, and that the problem solver may not be useful as a food labeler.

Figure 10:
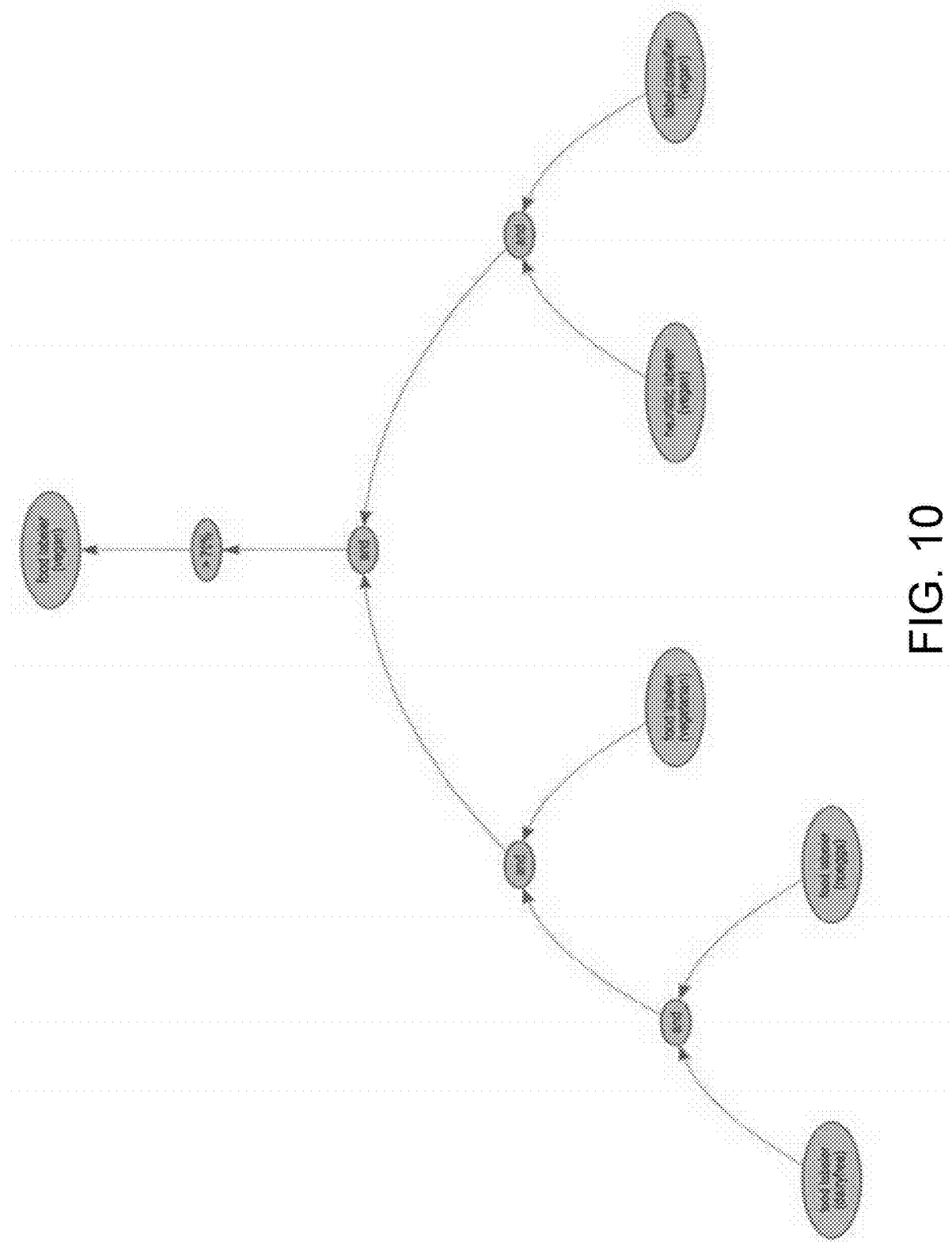
FIG. 10 illustrates a third exemplary pipeline of a food labeler in accordance with some embodiments.

In an example, a confidence threshold node of 70% can be added to the pipeline of the "vegan" food labeler illustrated in FIG. 9 to generate a new "vegan" food labeler with a pipeline illustrated in FIG. 10. The new "vegan" food labeler can be tested using a training set, and statistics including a utilization value can be reported. The utilization value of the new "vegan" food labeler can represent a fraction of the training set items that can pass the 70% confidence threshold defined in the problem solver pipeline of the new "vegan" food labeler. A table of multiple problem solvers and their respective statistical analyses are illustrated in FIG. 11.

The food analysis system 210 can use the labeling machine to analyze and map multiple types of data related to foods into the food ontology. The food analysis system 210 can automatically obtain data (images or texts) related to the foods (e.g. nutrition facts labels, manufacturer's product information, restaurant menu, recipes, etc.) from one or more sources (e.g., the Internet 120, grocery store websites, restaurant websites, recipe blogs, user input, etc.). The food analysis system 210 can leverage deep learning, OCR, and/or NLP capabilities to convert images of at least one consumer packaged food, at least one restaurant menu item, or at least one food recipe into structured data according to a preferred format of the system. The food analysis system 210 can also reorganize the obtained text data into structured data according to the preferred format of the system. With the newly structured data, the food analysis system 210 can, in real time, analyze, and classify features of, and map at least one consumer packaged food, at least one restaurant menu item, or at least one food recipe into the food ontology.

During analysis and classification of the foods, the food analysis system 210 can automatically parse and classify types and amounts of ingredients specified in the obtained data. During the analysis and classification of the foods, the food analysis system 210 can automatically estimate types and amounts of unknown ingredients based on the known ingredients specified in the obtained data or other similar foods in the food ontology. The food analysis system 210 can use at least a probabilistic model to estimate ingredients that must or may appear in the foods (e.g. a restaurant dish). The food analysis system also can calculate a probability (or confidence level) of the foods having the estimated ingredients, as well as the expected ranged of amounts of each estimated ingredient.

Food classification can comprise matching the text for a raw ingredient to an equivalent elementary food item in the food ontology. The food classification can be implemented for example in scikit-learn via the following pipeline. First, word singularization can be performed, by processing the raw text using an inflect library to transform all nouns to their singular form. The inflect library can be used to correctly generate plurals, singular nouns, ordinals, indefinite articles, and convert numbers to words. Next, a count vectorizer can be used to extract the features as word vectors. Next, the k-best features are selected, according to the chi-squared test. Lastly, classification can be performed with multinomial logistic regression. The above pipeline can be executed in a grid search with cross validation to find the best k value.

Figure 54:
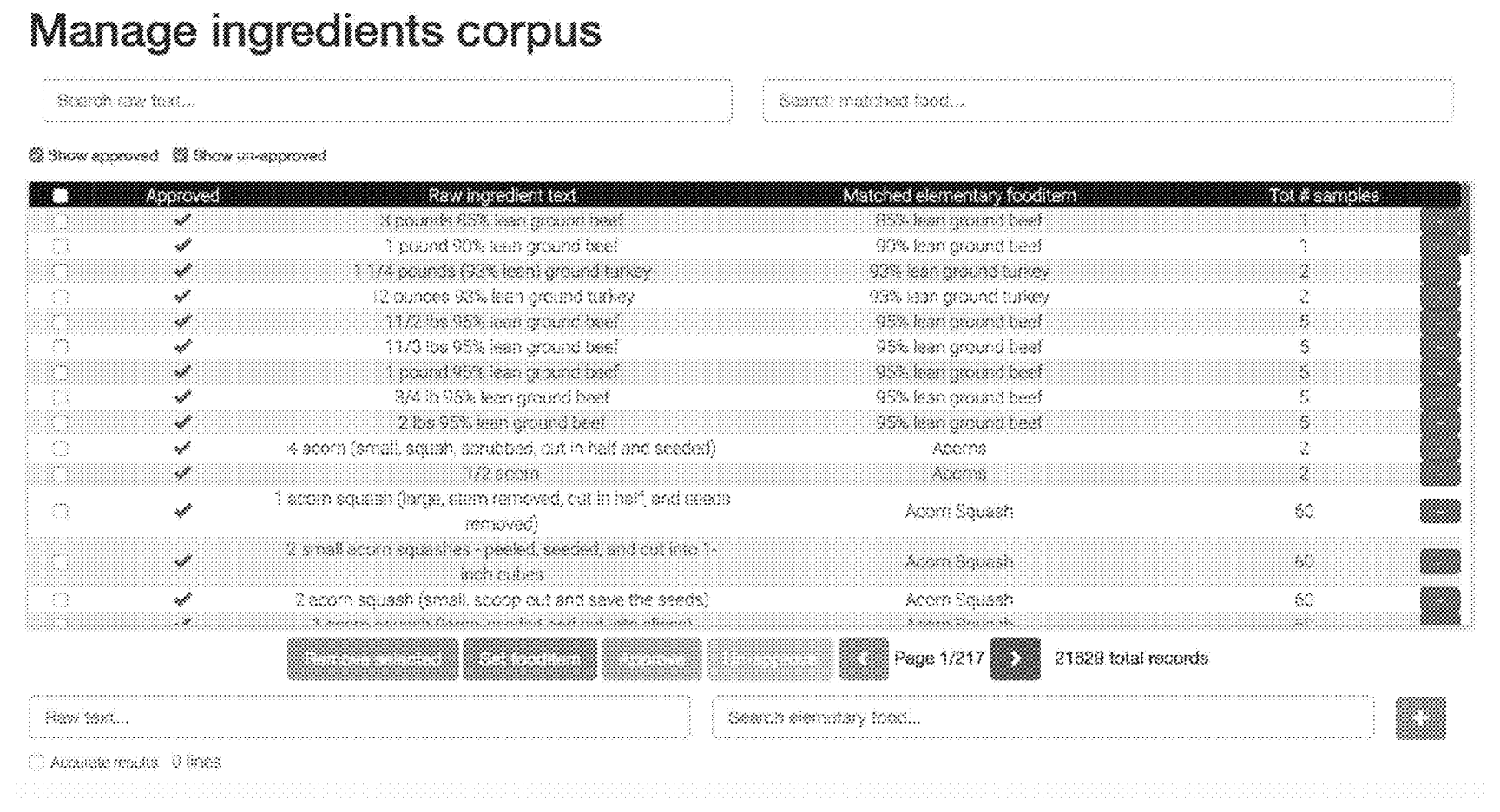

FIG. 54 shows a graphical user interface (GUI) for managing the training set for food classification. The GUI enables the following capabilities for the training set management. For example, training samples (a mapping of text to an elementary food) can be added. While adding samples, it is possible to search recipe ingredients for sample text. Conversely, training samples can be removed. The interface also allows existing training samples to be viewed, and their mapped food items to be changed. Samples can be approved. Additionally, approval of some samples can be removed if those samples were created automatically and are not very accurate. The interface can also allow the data to be filtered by text/food item/approval state. The interface can allow relevant information to be accessed easily/conveniently by users.

Figure 55:
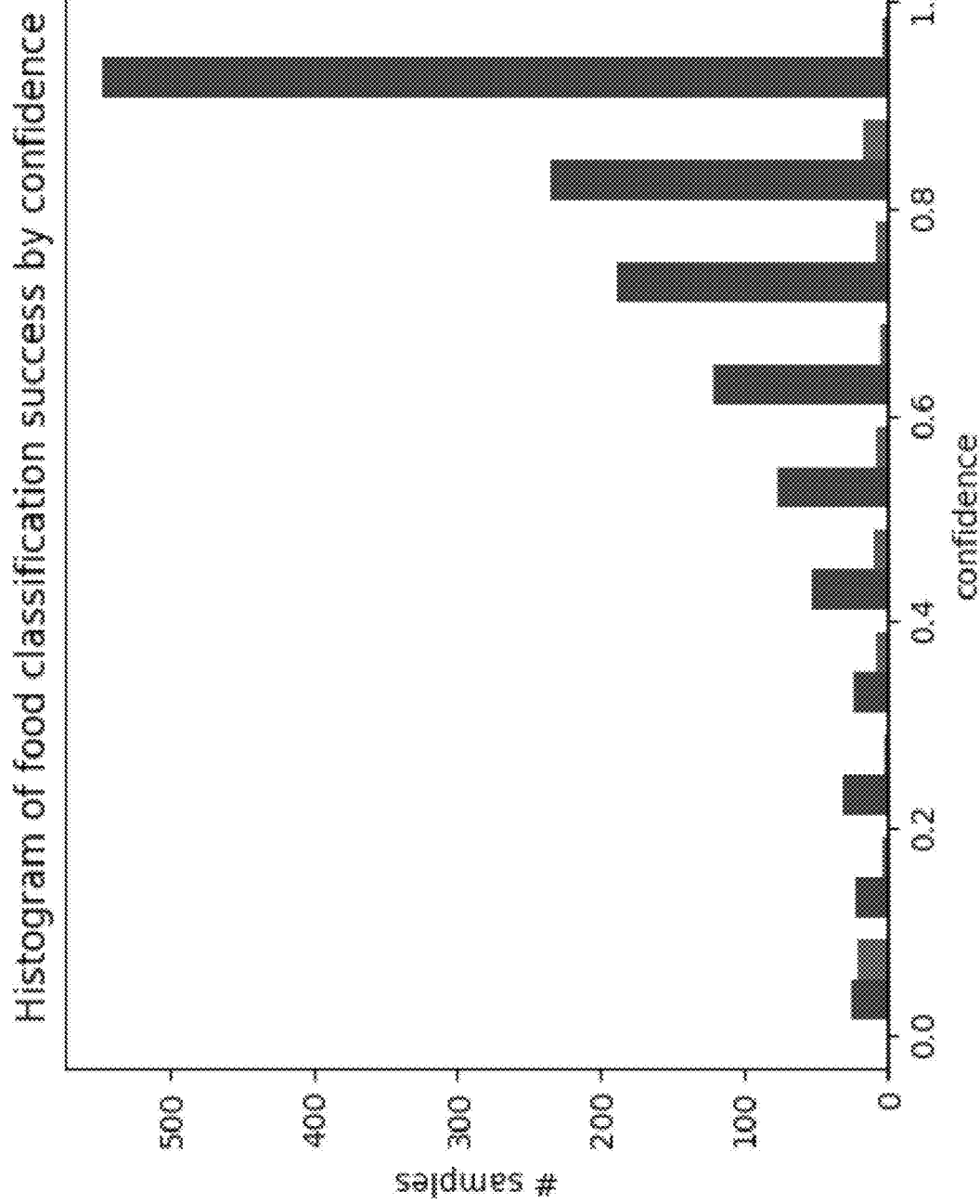
FIG. 55 shows a histogram of food classification success by confidence in accordance with some embodiments.

The food classification can include a confidence score which can be used to filter or add human verification input for results. FIG. 55 shows a histogram of food classification success by confidence in accordance with some embodiments. As an example, if a confidence threshold of 0.7 were selected on the sample dataset, there may be 971 correct ingredient matches and 29 incorrect ingredient matches above the threshold, and 353 correct ingredient matches and 55 incorrect ingredient matches below the threshold.

As previously described, different food categories can present ingredients information in different ways, and therefore may need to be analyzed differently. In some embodiments, the food categories can be classified into a number of different models (e.g. 4 different models), each of which builds upon the results of the previous model.

A first model may include a food classification model. The first model may utilize the food classification techniques described elsewhere herein. Relevant food categories for the first model may include packaged foods, certain restaurant menus, and in some instances recipes (although recipes may not be commonly input to the first model). The input to the first model may comprise free text describing a food item, e.g. "cane sugar" or "brown rice," and the output of the first model may comprise a food identity (food ID).

A second model may include a food parsing model. Relevant food categories for the second model may include recipes, and in some instances packaged foods (although packaged foods may not be commonly input to the second model), and in some instances restaurant dishes (although restaurant dishes may be rarely input to the second model). The input to the second model may comprise free text describing a food item with its amount, e.g. "1 cup of couscous," and the output of the second model may comprise a food identity (food ID), amounts of ingredients, and measurement ID. Food parsing may comprise transforming a single raw-text ingredient (e.g., "1 cup brown sugar") into an equivalent food item, serving and/or amount according to the food ontology. Food parsing may be performed for example using the following process. First, the elementary food item can be determined using the food classification from the first model. A list of all possible measurements can be extracted from the text and standardized using a standards unit library, whereby each unit is associated with a respective amount. The above list can be further expanded with conversions between different units. For example, if 'tablespoon' was found in the text, but 'teaspoon' was not, then a 'teaspoon' measurement can be added that corresponds to 3 times the amount of 'tablespoon'. All measurement units of the matched food-item can be retrieved from the database (e.g. 'cup', 'tablespoon', etc.). The two lists are then matched to choose the most probable measurement with its amount. The food parsing functionality can be implemented as part of the food analysis system described herein.

A third model may include a free text analysis model. Relevant food categories for the third model may include restaurant dishes, and in some instances packaged foods (although packaged foods may be rarely input to the third model). The input to the third model may comprise a string of food description, for example: "House made deep fried chips tossed in a creamy chipotle salsa roja. Topped with cashew crema and cilantro. With chorizo and two hard-boiled eggs." The output of the third model may comprise a list comprising a food ID, amounts of ingredients, and measurement ID. In certain cases, the amounts or measurements are not provided as part of the free text. In those cases the model can be configured to extract the ingredients ID, and mark the measurement ID and amounts as unknown.

Free text analysis may comprise using any of the NLP algorithms described herein. Free text analysis may comprise performing entity extraction on free text to extract food information provided in the text. The entities may comprise objects representing ingredients. Additionally, the entities may also comprise objects that need not necessarily represent ingredients, but that nonetheless provide insights about the labels or nutrients of the food. For example, in the case of the description of a food item named "Totopos":

{{House made [deep fried]processing method [chips] food tossed in a creamy [chipotle salsa roja]food. Topped with [cashew crema]food and [cilantro]food. Served with [chorizo]food and [two]amount [hard-boiled eggs]food.}}

The entities may comprise for example: food items, amounts, measurement sizes, processing methods, dietary needs, restaurant names, among others. The free text analysis can associate each entity to one or more other relevant entities, for example the "two" at the end of the string is with reference to the "eggs." Once an entity has been detected as a "food entity", the entity can be run through the ingredients classifier to determine the exact food ID. Entity extraction can be solved using statistical methods such as conditional random fields (CRFs). In some cases, if the corpus of entities is sufficiently large, entity extraction can also be solved using Deep Learning techniques as well. In cases where a string contains food items separated by commas, entity extraction can be simplified, since the string can be split based on the commas separation before running the food parsing.

A fourth model may include a menu item analysis model. Relevant food categories for the fourth model may include restaurant dishes. The input to the fourth model may comprise name and description of a dish. The output of the fourth model may comprise a list comprising a food ID, amounts of ingredients, measurement ID, and probability of each ingredient being present in the dish.

Under menu item analysis, a menu item is different than pure textual description, as the menu item contains both the name of the dish and the description. The description need not always contain all of the ingredients, and therefore the name of the menu item can be used to estimate potential ingredients using any of the statistical methods described herein.

For example, consider the following two items from a menu:

(1) Name: Pad Thai with chicken. Description: Stir-fried steamed rice noodles with chicken, eggs, mushroom, onions, cilantro and peanuts.

(2) Name: Fried rice. Description: choice of beef, pork, or chicken.

The menu item analysis pipeline may include multiple steps. Under statistical name analysis, a complete ontology of foods (which can be represented by a tree via a taxonomy) is assumed to be present, and that a branch in the taxonomy can be found based on a food name.

The union of all ingredients in the elements in the branch can be taken, and the probability of each ingredient appearing in the food item can be calculated. For example: "Pad thai with chicken" can be either its own branch or a part of the general branch "Pad thai". All pad thais have rice noodles, 80% of them may have fish sauce, 23% of them may have mushrooms, etc. A probability for the occurrence of each food (calculated over the branch) can be given by: P(ingredient in food)=(number of food items containing ingredient)/(number of food items).

If a certain element in the branch has too few examples, the probability can be recalculated by going higher in the taxonomy.

The probability for the occurrence of each food can allow more information to be extracted from the menus. In some embodiments, the data can be further refined by crowdsourcing from users and/or restaurants about the occurrences of specific ingredients that the users are unsure about.

Free text analysis can be performed on the description, after which the probability of certain ingredients that were found in the previous step can be increased to 100% (or close to 100%). For example, in example (1) above, mushrooms may appear as an ingredient, and thus the confidence level for having mushrooms in the food item can be increased (e.g. from 23% to 100%). By estimating the ingredients amount, a list of probabilities can be generated for the occurrence of each ingredient. Next, a probabilistic model can be applied for the amount of each ingredient. Consider a threshold θ above which an ingredient is assumed to be a part of the dish. Initially this threshold can be assumed to be a value (for example 50%). In some embodiments, the threshold can be estimated by machine learning techniques to maximize the precision of the results.

In order to estimate the amounts, the branch in which the food item appears is again considered, and a probabilistic model is fitted for the amount of each ingredient. The probabilistic model is applied on all samples in the branch that contain the ingredient. Since the amounts are always positive, the probabilistic model can be a log-normal distribution which can provide both the expected amount as well as the standard deviation.

The food analysis system 210 can estimate unknown nutrients from at least one consumer packaged food, at least one restaurant menu item, or at least one food recipe. Once the types and amounts of known and unknown ingredients are abstracted or estimated using the OCR, NLP, labeling machine, or other algorithms of the food analysis system 210, such information can used to estimate nutrients that are not revealed by at least one consumer packaged food, at least one restaurant menu item, or at least one food recipe. The food analysis system 210 can estimate ranges of the nutrients that are not revealed. In some examples, the ranges of the nutrients can be in terms of their amounts (e.g., grams, milligrams, etc.) or their percent (%) daily value based on a recommended total daily requirement for each of the nutrients. In some examples, the nutrients that are not revealed can be macronutrients, including a breakdown of total fat (e.g. saturated fat, trans fat) or a breakdown of total carbohydrate (e.g., dietary fiber, total sugars, added sugars). In some examples, the nutrients that are not revealed can be micronutrients, including vitamins, macrominerals, and microminerals. The vitamins can include biotin, folic acid, niacin, pantothenic acid, riboflavin, thiamin, vitamin A, vitamin B6, vitamin B12, vitamin C, vitamin D, vitamin E, and vitamin K. The macrominerals can include calcium, phosphorus, magnesium, sodium, potassium, chloride, and sulfur. The microminerals can include iron, manganese, copper, iodine, zinc, cobalt, fluoride, and selenium. In some examples, the nutrients that are not revealed can be phytonutrients. The phytonutrients can be anthocyanins, ellagitannins, flavonoids, allylic sulfides, and isoflavones.

The food analysis system 210 can estimate unknown nutrients from at least one consumer packaged food. The food analysis system 210 can parse and classify data obtained from a nutrition facts label and a list of ingredients of at least one consumer packaged food. The nutrition facts label may show some but not all nutrients found in at least one consumer packages food. Additionally, the nutrition facts label may not disclose amounts (e.g., milligrams) of such nutrients. Thus, the food analysis system 210 can extrapolate known or unknown ingredients and their amounts from the data obtained using the labeling machine and other algorithms described in the disclosure. Using a nutritional breakdown of each of the known or unknown ingredient from the database(s) 240 of the platform 200, the food analysis system 210 can calculate types and amounts of nutrients that may be found in at least one consumer packaged food. By using the revealed items in the nutrition facts label (e.g., calories per serving, total fat, total carbohydrate, protein), the food analysis system 210 can compare its calculated values for the respective revealed items to validate its estimation.

The food analysis system 210 can estimate unknown nutrients from at least one food recipe. The food analysis system 210 can parse and classify a list of ingredients and their respective amounts from at least one food recipe using the labeling machine and other algorithms described in the disclosure. The food analysis system 210 can aggregate types and amounts of nutrients found in the ingredients and provide an estimate on a resulting nutritional value of the recipe. The nutrients can include at least one macronutrient, at least one micronutrient, or both. Such estimation can yield a high reliability as at least one macronutrient and at least one micronutrient are minimally affected by cooking methods. A pipeline to estimate unknown nutrients from at least one food recipe can include: (1) receiving a free text of a food recipe including ingredients, (2) parsing and classifying the ingredients and their respective amounts, and (3)

superposing estimated nutritional values of the ingredients using a nutritional breakdown of each of the ingredients from the database(s). Alternatively or in addition to, the food analysis system 210 can include at least one machine learning algorithm based on at least NLP, statistical analysis, and multiple chemistry databases to estimate one or more effects of food processing (e.g., frying, boiling, microwave, cooking time, etc.) on a food's nutrients and their nutritional values. In some examples, such machine learning algorithm can be referred to as a food processing algorithm. The food processing algorithm can include specific processing parameters (e.g., an absorption coefficient, evaporation coefficient, diffusion coefficient etc.) for one or more nutrients. The diffusion coefficient of each of one or more nutrients can take into consideration a size of a respective ingredient during cooking. An additional pipeline to estimate unknown nutrients from at least one food recipe can include: (1) receiving a free text of a food recipe including ingredients, cooking methods, and cooking time, (2) parsing and classifying the ingredients and their respective amounts by using at least the machine labeler and the food processing algorithm, and (3) superposing estimated nutritional values of the ingredients. During a cooking process, at least one ingredient can be used in two or more steps during cooking. Nutritional values of at least one ingredient can be calculated multiple times, respectively to the two or more steps during cooking.

The food analysis system 210 can estimate unknown nutrients from at least one restaurant dish. The food analysis system 210 can map at least one restaurant dish into the food ontology. Subsequently, the food analysis system 210 can use its algorithms described in the disclosure to detect which ingredients must or may appear in at least one restaurant dish. For each ingredient, the food analysis system 210 can calculate types and expected amounts of nutrients that may be found.

The food analysis system 210 can utilize automatic spider builders (also known as crawlers) to crawl the Internet to obtain all data related to foods, abstract and classify food-related information, and store the information in the database(s) 240. The Internet 120 can include websites of restaurants with their menus, food manufacturers, and recipe blogs. Each website can have a different structure, and can be disorganized and outdated. The automatic spider builders of the food analysis system 210 can detect the layout of each website by detecting an XPath corresponding to each food name, description, price, ingredients, etc. The XPath (or XML, path language) can be a query language for selecting data points from an XML (extensible markup language) data structure, such that of a restaurant's website. The automatic spider builders can scale up a data collection process of the food analysis system 210 by orders of magnitude. The automatic spider builders can allow a content management team without technical skills to easily add thousands of new foods into the food analysis system 210.

The food analysis system can analyze a picture of a food dish that does not have any textual information about the food. In an example, a user can take a picture of a food item at a restaurant using a mobile device. The food analysis system 210 that is connected to the mobile device can automatically receive the picture of the food item. The food analysis system 210 can use at least its deep learning and OCR capabilities to abstract and classify ingredients that may appear in the food item. The food analysis system 210 can compare the food item to similar dishes that are already in the food ontology to abstract and classify the ingredients that may appear in the food item. If proven successful by internal testing models of the food analysis system 210, the food item can be mapped in the food ontology. The food analysis system 210 can compare a first characteristic absorption profile in at least a first portion of the electromagnetic spectrum of the picture of the food item of the user to a second characteristic absorption profile in at least a second portion of the electromagnetic spectrum of at least one of the similar dishes that are already in the food ontology.

An example of abstracting and classifying information from a consumer food package will be described in detail below with reference to FIGS. 12A-12C.

Figure 12A:
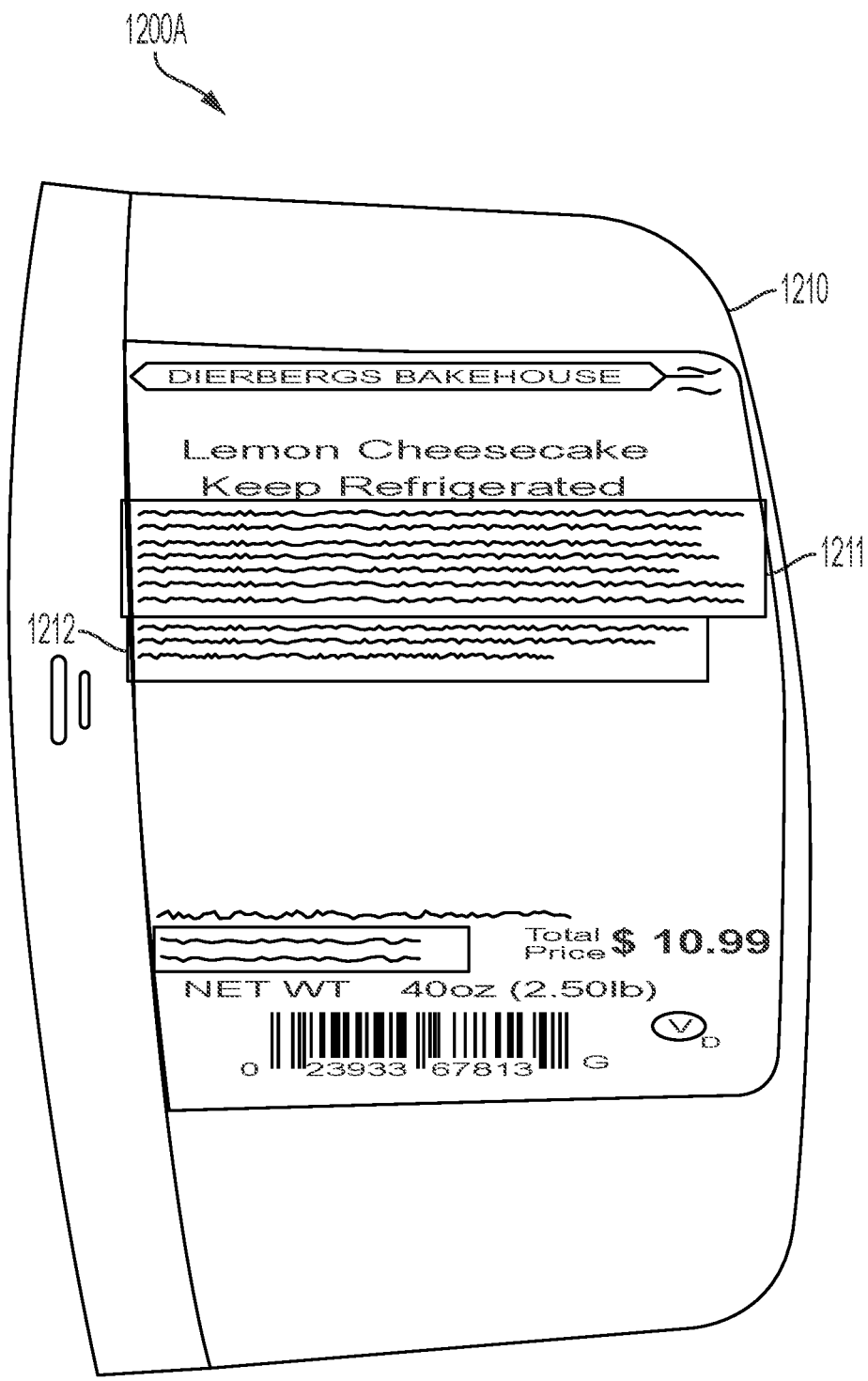

FIG. 12A illustrates a picture 1200 of Lemon Cheesecake 1210 from Dierbergs Bakehouse. Once imported into the platform 200, the food labeling system 210 in the platform 200 uses machine learning and OCR to automatically identify and draw a bounding box around one or more information sections 1211, 1212 of the picture 1200. A first information section 1211 contains ingredients in the Lemon Cheesecake, including milk, creak, sugar, barley flour, etc. A second information section 1212 contains warning disclaimers from the manufacturer, including other ingredients that have been utilized in the manufacturer's facility. The food labeling system 210 then uses NLP algorithms in real time to abstract every word from the information sections 1211, 1212. Subsequently, the food labeling system 210 uses the labeling machine to label and classify the information.

FIG. 12B illustrates a table 1220 of abstracted and classified information from the Lemon Cheesecake 1210. In the table 1220, the Lemon Cheesecake 1210 is identified by its product code 1230. The table 1220 presents a list of nutrients (e.g., calories, total fat, sodium, etc.) and their respective amount by weight (e.g., 130 g, 6 g, 170 mg, etc.) 1240-1250. The table 1220 presents a list of ingredients 1260, 1261. The table 1220 presents additional information from the manufacturer 1270-1275, including what the package contains, what the package may contain, what other products have been made by the same equipment from the same facility, and ingredients that have been utilized in the same facility. Importantly, the table 1220 presents one or more abstraction labels 1280, 1281 (e.g., contains added sugar, all natural ingredients, free from artificial colors, free from artificial flavors, etc.) generated by the labeling machine of the food analysis system 210 according to the abstracted and structured data in the table 1220. The table 1220 also contains a confidence score and an accuracy score for OCR and all food labelers used 1290-1297. The artificial intelligence-generated information can also be formatted in other formats, for example as illustrated in FIG. 12C. The labeling machine can work on a single picture or a batch of an unlimited number of pictures, and complete analysis in about 3 minutes to about 5 minutes total. If a picture has more than one packaged food, the food analysis system 210 can break down the picture into multiple sub-pictures. Each sub-picture can contain one packaged food.

FIG. 13 illustrates an exemplary table of a multitude of consumer packaged foods after abstraction and classification. The multitude of the consumer packaged foods can be organized by a machine generated numbering system or by their respective product codes. Each consumer packaged food can contain multiple pictures (e.g., of different years or from different angles, etc.). The table also keeps track of a number of ingredients, nutrients, allergens detected, as well as a number of food characteristic labels that have been found to be true (positive) and a number of food characteristic labels that have been found to be not applicable (negative) by the labeling machine.

Figure 14:
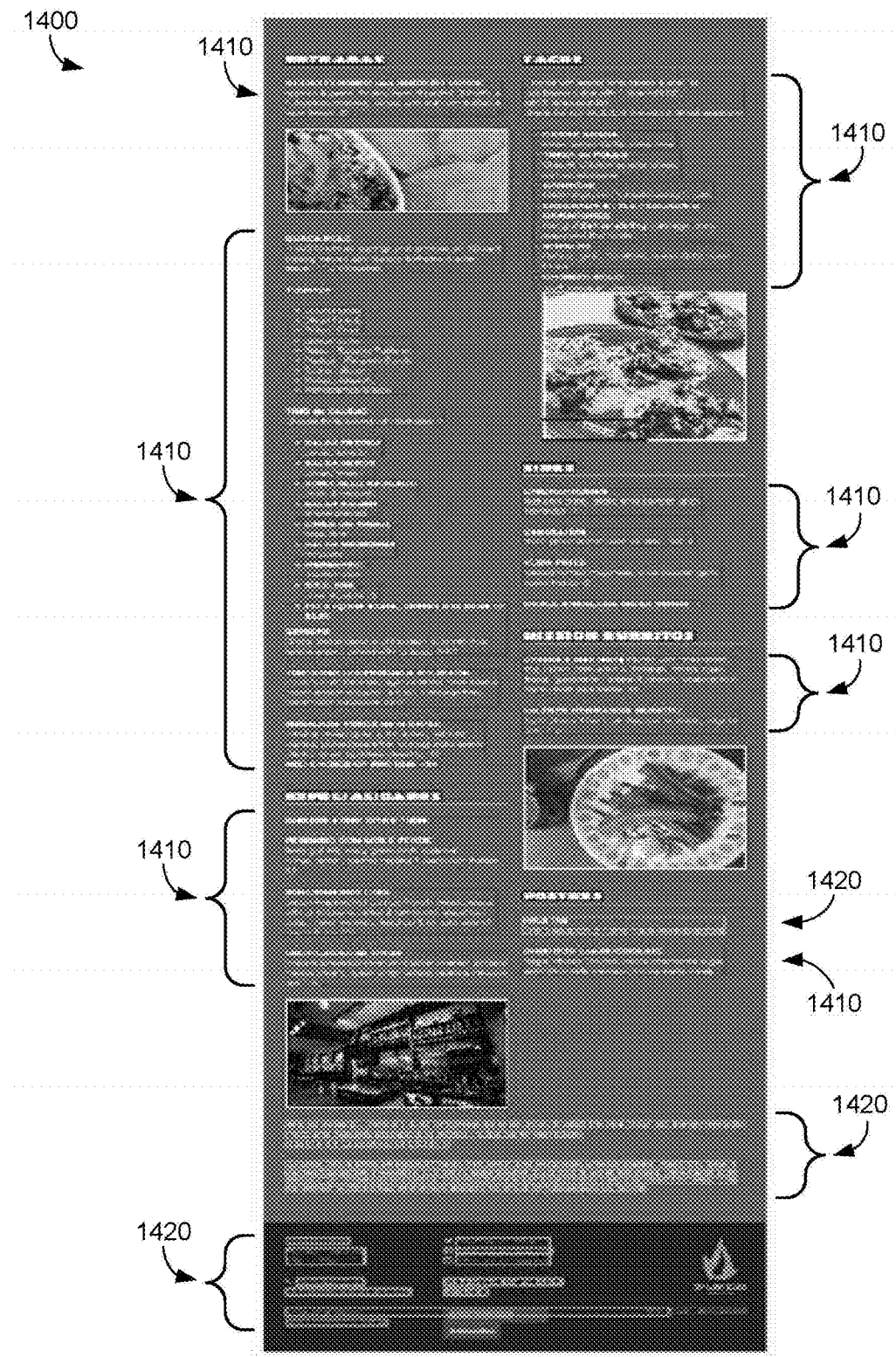
FIG. 14 illustrates an exemplary restaurant menu for food analysis in accordance with some embodiments.
Figure 15:
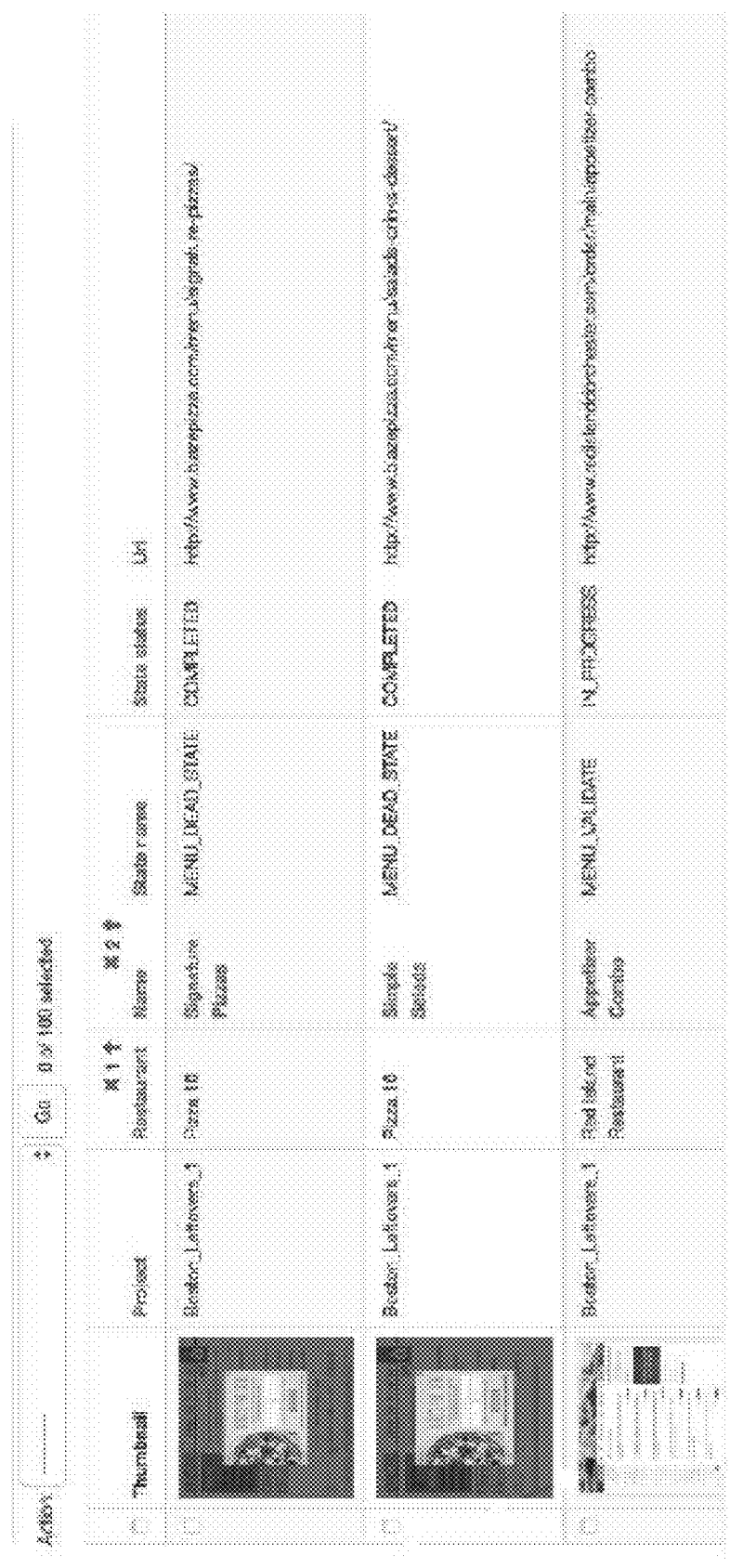

FIG. 14 illustrates an exemplary a restaurant menu obtained and analyzed by the food analysis system 210. The food analysis system 210 can use OCR and other algorithms to detect and draw bounding boxes around food dishes and their respective menu and sub-menu titles. As shown in FIG. 14, by way of example only, the food analysis system 210 can break down the menu 1400 into food dishes and their titles 1410 and other non-food related information 1420. FIG. 15 illustrates an exemplary table of information abstracted from restaurants menus. This is a scalable approach that can capture menus of at least about 350,000 restaurant locations across the U.S. using AI, OCR, and/or other algorithms. Additionally, the AI can continuously monitor the web for new websites or previously-analyzed websites to identify new menus and expand the database.

The food analysis system 210 of the platform 200 can compile all analyzed information into the food ontology. The food ontology can be used as a web of all foods. The food ontology can describe relationships among foods, ingredients, nutrients and other characteristics. The food ontology provided in the present disclosure may describe one or more relationships between two or more categories comprising or foods, ingredients, nutrients, and/or characteristics. The food ontology provided in the present disclosure may describe one or more relationships between two or more components within one of the abovementioned categories.

The food ontology can comprise a graphical representation depicting the information relating to different foods. The food ontology can further comprise displaying the graphical representation of the food ontology on an electronic display. The graphical representation of the food ontology can be two-dimensional. The graphical representation of the food ontology can be multi-dimensional comprising three or more dimensions.

The food ontology can be a graphical database. The graphical database can comprise one or more nodes. The node(s) can be connected to one or more edges. Each edge can represent a relationship between two nodes. Examples of the node(s) and edge(s) that are used in embodiments of the food ontology are abovementioned in the present disclosure.

The graphical database can comprise one or more "taxonomies" of food-related concepts (e.g., food items, ingredients, amounts, dimensions, volumes, processing methods, dietary needs, nutritional values, restaurant names, food dish names, dietary restrictions, geographical origin, etc.). A taxonomy can be a basic building block of the food ontology. A taxonomy can be represented by the node(s) (e.g., one or more food item nodes) and edge(s). A taxonomy can be at least a dimension in the "food space." Thus, one or more combinations of the taxonomies can represent the food ontology in a plurality of dimensions. One or more combinations of the taxonomies can allow analysis and/or visualization of the food space along any of the plurality of dimensions. In some cases, a taxonomy of the food ontology can be represented as a tree graph with the node(s) and edge(s), as abovementioned and described elsewhere in the present disclosure. In some examples, an edge can represent a "IS A" relationship between two nodes (e.g., "chicken" IS A "poultry product"; "cooking" IS A "processing method," etc.). In other examples, an edge can represent a "GOOD SUBSTITUTE FOR" relationship between two nodes.

In some cases, a taxonomy of the food ontology can be ingredients. The ingredients taxonomy can be operatively linked to one or more food databases (e.g., elementary food databases, such as, for example, United States Department of Agriculture (USDA) National Nutrient Database for Standard Reference, USDA Branded Food Products Database, etc.). In the ingredients taxonomy, each node can represent a food. A food can be either a specific food (e.g., Coca Cola, banana, etc.) or an abstract one (e.g., salad, tuna sandwich, mac and cheese, etc.) that can be a combination of one or more specific foods. In some cases, the food can be an abstract category of food that is a genus of the specific food (e.g., beef, nuts, vegetables, fruits, etc.). An edge can represent a relationship between two foods. Several types of relationship between the two foods can be allowed. In an example, two types of relationship between the two foods can be allowed. A first type of relationship between the two foods can be "IS_A," representing a food that may be a variety or a part of another food. Some examples can include (1) "Yellowfin tuna IS_A (variety of) Tuna" and "Tuna IS_A (variety of) Fish," and (2) "Chicken thigh IS_A (part of) Chicken" and "Chicken IS_A (variety of) Poultry." A second type of relationship between the two foods can be "CONTAINS," representing a first food that may contain a second food. The first food can contain the second food either after a type of processing, transformation, or directly. If such containment includes a processing of a single ingredient, the edge can include the processing method information. If such containment includes a processing of two or more ingredients, the node can include the processing method information. Some examples can include: (1) "Almond flour CONTAINS (grounded) Almonds," and (2) "Cooked white rice CONTAINS (White rice, Water)." The food ontology can have additional types of pre-defined edges to describe additional relationships between any pair of two nodes. The food analysis system 210 can generate one or more new edges for the food ontology.

As abovementioned, in some cases, a taxonomy of the food ontology can be one or more processing methods. The processing method(s) can represent various one or more processes that food components undergo during preparation at various stages (e.g., growing, harvesting, transportation, cooking, etc.). Examples of types of cooking that may be employed can include aging, baking, roasting, broiling, sautéing, braising, steaming, poaching, grilling, deep-frying, pan-frying, air-frying, impingement cooking, simmering, boiling, stewing, simmering, sous vide, smoking, cold-smoking, and/or any combination of the aforementioned, etc.

Nodes in the food ontology can be specific food items. The specific food items can include a specific kind of seed, a specific kind of vegetable, a specific kind of tuber, a specific type of edible fungi, a specific type of meat, etc. The specific food items can be referred to as leaf nodes (or leaves) of the graph database of the food ontology. A leaf node may be a node that does not have a child node. For example, Solanum tuberosum (Yukon Gold potato) cannot be broken down into sub-foods and can be registered as a leaf node in the food ontology. Thus, each of the leaf nodes can be a meta object existing above each specific food item. Additionally or in addition to, the food analysis system 210 can (i) receive data of specific food items from other nutrition services (e.g., USDA), (ii) analyze and map the data in the food ontology, and (iii) use at least one machine learning algorithm to learn how to generalize a group of specific food items and create a new leaf node. For example, "long brown rice" and "short brown rice" can be generalized into "brown rice," and the food ontology can have "long brown rice," "short brown rice," and "brown rice" leaf nodes. If the food analysis system 210 determines that an incoming data from a third party database is already generalized (e.g., "brown rice"), the data may be plotted as a leaf node in the food ontology.

Figure 16:
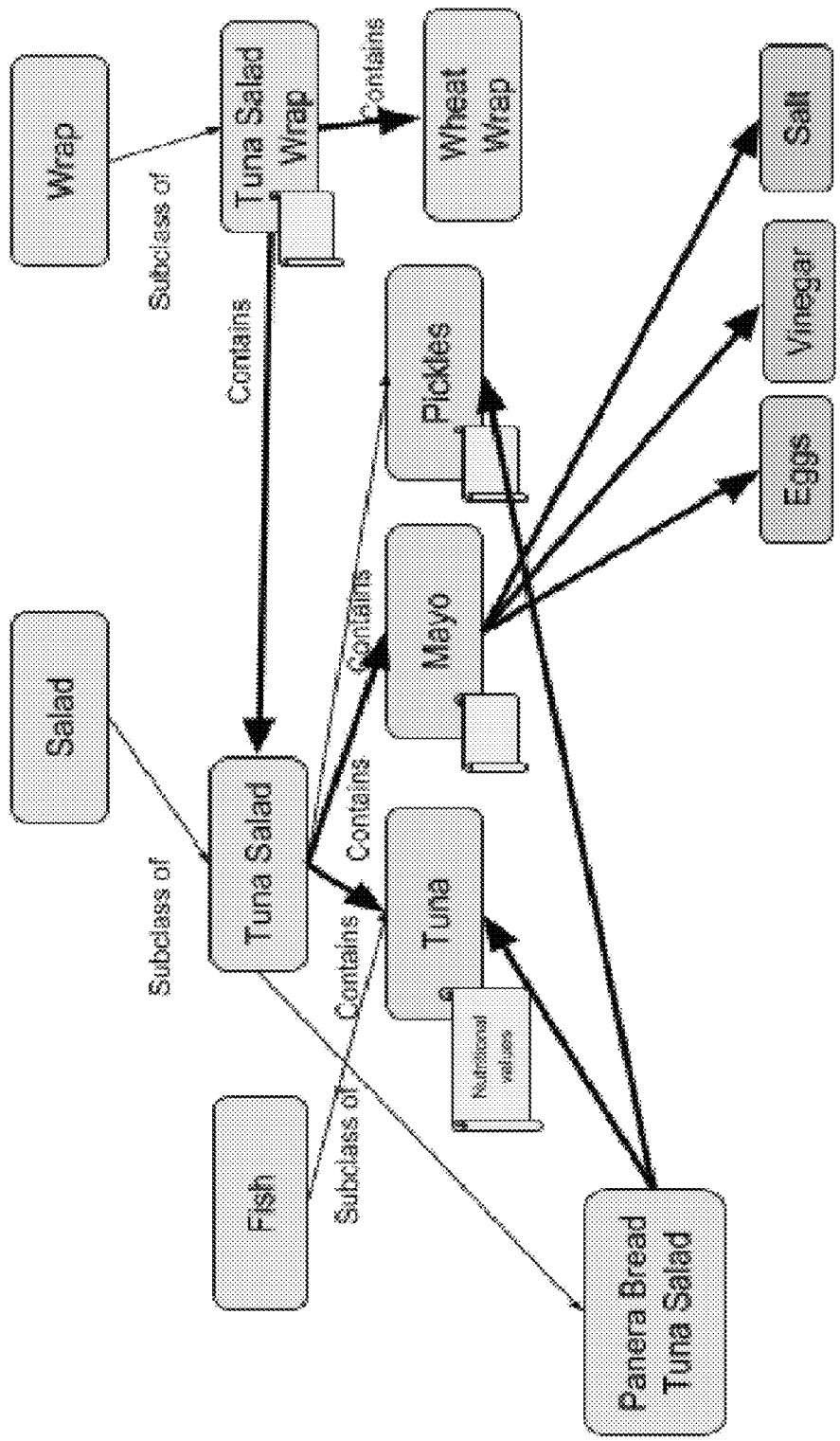
FIG. 16 illustrates an exemplary two-dimensional graphical representation of food ontology in accordance with some embodiments.
Figure 17A:
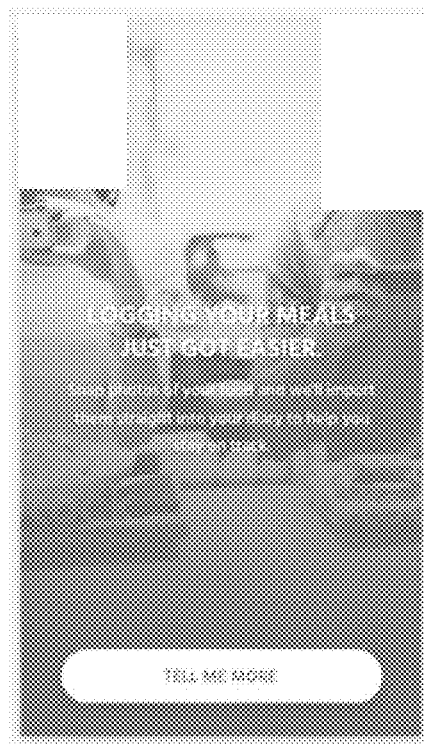
FIGS. 17A-17D illustrate exemplary windows of a GUI-based software interface for food image logging, in accordance with some embodiments.
Figure 17B:
Figure 17C:
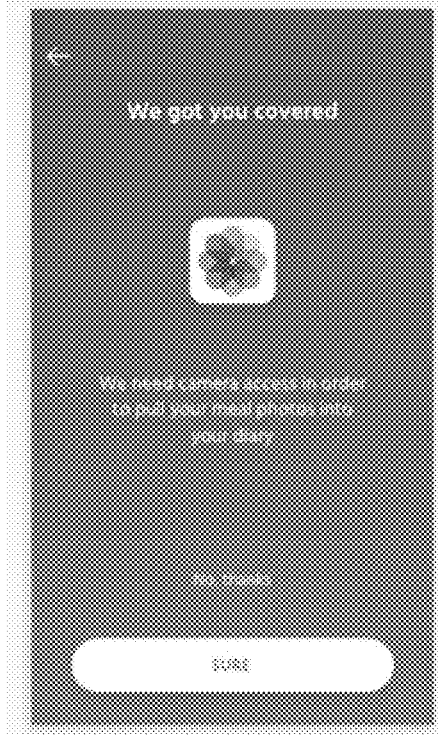
Figure 17D:
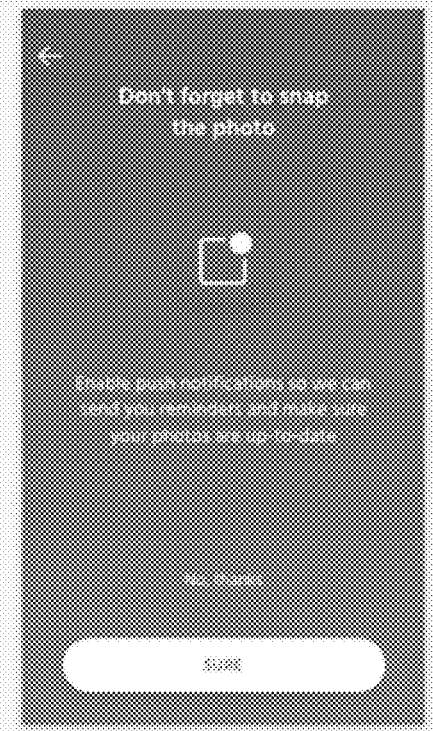

Graphical representation of the food ontology can be multi-dimensional, including two, three, or more dimensions. FIG. 16 illustrates an exemplary two-dimensional graphical representation of food ontology 1600 related to Panera Bread Tuna Salad. The food ontology 1600 contains multiple types of nodes. The food ontology contains multiple types of edges. A thick edge represents a relationship between two nodes that is directly abstracted from the raw input data. A thin edge represents a relationship between two nodes that is indirectly estimated by the food analysis system 210. A first type of node can be a consumer packaged food (e.g. Panera Bread Tuna Salad), an abstract food type (e.g., Tuna Salad, Salad, Wheat Wrap, Tuna Salad Wrap, or Wrap), or ingredients (e.g., Fish, Tuna, Pickles, Mayo, Eggs, Vinegar, or Salt). A node can be a subclass of a higher-class node, and such relationship can be represented by an IS_A edge. Some examples include "Panera Bread Tuna Salad IS_A (subclass of) Tuna salad" and "Tuna salad IS_A (subclass of) Salad," and "Tuna salad wrap IS_A (subclass of) Wrap." If the subclass as a whole is included in the higher-class node, such relationship can be represented by a CONTAINS edge. In an example, "Tuna Salad Wrap CONTAINS (Tuna Salad, Wheat Wrap)." Alternatively, a node can be an ingredient that is contained in a higher-ingredient node, and such relationship can be presented by the CONTAINS edge. As illustrated in FIG. 16, ingredients for Tuna Salad include Tuna, Mayo, Pickles, Eggs, Vinegar, and Salt. Since Tuna and Mayo are known ingredients, the food ontology describes Tuna and Mayo using a thick CONTAINS edge, as in "Tuna Salad CONTAINS (Tuna, Mayo)." Also, since Eggs, Vinegar, and Salt are known ingredients of Mayo, the food ontology automatically classifies the first three items using a thick CONTAINS edge, as in "Mayo CONTAINS (Eggs, Vinegar, Salt)." On the other hand, since Pickles is an unknown ingredient estimated by the food analysis system 210, the food ontology describe Pickles using a thin CONTAINS edge, as in "Tuna Salad CONTAINS (Pickles)." A node can have a scroll, indicating that the database(s) 240 of the platform 200 has specific nutritional values linked to the node item.

Figure 56:
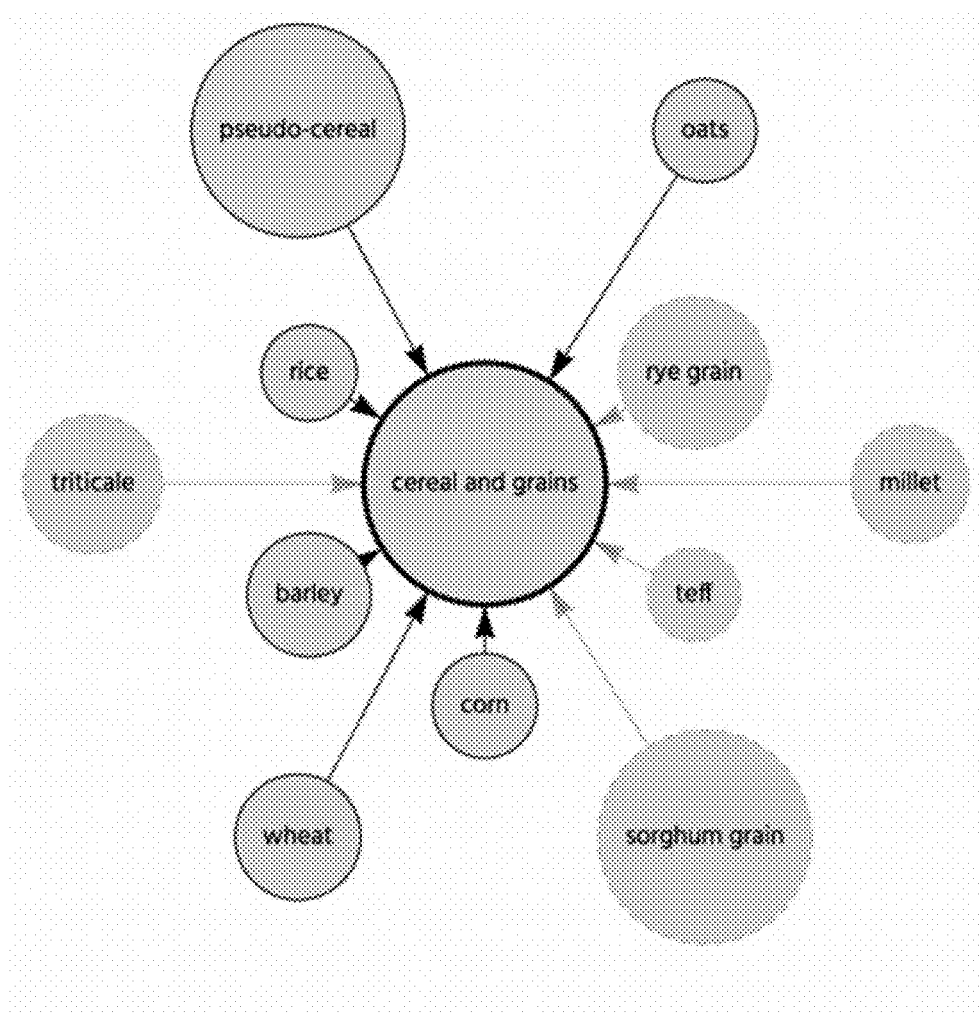
FIG. 56 illustrates an exemplary graphical representation of food ontology related to an ingredients taxonomy.

FIG. 56 illustrates an exemplary two-dimensional graphical representation of food ontology 1600 related to an ingredients taxonomy. A central "cereal and grains" node can be connected to each of a plurality of sub-nodes by an edge (wherein each edge is indicated by an arrow pointing in a direction from a sub-node to a central node). One or more of the sub-nodes may represent a known or unknown ingredient of the "cereal and grains" node. Examples of the sub-nodes (ingredients) of the "cereal and grains" node may include, pseudo-cereal, oats, rice, barley, wheat, corn, rye grain, millet, teff, sorghum grain, and triticale. The nature of the relationship between the node and each sub-node may be represented on the food ontology by a length of the edge (e.g., length of the arrow), width or color of the edge, distance between the node and the sub-node, color/shape/size of the sub-node, etc. Examples of the nature of the relationship between the node and each sub-node may include, for example, whether the ingredient sub-node must or may be present in the food node, origin of the ingredient, alternatives for the ingredient, etc.

The food ontology can be used to infer associations (e.g., known or unknown associations, abstract associations, etc.) among foods or among data related to the foods (e.g., among ingredients within each food) with one or more algorithms. The algorithm(s) may comprise one or more statistical methods. In some cases, the food ontology can be represented with at least two components: (1) taxonomies, which can be hierarchies of various "food space" dimensions (e.g. ingredients, processing methods, serving method, nutrient composition, cuisine, etc.), and (2) nodes and edges that make up each taxonomy (e.g., food item nodes). Such representation of the at least two components can be used to infer, generate, evaluate, confirm, or reject one or more associations among the nodes within taxonomy. In some cases, such food ontology structure can be used to infer common associations among nodes. In an example, in the context of recipes, a user may input "BLT," and the food ontology may reveal a recipe for a bacon-lettuce-tomato sandwich. In another example, in the context of meals, a user may input a given food item (or partial information about the food item), and the food ontology may predict which additional foods may be also included in the user input meal (e.g., either as a part of the food item or an addition to the food item).

Alternatively or in addition to, the food ontology can compare two or more taxonomies and generate a new taxonomy comprising new nodes and edges to represent previously unknown or unrecognized associations among food-related information.

The statistical method(s) may be used to generate statistical associations among foods or among data related to the foods. An example embodiment of generating such statistical associations is provided herein. Given a collection of recipes (i.e., "population") and a subset of the recipes (i.e., a "sample"), the statistical method(s) may identify two or more nodes with an association (e.g., nodes that are "strongly associated") in the ingredients taxonomy. For example, given 20,000 recipes comprising 12 recipes containing "BLT" as a part of the recipes (e.g., in the titles, descriptions, ingredients, etc.), the food ontology may use its algorithm(s) to find nodes (e.g., ingredient nodes) relevant to the "BLT" recipes. The algorithm(s) may utilize a plurality of steps. Each node in the ingredients taxonomy may be treated as a binary variable of the population (e.g., whether each recipe IS or IS NOT connected to "bacon," "lettuce," and/or "tomato"). In some cases, the algorithm(s) may make an assumption that the population is large enough to be representative of the general population, and treat the node's frequency in the population as a standardized approximation for the probability of a random recipe to contain the node. Subsequently, for each node the algorithm(s) may propose a null hypothesis (e.g., the sample IS NOT associated to the node, i.e., the probability of the node appearing in the sample is the same as the probability of the node appearing in the population), and test the null hypothesis by calculating a chance (e.g., a probabilistic score) that the sample would contain as many instances of the node as it contains. A threshold can be defined or predetermined, and when the probability of the observed data given the null hypothesis is below that threshold, the algorithm(s) may reject the null hypothesis and add the node to the list of the recipe's associations.

Mathematically, each node can be treated as a random binary variable with probability p=node's frequency in the population of recipes. If the sample (or subset sample) size is n, then the number of recipes connected to the node can be treated as a binomial random variable with a probability p and a number of repetitions n. In some cases, if k is an actual number of recipes connected to the node, then calculating a probability of the given scenario or one more extreme may comprise calculating the binomial survival function for p, n, and k−1. To accept or reject a null hypothesis, as aforementioned, a threshold range of about 0.01% to about 10% may be used. In some cases, the threshold may be at least about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. In some cases, the threshold may be at most about 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, or less. In an example, the aforementioned "BLT" example may use a threshold of 0.1%, which may be considered a more "strict" threshold in comparison to a 5% threshold.

Furthermore, the food ontology can utilize its statistical method(s) as a generalization tool to identify one or more significant statistical patterns. In some cases, two users may consume French fries (e.g., every day, every other day, once a week, once a month, etc.). One user may react negatively to fried food (e.g., experience allergic reactions, nausea, headache, etc. after consuming fried food), while the other user may react negatively to starchy vegetables (e.g., potatoes). The knowledge that French fries may be fried and contain ingredients of starchy vegetables may be stored in the food ontology and propagated (e.g., by using matrix multiplication) when searching for associations. As such, both users' meals that contain French fries may be connected to the nodes "friend" and/or "starchy vegetables," thereby allowing the statistical method(s) to generalize the patterns across all of the users' relevant meals (e.g., those containing other fried food for the first user and those containing other starchy vegetables for the second user).

FIGS. 57A and 57B illustrate an exemplary process of using the algorithms (e.g., statistical method(s)) to generate statistical associations among foods or among data related to the foods. FIG. 57A illustrates an exemplary result of the "BLT" textual query among a plurality of recipes to identify one or more samples (recipes) and how they are associated to "BLT." In this case, the query search of "BLT" (or "blt") has identified 12 samples, wherein the 12 samples are associated by the nodes, such as bacon, tomato, sandwich, lettuce, and basil. Each of the listed associations can be indicated by a probabilistic score of the identified node being associated to the query search.

FIG. 57B illustrates an exemplary way of applying the statistical method(s) to the food ontology for predictive meal logging. The food ontology can have mapped a plurality (e.g., thousands) of one or more users' meals. Each meal can be described as a list of food items, where each item may be described as a collection of nodes (e.g., a collection of ingredients). For a node that at least partially describe a food item a user has consumed (e.g., "egg"), the statistical method(s) can be applied to the food ontology to identify one or more nodes that have likely been consumed by the user(s) as part of the meal. Such node(s) may be identified with a probability score of likely having been consumed by the user(s), and/or ranked by such probability score. In some cases, the node(s) may be categorized by two or more associations, such as an "internal" association (one or more attributes describing the food item of interest, e.g., "boiled" for boiled egg, "fried" for fried egg, etc.) and an "external" association (e.g., one or more attributes describing different food items the user(s) has previously consumed along with an egg, such as cheese, bread, etc.). Each of the listed associations can be indicated by a probabilistic score of the identified node being associated to the query node.

As aforementioned, the food ontology can be used to for food generalization or meal generalization. A user may generate a food log (e.g., a collection of images or written list of foods or meals consumed by the user) directly (e.g., by writing down each meal on a digital diary) or indirectly (e.g., via taking and saving pictures of the meals on a mobile phone to post them on social media). In some cases, it may be advantageous to generalize the meals to one or more general meals to facilitate (e.g., automatically facilitate), the user's food logging experience and/or to understand common meal trends of the user.

The metrics for comparing a plurality of meals (e.g., at least 2, 3, 4, 5, 6, 7, 8, 9, 10 meals, or more; at most 10, 9, 8, 7, 6, 5, 4, 3, or 2 meals) can be similar to or based on the metrics for comparing and assessing similarities among elementary food items. For the elementary food items, various methods can be utilized to define a similarity between nodes in the food ontology. In some cases, the methods may emphasize specificity (e.g., "omelette" may be more specific to "egg" than "chicken, and the similarity metric increases as a distance between the nodes decrease in the food ontology), and/or common ancestors (e.g., "French fries" and "mashed potato" may share a common "potato" ancestor, and the similarity metric increase as a number of common ancestors between the nodes increase). In the context of meals, measuring or identifying a similarity between two meals may comprise iteratively identifying common components (e.g., food items) between the two meals, identifying the components that are more common than the other (i.e., closest components), "matching" the closest components and removing them from both of the meals. This process may be repeated until at least one of the two meals has no remaining component, wherein in the meal with no remaining component may be labeled a "smaller meal" and the meal with remaining components may be labeled a "larger meal." Subsequently, the similarity (or a similarity score) may be generated according to one or more metrics (e.g., a first percentage of the common components in the smaller meal, a second percentage of the common components in the larger meal, an average of the first and second percentages, a difference between the first and second percentages, the number of the common components, etc.).

By using one or more of the metrics described herein or their modifications thereof, the meals can be generalized by grouping the meals into one or more distinct groups (or sub-groups). One method of grouping the meals can comprise clustering, such as a hierarchical clustering, density-based spatial clustering of applications with noise (DB-SCAN), variations thereof, or combinations thereof. Another method of grouping the meals can comprise multidimensional scaling (MDS) to visually present and arrange the meals by their similarity, and develop an interface for a user, supervisor, and/or computational algorithms to group the meals.

Figure 58A:
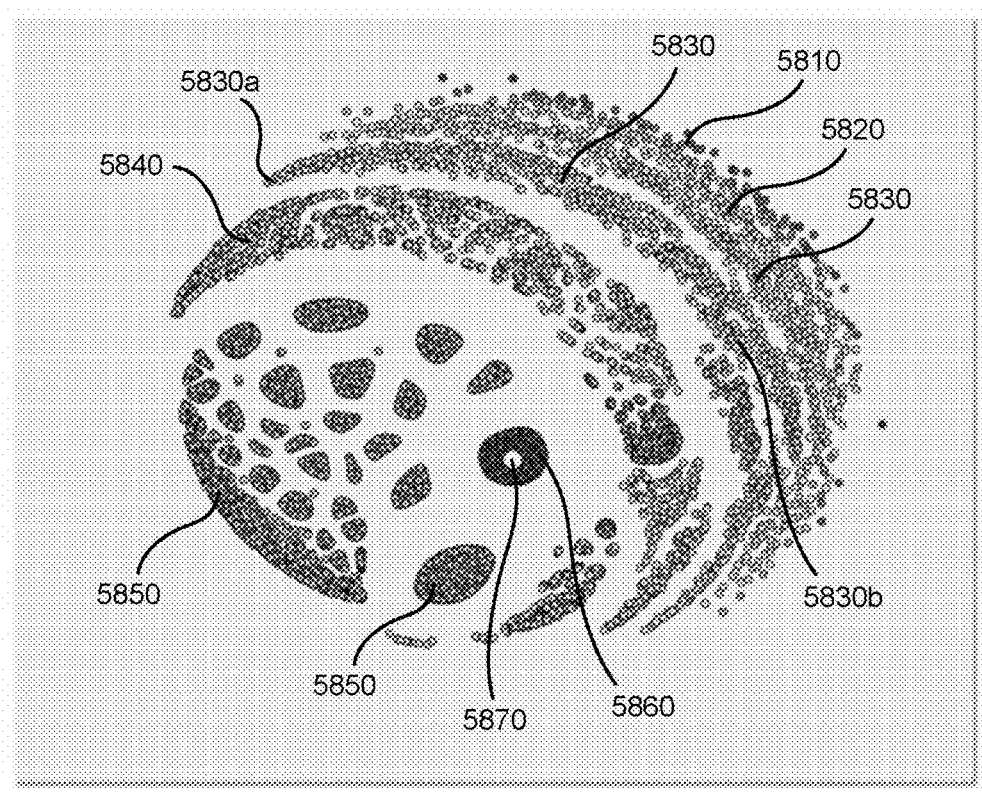
FIGS. 58A and 58B illustrate an exemplary process of grouping the meals for meal generalization.
Figure 58B:
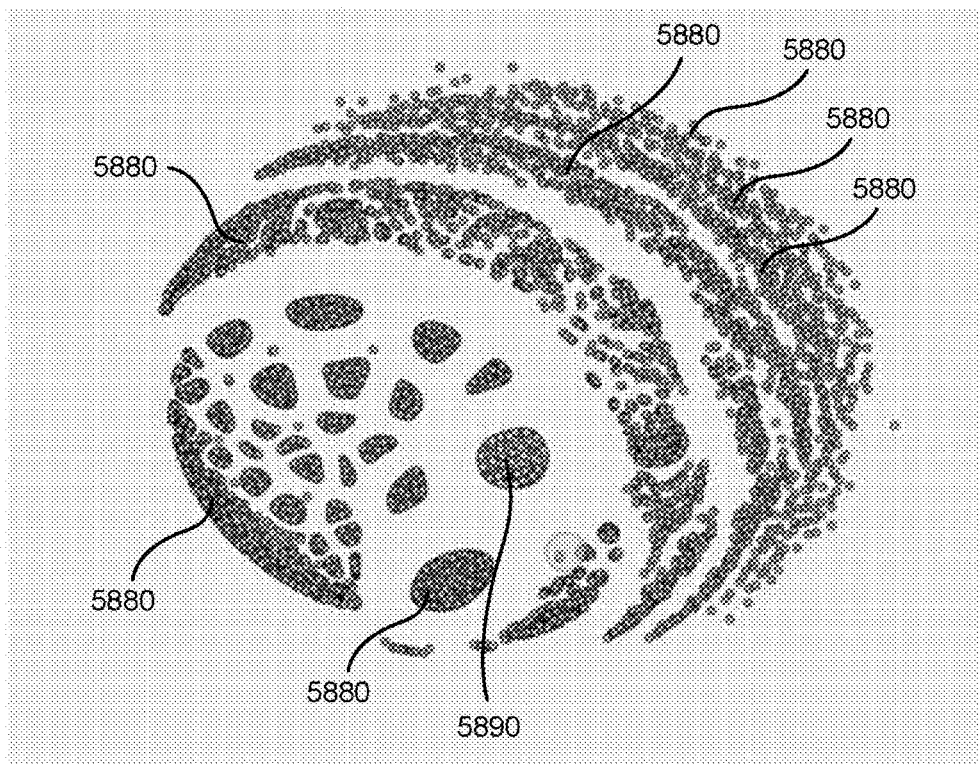

FIGS. 58A and 58B illustrate an exemplary process of grouping the meals based on the MDS. As illustrated in FIG. 58A, the MDS may visually present a plurality of meals (represented by a single dot or circle). The plurality of meals can be arranged by their similarities, and the similarities can be indicated by colors 5810, 5820, 5830, 5840, 5850, 5860, and 5870, and their respective locations relative to each other. For example, the foods indicated by the color 5830 may have a broad similarities as a group, in which the food 5830*a* arranged in the top left of the crescent and the food 5830*b* arranged in the bottom right of the crescent may exhibit the lowest degree of similarity between each other within the color 5830 group. For example, the color 5830 may indicate a plurality of fast food meals, in which the food 5830a may represent a vegetarian meal (e.g., Tofu Pad Thai) and the food 5830b may represent a non-vegetarian meal (e.g., Korean beef short rib barbeque). In some cases, the single food indicated by the color 5870 may represent a single meal. The graphical representation in FIG. 58A may be provided to the user, supervisor, and/or computation algorithms to group the meals.

FIG. 58B illustrates a result of grouping of the meals presented in FIG. 58A. As shown in FIG. 58B, the meals that have been previously arranged by the colors 5810, 5820, 5830, 5840, and 5850 are grouped into a new group 5880, whereas the meals that have been previously indicated by the colors 5860 and 5870 are grouped into a new group 5890.

For meal generalization, once the plurality of meals have been grouped into one or more groups (e.g., as illustrated in FIGS. 58A and 58B), a generalized meal can be identified (or generated) for each group. One approach can include identifying one or more branches (nodes within each meal) that appear in all the meals, and selecting one or more nodes that are the most common in the meals (most prevalent, e.g., in at least 30%, 40%, 50%, 60%, 70%, 80%, 90%, 99%, or more of the meals) within each group of meals. Alternatively or in addition to, the approach can include evaluating the nodes that may be common in the meals within each group of meals, then generating a new meal that most represent one or more nodes that are common in the meals (e.g., in at least 30%, 40%, 50%, 60%, 70%, 80%, 90%, 99%, or more of the meals). In some cases, the newly generated meal may be included into the pool of the plurality of meals, and such pool may be re-assessed for meal generalization to confirm that the newly generated meal is indeed a generalized meal that represents some or most of the previously identified group of meals.

Importantly, the food analysis system 210 can standardize data from other nutrition trackers. Data from such databases can be unstructured, fragmented, and/or disorganized, and can be often be incompatible with each other. The food analysis system 210 can (1) obtain data from the other nutrition trackers, (2) convert such data into structured data having one common format, and (3) organize the structured data into multiple layers of information in the food ontology. Thus, the food ontology can be used as a standardized meta object existing over existing food and/or nutrition databases. For example, the food analysis system 210 can analyze and map a "burrito" from each of multiple databases (e.g., MyFitnessPal, LoseIt, FatSecret, etc.) and track a user's food and/or beverage intake.

Figure 41:
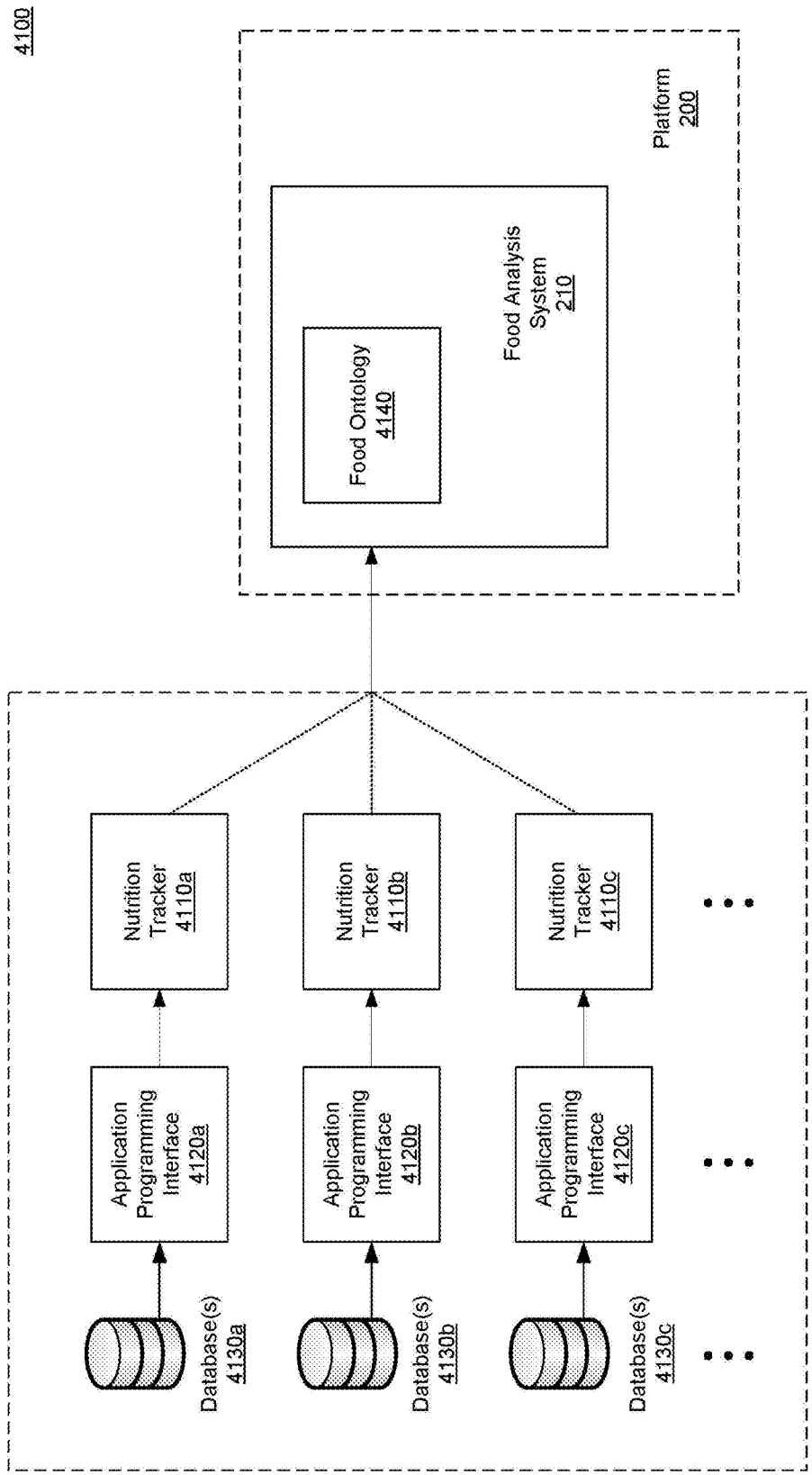
FIG. 41 illustrates an exemplary network layout in accordance with some embodiments.

FIG. 41 illustrates an exemplary network layout 4100 between the food analysis system 210 of the platform 200 and one or more nutrition trackers 4110a-4110c. One or more nutrition trackers 4110a-4110c can be in digital communication with APIs 4120a-4120c, respectively. The APIs 4120a-4120c can be in digital communication with (1) database(s) 4130a-4130c for storing data and (2) software and/or applications comprising a GUI for receiving the data from and/or sending the data to a user (not shown in FIG. 41). The APIs 4120a-4120c of one or more nutrition trackers 4110a-4110c can allow the user to record the user's food intake, and provide nutritional and caloric information of the user's food intake. The APIs 4120a-4120c can feed all data in the database(s) 4130a-4130c, respectively. The data in the database(s) 4130a-4130c are unstructured, fragmented, and/ or disorganized. Thus, while receiving the data relating to foods from one or more nutrition trackers 4110a-4110c, the food analysis system 210 uses one or more algorithms to (1) convert the data into structured data and (2) organize the structured data into multiple layers of information in the food ontology 4140. Such structured data are standardized into a common format of the food ontology 4140. Thus, a food item containing an abundance of information from the database(s) 4130a-4130c of the each of one or more nutrition trackers 4110a-4110c is mapped into the food ontology 4140, where the food ontology 4140 organizes the information by building one or more layers.

The food ontology, when combined with additional health-related data and/or machine learning algorithms of the platform 200, can be useful for a number of applications. Examples of such applications can include, but are not limited to: (1) estimate nutritional values for recipes and/or restaurant dishes; (2) provide food and health recommendations to a user, and to gain an understanding of the user's taste profile (e.g., user preference on food dishes or food types); (3) construct food logs; (4) generate missing elementary foods from existing packaged foods; (5) generate more accurate labels of food characteristics; (6) analysis of food costs; (7) model effects of cooking on nutritional values and estimate degree of food processing; (8) improved image classification or computer vision classification of foods; (9) improved analysis of voice-based food log; (10) identify food substitutes or alternatives (e.g., turn a recipe to gluten free, make a recipe less salty, make a recipe "healthier," etc.); and (11) creation of one or more new foods (e.g., generation of new food dishes from existing foods, generation of new elementary foods from existing packaged foods, etc.).

Device/Data Hub

The device/data hub 220 can generate a user's personalized data network between the platform 200 and the devices 110 and third-party database(s) 130. The device/data hub 220 can be in digital communication with (i) one or more devices (e.g., person devices such as a mobile phone) comprising food, health, and/or nutritional data, and/or (ii) one or more databases comprising food, health, and/or nutritional data. The device/data hub 220 can collect and aggregate food, health, or nutritional data. The device/data hub 220 can be a system used to collect and aggregate a plurality of data sets from a plurality of application programming interfaces (APIs). The plurality of data sets can be provided in two or more different formats. The plurality of data sets can include a plurality of physiological inputs associated with the user. The plurality of data sets can be collected from additional sources, such as the third-party database(s) 130 (e.g. healthcare providers). The device/data hub 220 can automatically aggregate food, biomarker, and health data of the user (e.g. nutrition, activity, sleep, genetics, glucose, menstrual cycle, etc.). Such data of the user can be continuously streamed by the device/data hub 220. The device/data hub 220 can be connected to one or more devices and/or one or more services, and collect one or more data points per month. The device/data hub 220 can be connected to over 100 devices and services and collect about 400 million or more data points per month. All incoming data, regardless of its source, can be fully integrated to a format of the device/data hub 220. The all incoming data can be fully integrated to software frameworks of the device/ data hub. The software frameworks can be a web framework (WF) or a web application framework (WAF).

The device/data hub 220 can be a serverless system to store raw data from the devices 110 prior to analysis by the food analysis system 210 or the insights and recommendation engine 230. One or more changes in the APIs cannot affect the raw data stored in the device/data hub 220. Not one of the raw data can ever get lost in the device/data hub 220. The devices 110 and database(s) 130, and their respective APIs, that are compatible with the device/data hub 220 can include mobile devices, wearable electronics, medical devices, point-of-care (POC) devices or kits, sensors, etc. The sensors can include a glucose sensor, GPS receiver, heart rate monitor, galvanic skin response (GSR) sensor, skin temperature sensor, capacitive sensor, and metabolic sensor. The sensors can each be a discrete device with a discrete API. The sensors can each be an integrated component or function of one or more of the devices 110.

Examples of the devices 110 and their respective data types are provided. From Abbott glucose monitors, data of blood glucose levels can be obtained. From Fitbit, data including activity, steps, weight, and sleep can be obtained. From Jawbone, data including activity, steps, weight, and sleep can be obtained. From GoogleFit, data including activity and steps can be obtained. From Moves, data on activity can be obtained. From Runkeeper, data including activity, weight and sleep can be obtained. Additional types of the devices 110 can include a smart clothing item with a heart rate monitor, a sensor-enabled mattress that tracks and adjusts to an individual's snoring, earbuds equipped with an in-ear thermometer, an artificial intelligence-embedded toothbrush that collects tooth brushing data through sensors (frequency, duration, brushed area, etc.), a smart ring that tracks an individual's biomarkers (e.g., activity, steps, sleep, heart rate, etc.), a wearable electrocardiography monitor, a portable air-quality tracker, a medication adherence hub that is designed to be placed adjacent to a user's medication pills and alert the user of scheduled medications, an e-cigarette or a vapor, smart utensils designed to offset hand tremors from Parkinson's Disease and other unsteadiness-causing conditions, a pregnancy-tracking wearable that can help women track and understand contractions, hearing aids, a sensor to measure antioxidants in the skin, implantable (e.g. by swallowing) sensors for diagnosing gastrointestinal problems or measuring food intake and/or digestive conditions, a device that sits in the mouth to detect a sound made by chewing of foods, a portable spectrometer to measure absorption spectrum of foods, and a portable mass spectrometer to provide a partial chemical composition of foods.

The platform 200, including the device/data hub 200, can be implemented in a GUI-based software interface. The GUI-based software interface can connect the platform 200, including the device/data hub 220, to a user device (e.g., a personal computer, a smartphone, etc.). The GUI-based software interface can be compatible with any operating system of the user device. When in use, the GUI-based software interface can gain unlimited access to data in the user device or data accessible through the user device. The GUI-based software interface can automatically collect the data without dependency on the user input. The data in the user device can include pictures, videos, voice recordings, texts, location services, etc. The data accessible through the user device can also include data in the user's cloud storage services. The data accessible through the user device can include data from at least one third-party application that connects the user device to one or more third-party devices (e.g., a glucose monitor, temperature sensor, etc.).

The device/data hub 220 can be a seamless food image logger. By using the GUI-based software interface that can be installed in a user device, the device/data hub 220 can gain unlimited access to a camera roll of the user device. Every time an image is taken by the user device, a convolutional network of the device/data hub 220 can analyze the image to decide whether or not the image contains at least one food or beverage. The convolutional network can analyze the image when the user is using an application other than the GUI-based software interface (e.g., a photo application of the user device, Instagram, etc.). If the convolutional network can identify at least one food or beverage in the image, the image is automatically aggregated in the database(s) 240 with a timestamp and geolocation. The stored data of the image can be used for analyses by the food analysis system 210 and the insights and recommendation engine 230. The analyses can include studying how body metrics (e.g., blood glucose level, sleep time, steps, etc.) of the user can be affected by at least one food or beverage in the image. The seamless food image logger function of the device/data hub 220 can facilitate a tedious and incessant process of food tracking required for the food analysis system 210. Exemplary windows of the GUI-based software interface for the seamless food image logger function are illustrated in FIGS. 17A-17D. During or after installation in the user device, the GUI-based software interface can ask users for access to the camera roll of the user device.

The device/data hub 220 can perform food tracking by textual and voice recognition analysis. By using the GUI-based software interface installed in the user device, the user can record and store at least one free text or at least one voice message about foods (e.g., foods the user has eaten, foods the user plans to eat, foods the user wants to learn more about, etc.) to the device/data hub 220. The device/data hub 220 can utilize a third-party service (e.g., Speech2Text) to automatically convert at least one voice message into a respective free text. The stored data of at least one free text or at least one voice message can be used for analyses by the food analysis system 210 and the insights and recommendation engine 230. In an example, if the user types a free text, "1 slice of bread with two eggs and a cup of coffee," to the GUI-based software interface, the device/data hub 220 can save data of the free text to the database(s) 240 and instruct the food analysis system 210 for analysis of the data. The food analysis system 210 can abstract and classify nutritional information (e.g., carbohydrate or nutrient intake) of foods mentioned in the free text, and map the foods into the food ontology. Subsequently, the device-data hub 220, in communication with the food analysis system 210, can inform the user results of the analysis. The textual and voice recognition function of the device/data hub 220 can facilitate a tedious and incessant process of food tracking required for the food analysis system 210. Exemplary windows of the GUI-based software interface for the voice recognition analysis function are illustrated in FIGS. 18A-18C. The GUI-based software interface window can display example sentence structures that users may use to record a voice message to the device/data hub 220, as shown in FIG. 18A. After automatically converting the voice message into a free text, the GUI-based software interface window can display the free text to the user, as shown in FIG. 18B. After immediately analyzing food-related information from the free text, the GUI-based software interface window can display the results of the analysis (e.g. a food item and predicted calories and serving size), and also ask the user to validate or edit the result for accuracy prior to saving the result in the database(s) 240, as shown in FIG. 18C.

The device/data hub 220 can be in communication with a number of medical devices and healthcare databases to continuously stream and store a user's personalized data. The stored users' personalized data can be used for analysis by the insights and recommendation engine 230. The user's personalized data can include glucose levels. The device/ data hub 220 can be in communication with a glucose meter. The device/data hub 220 can be in communication with a continuous glucose monitoring (CGM) device, otherwise known as a real-time CGM (RT-CGM) device. The CGM device, in combination with its corresponding GUI on the device and/or on a user device, can determine glucose levels in the blood on a continuous basis. The CGM device can monitor glucose levels of the interstitial fluid as a close correlation to the blood glucose levels. A measurement of a glucose level of the interstitial fluid can have at most about 15, 14, 13, 12, 11, 10, 9, 8, 7, 6, 5% or less error than a respective blood glucose level. The measurement of a glucose level of the interstitial fluid can have a shorter delay in response than a measurement of a blood glucose level. The CGM device can remain functional during a user's daily activities, including showering, exercising, sleeping, etc. The CGM device can be used for a user with type 1 diabetes or type 2 diabetes in order to assess when the user should inject insulin. The CGM device can be useful for athletes to optimize their athletic performance. The CGM device can be useful for individuals interested in tracking food intake as way to monitor their weight loss diet. The CGM device can include any suitable continuous glucose monitoring apparatus.

A network according to the present disclosure may comprise device/data hub 220, devices 110, third-party database(s) 130, and database(s) of the platform 240. The platform 240 can be a virtual private cloud (VPC) (e.g. Amazon VPC) for data storage. The network may utilize many independent software components that are collectively known as the open-source Apache Hadoop™ stack. These components may include products such as: Cassandra™, CloudStack™, HDFS, Continuum™, Cordova™, Pivot™, Spark™, Storm™, and/or ZooKeeper™. The machine learning/NLP algorithms described herein may leverage state-of-the-art machine learning libraries, including public libraries such as those built upon the Apache Spark™ and Python® systems.

Insights and Recommendation Engine

Figure 20:
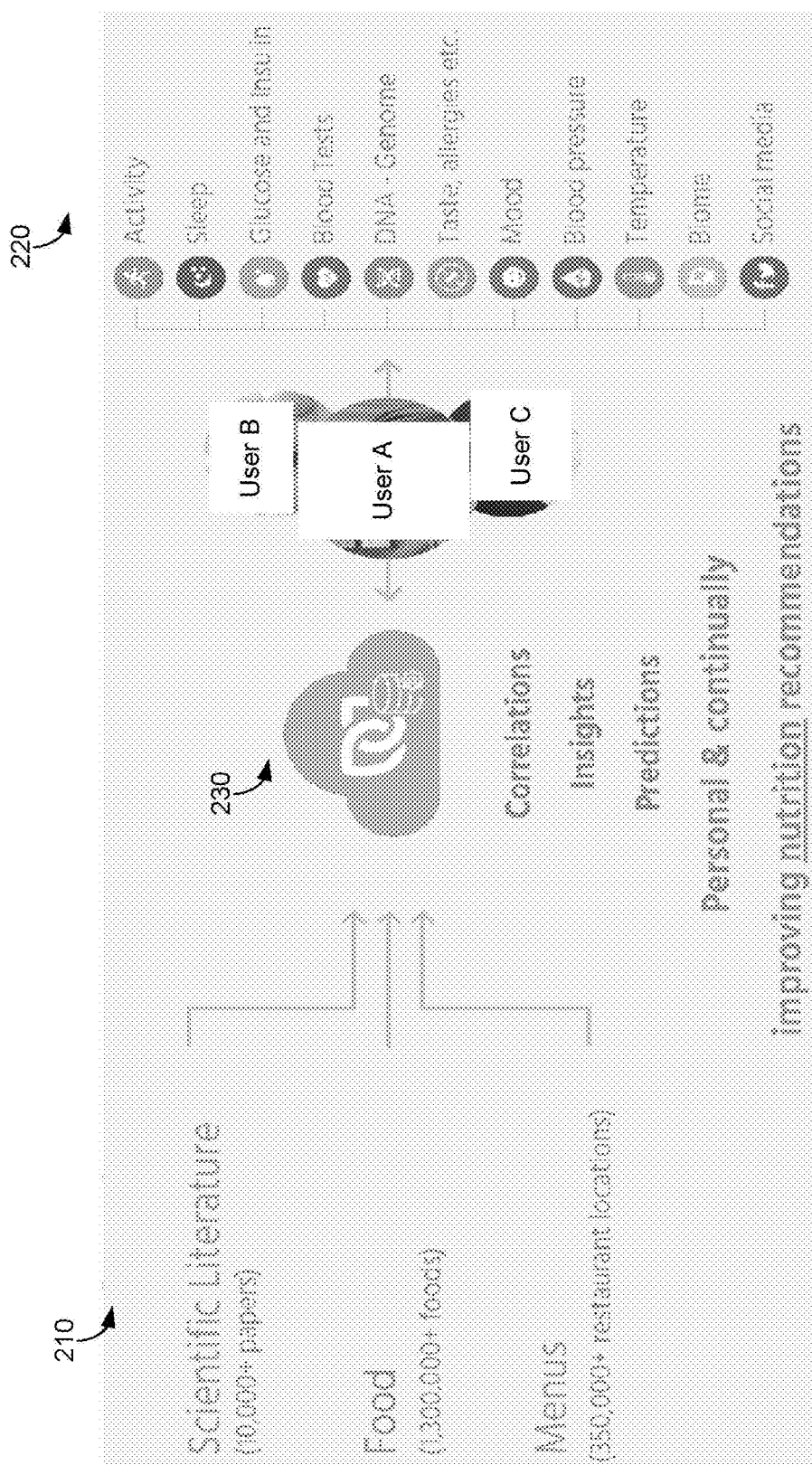
FIG. 20 illustrates features of an insight and recommendation engine in accordance with some embodiments.
Figure 21:
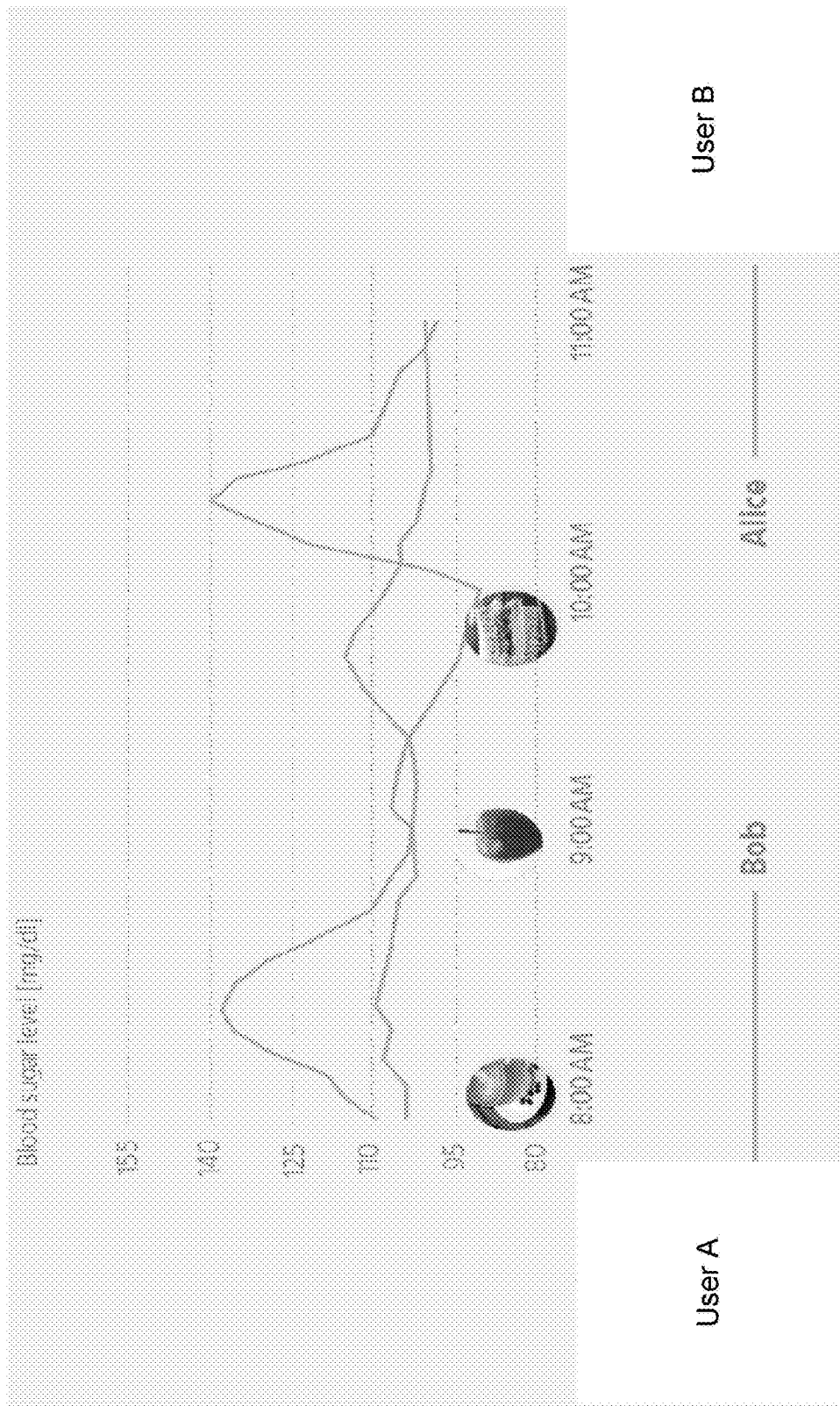
FIG. 21 is a graph of blood glucose levels of two individuals.
Figure 22:
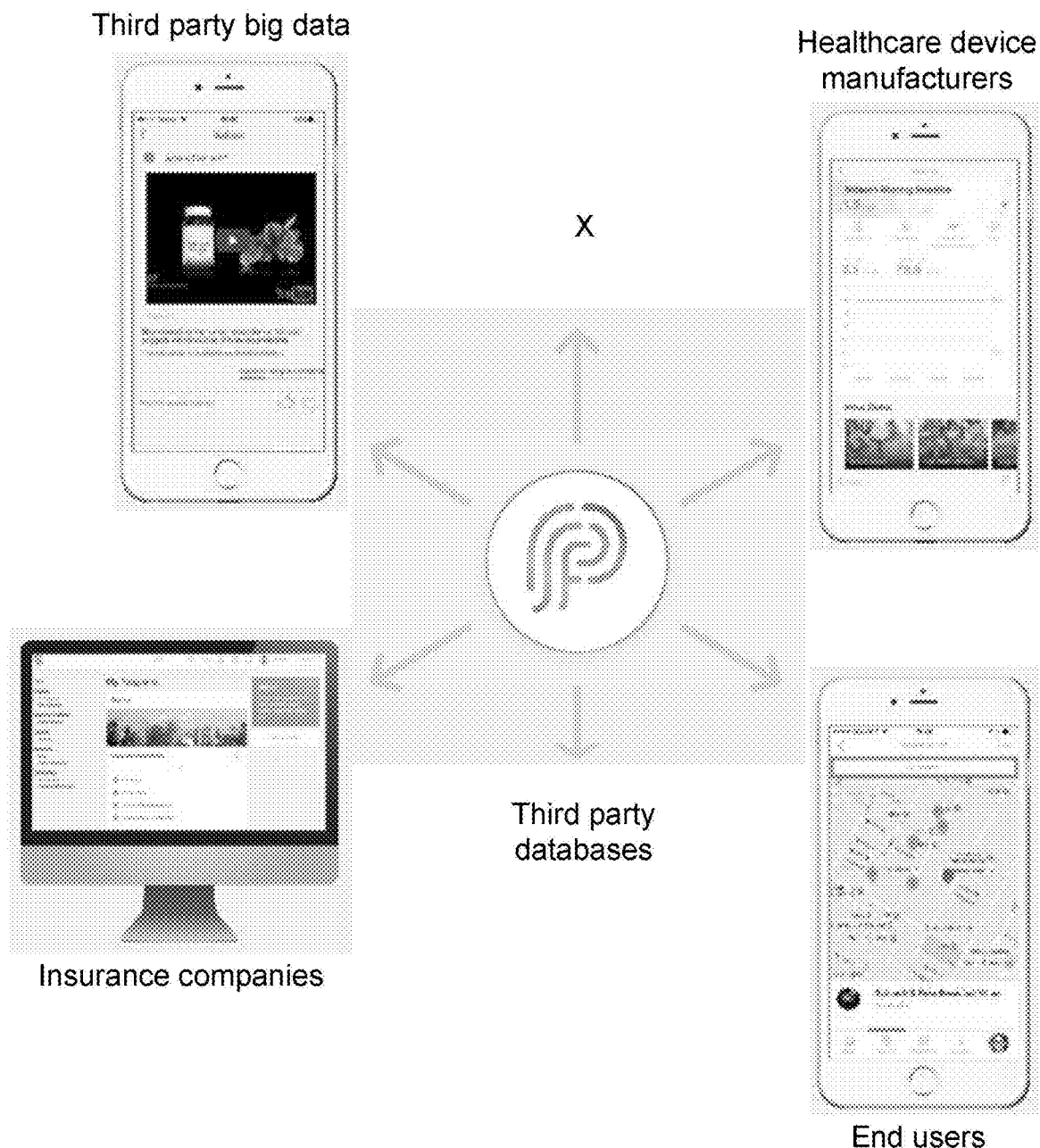
FIG. 22 illustrates potential entity partners utilizing embodiments of the present disclosure.

The insights and recommendation engine 230 can (1) access the food ontology in the food analysis system 210, (2) access a plethora of personal biomarkers data from the device/data hub 220, (3) analyze how foods affect a user's biomarkers, and (4) continually generate personal nutrition recommendations to the user. The relationship among the three components of the platform 200 is illustrated in FIG. 20. Upon analyzing and validating how foods may affect the user's biomarkers, the insights and recommendation engine 230 can generate one or more personalized digital signatures unique for the user. A personalized digital signature can be an algorithm to estimate the response of a specific biomarker of the user to consumption of a specific food item. For example, a digital signature for blood glucose (or sugar) level can take into consideration that blood glucose levels of two individuals may respond differently to consumption of identical food items (coffee, apple, and a sandwich) at identical times, as shown by graph in FIG. 21. One or more personalized digital signatures can be unique to a number of other factors related to the individual, including gender, age, race, genetics, microbiome, religious dietary restrictions, geography, height, weight, and time of the day, month, or year. In addition to end users of the insights and recommendation engine 230 and other functions provided in the present disclosure, additional partners that may benefit include healthcare device manufacturers, third party big data, third party databases, and insurance companies, as shown in FIG. 22.

The insights and recommendation engine 230 can determine various effects of food consumption on the user's body by applying at least one predictive model to a plurality of data sets. The plurality of data sets can include foods consumed by the user and physiological inputs associated with the user. Such data can be obtained from a plurality of sources, including discrete APIs. The plurality of data sets can also include information about the foods consumed by the user from the food ontology. Applying at least one predictive model to the plurality of data sets can generate a plurality of personalized food and health metrics for the user.

The insights and recommendation engine 230 can include a number of analytics and deep learning algorithms, including statistical analysis and artificial neural networks (ANN). The ANN can be a mathematical or computational model that is inspired by the structural or functional aspects of biological neural networks. The ANN can include a group of artificial neurons (units) that are interconnected. The ANN can be an adaptive system that is configured to change its structure (e.g., the connections among the units) based on external or internal information that flows through the network during the learning phase. The ANN can be used to model complex relationships between inputs and outputs or to find patterns in data, where the dependency between the inputs and the outputs cannot be easily attained. In some examples, the complex relationships can include how foods affect the user's body in a multitude of biomarkers.

As an alternative or in addition to the ANN, the insights and recommendation engine 230 can include biomathematical predictive models that use metric spaces, decision trees, and decision tree learning algorithms. A metric space can provide a "ruler" or an absolute measurement of how different two feature vectors are. The metric space can be used to define a "distance" between the two feature vectors. A decision tree can be a support tool that uses a tree-like graph or model of decisions and their possible consequences. The decision tree can include one or more leaf nodes (leaves) that represent final decisions. An entire path leading to one or more leaf nodes can represent a rule for arriving at one or more decisions, respectively. A decision tree learning algorithm can be an inductive machine learning mechanism that extrapolates accurate predictions about future events (unknown) from a given set of past (known) events. The decision tree learning algorithm can also provide a measure of confidence that the predictions are correct (e.g., a coverage rate, accuracy rate, and confidence interval). The minimum confidence interval for the tree learning algorithm's accuracy rate can be maintained to at least about 70, 75, 80, 85, 90, 95% or more.

The insights and recommendation engine 230 can use data collected and analyzed by the food analysis system 210 and the device/data hub 220 to generate at least one decision tree learning algorithm. At least one decision tree learning algorithm can be used to predict how foods previously consumed by a user may affect personalized biomarkers of the user (e.g. glucose level). At least one decision tree learning algorithm can also be used to predict how foods that the user has never consumed or other lifestyle events that may affect the user's biomarkers (e.g. glucose level).

Figure 23:
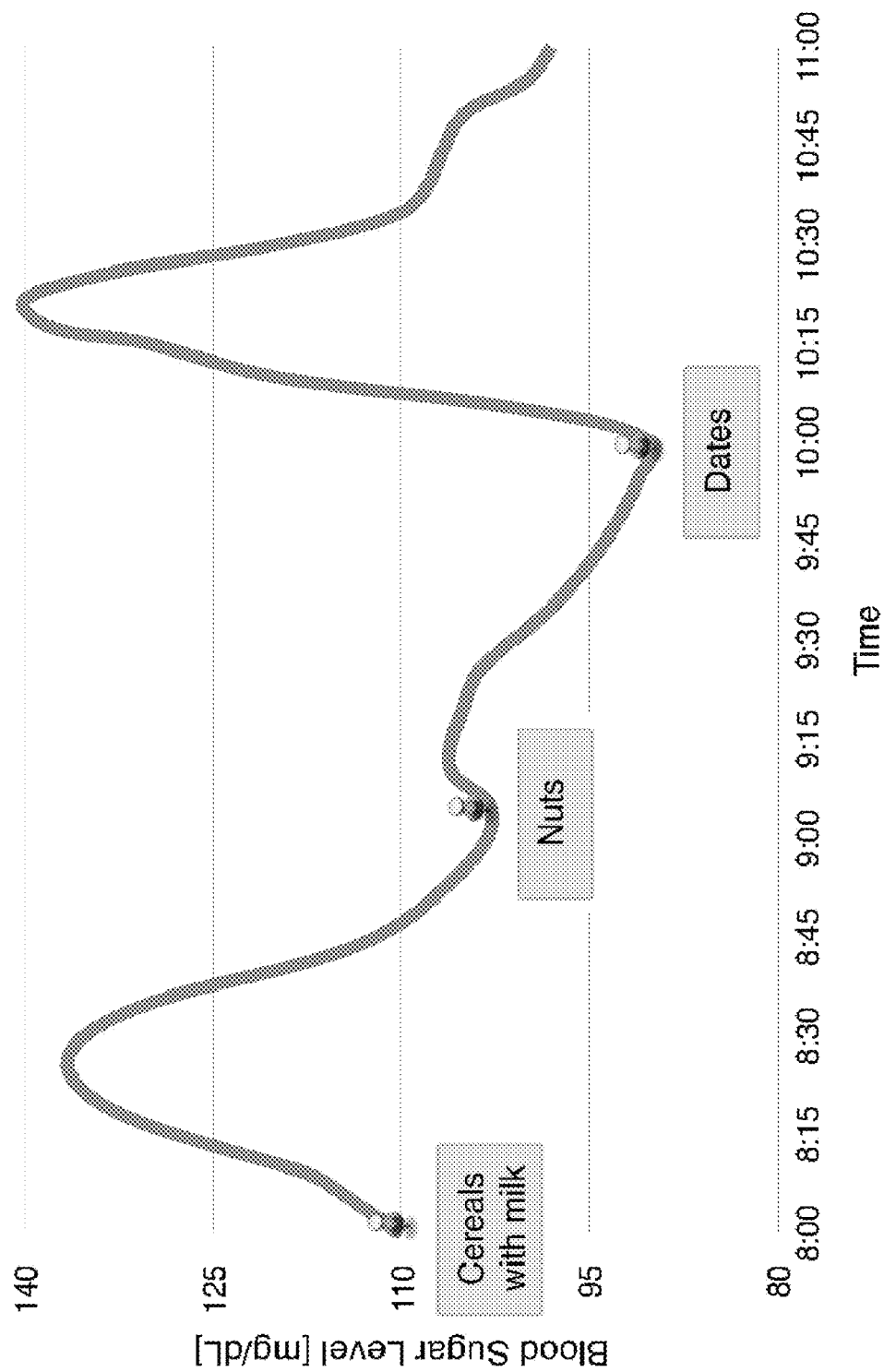
FIG. 23 is a graph of blood glucose level of an individual as a function of time in accordance with some embodiments.
Figure 24A:
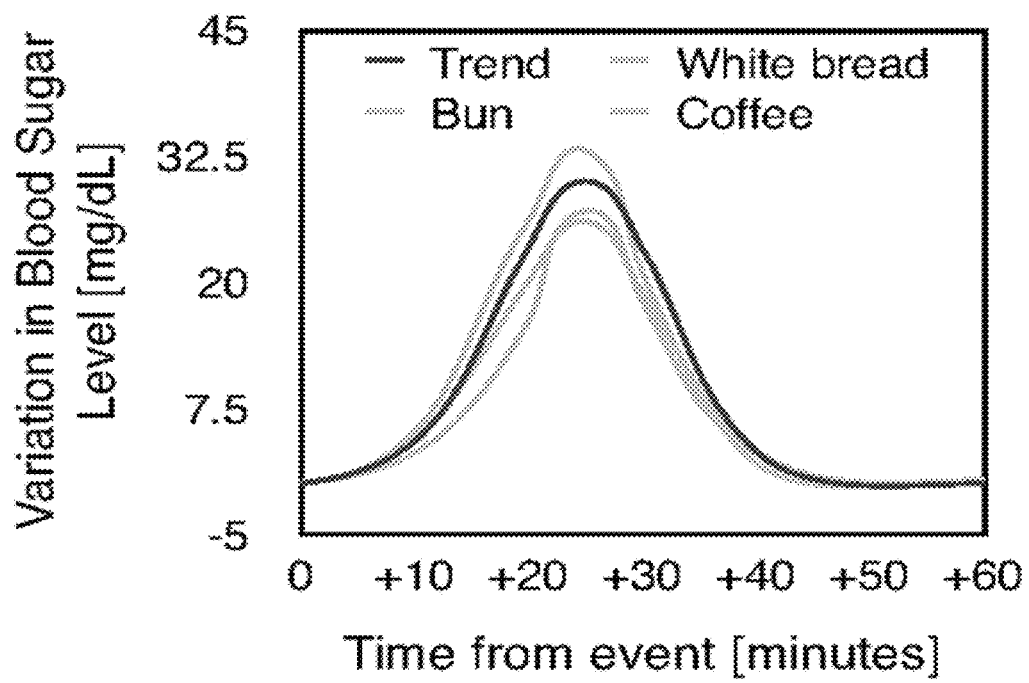
FIGS. 24A and 24B illustrate classification of foods according to their effects on a biomarker, in accordance with some embodiments.
Figure 24B:
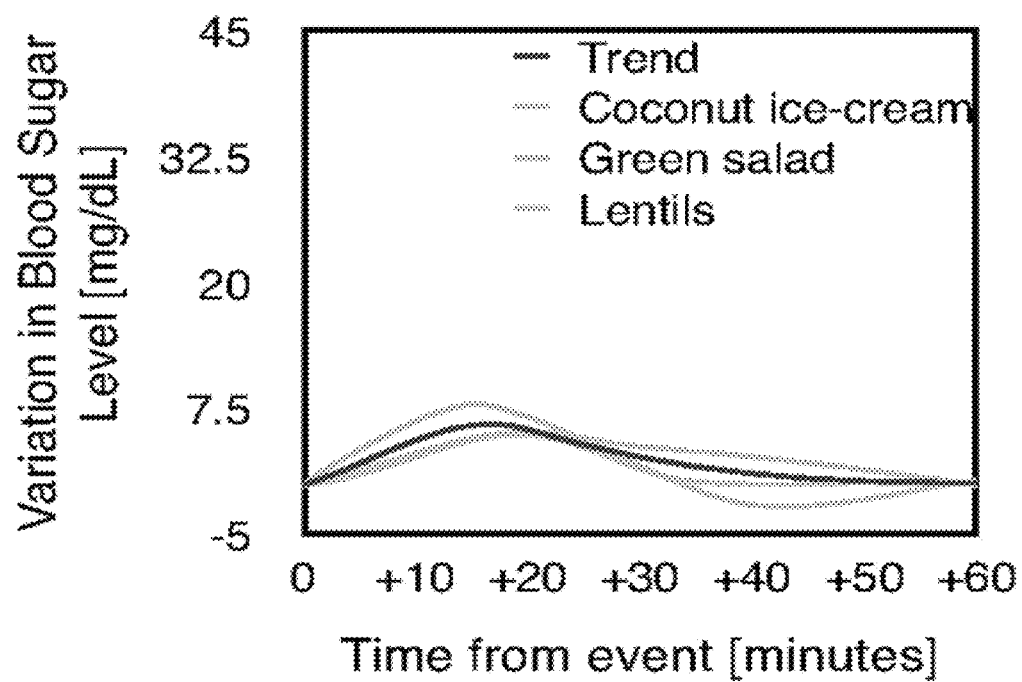

An example of how the insights and recommendation engine 230 can analyze a collection of data aggregated by the device/data hub 220 is described in detail. The device/data hub 220, in communication with a user's CGM device, can continually record the user's blood glucose level as a function of time, as demonstrated by graph in FIG. 23. The device/data hub 220 can also record what foods the user has consumed and their respective timestamps. FIG. 23 shows that the user has eaten cereals with milk at 8:00 A.M., nuts at 9:00 A.M., and dates at 10:00 A.M. The data also shows different degrees of spikes in the blood sugar level plot. To partial data and generate a "blood glucose level" digital signature of the user, the insights and recommendation engine 230 can extract known events (e.g., food consumption) and its associated blood sugar levels, and classify the known events by a degree of change in blood glucose level in response to each event. The breakdown can be performed using a biomathematical predictive model. FIGS. 24A-24B illustrates how 6 different food items can be classified into two trend groups based on their effect on an individual's blood glucose level. Graph in FIG. 24A illustrates that white bread and buns (also from white wheat) can affect the user's blood glucose level similarly and negatively. A relatively large variation of blood glucose levels can imply insulin-mediated fat storage as a response to respective foods. On the other hand, graph in FIG. 24B illustrates that coconut ice-cream, lentils, and salads have a relatively small effect on the user's blood sugar level. Although not shown in FIGS. 24A-24B, other biomarkers can be analyzed in a similar approach.

The insights and recommendation engine 230 can generate and use one or more digital signatures of a user to provide one or more recommendations to the user. One or more recommendations can be related to food, health, or wellness. In some examples, the insights and recommendation engine 230 can suggest meal plan recommendations that are tailored to an individual's body and its responses. The recommendations can include which specific foods to consume, where to find the specific foods (e.g. name and location of a restaurant), basic ingredients for the specific foods, how to prepare the specific foods (e.g., methods of cooking), when to consume the specific foods (e.g., between 4:30-5:30 P.M.), how much to consume, which activities or steps to take (or avoid) after consumption of the specific foods, etc. The insights and recommendation engine 230 can also track what the user likes to eat and does not like to eat. The insights and recommendation engine 230 can also predict what other types of foods the user will like or dislike, and use such one or more predictions to generate personalized recommendations. The personalized recommendations can yield high rate of compliance by the user.

The insights and recommendation engine 230 can send one or more personalized messages to a user while the user is using the GUI-based software interface. Additionally, one or more personalized messages can be pop-up messages, voice messages, and e-mails to the user device while the user is not using the GUI-based software interface. One or more personalized messages can suggest the user to consume less (or more) of one or more food items, or stop (or start) consumption of one or more food items. The insights and recommendation engine 230 can send predicted effects of one or more foods to the user's body.

The insights and recommendation engine 230 can suggest recommendations that can drive a behavioral change in a user. The behavioral change can be a preference selected by the user, or a suggestion generated by the insights and recommendation engine 230. The behavioral change can include eating less carbohydrate to lose weight. For example, the user may eat pizza often for lunch, and the insights and recommendation engine 230 can detect that consumption of pizza is correlated with a spiked increase in the user's blood glucose level. The insights and recommendation engine 230 can identify other foods that, when eaten with pizza, can reduce the blood glucose level. The insights and recommendation engine 230 can also identify one or more alternative food items to replace pizza.

Figures 25A, 25B, 25C:
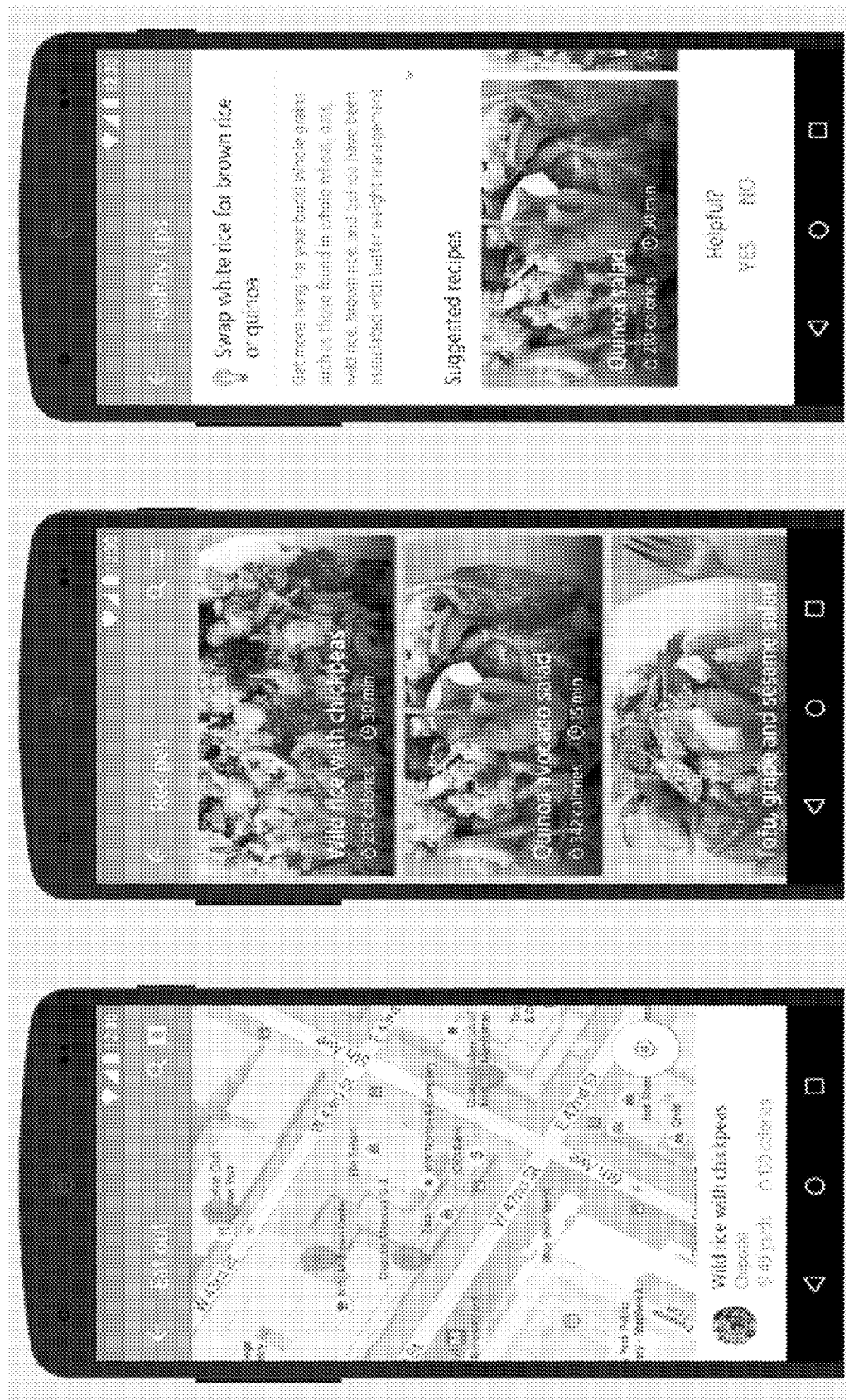
FIGS. 25A-25C illustrate exemplary windows of a GUI-based software interface for personal recommendations on menu items, in accordance with some embodiments.

By using the GUI-based software interface in a user device, the insights and recommendation engine 230 can receive a menu input, track a user's geolocation using GPS of the user device, search nearby restaurants, and recommend a different menu item available in the vicinity of the user. The insights and recommendation engine 230 can provide ordering tips and reasons for the different menu item. Exemplary windows of the GUI-based software interface for personal recommendations on menu items are illustrated in FIGS. 25A-25C.

The insights and recommendation engine 230 can be useful for individuals with type 1 diabetes or type 2 diabetes. An individual's blood glucose level can be affected by foods consumed and the individual's lifestyle (e.g., physical activity, sleep, stress, etc.). If the blood glucose level is too high, then the individual's body may secrete a hormone called insulin to help regulate the blood glucose by directing fat cells to absorb glucose. The insulin can also direct other cell types to absorb the blood glucose as a source of energy. For diabetics, the blood glucose level can be higher than normal due to the body's impaired ability to produce or respond to insulin. An individual with type 1 diabetes can have an insufficient production of insulin in the individual's body. An individual with type 2 diabetes can have an insufficient production of insulin and/or insulin resistance in the body. Individuals with the type 1 or type 2 diabetes can rely on insulin injections to control their blood glucose levels. Thus, the insights and recommendation engine 230 can (1) monitor a user's food intake, blood glucose levels (either continuously from a CGM device or in a discrete manner using a conventional glucose meter), as well as insulin levels for users using the insulin injection therapy, and (2) analyze relationships among specific food types, insulin injections, and blood glucose level responses. The insights and recommendation engine 230 can use the GUI-based software interface in the user device to display the recommendations to the user. From the recommendations, the user can find out specifically which food items the user's blood glucose level is most responsive to, which food items to avoid or consume more, an optimized time interval for insulin injection, etc. In an example, a recommendation may suggest that, "When you added avocado to your sandwiches your glucose response was over 30% lower [occurred 5 out of 6 times]." Other biomarkers that may be collected and correlated to insulin and blood glucose levels by the insights and recommendation engine 230 can include exercise, stress, activity, medications, menstrual cycle, etc. A combination of foods and at least one or more of the other factors can improve the quality of recommendations generated by the insights and recommendation engine 230.

Figure 26:
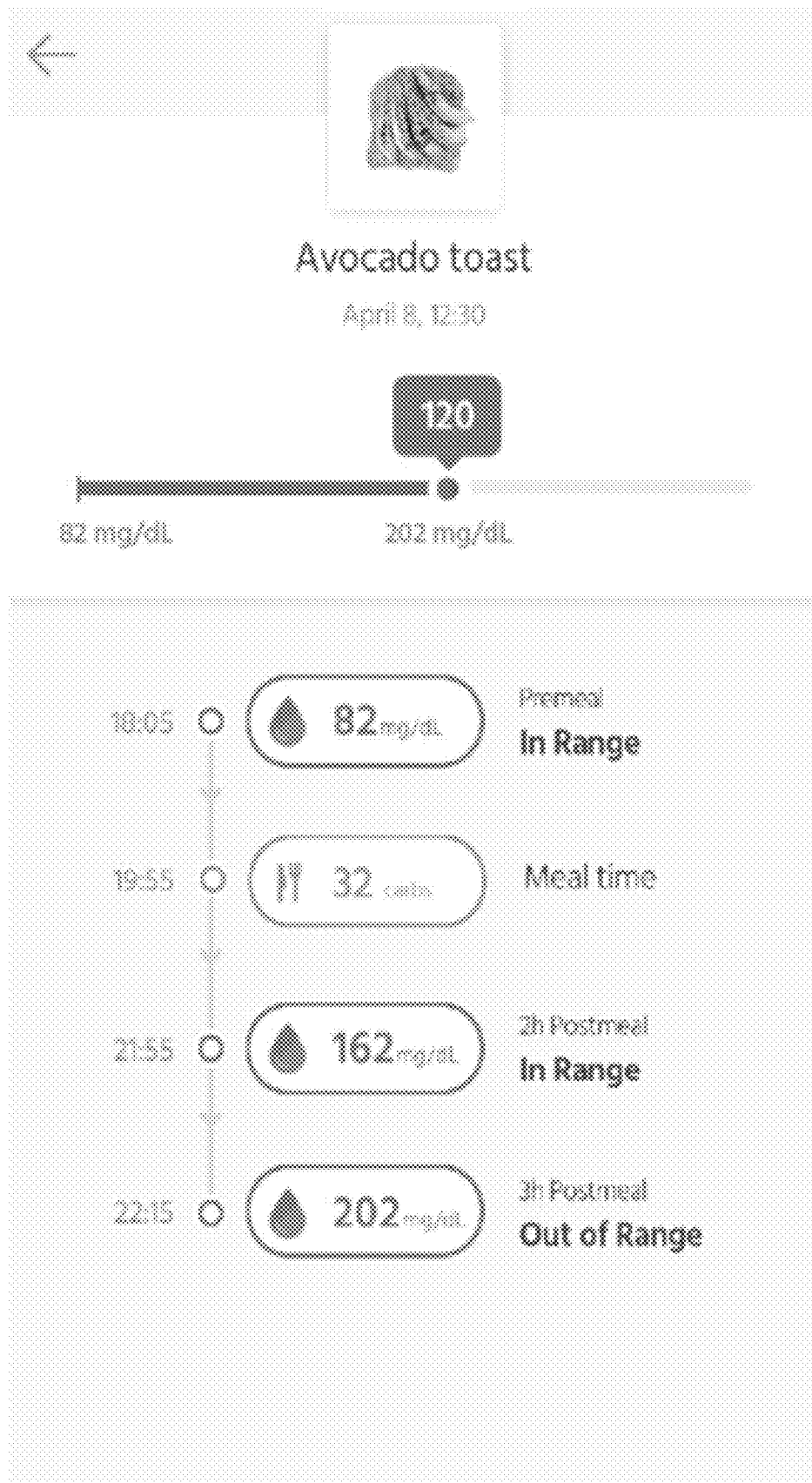
FIG. 26 illustrates an exemplary window of a GUI-based software interface for blood glucose logging, in accordance with some embodiments.

FIG. 26 illustrates an exemplary window of the GUI-based software interface for blood glucose logging. The blood glucose logging can be performed using a conventional glucose meter or a CGM device. The window can display a food item (e.g., Avocado toast) that has been consumed by the user. The window can display a change in the user's blood glucose level at one specific time point following consumption of the food item. Additionally, the window can display a report on the user's blood glucose level profile within a time period. The time period may capture time points before and after consumption of the food (e.g. pre-meal, or 2 and 3-hour post-meal). The insights and recommendation engine 230 can alter a length of the time period and a number of time points within the time period based on a profile of the food- and blood glucose-related data. Based on a recommended range of the blood glucose level, the insights and recommendation engine 230 can assess whether each of measured blood glucose levels is within or out of the recommended range, and display the assessment on the window.

Figure 27:
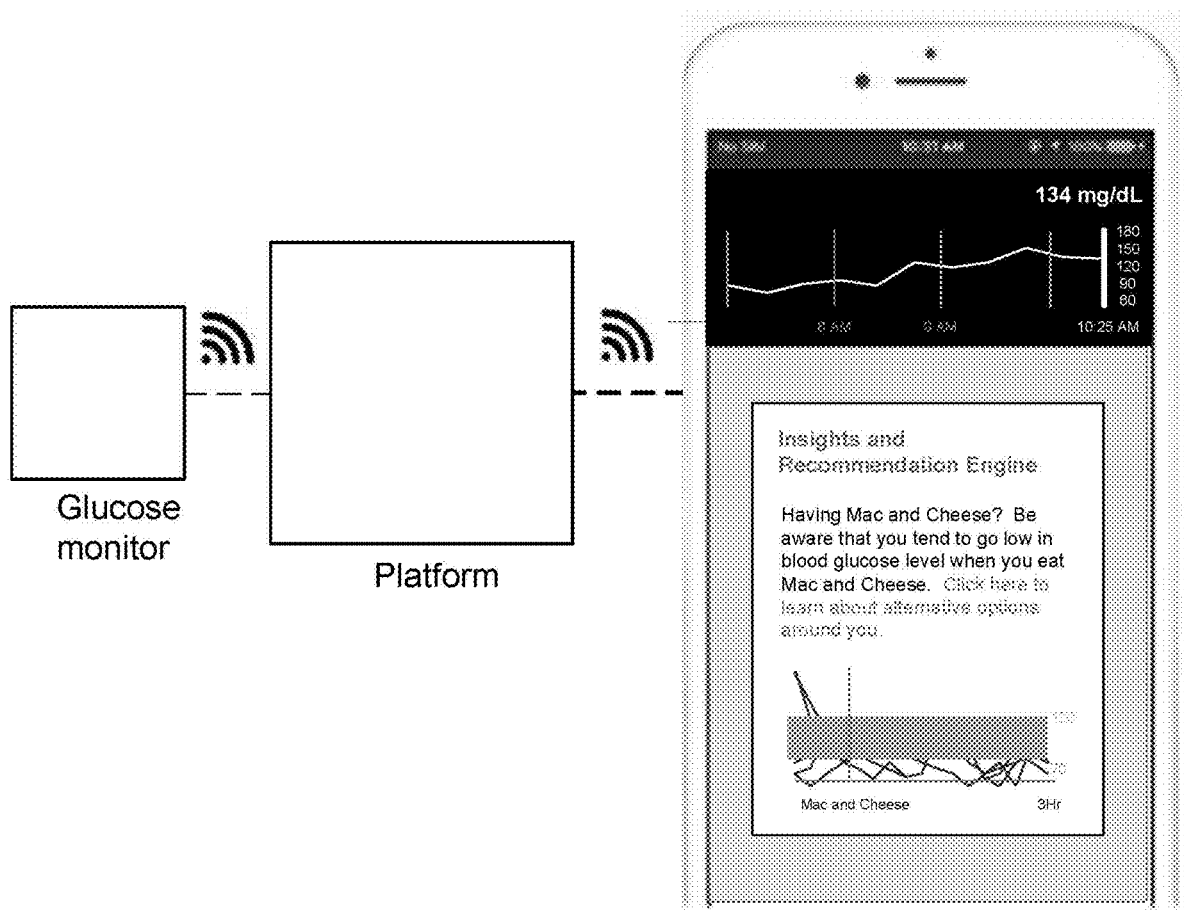
FIG. 27 illustrates an exemplary window of a GUI-based software interface for a recommendation based on an automatic blood glucose logging, in accordance with some embodiments.

FIG. 27 illustrates an exemplary window of a GUI-based software interface for displaying a recommendation based on an automatic blood glucose logging. The automatic blood glucose logging can use a CGM device. The CGM device may be in communication (e.g. via Bluetooth, Wi-Fi, etc.) with the GUI-based software interface in a user device. The GUI-based software interface can be connected to and leverage all features of the platform 200, including the food analysis system 210, the device/data hub 220, and the insight and recommendation engine 230. The window can display a graph of the user's blood glucose level, including a most recent measurement from the CGM device. For a food item that the user may be interested in consuming, the insights and recommendation engine 230 can generate an insight (e.g., a free text, image, graph, etc) on how the food item has affected the user's blood glucose level in the past. The insight can be displayed to the user on the window. The insight may help the user to make an informative decision regarding consumption of the food item. If the user has a wearable insulin delivery device, the insight on the window may also inform the user about different bolus options available in the wearable insulin delivery device.

The insights and recommendation engine 230 can use one or more biomathematical models described in the present disclosure to predict a user's general biomarkers. In an example, the insights and recommendation engine 230 can predict a user's glucose metabolism. The glucose metabolism process can begin with digestion. Upon digestion, glucose can be absorbed into the bloodstream upon entering the small intestine. When the blood glucose level increases, the pancreas can release a hormone called insulin to control blood sugar. Insulin can help with transfer of glucose into a number of cell types with insulin receptors. Examples of the cell types can include adipocytes (fat tissue), muscle myocytes (muscle), and hepatocytes (liver). Thus, the user's glucose metabolism can depend on one or more factors, including, but are not limited to, the user's glucose and insulin production levels, blood glucose level prior to food consumption, carbohydrate content in the food, insulin level in the body, blood pressure, physical activity, the user's insulin sensitivity, time of the day, stress, illness, pregnancy, medications, etc. Thus, there may be various ways to generate biomathematical models with one or more mathematical parameters to describe and predict relationships between such factors and the user's glucose metabolism. In some examples, some of the factors may be more relevant to the glucose metabolism than the others. In addition, relevance of such factors to the user may change over time.

Figure 28A:
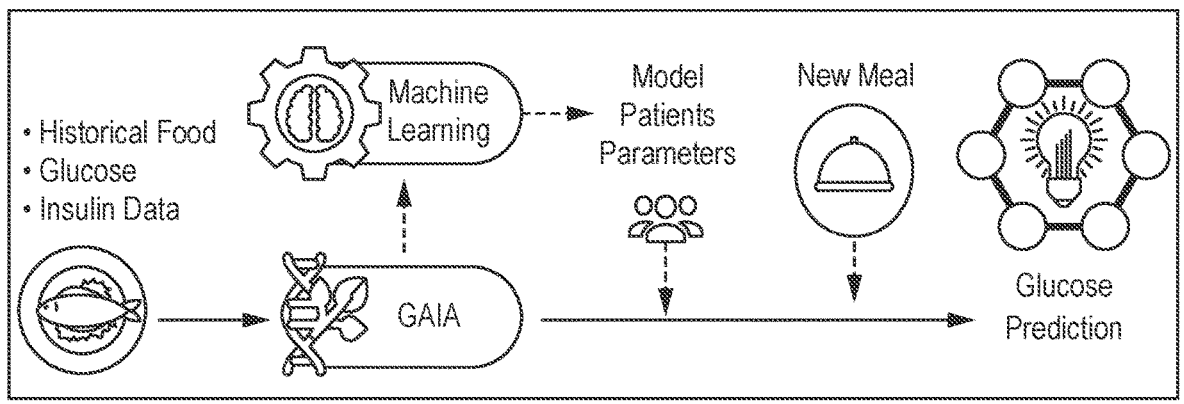
FIG. 28A is a flow chart of a method of modeling glucose and insulin interactions in the body, in accordance with some embodiments.
Figure 28B:
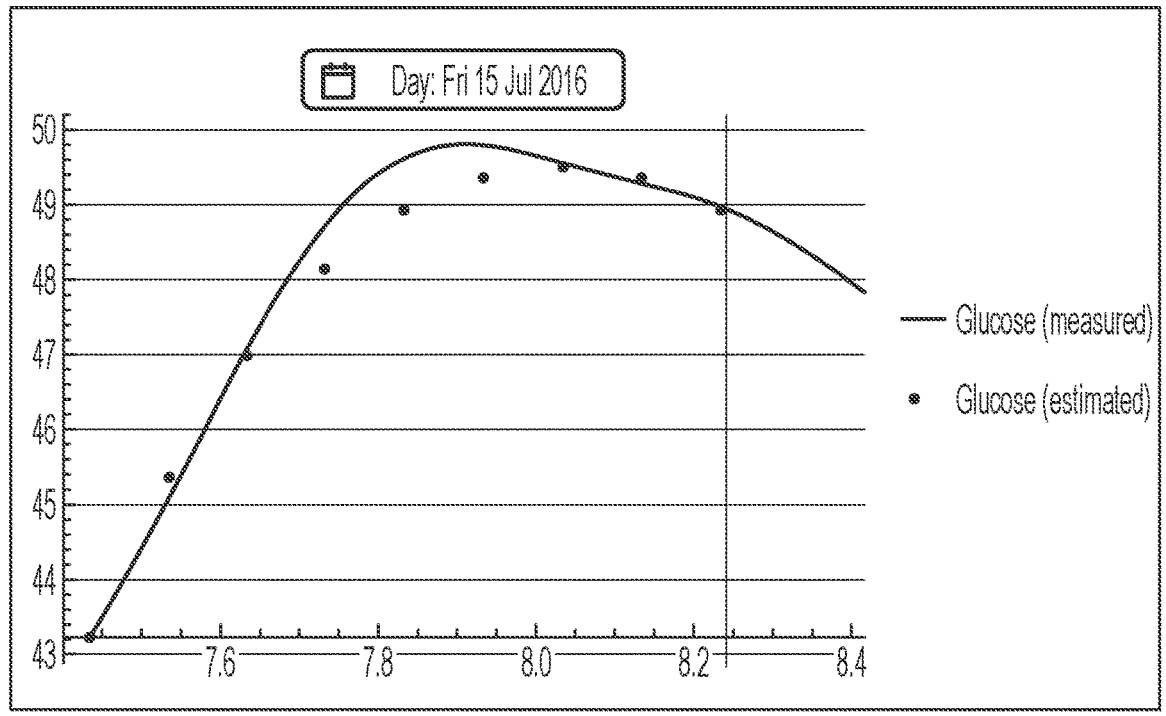
FIG. 28B is a graph plotting measured and estimated blood glucose levels, in accordance with some embodiments.

In an example, a Glucose Absorption and Insulin Assimilation (GAIA) model can be a biomathematical model to describe and predict the user's glucose metabolism and its interaction with insulin. The insulin may be injected insulin (exogenous) for patients who receive insulin injections or endogenous insulin. The GAIA model can use the user's historical data on food consumption as well as blood glucose and insulin levels to predict glucose responses. The GAIA model can use 2, 3, 4, 5, 6, 7, 8, 9, 10, 11, 12 or more historical meals from the user, coupled with their respective glucose and insulin levels, to predict the user's glucose and insulin responses to one or more new meals. FIG. 28A illustrates a flow chart of the GAIA model to predict glucose and insulin interactions in the body. An exemplary graph plotting measured glucose levels and GAIA-estimated blood glucose levels is shown in FIG. 28B.

The GAIA model can be defined by using one or more models for glucose G(t) and insulin I(t) in the blood. In an example, the glucose model can be a differential equation for the concentration of glucose in the blood as a function of time, as shown by the following equation:

$$\frac{dG}{dt} = a(t) + e(t) - u(t) - \phi(G, I)$$

where a(t) is the rate of glucose absorption from food in the blood, e(t) is the rate of endogenous glucose production by the liver, u(t) is the rate of glucose utilization by the body, and $\phi(G,I)$ represents the glucose-insulin interaction in the blood.

Figure 29:
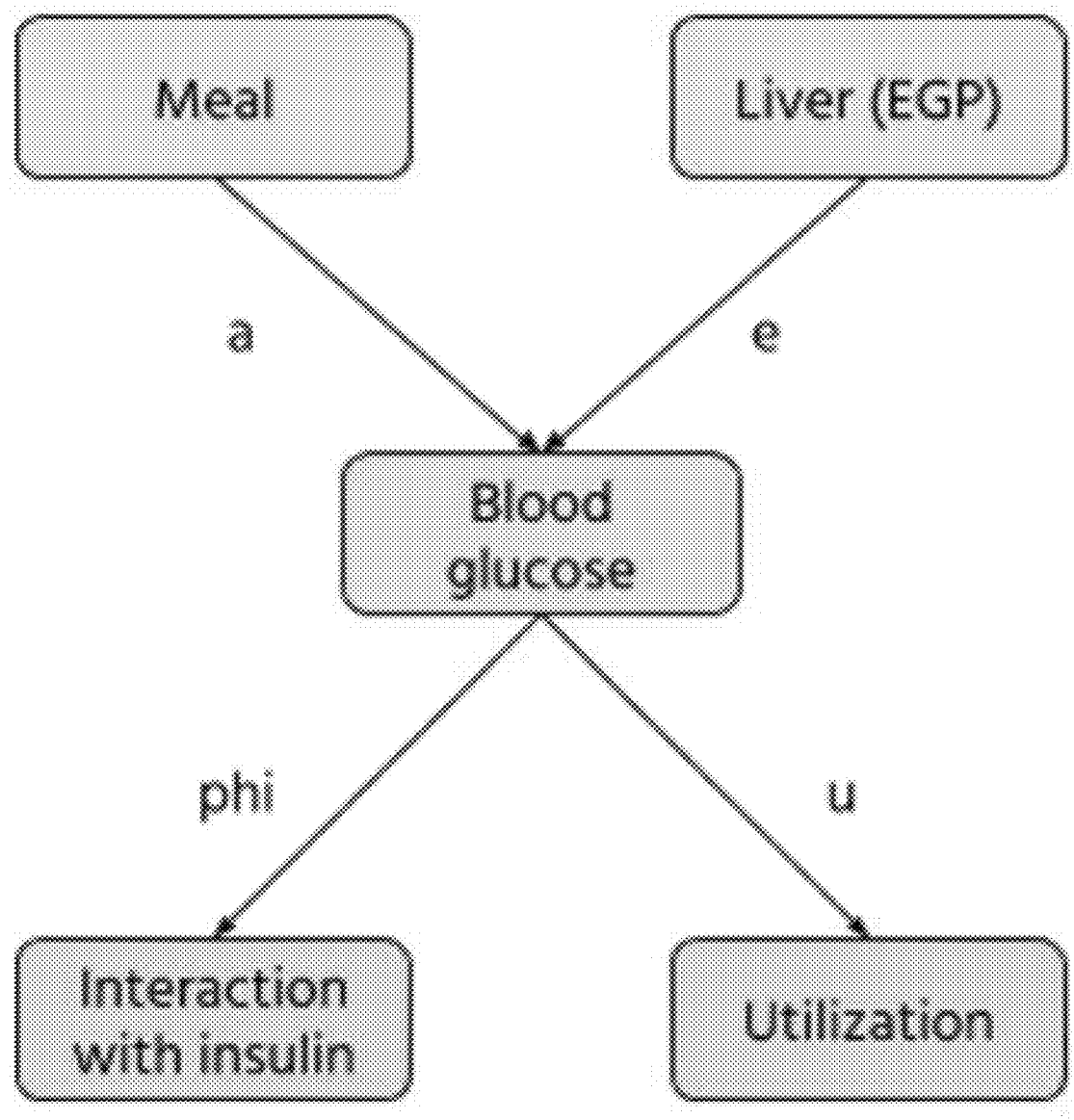
FIG. 29 illustrates a four-arm blood glucose model.

In healthy individuals with normal blood glucose levels, a total glucose uptake (utilization+interaction; or u(t)+$\phi$(G,I)) can range from about 1.9 to about 2.2 mg·kg$^{-1}$·min$^{-1}$. FIG. 29 illustrates a four-arm blood glucose model modeled using the above equation.

The rate of glucose absorption from food a(t) can depend on several parameters. Such parameters may be meal-dependent or meal-independent. For example, the rate of glucose absorption from food a(t) can be described by four meal-dependent parameters ($a_1$, $a_2$, $a_3$, $a_4$) that can represent a rate at which the glucose absorption increases or decreases, and the total amount of glucose absorbed after a given meal.

A simplified model can be constructed showing an expected glucose absorption rate for meals over an immediate duration after the meal (e.g., less than 2 hours) or for non-complex meals over an extended time period (e.g., more than 2, 3, 4, 5, 6, 7, 8, 9, 10 or more hours). If a meal contains substantial amounts of fats or protein, then the glucose absorption may be slower. As such, calculating the glucose absorption may include multiple maxima that are not captured by this model. In such cases, the model may only be used for the immediate duration after the meal (e.g., less than 2 hours).

The rate of endogenous glucose production (EGP) by the liver into the bloodstream e(t) can depend on several parameters. Such parameters may be meal-dependent or meal-independent. For example, the rate of EGP can be described by two meal-dependent parameters ($\varepsilon_1$, $\varepsilon_2$) and I(t) which is a function of insulin in blood, and where $\varepsilon_1$ represents a baseline endogenous glucose production in the absence of insulin, and $\varepsilon_2$ represents the rate of endogenous glucose production decrease with plasma insulin.

The rate of glucose utilization u(t) can depend on several parameters. Such parameters may be meal-dependent or meal-independent. For example, the rate of glucose utilization u(t) can be described as a function that grows nonlinearly for duration of a meal, which function can depend on three meal-independent parameters, where $v_1$ and $v_3$ represent the two asymptotes of the glucose utilization rate (at the initial time and final time respectively), and $v_2$ represents the rate at which the utilization rate u(t) varies. The rate of glucose utilization u(t) may be useful for breakfasts since glucose utilization is expected to surge in the mornings after an individual wakes up from sleep.

The glucose-insulin interaction in the blood $\phi$(G, I) can be meal-dependent or meal-independent. For example, the glucose-insulin interaction in the blood $\phi$(G, I) can be modeled as a non-linear interaction that is meal-independent. The glucose-insulin interaction in the blood $\phi(G, I)$ can be a function of different parameters, e.g. the blood glucose concentration $G(t)$, the plasma insulin concentration $I(t)$, an insulin sensitivity $\lambda$, and $G_0$ which represents how much insulin sensitivity decreases as blood glucose level increases for each patient. The interaction term $\phi(G, I)$ can be approximated using a Taylor series around different blood glucose concentrations.

Figure 30:
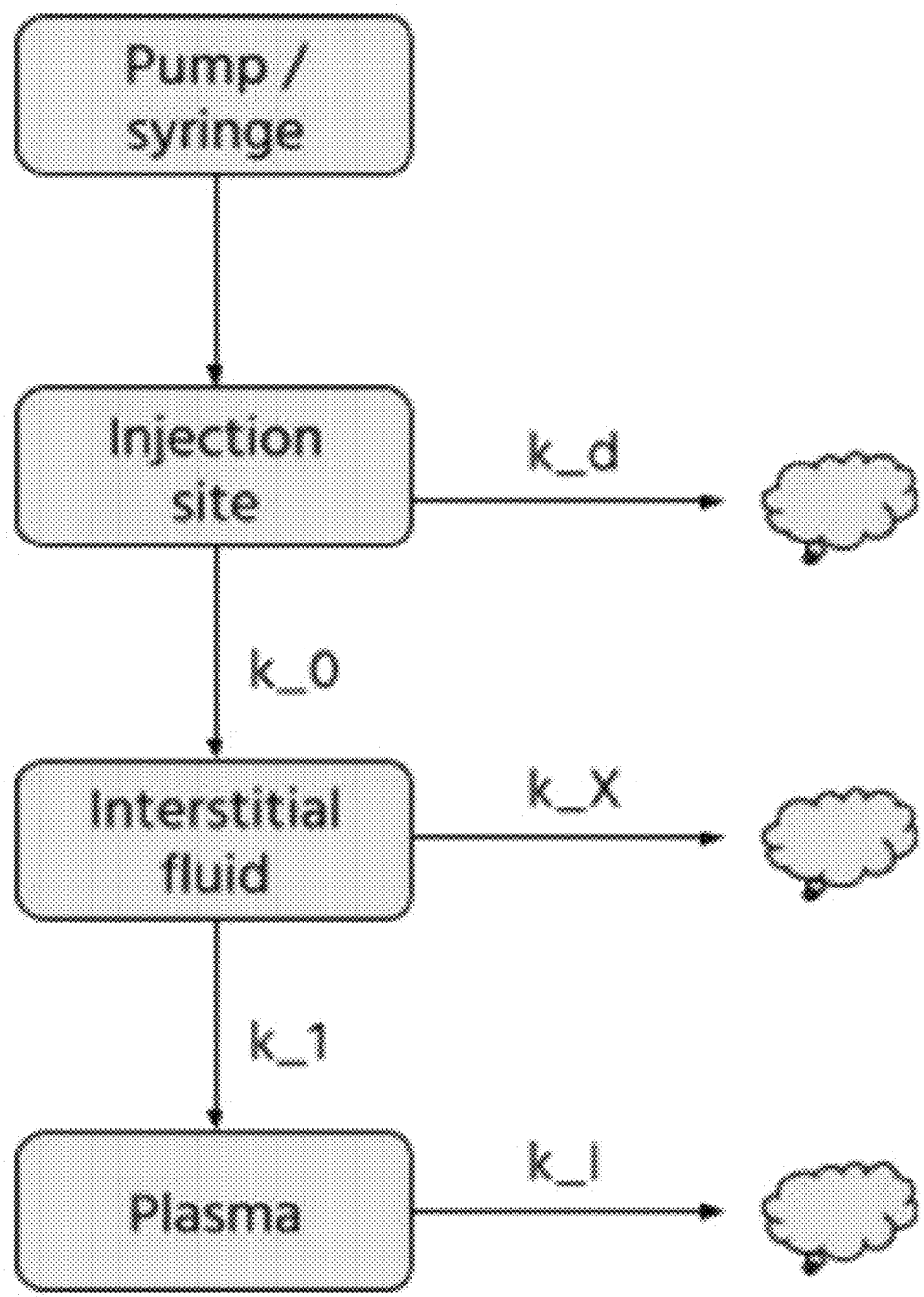
FIG. 30 is a flow chart of propagation of exogenous insulin into the body, in accordance with some embodiments.

The concentration of plasma insulin $I(t)$ can vary for each patient. For example, for patients living with type 1 diabetes for over a year, all insulin in the body may be assumed to have been provided by an exogenous source S. The source S can be either an insulin pump or a manual insulin injection. The insulin model for patients with type 1 diabetes can us a three-compartment model, as described by the following differential equation:

$$\frac{d}{dt}\begin{bmatrix} I_{inj} \\ I_{isf} \\ I \end{bmatrix} = M \begin{bmatrix} I_{inj} \\ I_{isf} \\ I \end{bmatrix} + \begin{bmatrix} S \\ 0 \\ 0 \end{bmatrix}$$

where $I_{inj}$ is a volume of insulin at an injection site,
$I_{isf}$ is a volume of insulin in the interstitium (interstitial fluid),
I is the plasma insulin concentration as a function of time,
S is the rate of insulin provided by the source (often an insulin pump).
The source S can be represented as a superposition of fixed basal rates, square boluses, and normal boluses (represented by delta functions). The rate constants of insulin transfer through the various compartments are represented by the matrix M:

$$M = \begin{bmatrix} -k_d - k_0 & 0 & 0 \\ k_0 & -(k_x - k_1) & 0 \\ 0 & \frac{k_1}{V_i m} & -k_I \end{bmatrix}$$

where m is the mass of the patient in kilograms,
$k_0$ is a rate constant for the transfer of insulin from the injection site to the interstitial fluid (1/hour),
$k_1$ is a rate constant for the transfer of insulin from the interstitial fluid to the plasma (1/hour),
$k_d$ is a rate constant for the insulin loss at site (1/hour),
$k_x$ is a rate constant for the transfer of insulin from the interstitial fluid outside of the blood (unused insulin; 1/hour),
$k_I$ is a rate constant for the disposing of plasma insulin (unused insulin; 1/hour), and
$V_i$ is an effective volume of plasma per body weight (liters per kilogram).
FIG. 30 illustrates a flow chart of such propagation of exogenous insulin from injection to the interstitial fluid to the plasma, as well as the respective rate constants. The flow chart also includes potential losses of insulin and their rate constants.

As illustrated in the above, by way of example only, the GAIA model can utilize 11 parameters, including 4 glucose absorption parameters ($a_1$, $a_2$, $a_3$, $a_4$), 2 endogenous glucose production parameters ($\varepsilon_1$, $\varepsilon_2$), 3 glucose utilization parameters ($v_1$, $v_2$, $v_3$), and 2 glucose-insulin interaction parameters ($\lambda$, $\phi$). Some of the parameters can be meal-dependent, thus may vary from one meal to another. Some of the parameters can be meal-independent, thus may remain fixed over duration of multiple meals. Some parameters may switch between meal-dependent to meal-independent, from meal to meal. The GAIA model can use at least one prediction pipeline to make at least one prediction on the changes in blood glucose level of a user. In an example, the pipeline can include the following steps: (1) identify one or more historical meals that have sufficient and reliable data (e.g., an historical meal with known ingredients, with respectively tracked glucose and insulin levels for 2 hours before the meal and 4 hours after the meal); (2) fit the measured glucose and insulin levels of each of one or more historical meals to the above models/equations, and obtain a parameter space of all physical values and 11 parameters of the GAIA model, in which the parameter space may be a set of all possible combinations of the physical values and the 11 parameters; (3) generate a distribution function of the parameter space; (4) repeatedly sample each combination from the parameter space by (i) recalculating the meal-dependent parameters with the generated meal-independent parameters, (ii) calculate the error in the fit for each meal, (iii) calculate the total error over all meals, and (iv) repeat (i)-(iii) as long as the total error decreases; and (5) use the finalized parameters to generate a prediction model that is personalized for the user. Furthermore, the insights and recommendation engine 230 can use the finalized parameters and machine learning to study how other biomarkers of the user may have affected the meal-dependent parameters.

Figure 31:
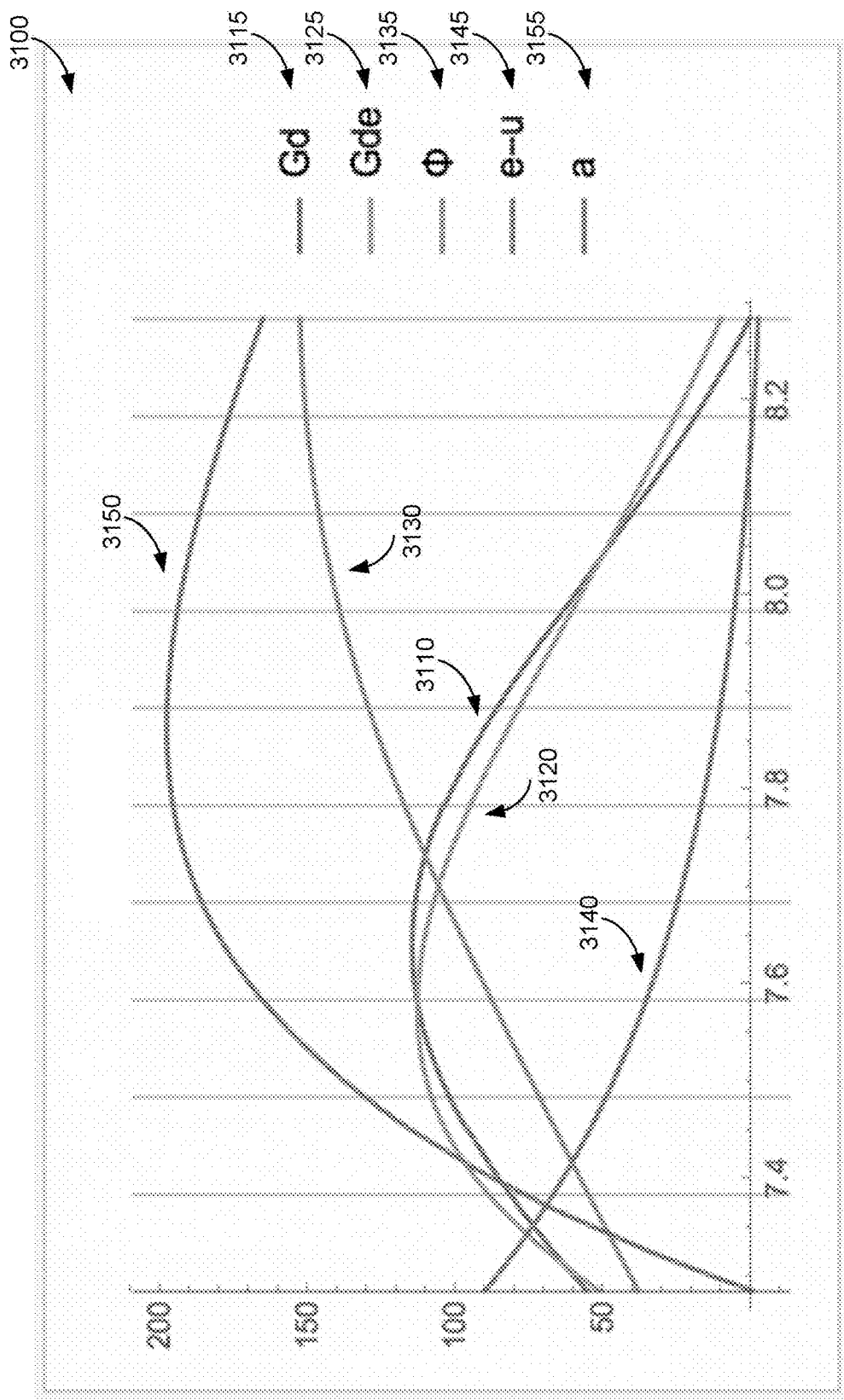
FIG. 31 illustrates an exemplary fitting of glucose absorption and insulin assimilation model, in accordance with some embodiments.

FIG. 31 illustrates an exemplary fitting 3100 of the GAIA model. Line 3110 is a measured rate of the change of the blood glucose level 3115. Line 3120 is an estimated rate of the change of the blood glucose level 3125. The estimated rate of the change of the blood glucose level is similar to the measured rate of the change of the blood glucose level. Line 3130 is the glucose-insulin interaction in the blood 3135. Line 3140 is a subtraction of the rate of glucose utilization by the body from the rate of endogenous glucose production by the liver 3145. Line 3150 is the rate of glucose absorption from food in the blood 3155.

The insights and recommendation engine 230 can be used for passive food tracking. Factors such as physical activity and sleep can be tracked passively and automatically via wearable devices (e.g., Apple Watch, Fitbit, Samsung Gear, Samsung Galaxy Watch, Android Wear, etc.). Additionally, the blood glucose level can be tracked passively and automatically via the CGM device. On the other hand, tracking food intake can require proactive and frequent interventions by a user (e.g. manual logging via voice or text). Such food intake tracking can be a tedious and unreliable process for data collection. By using machine learning, the insights and recommendation engine 230 can combine a group of user-specific parameters to generate a prediction model for passive food tracking. The parameters can include the user's geolocation using the GPS on a user device. The parameters can include changes in the user's blood glucose level monitored by the automatic blood glucose logging function. The parameters can include the user historical food and/or beverage consumption and blood glucose response data, as well as the food ontology of the food analysis system 210. In an example, when there is a spike in the user's blood glucose level, the insights and recommendation engine 230 can (1) search for the user's historical food items with a similar blood glucose response (e.g., intensity and duration); (2) generate a list of available foods in the vicinity of the user; (3) use the GAIA model to predict the user's blood glucose response to each of the available foods in (2); (4)

find food items that are repeatedly consumed by the user; (5) find common food items with a similar glucose profile among steps (1) to (4); and (6) predict which of the common food items the user most likely consumed in the past 2-3 hours. The steps aforementioned can be used to assist in the passive food tracking. Additional parameters for generation a prediction model for passive food tracking can include sound made from chewing foods, absorption spectrum of foods, and partial chemical composition of foods.

Figures 32A, 32B:
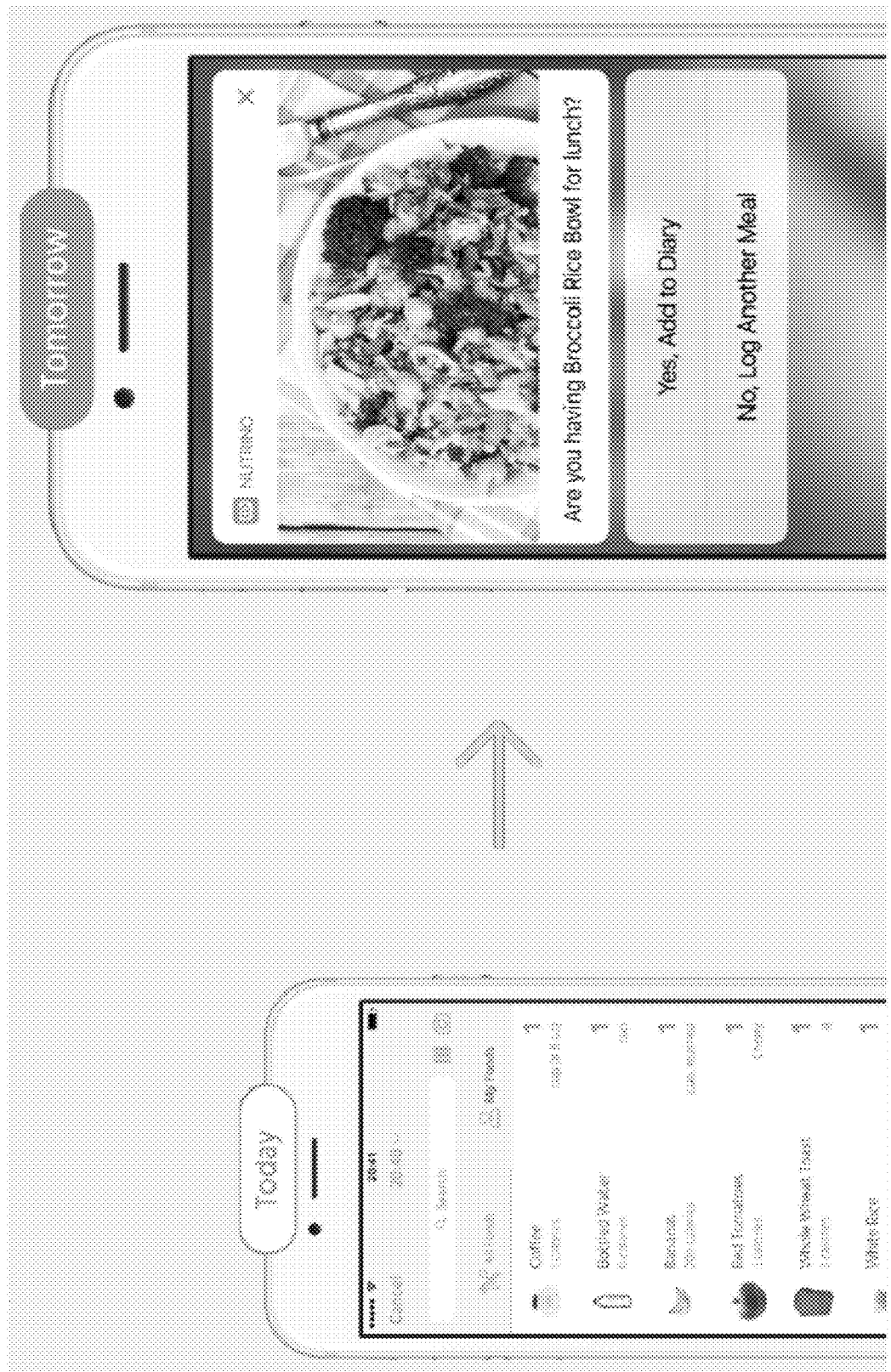
FIGS. 32A-32B illustrate exemplary windows of a GUI-based software interface showing prediction of eating patterns, in accordance with some embodiments.

The insights and recommendation engine 230 can predict a user's eating patterns or habits. As much as 78% of meals can repeat themselves for an individual's diet. The insights and recommendation engine 230 may find re-occurring patterns in the diet based on (1) the user's historical meal or beverage consumption data, (2) relations between different foods derived from the food ontology, and (3) location and/or time of day. For example, as illustrated in FIGS. 32A-32B, the user may have a habit of eating bananas, red tomatoes, whole wheat toast, and white rice on a first day, and a broccoli rice bowl on a second day. Next time the user consumes a sub-combination or an entirety of bananas, red tomatoes, whole wheat toast, and white rice, the insights and recommendation engine 230 may predict that the next meal would be the broccoli rice bowl. The insights and recommendation engine 230 can use the GUI-based software interface to ask the user to confirm or correct the prediction prior to logging the meal. Based on the user's response, the insights and recommendation engine 230 can confirm or improve its eating pattern prediction algorithm. In another example, a user can input "omelette" in the GUI-based software interface, and the insights and recommendation engine 230 may predict that the next most likely foods to be logged can be "bread" and "coffee" and auto-complete the user's meal as "Omelette with sliced bread and a cup of coffee." Such auto-completion capability can allow user clicks and/or inputs to be reduced by at least 30, 40, 50, 60, 70%, or more.

Thus, if the user opens the GUI-based software interface on a user device, the insights and recommendation engine 230 can (1) detect time and/or the user's geolocation using GPS; (2) search for the user's repeated historical meals at a similar time or geolocation; (3) generate a list of available meals in the vicinity of the user; (4) find common food items among (1)-(3); and (5) predict which of the common food items the user is most likely to consume soon. As shown in FIG. 32B, the insights and recommendation engine 230 may use the GUI-based software interface to ask and/or confirm if the prediction was correct. Based on the use response, the insights and recommendation engine 230 can confirm or improve its eating pattern algorithm.

The insights and recommendation engine 230 can also find food consumption patterns of each user and of a broad population. The broad population can be a collection of 5, 10, 100, 10,000, 100,000 or more individual users. The insights and recommendation engine 230 can combine the detected food consumption patterns of the user and the detected food consumption patterns of the broad population to determine in which type of a population that the user may belong.

In addition to glucose and insulin, the insights and recommendation engine 230 (herein referred to as the "engine") can be used to track and/or predict other factors that may affect and/or be affected by foods. The engine can be used to calculate antioxidant (e.g. thiols, vitamin C, etc.) levels. By using a device that can measure antioxidants at a position in the body (e.g. skin) automatically or with human intervention, the engine can generate one or more digital signatures for the user to track and predict antioxidant responses to foods. The engine can be used to calculate blood pressure levels. By using a continuous blood pressure monitoring device, the engine can provide insight on the relationships between foods and blood pressure, especially for users with hypertension or other cardiovascular conditions. The engine can be used to calculate digestion problems. By using an implantable (semi- or completely permanent) or swallowable (temporary) sensors, the engine can provide insight on the relationship between foods and the conditions of the digestive track (e.g., pH, contraction intensity and/or frequency, etc.). Such function may help patients with digestion problems (e.g., gastroesophageal reflux disease (GERD), Irritable bowel syndrome (IBS), etc.) eliminate foods that may hinder their quality of life. The engine can be used to calculate onset of migraines. By studying associations between foods and migraines (e.g., from manual user input), the engine can help users with chronic migraines to eliminate foods that may be predicted to cause migraines. The engine can be used to help users with sleep. The quality of sleep may be measured using a wearable device (e.g., Apple Watch, Fitbit, Samsung Gear, etc.). Sleep can be affected by food intake, but, conversely, sleep may also affect the user's hunger or metabolism. Thus, the engine can find correlations between the user's food intake and quality of sleep, and provide insights and recommendations accordingly. For example, the engine can use the GUI-based software interface to inform the user that "In 92% of the times you drank coffee after 4 P.M., you slept poorly." Alternatively or in addition to, the engine may relationships between foods and other factors including, but not limited to including, lethargy/fatigue, drowsiness, or cortisol levels. Any feature of a user's daily activity or physiology that can be measured by a wearable device or medical device may be analyzed by the engine to continuously provide users a better understanding of their bodies and/or a healthier diet.

Figures 33A, 33B, 33C:
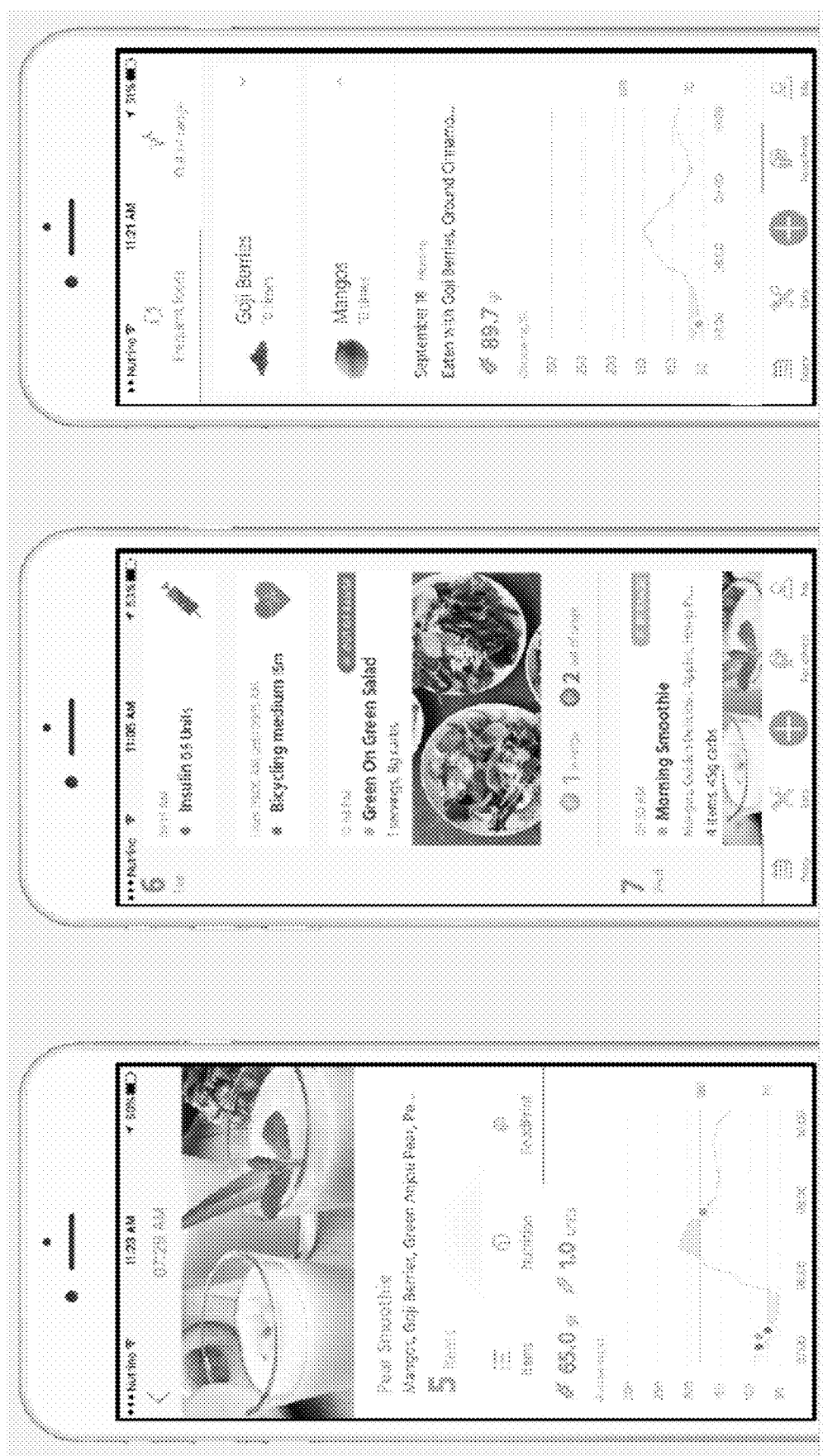
FIGS. 33A-33C illustrate exemplary windows of a GUI-based software interface showing multiple features, in accordance with some embodiments.

FIGS. 33A-33C illustrate exemplary windows of the GUI-based software interface showing multiple features. As shown in FIG. 33A, the window may display which food item the user has consumed (e.g. Pear Smoothie), how many ingredients are found or predicted to be present in the food item (e.g., Mangos, Goji Berries, Green Anjou Pear, etc), a generic or specific picture of the food item (e.g. directly imported from a respective restaurant's website), as well as a continuous tracking of the user's blood glucose level and insulin injection(s). As shown in FIG. 33B, the window may display a timeline of multiple events, including insulin injection and its dosing amount, daily activities (e.g. Bicycling), and food items or dishes (e.g., Green on Green Salad, Morning Smoothie). As shown in FIG. 33C, the window may display which food items the user has frequently consumed (e.g. Goji Berries, Mangos), and an average blood glucose response to such food items.

Figure 34B:
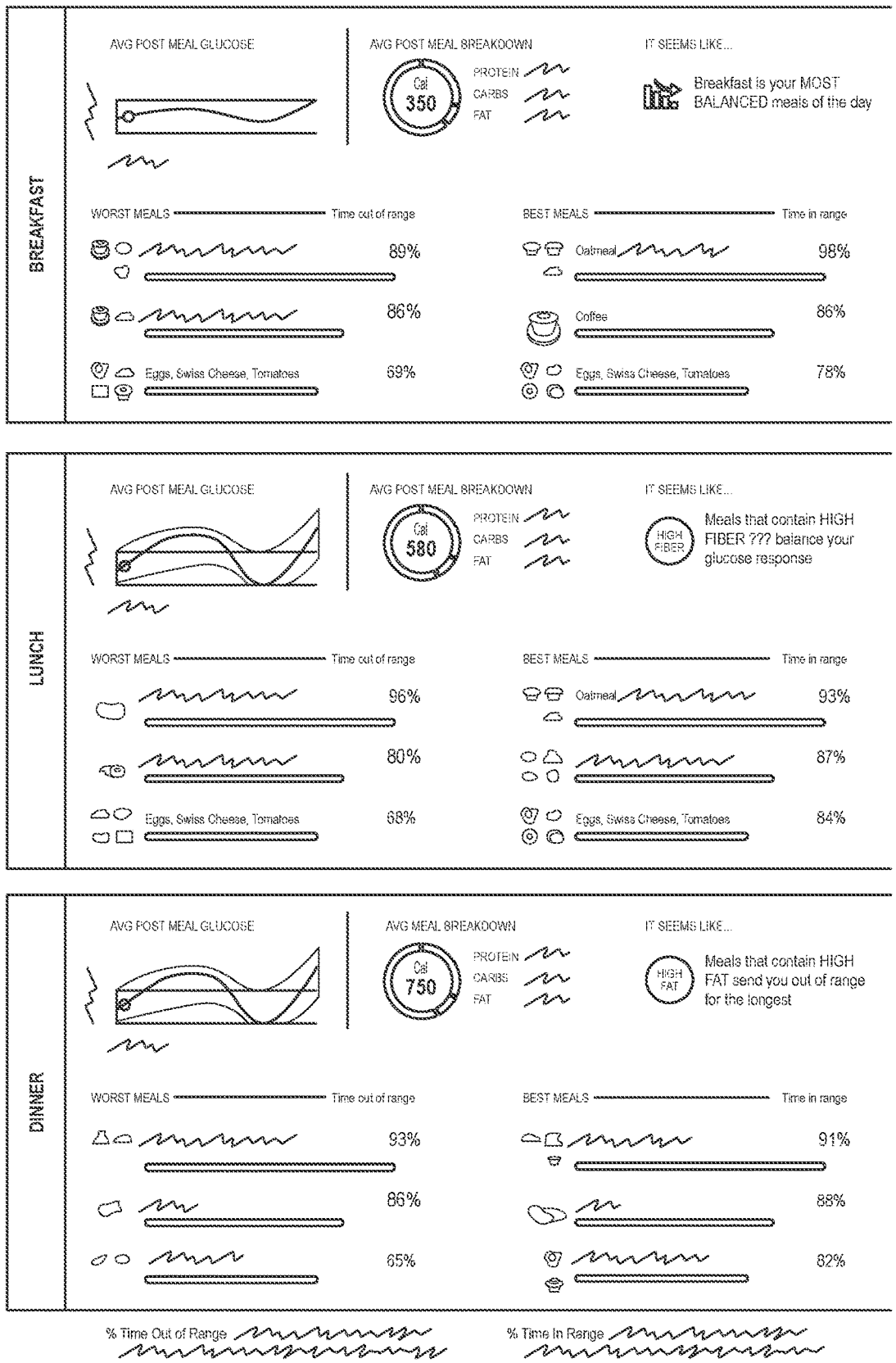
Figure 34C:
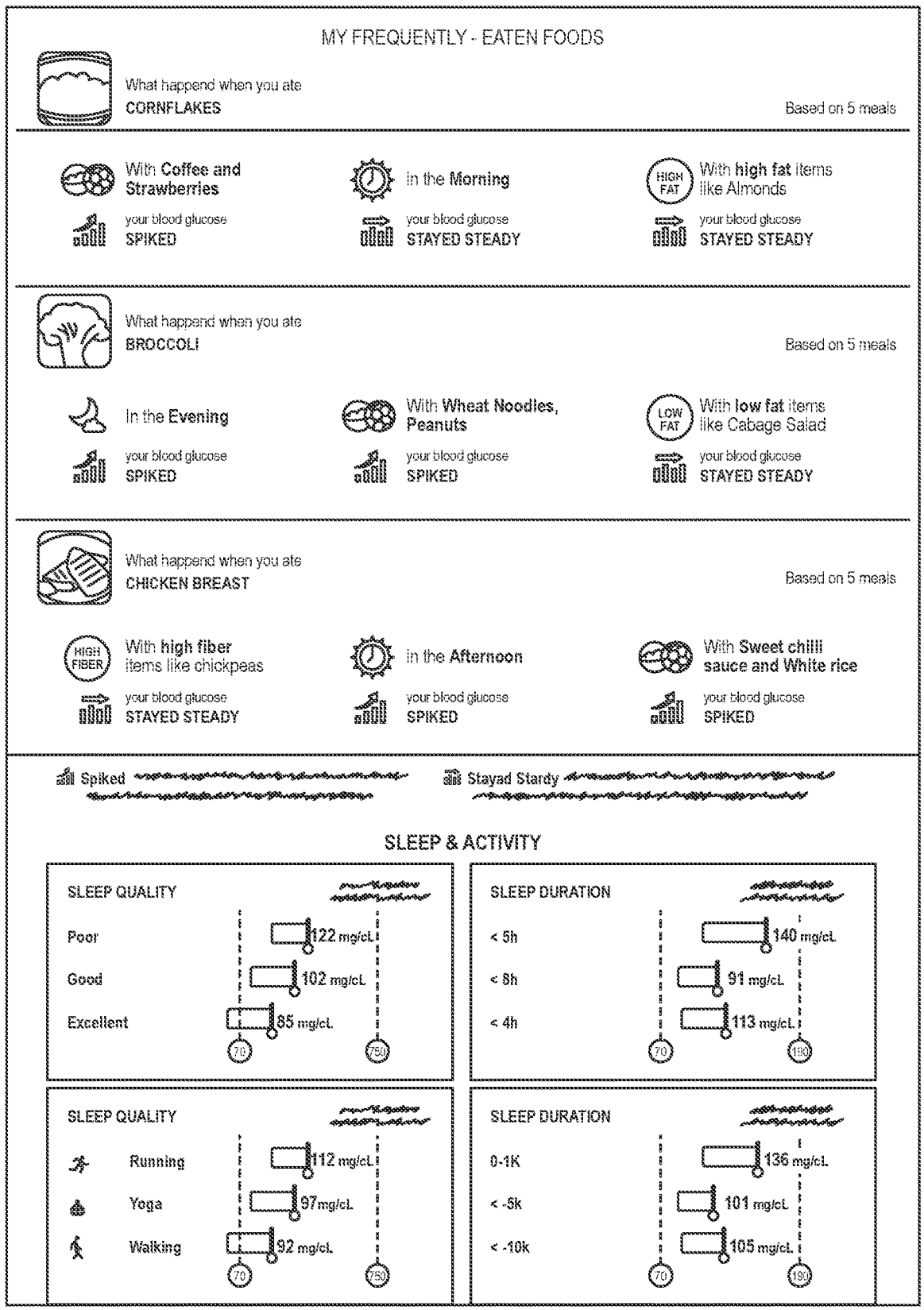

FIGS. 34A-34C illustrate exemplary windows of a GUI-based software interface showing a compressive report by the insights and recommendation engine 230. As shown in FIG. 34A, the window may display a graph showing a user's blood glucose measurements throughout the day. The window may display additional details about blood glucose, including the user's average weekly glucose level and its standard deviation value, the percentage of glucose measurements that have been in a predetermined target range (Time in target), below the target range, and above the target range. The window may also display popular eating hours, represented by the average of number of meals that have been consumed per every hour throughout the day, and a distribution plot of carbohydrates consumed (e.g., in grams)

per every hour throughout the day. The window may also display average glucose values at 2 hours post-meal (e.g., breakfast, lunch, and dinner). The window may also indicate whether the average glucose values at 2 hours post-meal are above or below the predetermined target range of blood glucose level. As shown in FIG. 34B, the window may display more details on the analyses of meals. Meals may be grouped into breakfast, lunch, and dinner. For each group, the window may display a minute-to-minute (or other intervals) change in blood glucose level during the 2 hour post-meal period, an average meal nutrition breakdown (e.g., protein, carbohydrates, fats, etc.), and an assessment of the balance of the average meal nutrition breakdown. In addition, the analyses of meals may include top three meals with significant changes in the blood glucose level, and top three meals with minimal changes in the blood glucose level. As shown in FIG. 34C, the window may display frequently eaten foods and their effects in the blood glucose level. In addition to foods, the window may also display correlations between the blood glucose level and other factors. The other factors can include sleep quality, sleep duration, activity type, and a number of daily steps.

Any of the embodiments described herein (e.g. relating to food analysis, food ontology, and personalized food/health/nutritional recommendations) are also suitable for use with the systems and methods for managing nutritional health as described in U.S. patent application Ser. No. 13/784,845 (published as US 2014/0255882) which is incorporated herein by reference in its entirety.

Calibration Kit

A calibration kit can be used to optimize the platform 200 to a user's physiological responsiveness to different foods. Optimizing the platform 200 may include optimizing the functions of the food analysis system 210, the device/data hub 220, and the insights and recommendation engine 230. As users can respond differently to the same food, and a wearable and/or medical device can have different compatibility to different users, the calibration kit may be used to set a food baseline for all users. Generating the food baseline profile for a user can include monitoring effects of different foods on the user's body as the user consumes one or more pre-packaged meals over a time period. One or more pre-packaged meals can contain known amounts of the foods. The monitored effects can be used to generate the food baseline profile. The calibration kit can be a modular kit. The calibration kit can include a monitoring system (e.g., a glucose monitoring system, a blood test, a genetic test, etc.) and one or more standardized meals (also referred to as "calibration meals"). The calibration meals can include food bars, beverages, or both. The platform 200 may know and have tested all features of the calibration meals (e.g., ingredient, nutrients, processing, etc.). In some examples, the user may put the device on the body (or perform the provided monitoring test), and consume one calibration meal per every morning. The user may be required to fast (e.g. for 12 hours) throughout the previous night. The device may measure the user's response to the calibration meal. The user can consume other foods throughout the day and track the foods to the platform 200 via the GUI-based software interface (e.g., food tracking by textual and voice recognition analysis, seamless food image logger, etc.). After a short period of time (e.g., a week), the platform 200 can use the data and predictions to set the baseline for the user. The baseline may be referred to as the user's unique, personalized food "finger print."

Figure 35:
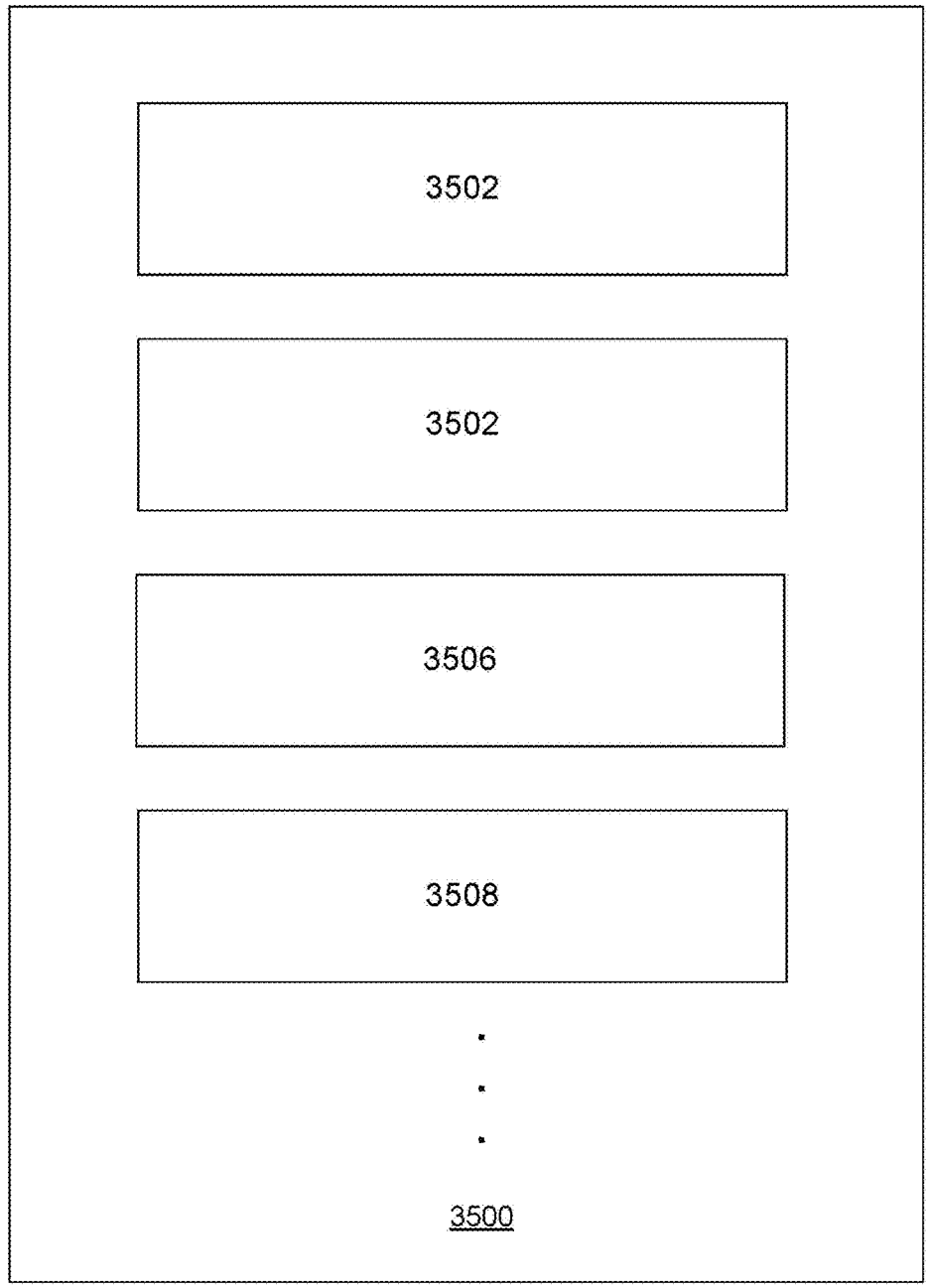
FIG. 35 shows an exemplary calibration kit in accordance with some embodiments.

FIG. 35 illustrates an exemplary calibration kit 3500. The calibration kit can contain a first box 3502 that includes a CGM device, a second box 3504 that includes a DNA collection kit for DNA testing (e.g., saliva collection kit), a third box 3506 that includes a biome collection kit for microbiome analysis (e.g., sample collected from gut, genitals, mouth, nose, and/or skin), a fourth box 3508 that includes one or more calibration meals. The calibration kit may optionally include any of the above boxes, or different combinations of the boxes. The calibration kit can include 1, 2, 3, 4, 5, or more calibration foods. The calibration kit can include 2, 3, 4, 5, 6, or more boxes. The calibration kit can include 1, 2, 3, 4, 5 or more monitoring systems. In some embodiments, the calibration kit may include one or more other components/devices (e.g. blood testing kits, wearable device, or other biomarker tests/devices) that aid in generating a baseline health status of a user. The calibration kit may also include a detailed list of instructions for a user to easily follow. If necessary, the calibration kit can include a container for each collection kit.

Example 1

Healthcare Providers

Figure 36:
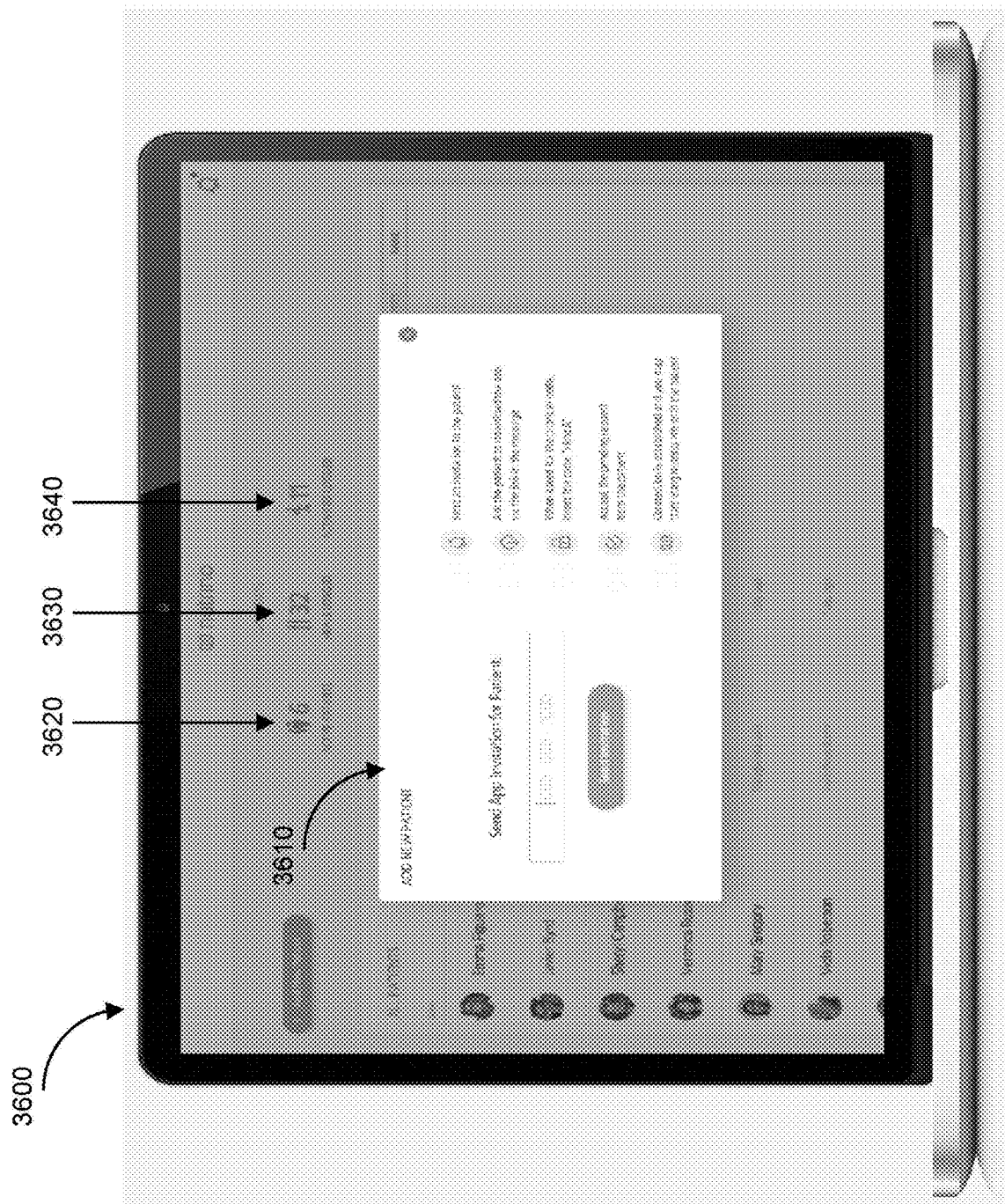
FIG. 36 illustrates an exemplary window of a web portal for healthcare providers in accordance with some embodiments.

End users of the insights and recommendation engine 230 and other features of the platform 200 can include healthcare providers. Healthcare providers can use a GUI-based software interface (e.g. a web portal) to monitor and study the effects that different foods may have on patients' bodies. The healthcare providers and the patients can share or exchange information by each connecting to the platform 200 as a hub. In some examples, the web portal can be used to monitor patients with type 2 and pre-diabetes. FIG. 36 illustrates an exemplary window 3600 of the web portal for the healthcare providers. On the web portal, as shown in the window 3600, the healthcare providers can invite new patient 3610, count a number of active patients that have accepted the invitation 3620, track how a number of meals 3630 and/or activities 3640 have been logged by the participants. The healthcare providers can select the meals 3630 and/or activities 3640 image on the window 3600 to connect to at least one additional window (not shown in FIG. 35) and access more data and analyses.

Figure 37:
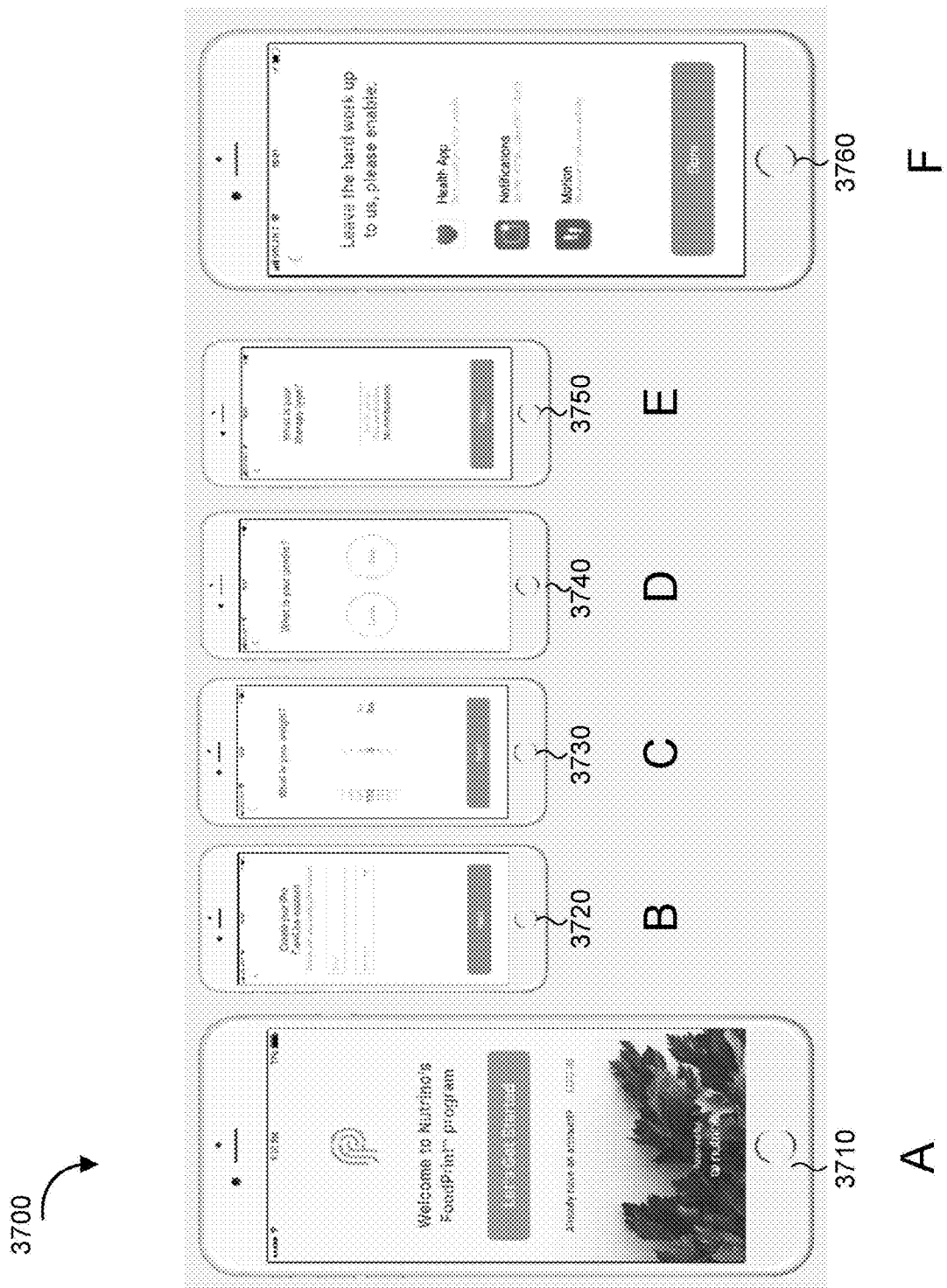
FIG. 37 (parts A through F) illustrate exemplary windows of a mobile application showing initial set up of the mobile application, in accordance with some embodiments.

A new user (e.g., a patient participant for a healthcare provider) can receive an invitation from the healthcare provider to install a GUI-based software interface (e.g. mobile application) on a user device (e.g. a smart phone). FIG. 37 (parts A through F) illustrate exemplary windows 3710-3760 of a mobile application on a user device. Subsequent to initiating the application for the first time (window 3710), the mobile application can ask the user to create an account (window 3720), input basic information about the patient, including weight (window 3730), height (not shown), gender (window 3740), diabetes therapy type, if any (window 3750), and enable access to other features on the user device (window 3760). The other features can include the notification function of the user device, or other mobile applications for health monitoring, motion detecting, photography, etc. Enabling access to the other features can automate multiple processes of the platform 200 and reduce its dependency on user input.

Figure 38:
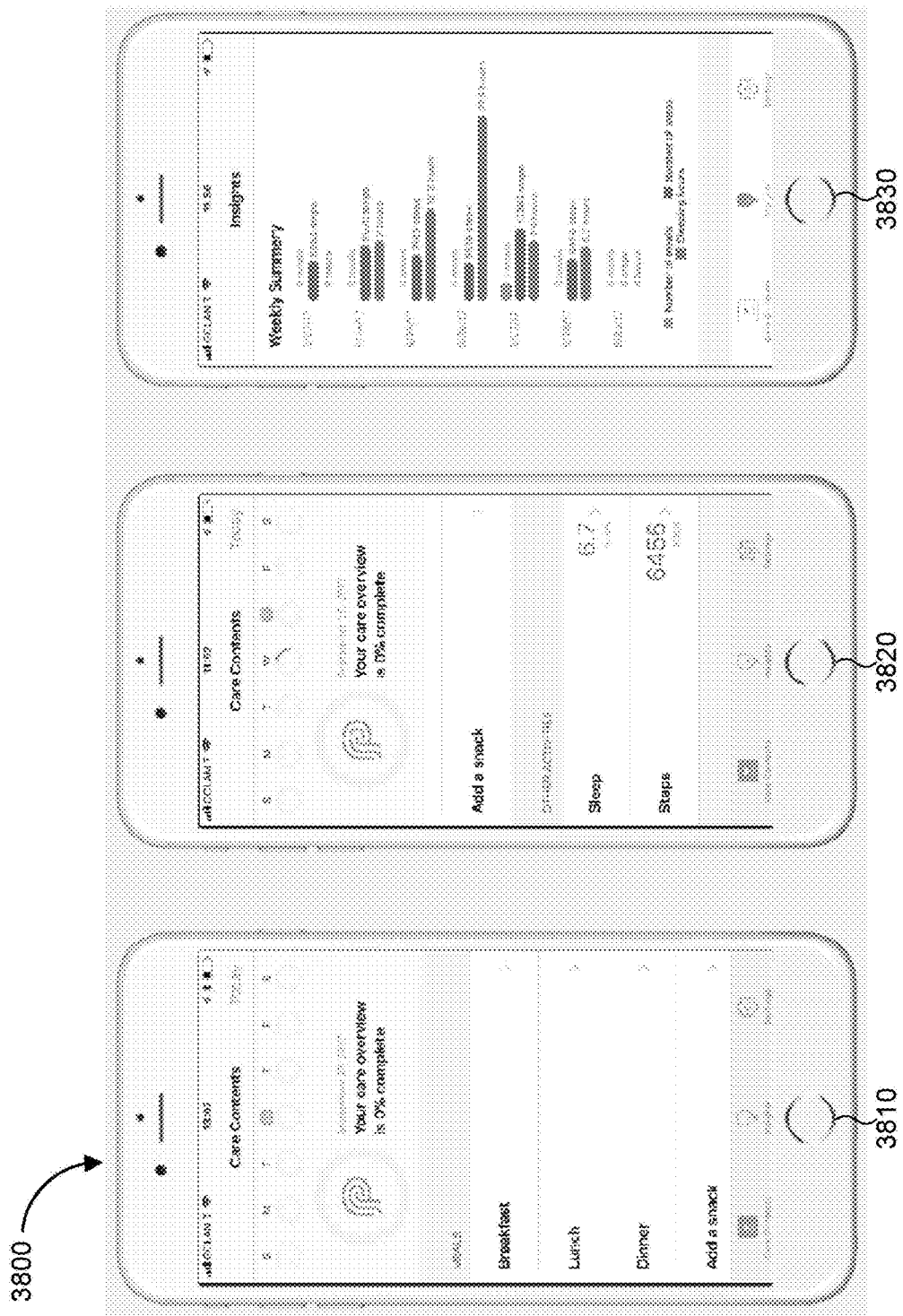
FIG. 38 (parts A through C) illustrate exemplary windows of a mobile application showing components of baseline data collection, in accordance with some embodiments.

The user can also receive a Calibration Kit to initiate optimization of the platform 200 to the patient's physiological responsiveness. The user can use one or more devices and consume one or more calibration foods included in the calibration kit for an initial short program (e.g., 1 week) for baseline collection. The user can also consume and track other foods and/or beverages. The platform 200 can use data and predictions generated from the initial short program to generate a baseline for the user. The baseline can reflect the user's physiological responsiveness to foods. FIG. 38 (parts A through C) illustrate exemplary windows 3810, 3820, and 3830 of the mobile application on the user device for baseline data collection. Data recorded can include meals (e.g., breakfast, lunch, dinners, etc.; window 3810), daily activities (e.g., sleep, steps, etc; not shown), and additional biomarkers (e.g. glucose level, insulin level, heart rate, etc.; window 3820). Data can be recorded by user input or by using trackers, such as wearable devices. During the baseline collection, the user can have access to summary of the data collected (insights). The summary can include a number of meals, walking steps, sleeping hours, etc.

Figure 39:
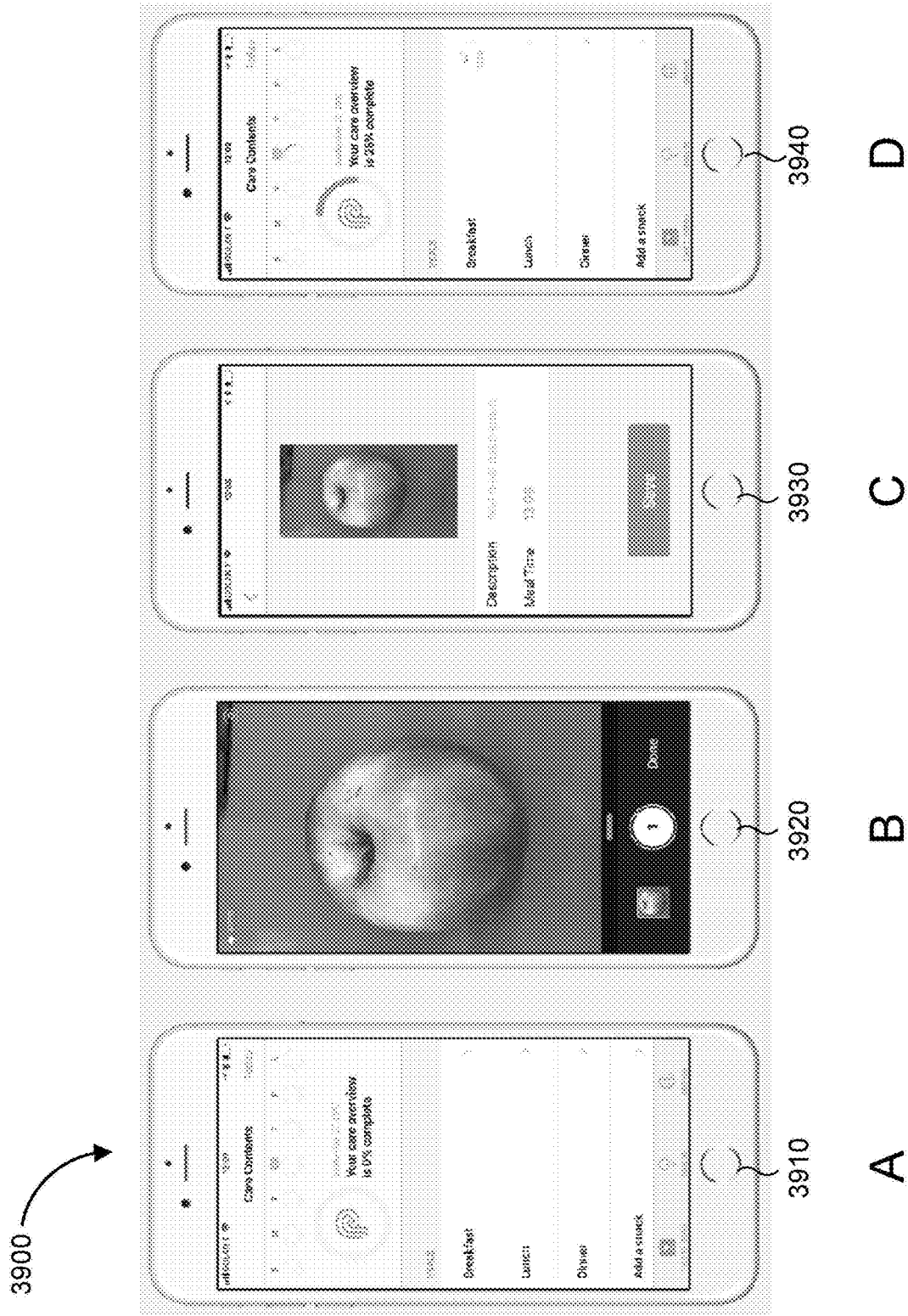
FIG. 39 (parts A through D) illustrate exemplary windows of a mobile application showing a food image logging interface, in accordance with some embodiments.

FIG. 39 (parts A through D) illustrate exemplary windows 3910-3940 of the mobile application on the user device showing food image logging interface. The user can select a meal (e.g., breakfast, lunch, or dinner; window 3910). For accurate logging and baseline data collection, the mobile application can allow the user to record snacks. The user can be prompted to the window 3920 to take a picture of a food item to be consumed (e.g., an apple). The picture of the food item can be recorded, and the mobile application can ask the user to input description and meal time for the food item (window 3930). If the user records the food item for breakfast, then the mobile application may check off breakfast from a list of meals to be recorded (window 3940).

Figures 40A, 40B:
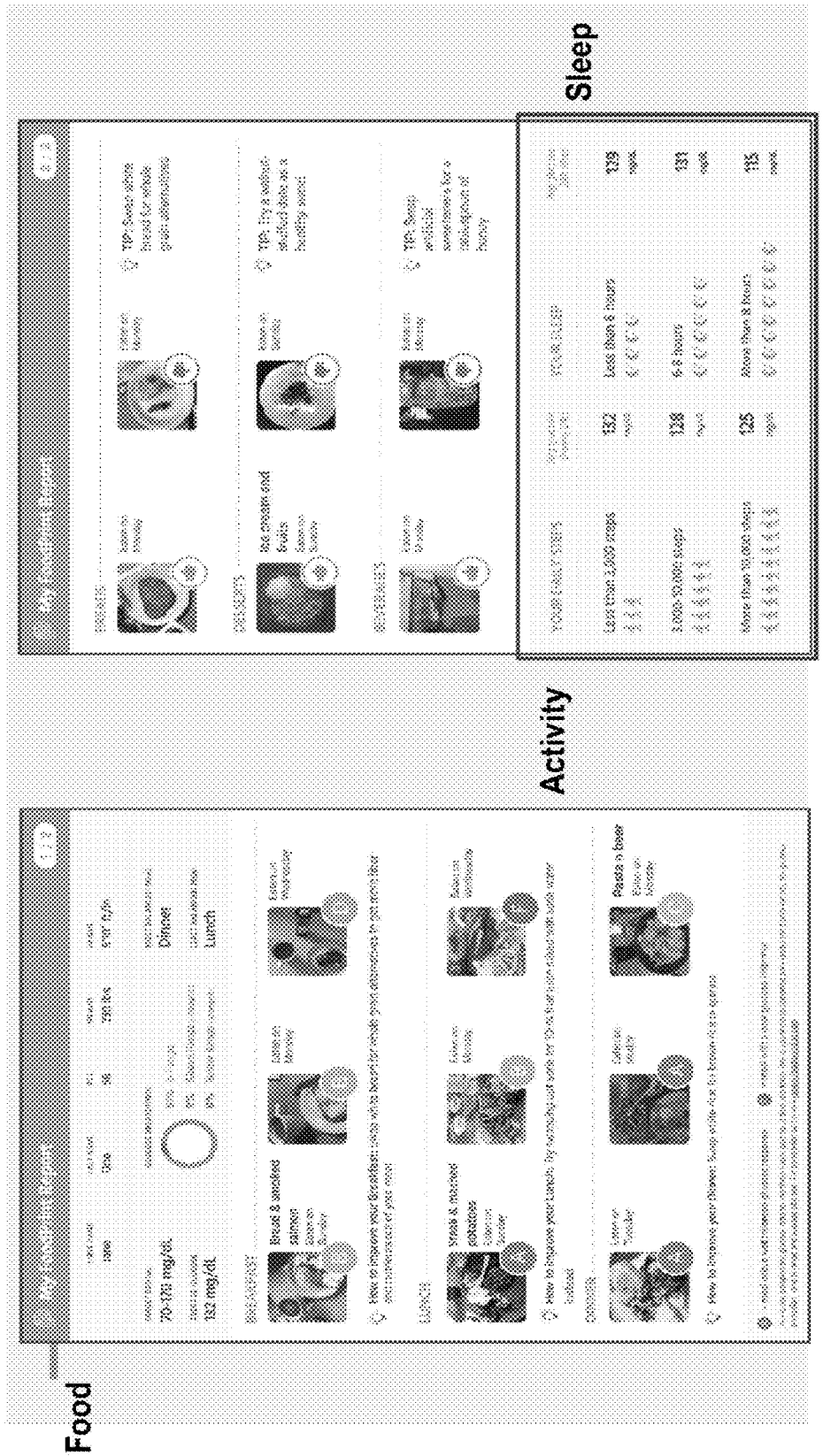
FIGS. 40A and 40B illustrate exemplary windows of a GUI-based software interface showing an analysis report of a user's data, in accordance with some embodiments.

After completion of the baseline data collection, the user can have access to a report of analyses and insights generated by the insights and recommendation engine 230. If the user is linked to a healthcare provider system or a health-related study, then the healthcare provider or a coordinator of the health-related study may have access to a portion or the entirety of the report. FIGS. 40A and 40B illustrate exemplary windows of a GUI-based software interface showing the report on the user's data. In some examples, the report may focus on factors that can influence blood glucose level: food, activity, and sleep. The report can inform a pre-defined target glucose level range (e.g. 70-170 mg/dL) for the user along with the user's average glucose level. The report can include assessment of one or more meals based on how the user's glucose level responded to one or more meals. The assessment can utilize a rating system (e.g., "A" for a balanced glucose response, "F" for a poor glucose response, etc.). The report can also show recommendations generated by the insights and recommendation engine 230. The recommendation can compare two food items consumed by the user and suggest if one of the two food items is a healthier option than the other of the two food items based on the user's physiological responses. In some examples, a recommendation can compare two types of breads (whole grain bread vs. white bread) and recommend swapping white brad for whole grain alternatives. Another recommendation can compare two types of desserts (ice cream and fruits vs. walnut-stuffed dates) and suggest that the walnut-stuff dates may be a healthier option than the ice cream fruits. A different recommendation can compare two types of beverages (a honey-containing drink vs. an artificial sweeteners-containing drink) and recommend swapping artificial sweeteners for a tablespoon of honey. Additionally, the report can show a correlation between to number of steps the user took and the user's respective average blood glucose level. The report can inform the user that the user's blood glucose level decreased from 132 mg/dL to 125 mg/dL when the user increased the number of steps from less than 3,000 steps to more than 10,000 steps per day. Furthermore, the report can show a correlation between sleep and blood glucose level. The report can inform the user that the user's blood glucose level decreased from 129 mg/dL to 115 mg/dL when the user increased a number of hours of sleep from less than 6 hours to more than 8 hours.

Example 2

Dietary Glucose Monitoring

Introduction

Every individual is unique. A body of each individual can process foods (e.g., meals, beverages, etc.) differently than those of other individuals. As a result, a same food (or foods) can have different effects on biomarkers (e.g., glucose levels) of different individuals. In addition the same food(s) can have different effects on the biomarkers of each individual when consumed at different times (e.g., in the morning and in the afternoon).

A plethora of databases and services are available to offer food, nutrition, and health advices. Examples of such databases and services include healthcare providers, food or nutrition manufacturers, restaurants, online and offline food recipes, and scientific articles. However, such nutritional and/or dietary guidelines available thus far are not tailored to each individual and limited in scope (e.g., types of foods, biomarkers, health conditions, etc.). Whether it be for recreational, cosmetic, medical, or other purposes, individuals inevitably have to rely on multiple sources of information to make food and nutrition-related decisions every day to improve or maintain health.

Thus, there is a need for systems and methods that can provide real time feedback on effects of the foods on each individual's health. There is a need for systems and methods that can continuously collect a vast amount of data (e.g., ingredients in a dish, nutrition information, glucose levels, blood pressures, temperature, etc.) from discrete sources, analyze and restructure the data into a common format, assess and predict correlations between an individual's consumed foods and biomarkers, and provide personalized nutrition recommendations based on the individual's health and metabolic state at any given time.

Dietary Glucose Monitor

The ecosystem 100 comprising the platform 200 that can be implemented as part of a dietary glucose monitor (DGM) 101 in accordance with some embodiments. The DGM 101 can provide each user with personalized nutrition insights based on effects of different foods on at least the user's glucose levels. The DGM 101 can provide real time feedback on effects of one or more foods that the user has consumed or will consume on the user's glucose level. The DGM 101 can provide recommendations on adjusting the user's diet or lifestyles to maintain or improve the user's glucose level, thereby maintaining the user's health. The DGM 101 can be applicable to any user, regardless of age, gender, race, health conditions, etc. The DGM 101 may or may not need calibration by the user prior to its usage.

The terms "food analysis system" and "food analysis module" (e.g., the food analysis system 210 as shown in FIG. 1) may be used interchangeably in the present disclosure.

The DGM 101 can comprise some or all components of the ecosystem 100, as shown in FIG. 1. In some embodiments, the DGM 101 can comprise the platform 200, which platform 200 comprising the food analysis module 210, the device/data hub 220, the insights and recommendation engine 230, and one or more of the devices 110. The components of the platform 200 can be in communication with each other. Thus, when describing a function of a component of the platform 200, one skilled in the art would be capable of understanding that it may be interpreted as a function of the component alone or in combination with one or more additional components of the platform 200. In an example, when describing a function of the food analysis module 201, one skilled in the art would be capable of understanding that it may be interpreted as a function of the food analysis module 201 alone or in combination with the device/data hub 220 and/or the insights and recommendation engine 230.

The DGM 101 can be applicable in a number of user applications. The DGM 101 can be used for a user with type 1 diabetes or type 2 diabetes in order to assess when the user should inject insulin. The DGM 101 can be useful for athletes to optimize their athletic performance. The DGM 101 can be useful for individuals interested in tracking food intake as way to monitor their weight loss diet.

Figure 59:
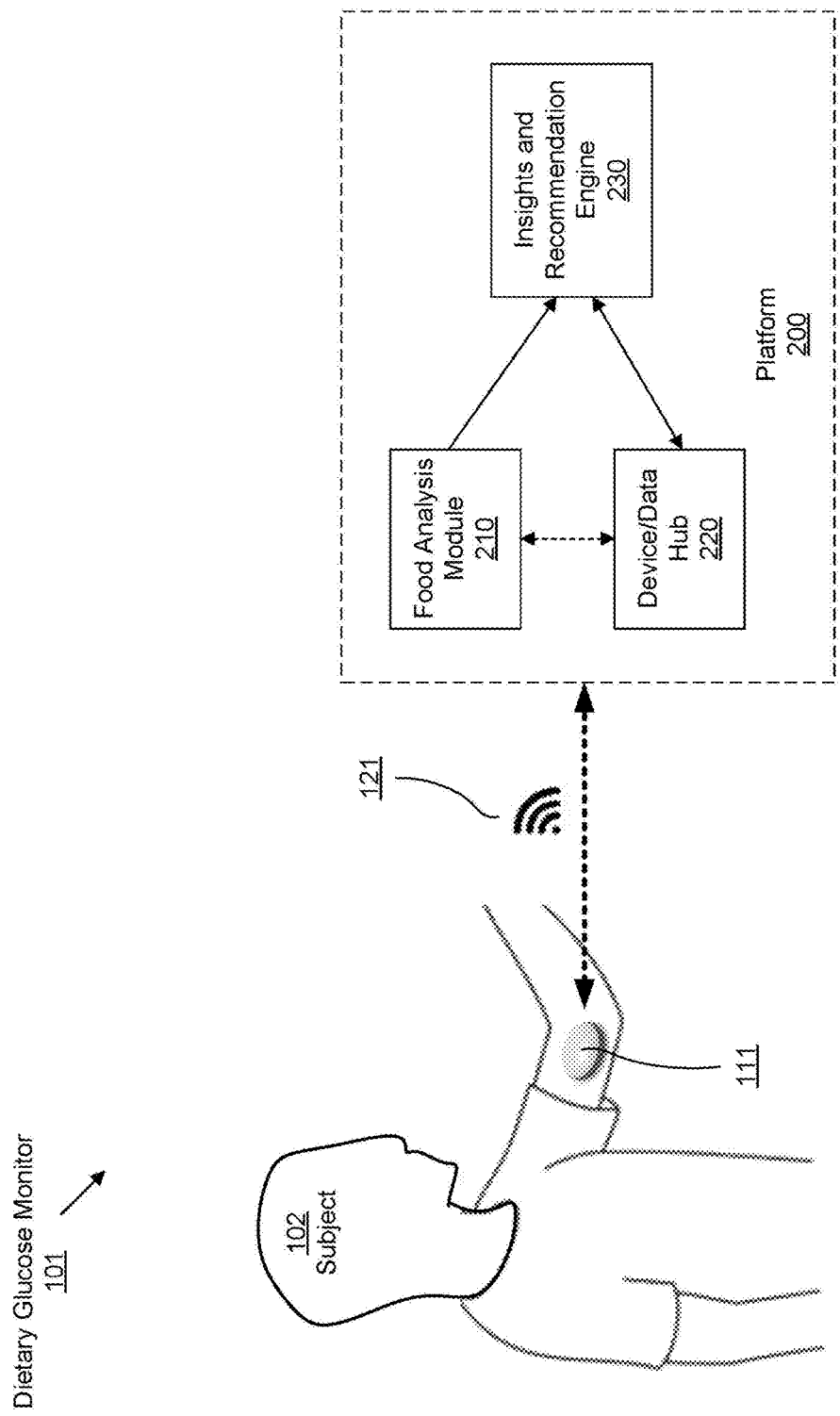
FIG. 59 illustrates an ecosystem for dietary glucose monitor for food analysis and personalized glucose level management, in accordance with some embodiments.

FIG. 59 illustrates an example of the DGM 101. The glucose level monitor 111 of the DGM 101 can be placed on or adjacent to the skin of the subject 102. The glucose level monitor 111 can be in communication 121 (e.g., Bluetooth, NFC, WiFi, etc.) with the platform 200 of the DGM 101.

Figure 60:
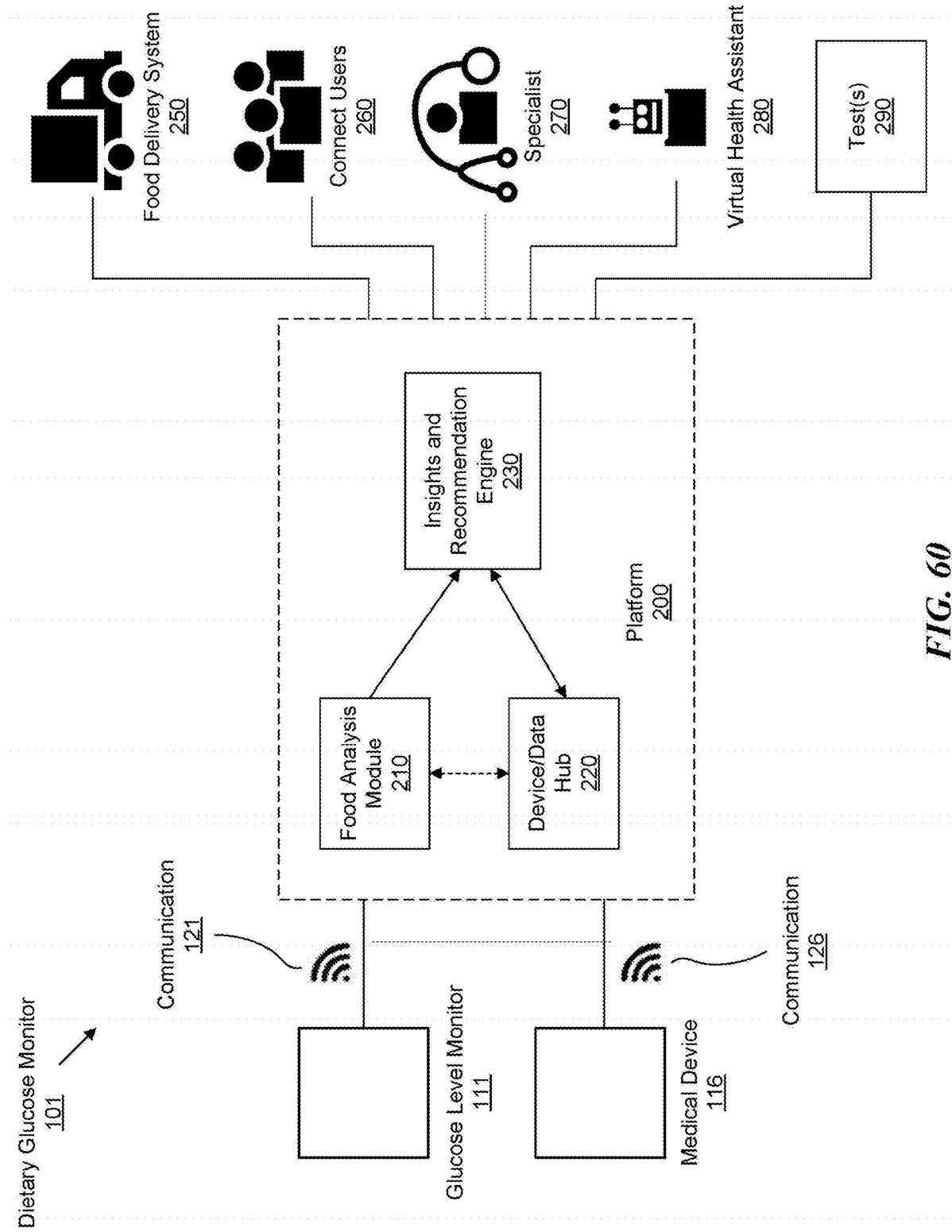
FIG. 60 illustrates another ecosystem for dietary glucose monitor for food analysis and personalized glucose level management, in accordance with some embodiments.

FIG. 60 illustrates further details of the DGM 101 in accordance with some embodiments. The DGM 101 can comprise the food analysis module 210 in communication with the glucose level monitor 111, wherein the food analysis module 210 is configured to (1) analyze data indicative of foods consumed by the user, and (2) determine an effect of individual foods on a glucose level of the user, based on changes to the user's glucose level as measured by the glucose level monitor. The DGM 101 can comprise the glucose level monitor 111.

The glucose level monitor 111 may be functional upon placement on anywhere in the body of the subject 102. The glucose level monitor 111 may be in operative and/or digital communication with the platform 200, such that any data collected by the glucose level monitor can be transmitted to one or more components of the platform (e.g., the device/data hub 220, the insights and recommendation engine 230, etc.) in real time. In some cases, the glucose level monitor 111 may be configured to transmit a collection of data in a predetermined time period (e.g., at least once every 5, 10, 20, 30, 60 minutes, 2, 3, 4, 5, 6, 8, 12, 18, 24 hours, etc.). In some cases, the glucose level monitor 111 may be configured to transmit a collection of data once a digital size (e.g., bytes) the collection of data reaches a predetermined threshold (e.g., 5 megabytes).

In some cases, the glucose level monitor 111 may be a "one size fits all" glucose level monitor that can be applicable to a variety of users regardless of age, gender, height, weight, disease (e.g., Type 1 vs Type 2 diabetes), etc. In some cases, the glucose level monitor 111 may be a personalized glucose level monitor for each user (e.g., specific shape for a specific location of a specific user, specific detection mechanism for a specific disease of the user, etc.).

The foods can be elementary foods (e.g., fruits, vegetables, milk, eggs, meat, poultry, fish, nuts, etc.), recipes of foods, packaged foods, restaurant dishes, home-cooked dishes, etc. The individual foods can be ingredients and/or nutrients of the elementary foods. In an example, the food is a dish of pad thai, and the individual foods can be ingredients of pad thai, such as, for example, noodles, oil, garlic, eggs, soy sauce, lime juice, brown sugar, fish sauce, onions, basil leaves, peanuts, tofu, shrimp, etc.

The glucose level monitor 111 can measure the amount of glucose in the bodily fluid (e.g., interstitial fluid, blood, etc.) at a moment of time. In some cases, the glucose level monitor 111 can measure the amount of glucose in a non-blood fluid as an indication of the blood glucose level. In some cases, the glucose level monitor 111 can measure the amount of glucose directly in the blood. The DGM 101 (e.g., the insights and recommendation engine 230 of the DGM 101) can use data obtained from the glucose level monitor 111 and from the food analysis module 210 to quantify personalized effects of foods (or individual foods) on individuals. The DGM 101 can detect a change in the glucose level over a period of time (e.g., a slope of a graph of the glucose level over time) as an indicator of a change in the glucose level.

The glucose level monitor can be configured to measure a range of glucose levels from about 0.1 millimoles per litre (mmol/L) to about 100 mmol/L. The glucose level measured by the glucose level monitor can be at least about 0.1 mmol/L, 0.2 mmol/L, 0.3 mmol/L, 0.4 mmol/L, 0.5 mmol/L, 1 mmol/L, 2 mmol/L, 3 mmol/L, 4 mmol/L, 5 mmol/L, 10 mmol/L, 20 mmol/L, 30 mmol/L, 40 mmol/L, 50 mmol/L, 100 mmol/L, or more. The glucose level measured by the glucose level monitor can be at most about 100 mmol/L, 50 mmol/L, 40 mmol/L, 30 mmol/L, 20 mmol/L, 10 mmol/L, 5 mmol/L, 4 mmol/L, 3 mmol/L, 2 mmol/L, 1 mmol/L, 0.5 mmol/L, 0.4 mmol/L, 0.3 mmol/L, 0.2 mmol/L, 0.1 mmol/L, or less.

The glucose level monitor can be configured to measure a range of glucose levels from about 1 milligrams per decilitre (mg/dL) to about 500 mg/dL. The glucose level measured by the glucose level monitor can be at least about 1 mg/dL, 2 mg/dL, 3 mg/dL, 4 mg/dL, 5 mg/dL, 10 mg/dL, 20 mg/dL, 30 mg/dL, 40 mg/dL, 50 mg/dL, 100 mg/dL, 200 mg/dL, 300 mg/dL, 400 mg/dL, 500 mg/dL, or more. The glucose level measured by the glucose level monitor can be at most about 500 mg/dL, 400 mg/dL, 300 mg/dL, 200 mg/dL, 100 mg/dL, 50 mg/dL, 40 mg/dL, 30 mg/dL, 20 mg/dL, 10 mg/dL, 5 mg/dL, 4 mg/dL, 3 mg/dL, 2 mg/dL, 1 mg/dL, or less.

There can be multiple ways of quantifying the blood glucose response of a single meal as a single meal: (1) an incremental area under the curve (iAUC); (2) percent in-range (% in-range); (3) spike; and (4) total variation. First, the iAUC can be calculated as the area between the glucose curve and above the baseline glucose at the beginning of the meal. The iAUC can have a unit of mg·hours/dL (mg·hr/dL). The iAUC can allow a continuous range of values. The iAUC can sample an entire glucose level curve over time. Second, the % in-range can be a percentage of post-meal time that the glucose level is in a predefined range. In some cases, the predefined range can be provided or suggested by a physician for a user or a group of users. Third, the spike can be a difference between the "peak" and the baseline glucose levels. In some cases, the baseline glucose levels can be an average of the user's glucose levels over a period of time when the user is not consuming any food or any significant amount of food. Fourth, the total variation can be defined as the sum of the absolute difference between all consecutive values.

The platform 200 of the DGM 101 can be implemented using one or more GUIs (not shown in FIG. 3) to enable the user to select and employ features of the three components 210, 220, and 230. The GUIs can be rendered on a display screen on a user device. As such, the DGM 101 (e.g., the food analysis module 210) can be in communication with the user device displaying the GUIs. Examples of the user device can include one or more of the devices 110, such as the mobile device 114 or the wearable device 112. One or more components of the DGM 101 can be in communication with each other (e.g., share data). In some cases, the insights and recommendation engine 230 can (1) use information from the food analysis module 210 regarding the foods consumed by the user and information from the device/data hub 220 regarding a biological signal of the user, and (2) analyze any correlation (e.g., causation) between the foods consumed by the user and the biological signal.

The food analysis module 210 can be configured to analyze data indicative of foods consumed by the user and other data indicate of foods that are not consumed by the user. Such data indicative of foods may be structured or unstructured when initially received (e.g., collected) by the food analysis module 210. The food analysis module 210 can be capable of mapping such unstructured (e.g., different formats) data into a structured (e.g., a same format) data. The food analysis module 210 can represent such structured data relating to all foods as a map of foods (i.e., a web of foods, food ontology).

The data indicative of foods consumed by the user can comprise one or more images of the foods consumed by the user, one or more videos of the foods, one or more voice logs of the foods, one or more text logs of the foods, one or more barcodes on each package of the foods. Thus, food analysis module 210 can be configured to structure and/or analyze the data (e.g., image(s), video(s), voice log(s), text log(s), barcode(s), etc.) using information from the food ontology to predict (or determine) one or more ingredients within the foods. The food analysis module 210 can further be configured to use information from the food ontology to determine one or more nutrients (e.g., calories, total fat, sodium, etc.) and their estimated amounts from the one or more predicted (or determined) ingredients.

The food analysis module 210 can be in communication with the mobile device 114 or the wearable device 112. The mobile device 114 or the wearable device 112 can be configured to collect in part the data (e.g., image(s), video(s), voice log(s), text log(s), barcode(s), etc.) indicative of foods consumed by the user. The food analysis module 210 can be configured to abstract and/or analyze information relating to foods from the captured image(s), food(s), voice log(s), text log(s), or barcode(s) of foods or food packages, for example, by using the food ontology. The food analysis module 210 can further be configured to update the food ontology based on such data obtained from one or more user devices of the user and other users of the DGM 101 (or the ecosystem 100). The food analysis module 210 can further be in communication with the smart home device 118 (e.g., a smart refrigerator). In an example, the food analysis module 210 can be in communication with the smart refrigerator. The smart refrigerator can be configured to track movement of the foods in and out of the refrigerator to track or predict food consumption by the user. The smart refrigerator may track movement of the foods by using a sensor (e.g., a camera) that captures images or videos of the foods or that reads the barcode of pre-packaged foods or meals.

The GUI(s) of the DGM 101 can be configured to visually annotate the data (e.g., image(s), video(s), voice log(s), text log(s), barcode(s), etc.) of the foods consumed by the user, with a name of each food item predicted to be present in the data and the ingredients within each food item. In some cases, the GUI(s) of the DGM 101 (i.e., one or more graphics modules of the DGM 101) can be configured to visually annotate the image(s) of the foods consumed by the user, with a name of each food item and/or the ingredients within each food item.

The glucose level monitor 111 can comprise a blood glucose monitor, a continuous glucose monitor (CGM), a flash glucose monitor (FGM), or a glucose sensing bio-implant. The glucose level monitor 111 can be configured to measure the user's glucose level in an analyte (e.g., a bodily fluid) comprising blood, interstitial fluids, sweat, tear, and/or saliva. The glucose level monitor 111 can be placed on or adjacent to the user's skin, or inside the user's body (e.g., underneath the skin). In some cases, a portion of the glucose level monitor 111 can be in fluid communication with the user's analyte to measure the glucose level in the analyte. In some cases, the glucose level monitor 111 can be a non-invasive device (e.g., a non-invasive medical device) that is capable of measuring the user's glucose level without piercing and drawing blood from the user's skin. In an example, the glucose level monitor 111 may direct the electromagnetic radiation (e.g., radio wave, microwave, infrared light, visible light, ultraviolet (UV) light through the user's skin and towards the user's bodily fluid. Afterwards, the glucose level monitor 111 may read at least a portion of the directed electromagnetic radiation that is transmitted or reflected by the user's bodily fluid, which transmission or reflection reading indicative of the glucose level of the bodily fluid. The electromagnetic radiation may comprise one or more wavelengths (e.g., a laser with one wavelength). Similarly, the glucose level monitor 111 may utilize electrical signals to non-invasively detect the user's glucose level.

The device/data hub 220 can be in communication with the CGM to continuously stream and store a user's personalized data regarding the glucose level. The stored users' personalized data can be used for analysis by the insights and recommendation engine 230. A measurement of the CGM of the interstitial fluid can have at most about 15, 14, 13, 12, 11, 10, 9, 8, 7, 6, 5% or less error than a respective blood glucose level. The measurement of a glucose level of the interstitial fluid can have a shorter delay in response than a measurement of a blood glucose level. The CGM can remain functional during a user's daily activities, including showering, exercising, sleeping, etc. The glucose level monitor 111 can include any suitable continuous glucose monitoring apparatus.

The device/data hub 220 can be in communication with the FGM. The FGM can be a small sensor that is put on or a skin of the user. A portion of the FGM can sit underneath the skin to be in fluid communication with the interstitial fluid. The FGM can determine glucose levels of the interstitial fluid as a close correlation to the blood glucose levels. The FGM can record the user's glucose levels continuously or intermittently (e.g., once every 5, 10, 15, 20, 30, 60 minutes, more frequently, less frequently, etc.), and the user can access data comprising the user's collected glucose levels by scanning the FGM with a separate scanner (e.g., a specific monitor, or a user device, such as a mobile device).

The glucose monitor (e.g., the CGM or FGM) can be worn by the user for about 10 to 30 days. The glucose monitor can be worn by the user for at least about 5, 10, 15, 20, 25, 30, 40, 50, or more days. The glucose monitor can be worn by the user for at most about 50, 40, 30, 25, 20, 15, 10, 5, or less days. After use, the glucose monitor may be removed and replaced with a new glucose monitor. The new glucose monitor may or may not need calibration to the user.

The glucose level monitor 111 can be in communication with the user device to transmit data indicative of the user's glucose level. The communication can comprise electromagnetic radiation, sound, the Institute of Electrical and Electronics Engineers (IEEE) 802.11 wireless local area network (WLAN) standards, Bluetooth, Zigbee, Z-Wave, near-field communication (NFC), magnetic secure transmission (MST), a functional modification thereof, or a combination thereof. In some cases, the glucose level monitor 111 can be hardwired with the user device.

The glucose level monitor 111 can measure the glucose level of the user at a frequency of at least about one measurement (or reading) per every 0.5, 1, 2, 3, 4, 5, 10, 15, 20, 30, 60, 90, 120 minutes, or more. The glucose level monitor 111 can measure the glucose level of the user at a frequency of at most about one measurement (or reading) per every 120, 90, 60, 30, 20, 15, 10, 5, 4, 3, 2, 1, 0.5 minutes, or less. The glucose level monitor 111 may measure one or more glucose levels of the user at an irregular pattern. In some cases, the glucose level monitor 111 may be adaptive. In some cases, the glucose level monitor 111 may be configured to monitor the glucose level of the user at a first rate, and when the glucose level monitor 111 detects a drastic change (e.g., an increase or a decrease) in the glucose level (e.g., by comparing it to a history of the user's glucose levels, a predetermined reference glucose level, or a predetermined reference glucose level range, etc.), the glucose level monitor 111 may begin to monitor the glucose level of the user at a second rate that is higher than the first rate. Such shift in the rate of glucose level detection may be automatic (e.g., without human intervention or instruction at the instant moment) or user assisted (e.g., the glucose level monitor 111 may prompt the user via the user device to approve the change of the rate of glucose detection).

The glucose level monitor 111 can be further capable of measuring an additional biomarker level of the user. The glucose level monitor 111 can be capable of measuring at least about 1, 2, 3, 4, 5, 6, 7, 8, 9, 10, or more additional biomarker levels of the user. The glucose level monitor 111 can be capable of measuring at most about 10, 9, 8, 7, 6, 5, 4, 3, 2, or 1 additional biomarker level of the user. In such a case, the food analysis module can be further configured to (1) analyze the data indicative of foods consumed by the user, and (2) determine an effect of individual foods on the additional biomarker level of the user, based on changes to the user's additional biomarker level as measured by the glucose level monitor.

The additional biomarker can comprise genes, peptides, proteins, lipids, metabolites, etc. Examples of the additional biomarker include insulin, lactic acid, ketone, antioxidants, neurotransmitters, amines, vitamins, cholesterols, carbohydrates, alcohols, amino acids, nucleic acids, etc. The additional biomarker can further include additional biological features of the user, such as body temperature, heart rate, perspiration, or movement of the body.

Alternatively or in addition to, the food analysis module can be further in communication 126 with the medical device 116 (as shown in FIG. 60) configured to measure the additional biomarker in the user's body. The medical device 116 can be capable of measuring at least about 1, 2, 3, 4, 5, 6, 7, 8, 9, 10, or more additional biomarker levels of the user. The medical device 116 can be capable of measuring at most about 10, 9, 8, 7, 6, 5, 4, 3, 2, or 1 additional biomarker level of the user. In such a case, the food analysis module can be further configured to (1) analyze the data indicative of foods consumed by the user, and (2) determine an effect of individual foods on the additional biomarker level of the user, based on changes to the user's additional biomarker level as measured by the medical device. The medical device 116 can comprise heart rate monitors, blood pressure monitors, sweat sensors, galvanic skin response (GSR) sensors, electrocardiogram (ECG) monitors, bioelectrical impedance analysis (BIA) monitor (e.g., a body fat monitor), functional modifications thereof, or combinations thereof. The medical device 116 can comprise an emotion monitor, such as, for example, a stress monitor placed on or adjacent to the user's skin and configured to measure skin temperature, skin conductance, and/or arterial pulsewave as an indication of the user's stress level.

The medical device 116 can be in communication with the user device to transmit data indicative of the additional biomarker of the user. The communication can comprise electromagnetic radiation, sound, the Institute of Electrical and Electronics Engineers (IEEE) 802.11 wireless local area network (WLAN) standards, Bluetooth, Zigbee, Z-Wave, near-field communication (NFC), magnetic secure transmission (MST), a functional modification thereof, or a combination thereof. In some cases, the medical device 116 can be hardwired with the user device.

The medical device 116 can measure the additional biomarker level of the user at a frequency of at least about one measurement (or reading) per every 0.5, 1, 2, 3, 4, 5, 10, 15, 20, 30, 60, 90, 120 minutes, or more. The medical device 116 can measure the additional biomarker level of the user at a frequency of at most about one measurement (or reading) per every 120, 90, 60, 30, 20, 15, 10, 5, 4, 3, 2, 1, 0.5 minutes, or less. The medical device 116 may measure the additional biomarker level of the user at an irregular pattern. In some cases, the medical device 116 may be adaptive. In some cases, the medical device 116 may be configured to monitor the additional biomarker level of the user at a first rate, and there is a drastic change (e.g., an increase or a decrease) in the glucose level (e.g., by comparing it to a history of the user's glucose levels, a predetermined reference glucose level, or a predetermined reference glucose level range, etc.) or the additional biomarker level (e.g., a similar approach as that of the glucose level), the medical device 116 may begin to monitor the additional biomarker level of the user at a second rate that is higher than the first rate. Such shift in the rate of additional biomarker level detection may be automatic (e.g., without human intervention or instruction at the instant moment) or user assisted (e.g., the medical device 116 may prompt the user via the user device to approve the change of the rate of glucose detection).

In some cases, the wearable device 112 (as shown in FIG. 1) maybe used in addition to or in place of the medical device 116 to monitor the additional biomarker level of the user. Examples of the wearable device 112 include, but are not limited to, Apple Watch, Fitbit, Samsung Gear, Android Wear devices, etc.

The food analysis module 210 can be further configured to determine a correlation between the glucose level of the user and the additional biomarker level of the user. In an example, the food analysis module can determine how a change in the glucose level from consumption of a food affects the user's lactic acid level (e.g., in the blood) or the user's body temperature.

Due to the relationship between glucose and insulin, the dietary glucose monitor can also measure insulin indirectly by calculating the insulin levels using a glucose-insulin model. The glucose-insulin model can be a biomathematical model e.g. the GAIA model described above, a machine learning model, or any other suitable model. Since insulin is considered to be the main regulator of fat storage in the body, this allows leveraging the dietary glucose monitor as an aid for weight loss. While glucose is a relatively good proxy for insulin, the relationships between them may not be trivial (see, e.g., Holt SHA, Brand Miller J C, Petocz P. An insulin index of foods: the insulin demand generated by 1000-kJ portions of common foods., Am. J. Clin. Nutr. 66, 1264-1276 (1997)), and may require use of a suitable model to derive estimated insulin levels. Once the insulin levels are estimated the dietary glucose monitor can thus provide insights and recommendations as to which foods, combination of foods or lifestyle events affect an individual's weight, thus providing a personalized weight loss program that is based on biomarker measurements.

The food analysis module 210 (and/or the insights and recommendation engine 230 that is in communication with the food analysis module 210) can be further configured to provide one or more recommendations to the user for managing the user's glucose level based on the effects of different foods on the user's glucose level. The food analysis module 210 can be further configured to provide one or more recommendations to the user for managing the user's additional biomarker level based on the effects of different foods on the user's additional biomarker level. The one or more recommendations can comprise a change in the user's diet. For instance, the user can be diabetic, and the user may have been recommended a special diet by her physician.

The one or more recommendations can comprise at least one food to consume or avoid, a combination of two or more foods to consume or avoid, or at least a time to consume or avoid at least one food. In some cases, the food analysis module 210 can detect a decrease or maintenance in the glucose level of the user when two particular foods are consumed together (e.g., at the same time as two items or as ingredients in a same dish) or right after one another, and recommend the user to consume such combination of foods. In some cases, the food analysis module 210 can detect a sudden increase in the glucose level of the user when two particular foods are consumed together (e.g., at the same time as two items or as ingredients in a same dish) or right after one another, and recommend the user to avoid consuming such combination of foods. In some cases, the food analysis module 210 can detect a more dramatic increase in the user's glucose level when consuming a food (e.g., a donut, ice cream, pasta, etc.) late in the evening (e.g., past 9 P.M.) than an increase in the user's glucose when on consuming the same food at an earlier time of the day (e.g., before 6 P.M.). In such a case, the food analysis module 210 can recommend the user to avoid consumption of such food past a certain time (e.g., 6 P.M.).

Referring to FIG. 60, the food analysis module 210 can be further configured to direct a delivery of one or more foods to the user. The food analysis module 210 can be in communication with one or more food delivery or meal plan services 250, such as, for example, HelloFresh, Green Chef, EveryPlate, Sun Basket, Home Chef, Blue Apron, BistroMD, Freshly, NutriSystem, Plated, Purple Carrot, GreenBlender, PeachDish, Chef d, Terra's Kitchen, Fresh Direct, Daily Harvest, Instacart, Uber Eats, etc. The food analysis module 210 can suggest a meal provided by the food delivery or meal plan service(s) 250 that align with its one or more recommendations comprising at least one food to consume or avoid, a combination of two or more foods to consume or avoid, or at least a time to consume or avoid at least one food. The food analysis module 210 can automatically direct the food delivery or meal plan service(s) 250 to deliver such meal (and/or supplements) to the user with or without the user's confirmation. The user may provide a prior consent such that the food analysis module 210 can automatically direct the order and delivery of recommended foods or meals. the food delivery or meal plan service(s) 250 may provide a personalized and curated grocery list (e.g., by automatically generating a grocery list on Instacart), recipes, and advice. The provided recipes may be an existing recipe or a new recipe generated by the system described herein for the user. The food analysis module 210 can direct a delivery of about 1, 2, 3, 4, 5, 6, 7, 8, 9, 10 or more foods (e.g. at once). The food analysis module 210 can direct delivery of 1, 2, 3, or more meals per day. The food analysis module 210 can direct the delivery of foods for at least about 1, 2, 3, 4, 5, 6, 7, 8, 9, 10 or more times a week. The food analysis module 210 can direct the delivery of foods for at most about 10, 9, 8, 7, 6, 5, 4, 3, 2, or 1 time a week. The food analysis module 210 can update or change a preference of the foods that are being ordered and delivered based on the user's preference, rating of the foods, or response in the glucose level or the additional biomarker level. Additionally, the food analysis module 210 can be in communication with courier services, such as, for example, United States Postal Service (USPS), Federal Express (FedEx), United Parcel Service (UPS), Dalsey, Hillblom and Lynn (DHL), Google Express, Amazon, etc. to track and update the user on the delivery of the one or more foods to the user.

The food analysis module 210 can be further configured to recommend a recipe of a meal or diet plan to the user, wherein the recipe reflects the recommendation(s) provided to the user. The food analysis module 210 can be in communication with one or more sources (e.g., websites, on- or offline publications, etc.) to recommend such recipe. Examples of the source(s) can include, but are not limited to, cookpad, allrecipes, chefkoch, dianping, marmiton, foodnetwork, russianfood, geniuskitchen, bbcgoodfood, thekitchn, cuisineaz, epicurious, seriouseats, 1000.menu, yummly, foodandwine, bonappetit, taste, allrecipes, eater, tasty, etc.

The recommendation(s) provided by the food analysis module 210 can further comprise a change in the user's lifestyle. In some cases, based on the history of the user or compiled histories of two or more users, the food analysis module 210 can suggest a change in the user's lifestyle that can directly or indirectly provide a change or maintenance of the glucose level or the additional biomarker level of the user. The user's lifestyle can comprise exercising, walking, standing, sitting, stress management, meditation, medication, dietary supplementation, sexual activity, or sleeping. The food analysis module 210 can be in communication with one or more user devices (e.g., the glucose level monitor 111, the wearable device 112, the mobile device 114, or the medical device 116, etc.) to determine a relationship between one or more of the group comprising: the user's lifestyle, consumption of food(s) or individual food(s), or the glucose level or the additional biomarker level of the user. The food analysis module 210 can suggest a change in the user's lifestyle that has been shown to or is predicted to (e.g., by a healthcare professional or by using machine learning algorithms) help maintain or change the user's glucose level or additional biomarker level.

The GUI(s) of the DGM 101 can be configured to visually annotate the data (e.g., image(s), video(s) or one or more screenshots thereof, transcription of the voice log(s), text log(s), etc.) of the foods with the ingredients within each food item, a rating or ranking for each food item, fan insight for each food item, and/or a dietary recommendation. The rating or ranking may be indicative of an effect (e.g., positive or negative) of the foods to the user's glucose level and/or the additional biomarker level.

The rating can be a numerical rating, alphabetical rating, alphanumerical rating, percentage, graphical system, etc. In some cases, the ratings can be provided based on a scale, wherein a higher rating can have a more positive effect on the user's glucose level compared to a lower rating. In some cases, the rating can be based on a 0 percent (%) to 100% scale, a higher percentage value representing a more positive effect on the glucose or additional biomarker level of the user. The rating can be at least about 0%, 1%, 2%, 3%, 4%, 5%, 6%, 7%, 8%, 9%, 10%, 20%, 30%, 40%, 50%, 60%, 70%, 80%, 90%, 99%, or more. The rating can be at most about 100%, 90%, 80%, 70%, 60%, 50%, 40%, 30%, 20%, 10%, 9%, 8%, %, 6%, 5%, 4%, 3%, 2%, 1%, or less. In some cases, the rating can be based on another numerical scale, such as, for example, a 0 to 10 scale (e.g., 0, 1, 2, 3, 4, 5, 6, 7, 8, 9, and 10 in an order of positive effects). In some cases, the rating can be based on a graphical scale, such as, for example, a 1 to 5 stars scale (e.g., 1, 2, 3, 4, and 5 starts in an order of positive effects). In some cases, the rating can be an alphabetical rating system, such as, for example, one or more of D−, D, D+, C−, C, C+, B−, B, B+, A−, A, and A+.

Each of the ratings can be indicative of a measured or predicted effect of a corresponding food item or ingredient on the user's glucose level or the additional biomarker level. In some cases, the DGM 101 can determine when the user is eating or has consumed one or more foods (e.g., by user input or based on geolocation of the user). The DGM 101 can abstract information about the food(s) (e.g., ingredients, nutrition, etc.) based on data of the food(s). Afterwards, the DGM 101 can provide ratings of the food(s) based on their past effect on the glucose level or additional biomarker level of the user or a population of users. Alternatively or in addition to, the DGM 101 can use real time data of the glucose levels or additional biomarker levels of the user at or around the time of consumption of the food(s), then provide ratings of the food(s) based on their effect on the glucose levels or additional biomarker levels.

The positive effect on the user's glucose level can comprise an increase or decrease in the user's glucose level. For some users, a positive effect of the foods may be an increase of the glucose level or the additional biomarker level. For some users, a positive effect of the foods may be a decrease of the glucose level or the additional biomarker level. For some users, a negative effect of the foods may be an increase of the glucose level or the additional biomarker level. For some users, a negative effect of the foods may be a decrease of the glucose level or the additional biomarker level. For some users, a positive effect of the foods may be maintenance of the glucose level or the additional biomarker level within a predefined range for the users. For some users, a negative effect of the foods may be maintenance of the glucose level or the additional biomarker level within the predefined range for the users. Such predefined range may be user defined (e.g., user's personal goal) or suggested by a medical professional or dietician.

The food analysis module 210 can be configured to determine the effect of the individual foods on the glucose level of the user in real time, periodically, or at one or more predetermined time points. The food analysis module 210 can determine the effect of the individual foods on the glucose level or the additional biomarker level of the user in real time, e.g., simultaneously and/or for a duration of time around the time of consumption of the individual foods (or the foods comprising the individual foods). The food analysis module 210 can determine the effect of the individual foods on the glucose level or the additional biomarker level of the user periodically by analyzing previously collected data every 1 hour, 2 hours, 3 hours, 4 hours, 6 hours, 8 hours, 12 hours, 24 hours, 2 days, 3 days, 4 days, 5 days, 6 days, 1 week, 2 weeks, 3 weeks, 4 weeks, 1 month, etc. The food analysis module 210 can determine the effect of the individual foods on the glucose level or the additional biomarker level of the user at one or more predetermined time points, such as, for example, at 6 A.M. (e.g., such that the food analysis module 210 can provide recommendations before the user consumes breakfast), 11 A.M. (e.g., such that the food analysis module 210 can provide recommendations before the user consumes lunch), 5 P.M. (e.g., such that the food analysis module 210 can provide recommendations before the user consumes dinner), 10 P.M. (e.g., such that the food analysis module 210 can provide summary of correlations between the foods consumed and the glucose or additional biomarker level before the user sleeps), etc.

FIGS. 61A and 61B illustrate examples of visual annotations via the GUI(s) of the DGM 101 in accordance with some embodiments. Referring to FIG. 61A, the user can access the GUI(s) of the DGM 101 via a user device (e.g., the mobile device 114). The user can use the GUI(s) of the DGM 101 to capture an image 6105 of a dish (e.g., a salad) to be consumed. In some cases, the user can use other GUI(s) of the mobile device 114 (e.g., a camera application) to capture the image 6105 of the dish to be consumed. In some cases, the user can obtain the image 6105 of the dish from other sources, such as, for example, a website of the restaurant or one or more SNS networks (e.g., Yelp). In some cases, a video of the dish to be consumed can be captured instead of the image 6105, and the DGM 101 can be configured to generate at least the image 6105 of the dish from such video. The GUI(s) of the DGM 101 can scan 6110 the image 6105 to identify one or more food items (e.g., individual foods or ingredients in the dish) from the image 6105. The names of the food item(s) of the image 6105 can be visually annotated by the DGM 101 on the GUI(s) of the DGM 101. Referring to FIG. 61B, the DGM 101 can analyze the food item(s) 6115 and provide one or more ratings 6120 (or rankings) for the food item(s) 6115. The rating(s) 6120 can be indicative of an effect of the food item(s) 6115 on the user's glucose level and/or the additional biomarker level. In an example, the rating(s) 6120 of the food item(s) 6115 may be an alphabetical system, wherein the highest rating of A+ indicates least increase in the user's glucose level and a lower rating (e.g., B, C, D, etc.) indicates a higher increase in the user's glucose level than the rating of A+. In addition, the DGM 101 can predict the dish that the user is consuming based on the food item(s) predicted (or identified) from the image 6105, then show on the GUI(s) one or more predictions 6125 of the dish (e.g., quinoa salad, French shrimp salad, Ceasar salad, etc.). In some cases, the food prediction 6125 function may allow the user to provide a name of the dish.

Figures 62A, 62B:
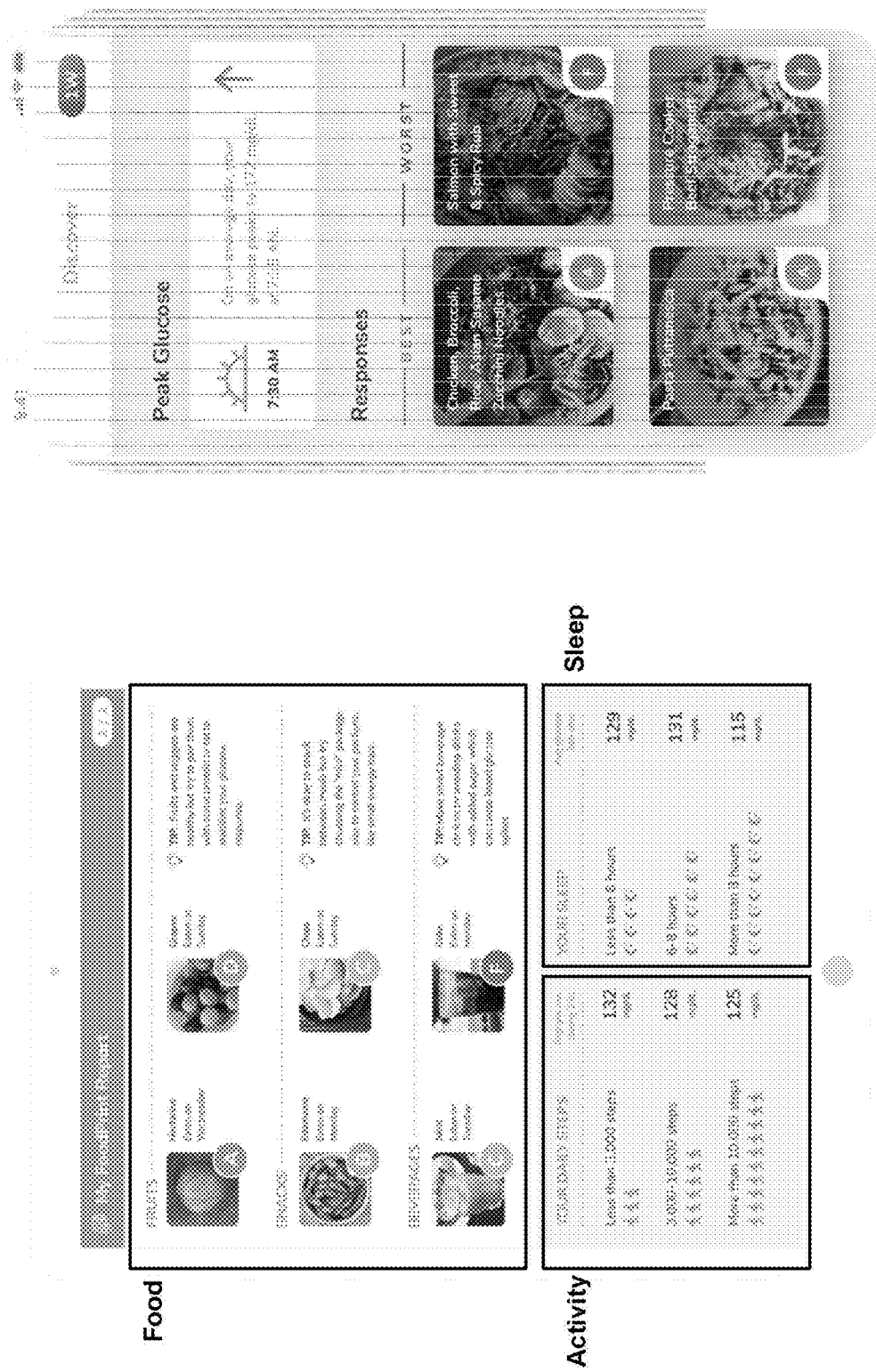
FIGS. 62A and 62B illustrate exemplary windows of a GUI-based software interface showing an analysis report of a user's data, in accordance with some embodiments.

FIGS. 62A and 62B illustrate exemplary windows of a GUI-based software interface showing an analysis report of the user's food data, in accordance with some embodiments. Referring to FIG. 62A, the analysis report can focus on factors that can influence blood glucose level: food, activity, and sleep. The report can be based on a pre-defined target glucose level range (e.g., 70-170 mg/dL) for the user. The report can include assessment of one or more meals based on how the user's glucose level responded to one or more meals. The assessment can utilize a rating system (e.g., "A" for a balanced glucose response, "F" for a poor glucose response, etc.). The report can also show recommendations generated by the insights and recommendation engine 230. The recommendation can compare two food items (consumed by the user and suggest if one of the two food items is a healthier option than the other of the two food items based on the user's physiological responses. In some examples, a recommendation can compare two types of fruits (nectarine vs. grapes) and also recommend pairing either fruit with protein or fat. Another recommendation can compare two types of snacks (edamame vs. chips) and suggest that small energy bars may be a healthier option for snacks. A different recommendation can compare two types of beverages (juice vs. coke) and recommend avoiding drinks with added sugar. Additionally, the report can show a correlation between a number of steps the user took and the user's respective average blood glucose level. The report can inform the user that the user's blood glucose level decreased from 132 mg/dL to 125 mg/dL when the user increased the number of steps from less than 3,000 steps to more than 10,000 steps per day. Furthermore, the report can show a correlation between sleep and blood glucose level. The report can inform the user that the user's blood glucose level decreased from 129 mg/dL to 115 mg/dL when the user increased a number of hours of sleep from less than 6 hours to more than 8 hours. Referring to FIG. 62B, another analysis report can include a report on an average peak glucose level of the user over a set time period (e.g., 1, 2, 3, 4, 5, 6, 7, 8, 9, 10 days or more). In an example, the analysis report can inform the user that the user's glucose level peaked to 172 mg/dL at 7:35 A.M. on an average day from 1 week of data collection. Additionally, the analysis report can inform the user one or more dishes that the user has consumed over a given period (e.g., 1 week) with balanced glucose response (e.g., dishes with the "A" rating). The analysis report can also inform the user one or more dishes that the user has consumed over a given period (e.g., 1 week) with a poor glucose response (e.g., dishes with the "F" rating).

Referring to FIG. 60, the DGM 101 can be a tool to connect two or more users 260. The DGM 101 can be a tool for group therapy, support groups, or peer-to-peer support for diet and/or health management. Such group therapy, support groups, or peer-to-peer support can help promote or maintain a behavioral change for better glucose level or additional biomarker level management. The food analysis module 210 can be further configured to start a group of two or more users based on the comparison. Even if the two or more users were not designated to a pre-defined group, the food analysis module 210 can automatically start a group of two or more users based on different factors, such as, for example, gender, age bracket, race, geolocations, work hours, profession, conditions or diseases, etc. In addition, the food analysis module 210 can be further configured to generate one or more subgroups of the group.

The DGM 101 can be further configured to allow the user to share any information collected and/or generated by the DGM 101 for the user with others who may or may not be a user of the DGM 101. The DGM 101 can be configured to allow the user to share the information with a CDE, nutritionist, dietitian, physician, nurse, or a physical trainer. The DGM 101 can be configured to allow the user to share the information with a friend or family member. Examples of the information collected and/or generated by the DGM 101 for the user can include the analysis of foods consumed by the user, the glucose or additional biomarker level of the user, or a correlation and/or prediction thereof between the foods consumed and the glucose or additional biomarker level of the user.

The food analysis module 210 can be further configured to compare the effect of individual foods on the glucose levels between two or more users. Users of the DGM 101 can use the same platform 200, and as such, the platform 200 comprising the food analysis module 210 can correlate and compare data related to two or more users. The food analysis module 210 can correlate and compare data (e.g., glucose levels or additional biomarker levels) of two or more user of a same gender, age bracket (e.g., 10-20, 20-30, 30-40, 40-50, 50-60, 60-70, 70-80 years old, etc.), race, geolocations (e.g., by continent, country, cities, towns, schools, etc.), work hours (e.g., day shift, night shift, etc.), profession (e.g., athletes, doctors, students, restaurant workers, stay home parents, office clerks, mail delivery personnel, etc.), conditions or diseases (e.g., healthy, type 1 or 2 diabetes, hypertension or hypotension, partial or full paralysis, history of a stroke, viral infections, cancer, sleep disorder, mood disorder, etc.).

The food analysis module 210 can correlate and compare data (e.g., glucose levels or additional biomarker levels) of two or more users of a pre-defined group. A healthcare provider can have access (limited access) to the DGM 101 that is synced with two or more users. The healthcare provider can assign two or more users in a group, e.g., a group for a study for specific foods or conditions. For example, the healthcare provider can generate a group of patients with type 1 diabetes within the DGM 101 and use the DGM 101 to track their glucose levels (e.g., by the glucose level monitor 111 on each of the users) and/or provide recommendations to the users in the group. In addition, the users in the group can have access (limited access) to each other's information, and this may in some cases promote a competition and motivation to the users to follow a recommended diet.

Whether in a pre-defined group or a group generated by the food analysis module 210, the food analysis module 210 is further configured to allow the group of two or more users to communicate with one another via a GUI on a user device associated with each user (e.g., via the GUIs of the DGM 101). The two or more users can communicate with one another via the GUI on each other's mobile device 114 or wearable device 112. The communication between the group of two or more users can comprise information shared via the graphical user interface, the information comprising a text, image, video, and/or voice recording.

Referring to FIG. 60, the DGM 101 can be further configured to connect the user to a healthcare or fitness specialist 270. The DGM 101 (e.g., the food analysis module 210 and/or the insights and recommendation engine 230) can be configured to identify the healthcare or fitness specialist 270 for the user based on the effect of individual foods on the glucose level or the additional biomarker level of the user. The healthcare or fitness specialist 270 can comprise a certified diabetes educator (CDE), nutritionist, dietitian, physician, nurse, or a physical trainer. The healthcare or fitness specialist 270 can provide telemedicine (e.g., providing diagnosis or treatment of a health condition or disease by telelcommunication), nutritional advice (e.g., regarding the glucose management and its relation to diet and other lifestyles), and coaching (e.g., exercise routines).

Figure 63:
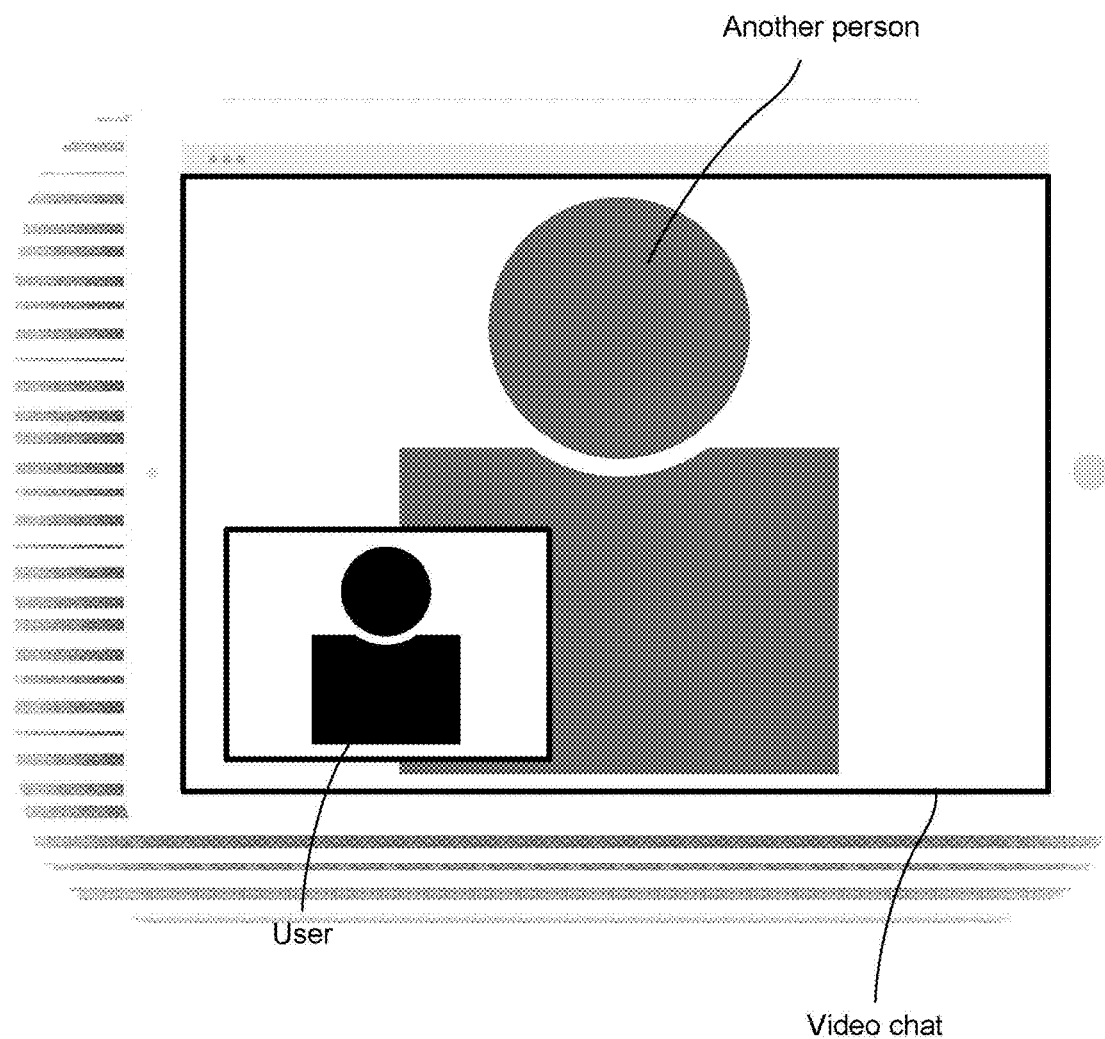
FIG. 63 illustrates an exemplary window of a GUI-based software interface showing a video chat between the user and another person.

FIG. 63 illustrates an exemplary window of a GUI-based software interface showing a video chat between the user and another person. The DGM 101 can provide the GUI-based software interface for the user to talk to other user(s) of DGM 101. The other user(s) may have a similar diet plan and/or health conditions (e.g., type 2 diabetes) as the user. The other user(s) may have already gone through the diet plan that the user is currently on, and the other user(s) may provide support and encouragement to the user. The DGM 101 can provide the GUI-based software interface for the user to talk to the healthcare or fitness specialist 270. In some cases, a live feedback from the healthcare or fitness specialist 270 may be more effective in the user's compliance to the diet and dietary goals.

Referring to FIG. 60, the DGM 101 can be further configured to remind the user about one or more tests 290 relevant to the user's health. The test(s) 290 can be relevant to the user's diet, glucose level, additional biomarker level, disease, and/or other conditions. In some cases, the test(s) 290 can be a biyearly or quarterly testing of A1C test. The A1C test may be a blood test that can provide information about the user's average levels of blood glucose over a time period (e.g., past 3 months). The A1C test can be used to diagnose type 2 diabetes and/or prediabetes. The A1C test can also be used as diabetes management. The A1C test may also be referred to as the hemoglobin A1C, HbA1c, glycated hemoglobin, or glycohemoglobin test. The A1C test result may be reported as a percentage (e.g., the higher the percentage, the higher the user's blood glucose levels have been). In an example, a healthy A1C level may be below 10 percent (e.g., 5.7 percent). In some cases, the DGM 101 can make an appointment for the test(s) 290. The DGM 101 may be operatively linked to a database for the test(s) 290 to receive or retrieve user's results of the test(s) 290 for further analysis.

Referring to FIG. 60, the DGM 101 can be further configured to connect the user to a virtual health assistant 280. The virtual health assistant 280 can be in communication with one or more components of the DGM 101 (e.g., the food analysis module 210 and/or the insights and recommendation engine 230). The virtual health assistant 280 can be configured to automatically generate and provide the one or more recommendations to the user. The virtual health assistant 280 can be configured to communicate with the user via the user device (e.g., the mobile device 114). The virtual health assistant 280 and the user may communicate via the GUI(s) of the DGM 101 on the user device. The virtual health assistant 280 can use artificial intelligence comprising one or more machine learning algorithms to (1) understand a question or comment from the user; (2) identify the one or more recommendations based on the effect of individual foods on the glucose level of the user; and (3) generate and provide the recommendation(s) to the user. The virtual health assistant 280 can use artificial intelligence comprising one or more machine learning algorithms to (1) understand a question or comment from the user; (2) identify the one or more recommendations based on the effect of individual foods on the glucose level and/or the additional biomarker level of the user; and (3) generate and provide the recommendation(s) to the user. The machine learning algorithm(s) can include a natural language processing (NLP), optical character recognition (OCR) capabilities, a computer vision system, or a statistical model.

The machine learning algorithm(s) can include one or more training data sets that comprise example questions or comments from the user regarding foods, individual foods, glucose level of the user, additional biomarker level of the user, lifestyles of the user, any prediction thereof, or any correlation therebetween. The training data set(s) can callow the machine learning algorithm(s) to learn a plurality of parameters to generate one or more models (e.g., mathematical models, classifiers) that can be used to distinguish or differentiate different aspects of the user's questions or comments, thereby to provide appropriate answers or comments back to the user.

In an example, the user can ask the virtual health assistant 280 (e.g., via sending a voice message or a text message) "How is my glucose level doing?", the virtual health assistant 280 may provide a summary of the user's glucose level, such as: (1) "There was a drop of your glucose level after 2:30 P.M., when you consumed coffee with a muffin"; (2) "There was a peak in your glucose level after consuming the meatball pasta"; (3) "Within the past 2 months, we noticed a peak in your glucose level when you eat dinner past 8 P.M."; (4) "Running or swimming has been more effective in managing your glucose level than weight lifting"; or (5) "There is an unusual trend in your glucose level within the past 2 days. Please see an endocrinologist soon. Dr. Christine Emdy is a highly rated endocrinologist in your insurance network and may be available this week for an appointment." The virtual health assistant 280 may be in communication with healthcare providers and the user's healthcare insurance information to make an appointment (e.g., with a nurse, general physician, specialist, dentist, optometrist, etc.) automatically, with or without the user's consent (e.g., by voice or text messaging).

The one or more recommendations by the DMG 101 (e.g., by the food analysis module 210) can be automatically generated and provided to the user by the virtual health assistant 280. The virtual health assistant 280 can provide the recommendation(s) to the user at least once every 1 hour, 2 hours, 3 hours, 4 hours, 6 hours, 12 hours, 24 hours, 2 days, 3 days, 4 days, 5 days, 6 days, 1 week, 2 weeks, 3 weeks, 4 weeks, 2 months, or more. The virtual health assistant 280 can provide the recommendation(s) to the user at most once every 2 months, 4 weeks, 3 weeks, 2 weeks, 1 week, 6 days, 5 days, 4 days, 3 days, 2 days, 25 hours, 12 hours, 6 hours, 4 hours, 3 hours, 2 hours, 1 hour, or less.

The user can initiate a communication with the virtual health assistant 280 by providing (e.g., via voice or text messaging) a question (e.g., regarding the user's diet, glucose or additional biomarker level, etc.) to the virtual health assistant 280. The virtual health assistant 280 can provide an answer to the user's question in at least about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds, 1 minute, 2 minutes, 3 minutes, 4 minutes, 5 minutes, 10 minutes, 20 minutes, 30 minutes, 40 minutes, 50 minutes 1 hour, 2 hours, 3 hours, 4 hours, 5 hours, or more. The virtual health assistant 280 can provide an answer to the user's question in at most about 5 hours, 4 hours, 3 hours, 2 hours, 1 hour, 50 minutes, 40 minutes, 30 minutes, 20 minutes, 10 minutes, 9 minutes, 8 minutes, 7 minutes, 6 minutes, 5 minutes, 4 minutes, 3 minutes, 2 minutes, 1 minute, 50 seconds, 40 seconds, 30 seconds, 20 seconds, 10 seconds, 9 seconds, 8 seconds, 7 seconds, 6 seconds, 4 seconds, 3 seconds, 2 seconds, 1 seconds, or less. In some cases, the virtual health assistant 280 can provide the answer to the user's question one or more times. the virtual health assistant 280 can provide the answer at least about 1, 2, 3, 4, 5, 6, 7, 8, 9, 10, or more times.

In some cases, the virtual health assistant 280 can be configured to ask one or more questions to the user following receiving the user's question (e.g., the user's original question). The virtual health assistant 280 can ask the question(s) to receive more information regarding the user's question. The information regarding the user's question may help the virtual health assistant 280 to understand the user's question better and provide a relevant answer to the question.

Figure 64:
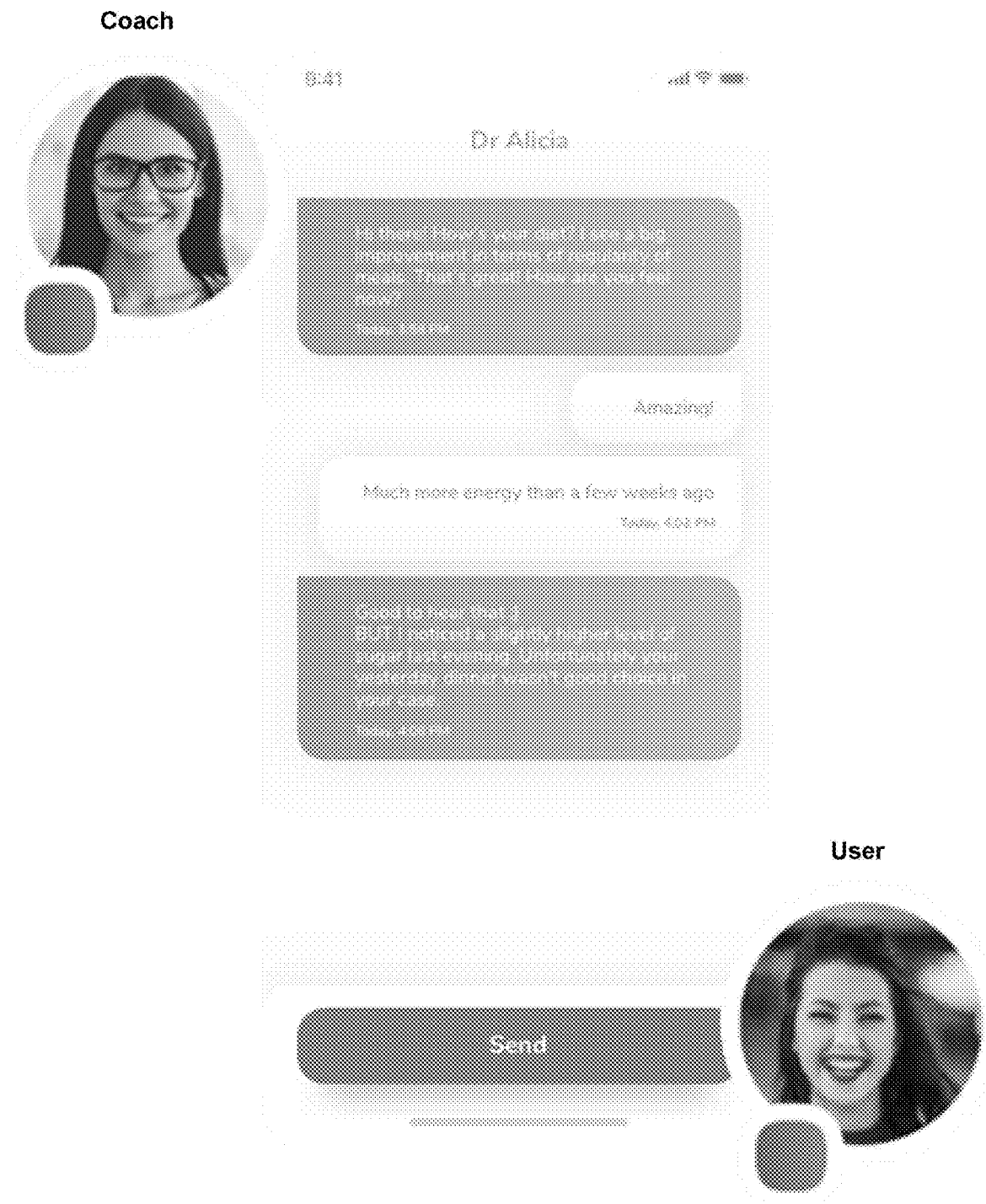
FIG. 64 illustrates an exemplary window of a GUI-based software interface showing an exchange of messages between the user and a coach.

FIG. 64 illustrates a window of a GUI-based software interface showing an exchange of messages (e.g., a conversation) between the user and a coach. The coach can be a specialist (e.g., a nurse, physician, dietician, etc.) with an unlimited or limited access to the user's data and its analysis by the DGM 101 (e.g., by the insights and recommendation engine 230). Alternatively or in addition to, the coach can be an artificial intelligence algorithm (e.g., a chatbot) that is operatively coupled to the platform 200 of the DGM 101. The artificial intelligence algorithm may use one or more of the abovementioned machine learning algorithms to communicate with the user. The conversation between the coach and the user can be initiated by the user. Alternatively, the conversation between the coach and the user can be initiated by the coach. The coach can inform the user of one or more recommendations generated by the DGM 101 (e.g., by the insights and recommendation engine 230). In some cases, the user may be more receptive (more motivated, encouraged, etc.) to the recommendation(s) when informed or instructed via a conversation with the coach than an analysis report generated by the DGM 101. In some examples, the coach can inform the user whether the user has been showing a balanced glucose response or not. In some examples, the coach and inform the user of any foods and/or times indicative of a poor glucose response. The coach may also provide recommendation(s) regarding the user's additional biomarker level(s). The coach may also ask a question to the user that may be necessary by the DGM 101 for further analysis of the user's data.

The DGM 101 can further comprise one or more prepackaged meals containing known amounts of foods, wherein the food analysis module 210 can be further configured to (1) monitor effects of the foods in the one or more pre-packaged meals on the user's glucose level and/or the additional biomarker level as the user consumes the one or more pre-packaged meals over a time period, and (2) generate a glucose and/or additional biomarker baseline profile of the user based on the monitored effects. The pre-packaged meal(s) can be provided to the user in a calibration kit, which calibration kit can be used to optimize the DGM 101 (e.g., the platform 200 of the DGM 101) to the user's physiological responsiveness to different foods.

Optimizing DGM 101 (e.g., the platform 200 of the DGM 101) can include optimizing the functions of the food analysis module 210, the device/data hub 220, and the insights and recommendation engine 230, as well as at least the glucose level monitor 111 in communication with these components. As users can respond differently to the same food, and the glucose level monitor 111 and the medical device 116 can have different compatibility to different users, the calibration kit may be used to set a food baseline for one or more users. Generating the food baseline profile for a user can include monitoring effects of different foods (or individual foods) on the user's body as the user consumes one or more pre-packaged meals over a time period. One or more pre-packaged meals can contain known amounts of the foods. The monitored effects can be used to generate the food baseline profile. The calibration kit can be a modular kit. The calibration kit can include a monitoring system (e.g., the glucose level monitor 111, the medical device 116, a blood test kit, a genetic test, etc.) and one or more standardized meals (also referred to as "calibration meals"). The calibration meals can include food bars, beverages, or both. The platform 200 of the DGM 101 may know and have tested all features of the calibration meals (e.g, ingredient, nutrients, processing, etc). In some examples, the user may put the device (e.g., the glucose level monitor 111) on the body (or perform the provided monitoring test, such as, for example, the blood test kit), and consume one calibration meal per every morning. The user may be required to fast (e.g. for 12 hours) throughout the previous night. The device may measure the user's response to the calibration meal. The user can consume other foods throughout the day and track the foods to the platform 200 via the GUI-based software interface (e.g., food tracking by textual and voice recognition analysis, seamless food image logger, etc.). After a short period of time (e.g., a week), the platform 200 can use the data and predictions to set the baseline for the user. The baseline may be referred to as the user's unique, personalized food "finger print."

Figure 65:
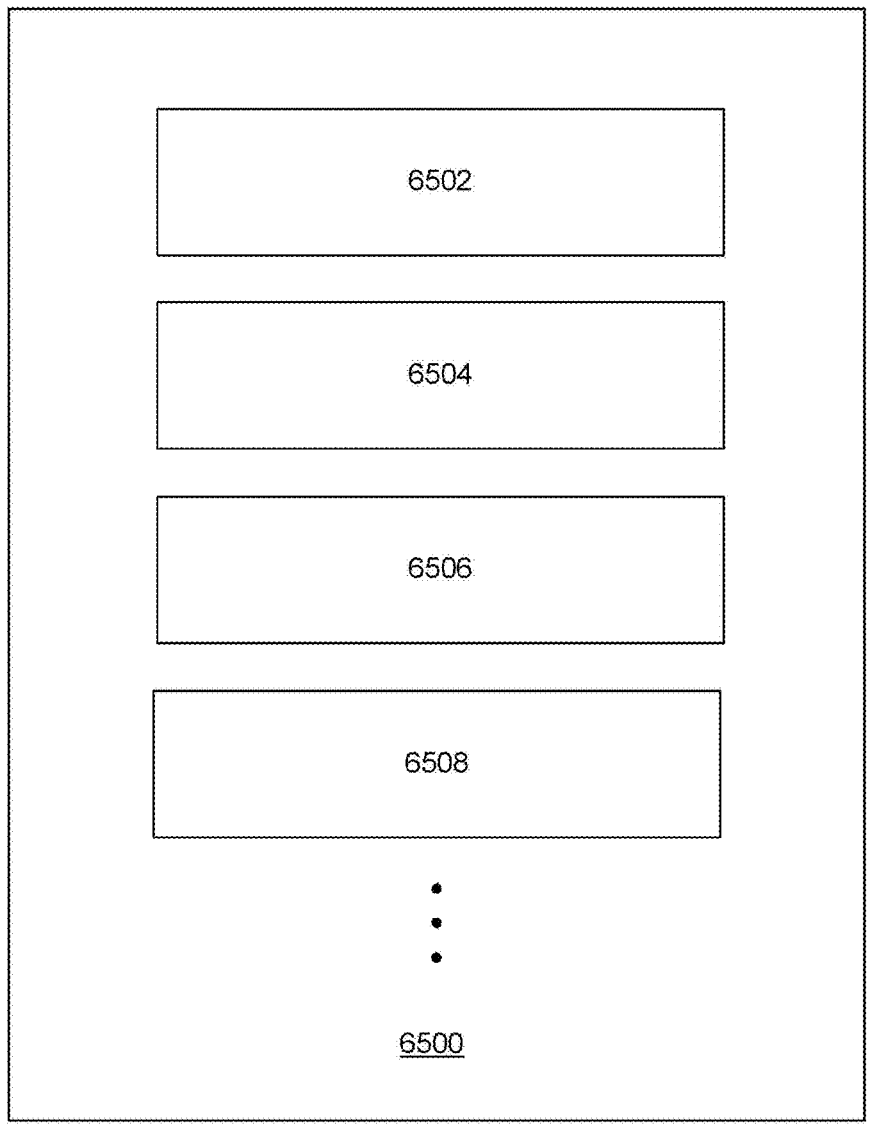
FIG. 65 shows an exemplary calibration kit in accordance with some embodiments.

FIG. 65 illustrates an exemplary calibration kit 6500. The calibration kit can contain a box 6502 that includes the glucose level monitor 111, and an additional box 6504 that includes one or more calibration meals. The calibration kit can contain a different box 6506 that includes a DNA collection kit for DNA testing (e.g., saliva collection kit). The calibration kit can contain another different box 6508 that includes a biome collection kit for microbiome analysis (e.g., sample collected from gut, genitals, mouth, nose, and/or skin). The calibration kit may optionally include any of the above boxes, or different combinations of the boxes. The calibration kit can include 1, 2, 3, 4, 5, or more calibration foods. The calibration kit can include 2, 3, 4, 5, 6, or more boxes. The calibration kit can include 1, 2, 3, 4, 5 or more monitoring systems. In some embodiments, the calibration kit may include one or more other components/devices (e.g. the medical device 116, wearable device, or other biomarker tests/devices) that aid in generating a baseline health status of a user. The calibration kit may also include a detailed list of instructions for a user to easily follow. If necessary, the calibration kit can include a container for each collection kit.

Computer Systems

Figure 66:
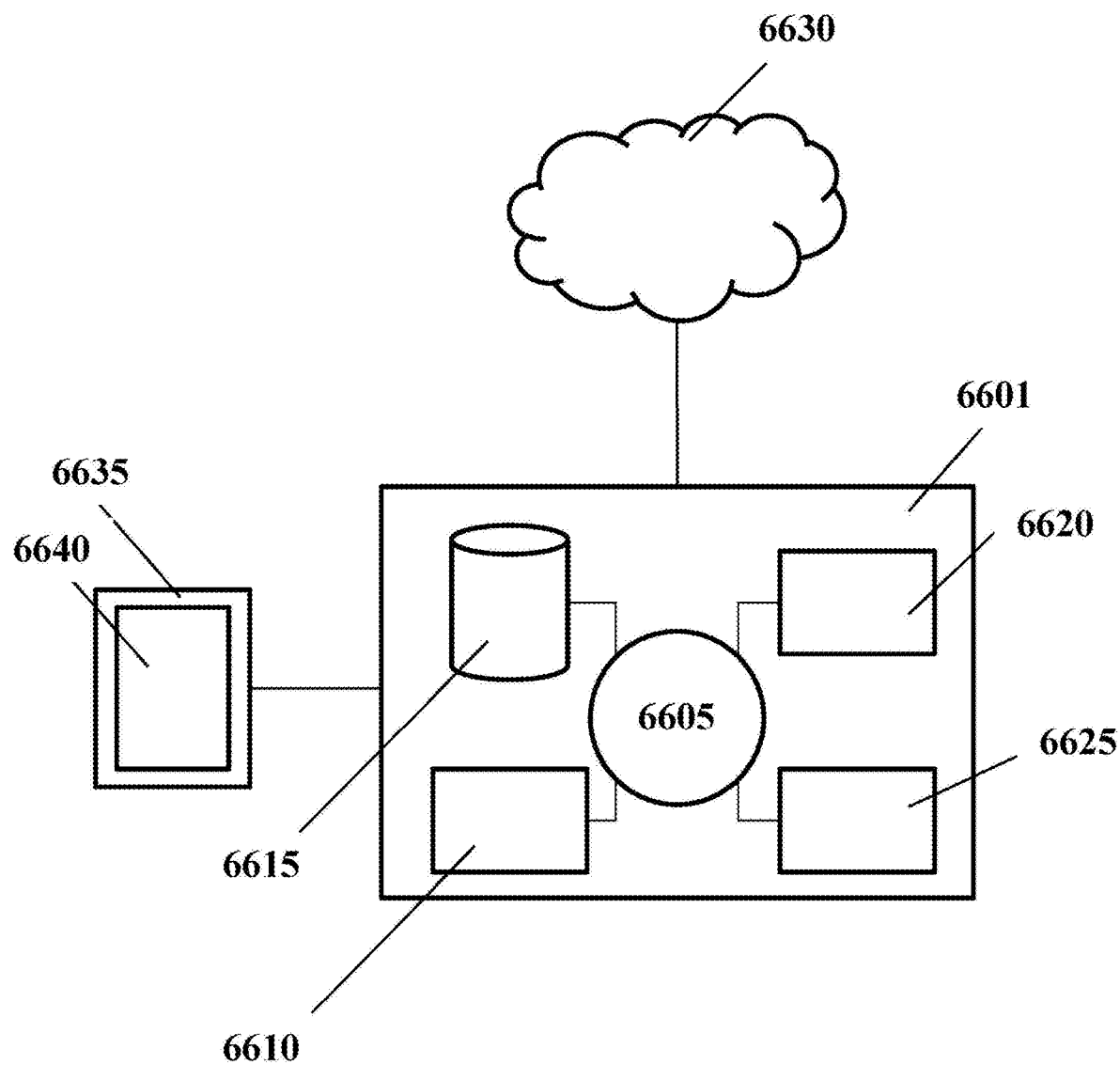
FIG. 66 shows a computer system that is programmed or otherwise configured to implement methods provided herein.

The present disclosure provides computer systems that are programmed to implement methods of the disclosure. FIG. 66 shows a computer system 6601 that is programmed or otherwise configured to operate the DGM 101. The computer system 6601 can regulate various aspects of the DGM 101 of the present disclosure, such as, for example, the platform 200 that comprises the food analysis module 210, the device/data hub 220, and the insights and recommendation engine 230. The computer system 6601 can be an electronic device of a user or a computer system that is remotely located with respect to the electronic device. The electronic device can be a mobile electronic device.

The computer system 6601 includes a central processing unit (CPU, also "processor" and "computer processor" herein) 6605, which can be a single core or multi core processor, or a plurality of processors for parallel processing. The computer system 6601 also includes memory or memory location 6610 (e.g., random-access memory, read-only memory, flash memory), electronic storage unit 6615 (e.g., hard disk), communication interface 6620 (e.g., network adapter) for communicating with one or more other systems, and peripheral devices 6625, such as cache, other memory, data storage and/or electronic display adapters. The memory 6610, storage unit 6615, interface 6620 and peripheral devices 6625 are in communication with the CPU 6605 through a communication bus (solid lines), such as a motherboard. The storage unit 6615 can be a data storage unit (or data repository) for storing data. The computer system 6601 can be operatively coupled to a computer network ("network") 6630 with the aid of the communication interface 6620. The network 6630 can be the Internet, an internet and/or extranet, or an intranet and/or extranet that is in communication with the Internet. The network 6630 in some cases is a telecommunication and/or data network. The network 6630 can include one or more computer servers, which can enable distributed computing, such as cloud computing. The network 6630, in some cases with the aid of the computer system 6601, can implement a peer-to-peer network, which may enable devices coupled to the computer system 6601 to behave as a client or a server.

The CPU 6605 can execute a sequence of machine-readable instructions, which can be embodied in a program or software. The instructions may be stored in a memory location, such as the memory 6610. The instructions can be directed to the CPU 6605, which can subsequently program or otherwise configure the CPU 6605 to implement methods of the present disclosure. Examples of operations performed by the CPU 6605 can include fetch, decode, execute, and writeback.

The CPU 6605 can be part of a circuit, such as an integrated circuit. One or more other components of the system 6601 can be included in the circuit. In some cases, the circuit is an application specific integrated circuit (ASIC).

The storage unit 6615 can store files, such as drivers, libraries and saved programs. The storage unit 6615 can store user data, e.g., user preferences and user programs. The computer system 6601 in some cases can include one or more additional data storage units that are external to the computer system 6601, such as located on a remote server that is in communication with the computer system 6601 through an intranet or the Internet.

The computer system 6601 can communicate with one or more remote computer systems through the network 6630. For instance, the computer system 6601 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 6601 via the network 6630. Other examples of remote computers systems include the glucose level monitor 111 and the medical device 116.

Methods as described herein can be implemented by way of machine (e.g., computer processor) executable code stored on an electronic storage location of the computer system 6601, such as, for example, on the memory 6610 or electronic storage unit 6615. The machine executable or machine readable code can be provided in the form of software. During use, the code can be executed by the processor 6605. In some cases, the code can be retrieved from the storage unit 6615 and stored on the memory 6610 for ready access by the processor 6605. In some situations, the electronic storage unit 6615 can be precluded, and machine-executable instructions are stored on memory 6610.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 6601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 6601 can include or be in communication with an electronic display 6635 that comprises a user interface (UI) 6640 for providing, for example, food image rating, analysis report, and/or one or more recommendations. Examples of UI's include, without limitation, a graphical user interface (GUI) and web-based user interface.

Remarks

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein may be employed. It is intended that the following claims define the scope of the disclosure, and that methods and structures within the scope of these claims and their equivalents be covered thereby.

What is claimed is:

1. A system comprising:
one or more processors; and
one or more processor-readable storage media storing instructions which, when executed by the one or more processors, cause performance of:
obtaining user input that includes textual input indicating quantitative information for a food item;
determining, based on the quantitative information for the food item, nutritional information for the food item, wherein the quantitative information for the food item is different from the nutritional information for the food item; and
generating, based on the nutritional information, an insulin delivery recommendation.

2. The system of claim 1, wherein the nutritional information comprises a carbohydrate content of the food item.

3. The system of claim 1, wherein generating the insulin delivery recommendation comprises accessing an equation modeling a relationship between carbohydrates and insulin.

4. The system of claim 1, wherein the quantitative information includes a quantity, a serving size, or both for the food item.

5. The system of claim 1, wherein the food item is to be consumed by a user of a wearable insulin delivery device.

6. The system of claim 1, wherein the insulin delivery recommendation comprises bolus information.

7. The system of claim 1, wherein the insulin delivery recommendation comprises a timing for insulin delivery.

8. A processor-implemented method comprising:
obtaining user input that includes textual input indicating quantitative information for a food item;
determining, based on the quantitative information for the food item, nutritional information for the food item, wherein the quantitative information for the food item is different from the nutritional information for the food item; and
generating, based on the nutritional information, an insulin delivery recommendation.

9. The processor-implemented method of claim 8, wherein the nutritional information comprises a carbohydrate content of the food item.

10. The processor-implemented method of claim 8, wherein generating the insulin delivery recommendation comprises accessing an equation modeling a relationship between carbohydrates and insulin.

11. The processor-implemented method of claim 8, wherein the quantitative information includes a quantity, a serving size, or both for the food item.

12. The processor-implemented method of claim 8, wherein the food item is to be consumed by a user of a wearable insulin delivery device.

13. The processor-implemented method of claim 8, wherein the insulin delivery recommendation comprises bolus information.

14. The processor-implemented method of claim 8, wherein the insulin delivery recommendation comprises a timing for insulin delivery.

15. One or more non-transitory processor-readable storage media storing instructions which, when executed by one or more processors, cause performance of:
Obtaining user input that includes textual input indicating quantitative information for a food item;
determining, based on the quantitative information for the food item, nutritional information for the food item, wherein the quantitative information for the food item is different from the nutritional information for the food item; and
generating, based on the nutritional information, an insulin delivery recommendation.

16. The one or more non-transitory processor-readable storage media of claim 15, wherein the nutritional information comprises a carbohydrate content of the food item.

17. The one or more non-transitory processor-readable storage media of claim 15, wherein generating the insulin delivery recommendation comprises accessing an equation modeling a relationship between carbohydrates and insulin.

18. The one or more non-transitory processor-readable storage media of claim 15, wherein the quantitative information includes at least one of a group comprising a plurality of serving sizes.

19. The one or more non-transitory processor-readable storage media of claim 15, wherein the insulin delivery recommendation comprises bolus information.

20. The one or more non-transitory processor-readable storage media of claim 15, wherein the insulin delivery recommendation comprises a timing for insulin delivery.

* * * * *